(12) United States Patent
Mueller et al.

(10) Patent No.: US 12,259,387 B2
(45) Date of Patent: *Mar. 25, 2025

(54) SYSTEM, METHOD, APPARATUS AND DIAGNOSTIC TEST FOR PLASMODIUM VIVAX

(71) Applicant: The Walter and Eliza Hall Institute of Medical Research, Parkville (AU)

(72) Inventors: Ivo Mueller, Mount Macedon (AU); Takafumi Tsuboi, Ehime Prefecture (JP); Michael White, Melbourne (AU); Rhea Longley, Brunswick West (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,736

(22) Filed: Oct. 11, 2023

(65) Prior Publication Data

US 2024/0295554 A1    Sep. 5, 2024

Related U.S. Application Data

(63) Continuation of application No. 16/472,269, filed as application No. PCT/IB2017/001776 on Dec. 21, 2017, now Pat. No. 11,835,520.

(60) Provisional application No. 62/438,963, filed on Dec. 23, 2016.

(51) Int. Cl.
| | | |
|---|---|---|
| *G01N 33/573* | (2006.01) | |
| *C07K 14/415* | (2006.01) | |
| *C07K 16/20* | (2006.01) | |
| *G01N 33/569* | (2006.01) | |
| *G01N 33/68* | (2006.01) | |

(52) U.S. Cl.
CPC ..... *G01N 33/56905* (2013.01); *C07K 14/415* (2013.01); *C07K 16/205* (2013.01); *G01N 33/6857* (2013.01); *G01N 2333/445* (2013.01)

(58) Field of Classification Search
None
See application file for complete search history.

(56) References Cited

PUBLICATIONS

Chuquiyauri et al (Amer. J. Trop. Med and Hygiene. Oct. 7, 2015; 93(4): 801-809 ).*
Kerkhof, K. et al. ('Serological markers to measure recent changes in malaria at population level in Cambodia', Malaria journal. Dec. 2016. vol. 15. No. 1. e.529).*

\* cited by examiner

*Primary Examiner* — Jennifer E Graser
(74) *Attorney, Agent, or Firm* — Hoffmann & Baron LLP

(57) ABSTRACT

A system, method, apparatus and diagnostic test for *Plasmodium vivax*, to determine a likelihood of a specific timing of infection by *P. vivax* in a subject, and hence identify individuals with a high probability of being infected with otherwise undetectable liver-stage hypnozoites. The system, method, apparatus and diagnostic test relate to the identification of hypnozoites ("dormant" liver-stages), or at least of the likelihood of the subject being so infected. Optionally and preferably, the specific timing relates to recent infections, for example within the last 9 months.

21 Claims, 30 Drawing Sheets
Specification includes a Sequence Listing.

a) Initial down-selection b) Model-based down-selection

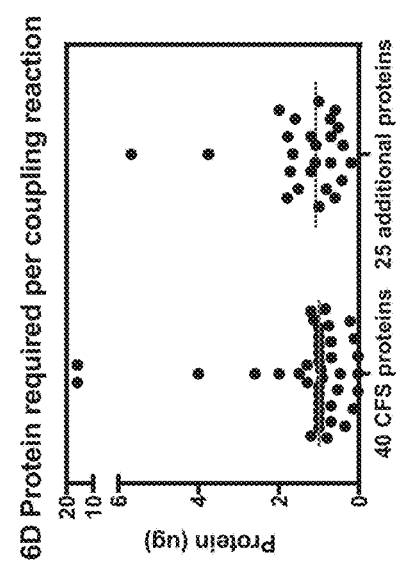
Fig 6D Protein required per coupling reaction
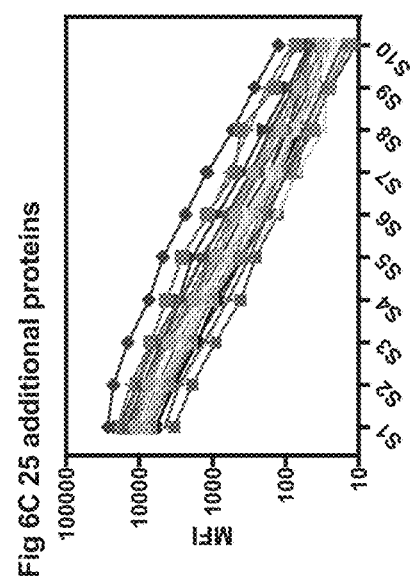
Fig 6C 25 additional proteins
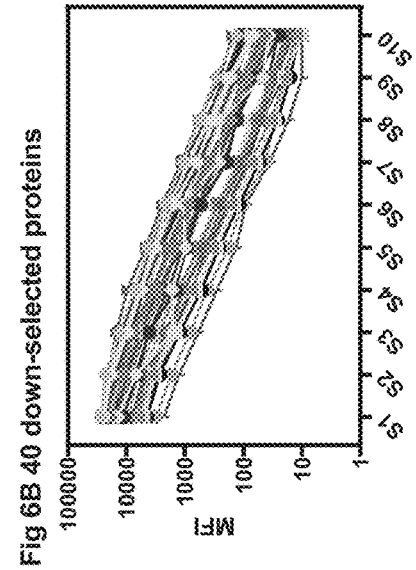
Fig 6B 40 down-selected proteins

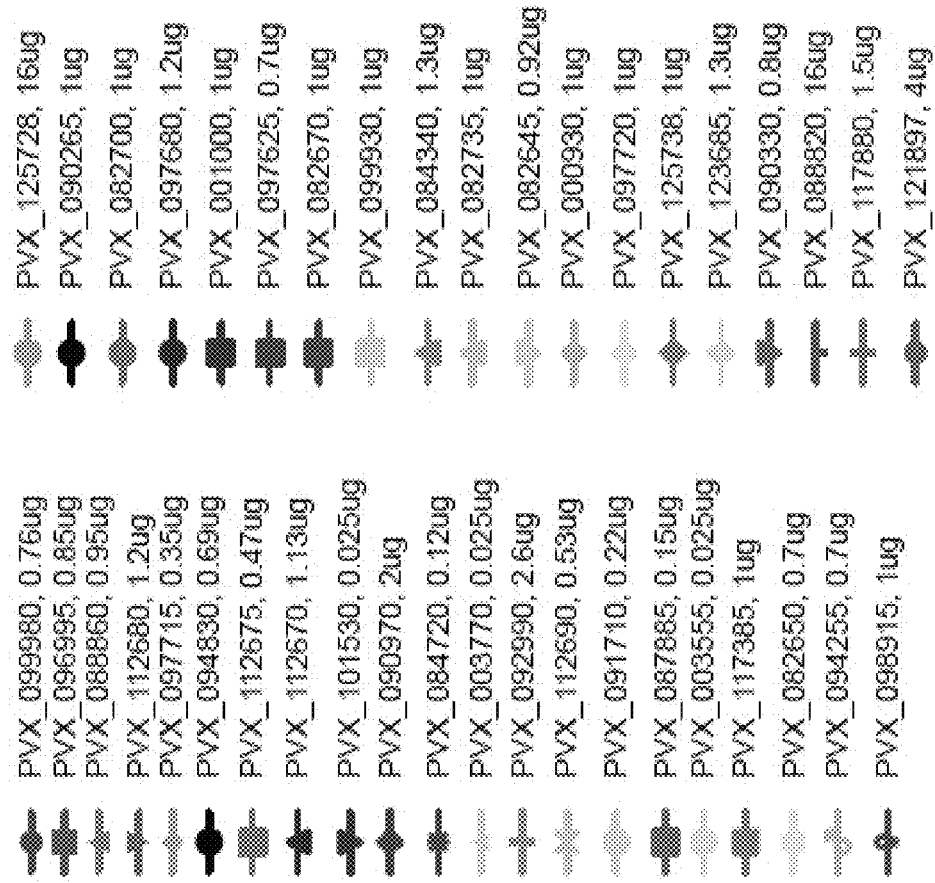
Figure 6E (key to Figure 6B)

Figure 6F (key to Figure 6C)

PVX_003795, 0.82ug
PVX_094350, 1.66ug
PVX_087110, 1.72ug
PVX_087670, 0.71ug
PVX_099930, 1.52ug
PVX_081330, 3.76ug
PVX_088820, 5.68ug
PVX_080665, 0.7ug
PVX_092995, 1.1ug
PVX_087885, 0.42ug
PVX_114330, 0.6ug
Pv DBP (SacI), 0.72ug

PVX_122805, 1.78ug
PVX_098585, 1.2ug
PVX_098582, 1.6ug
PVX_121920, 1.8ug
PVX_094255, 0.52ug
PVX_090325, 0.6ug
PVX_101590, 2ug
PvDBP R3-5, 0.4ug
PvGAMA, 1.2ug
PvRipr, 1ug
PvCYRPA, 1ug
Pv DBPII (AH), 1.08ug
PvEBP, 0.2ug

SYSTEM, METHOD, APPARATUS AND DIAGNOSTIC TEST FOR PLASMODIUM VIVAX

CROSS REFERENCE TO RELATED APPLICATIONS

The present invention is a continuation of U.S. application Ser. No. 16/472,269 filed Jun. 21, 2019, which is a national stage application which claims priority from PCT Application No. PCT/IB2017/001776 filed Dec. 21, 2017, and U.S. Application No. 62/438,963 filed Dec. 23, 2016. Applicants claim the benefits of 35 U.S.C. § 120 as to the said priority U.S. and PCT applications, and priority under 35 U.S.C. § 119 as to the said U.S. provisional application, and the entire disclosures of all applications are incorporated herein by reference in their entireties.

SEQUENCE LISTING

This application contains a Sequence Listing, submitted in, XML format via PatentCenter and hereby incorporated by reference in its entirety. The XML copy, created on May 7, 2024, is named "2762-9_PCT_US_CON_2024-05-07.xml" and is 248,294 bytes in size.

FIELD OF THE INVENTION

The present invention is of a system, method, apparatus and diagnostic test for relapsing *Plasmodium* species (i.e *Plasmodium vivax* and *Plasmodium ovale*), and in particular, to such a system, method, apparatus and diagnostic test for *Plasmodium vivax* for characterizing at least one aspect of infection in a subject or a population of subjects.

BACKGROUND OF THE INVENTION

*Plasmodium vivax* (*P. vivax*) is one of five species of parasites that cause malaria in humans. This disease is marked by severe fever and pain, and can be fatal. The symptoms are caused by the parasite's infection, and destruction, of red blood cells in the subject. Infection of new subjects occurs when infectious mosquitoes take a blood meal from humans and inoculate parasites with their saliva.

Like one other species that infects humans, *P. ovale*, *P. vivax* has the ability to "hide" in the liver of a subject and remain dormant—and asymptomatic—before (re-)emerging to cause renewed bloodstage infections and malarial symptoms. Transmission from humans to mosquitoes can only occur when the sexual stages of the parasite (gametocytes) are circulating in the blood. Liver-stage infection with hypnozoites is completely undetectable and asymptomatic, and transmission to mosquitoes is not possible. *P. falciparum* and *P. knowlesi* do not have this ability. *P. malariae* can cause recurrent infections but it remains unclear if these infections persist in the bloodstream, the liver or another organ. This ability to hide from the immune system in the liver for prolonged periods makes *P. vivax* and *P. ovale* particularly difficult to detect and treat.

FIG. 1 shows the overall life cycle of the *P. vivax* parasite (see Mueller, I. et al. Key gaps in the knowledge of *Plasmodium vivax*, a neglected human malaria parasite. Lancet Infectious Diseases 9, 555-566 (2009)). During a blood meal, a malaria-infected female *Anopheles* mosquito inoculates sporozoites into the human host (1). Sporozoites infect liver cells (2) and either enter a dormant hypnozoite state or mature into schizonts (3), which rupture and release merozoites (4). After this initial replication in the liver (exo-erythrocytic schizogony A), the parasites undergo asexual multiplication in the erythrocytes (erythrocytic schizogony B). Merozoites infect red blood cells (5). The ring stage trophozoites mature into schizonts, which rupture releasing further merozoites into the blood stream (6). Some parasites differentiate into sexual erythrocytic stages (gametocytes) (7). Blood stage parasites are responsible for the clinical manifestations of the disease.

The gametocytes, male (microgametocytes) and female (macrogametocytes), are ingested by an *Anopheles* mosquito during a blood meal (8). The parasites' multiplication in the mosquito is known as the sporogonic cycle (C). While in the mosquito's stomach, the microgametes penetrate the macrogametes generating zygotes (9). The zygotes in turn become motile and elongated (ookinetes) (10) which invade the midgut wall of the mosquito where they develop into oocysts (11). The oocysts grow, rupture, and release sporozoites (12), which make their way to the mosquito's salivary glands. Inoculation of the sporozoites (1) into a new human host perpetuates the malaria life cycle.

Diagnosis of subjects with *P. vivax* infections is of paramount importance to reducing or even eliminating transmission in a population. Such diagnosis would also significantly help individual subjects to receive proper treatment, including those that have only silent liverstage infections. Given the high degree of population mobility today, particularly in response to natural disasters or human conflicts, accurate and rapid diagnosis of all *P. vivax* infections has become even more important to controlling the disease. In addition, as transmission in countries decreases (as each population approaches elimination of the disease), population-level surveillance becomes increasingly important. This surveillance will aid in determining residual areas of transmission within a country, and can also be used to provide evidence for the absence of transmission indicating that elimination has been achieved.

Some proteins have been very well studied and characterized for diagnostic purposes. For example, merozoite surface protein 1 (MSP1), in particular certain C-terminal MSP1-19 fragments and the N-terminal Pv200L fragments have been described as suitable diagnostic antigens. Some examples of prior publications related to this protein include U.S. Pat. No. 6,958,235, which focuses on a fragment of this protein for diagnostic purposes; WO9208795A1, which focuses on this protein for diagnosis; and US20100119539. Merozoite surface protein 3 (MSP3) is described with regard to a diagnostic tool in U.S. Pat. No. 7,488,489. MSP3.10 [merozoite surface protein 3 alpha (MSP3a)] is described as part of the family of merozoite surface protein 3 like proteins for diagnostic and other purposes in US20070098738. Rhoptry associated membrane antigen is described with regard to a diagnostic tool in EP0372019 B1. Many other proteins were described in relation to their immunogenicity and hence their therapeutic utility as part of a vaccine. Some non-limiting examples are given below.

| UniProt | Annotation[1] | Patent information |
|---|---|---|
| A5K3N8 | rhoptry neck protein 2, putative (RON2) | Vaccine including this protein (US20160158332); specifically described and claimed for diagnosis in EP2520585, no family members, abandoned in 2013 |
| A5KBS6 | hypothetical protein, conserved (PvLSA3[d]) | WO2015091734 (vaccine) |
| A5K4Z2 | apical merozoite antigen 1 (PvAMA1) | U.S. Pat. No. 9,364,525 (one of a list of antigens for a vaccine, downloaded as US20100150998); WO2006037807-structure of this antigen; U.S. Pat. No. 7,150,875-vaccine specifically directed at this antigen |
| A5K0N7 | translocon component PTEX150, putative (PTEX150) | US20140348870-Especially preferred antigens are post-challenge immunity associated antigens that are identified via pre-infection suppressive treatment, controlled sub-symptomatic infection to develop immunity, and comparative proteomic differential analysis. WO2010127398-more focused on treatment |
| A5KBL6 | merozoite surface protein 5 | WO2014186798-immune stimulation (1 of a long list of diseases and antigens); U.S. Pat. No. 8,350,019 (focuses on this protein for diagnostic use); WO2015031904-use of this protein to determine if an individual is protected against malaria; WO2016030292-focused on treatment; US20110020387-malaria vaccine |
| A5K800 | MSP7 [merozoite surface protein 7 (MSP7)] | EP2990059-therapeutic but mentions MSP7 specifically |
| A5K736 | reticulocyte binding protein 2b (RBP2b) | U.S. Pat. No. 8,703,147-treatment and prevention of malaria |
| A5KAV2 | merozoite surface protein 3 (MSP3.3) | EP2223937-prevention and treatment of malaria; describes the gene family that includes this protein for diagnosis and treatment-EP1689866 |
| A5KAU1 | merozoite surface protein 8, putative | US20140348870-identified this protein as immunogenic |
| A5K806 | thrombospondin-related anonymous protein (PvTRAP/SSP2) | Immunogenic, part of a vaccine: US20100272745, U.S. Pat. No. 7,790,186, U.S. Pat. No. 7,150,875, WO2013142278, WO2015091734 |
| A5KDR7 | Duffy receptor precursor (DBP) | mentioned as immunogenic protein, part of a vaccine: U.S. Pat. No. 7,790,186 |
| A5KAW0 | MSP3.10 [merozoite surface protein 3 alpha (MSP3a)] | US20070098738-describes entire protein family; US707129-describes various members of this family as being immunogenic |

Still other proteins have barely been described or characterized in the literature. In some cases, these proteins have not yet been described with regard to their stage in the *P. vivax* life cycle. In other cases, an initial determination of the stage has been made but their diagnostic or therapeutic utility is not known. A non-limiting list of some of these proteins is provided below. A further list is provided with regard to Appendix I, although optionally any annotated proteins from *P. vivax* in Uniprot (http://www.uniprot.org/uniprot/) or another suitable protein database could be included.

| Uniprot | Protein name |
|---|---|
| A5K7E7 | hypothetical protein, conserved |
| A5K482 | hypothetical protein, conserved |
| A5K0Q6 | hypothetical protein, conserved |
| A5K4N0 | hypothetical protein, conserved |
| A5KAP7 | hypothetical protein, conserved |
| A5K4I6 | hypothetical protein, conserved |
| A5K659 | hypothetical protein, conserved |
| A5KB45 | hypothetical protein, conserved |

Very few attempts have been made to characterize the life cycle of the parasite within the body for diagnostic purposes, in terms of the dynamics of the proteins or antibody responses to specific proteins present in the blood. For example, an assay for determining a state of protective immunity is described in US20160216276. However, the disclosure relates to diagnostic assays for identifying individuals that are protected against *Plasmodium falciparum* caused malaria. As noted above, *P. falciparum* does not have a dormant liver stage with long-latency giving rise to relapses. This patent application does not mention *P. vivax*.

Other prior art disclosures for diagnostics focus only on the blood stage of *P. vivax*, which again prevents a complete picture of the dynamics of the infection in the subject from being determined. U.S. Pat. No. 6,231,861 and US20090117602 both suffer from this deficiency.

In other cases, where a plurality of antigens were examined for malarial diagnostics of *P. vivax*, the results still did not provide a complete picture of the dynamics of the infection in the subject. For example, "Genome-Scale Protein Microarray Comparison of Human Antibody Responses in *Plasmodium vivax* Relapse and Reinfection" (Chuquiyauri et al; Am. J. Trop. Med. Hyg., 93(4), 2015, pp. 801-809) suffered from the following drawbacks:
  i) It only features antibody signatures that differentiate between blood-stage infections that are thought to stem either from direct infections or relapsing infections;
  ii) The phenotypes are of poor quality because they are focused on genotyping with only one gene, so may overestimate the number of new infections vs relapses;
  iii) They are only looking at the presence and titer of antigens at one timepoint (i.e. at the time of infection).

In another example, "Serological markers to measure recent changes in malaria at population level in Cambodia" (Kerkhof et al; Malaria Journal, 15 (1), 2016, pp. 529, the authors calculated estimated antibody half-lives to 19 *Plasmodium* proteins, including 5 *P. vivax* proteins. These 5 proteins are well-known vaccine candidates (CSP, AMA1, EBP, DBP and MSP1), and the work included no formal antigen down-selection. A major limitation of this study is that individuals were only assessed for malaria prevalence every 6 months, and hence the estimated half-lives are not a true biological reflection of what occurs in the absence of reinfection. The authors only identified one *P. vivax* antigen, EBP, that had an estimated antibody half-life of less than 2 years.

BRIEF SUMMARY OF THE INVENTION

The present invention, in at least some embodiments, is of a system, method, apparatus and diagnostic test for *Plasmodium vivax*, to determine a likelihood of a specific timing of infection by *P. vivax* in a subject, and hence identify individuals with a high probability of being infected with otherwise undetectable liver-stage hypnozoites. According to at least some embodiments, the system, method, apparatus and diagnostic test relate to the identification of hypnozoites ("dormant" liver-stages), or at least of the likelihood of the subject being so infected. Optionally and preferably, the specific timing relates to recent infections, for example within the last 9 months. Without wishing to be limited by a closed list, the present invention is able to identify such recent infections, and not just current infections.

Non-limiting examples of elapsed time periods since an infection include time since infection ranging from 0 to 12 months, and each time period in between, by month, by week, and/or by day. Optionally and preferably a particular time period is determined as a binary decision of a more recent or an older infection, with each time point as a cut-off. As a non-limiting example, one such cut off could determine whether an infection in a subject was within the past 9 months or later than the past 9 months.

Optionally the timing of such an infection may also be determined, such that one or more of the following parameters may be determined. One such parameter is optionally whether the infection is a first infection in the patient, of *P. vivax* generally or of a particular strain of *P. vivax*. As there is no sterilizing immunity in malaria, immunity to one strain does not necessarily confer immunity to another, different strain. However, as described in greater detail below with regard to the examples, the present invention was tested by using samples from three different regions (including Brazil, Thailand and the Solomon Islands). These three populations are genetically highly diverse and represent the major part of the global genetic variation in *P. vivax*. Consequently, the present inventors believe, without wishing to be limited by a single hypothesis, that it will work anywhere in the world. Other parameters relate to time elapsed from the previous infection.

According to at least some embodiments, the antibody measurements may optionally be used to provide an estimation of elapsed time since last infection. An estimate of the time since last *P. vivax* blood-stage infection-depending on the available calibration data—can be defined either as the time since last PCR-detectable blood-stage parasitemia, or as the time since last infective mosquito bite. Time since last infection can be estimated continuously or categorically. Concurrent estimation of uncertainty will be important.

According to at least some embodiments, the antibody measurements may optionally be used to provide a determination of medium-term serological exposure, for example a frequency of infections during a particular time period and/or time since last infection.

According to at least some embodiments, there is provided a system, method, apparatus and diagnostic test for detection of a "silent" (asymptomatic or presymptomatic) infection by *P. vivax*.

According to at least some embodiments, there is provided a system, method, apparatus and diagnostic test for detection of a dormant infection, in which *P. vivax* is present in the liver but is not present at detectable levels in the blood. As described herein, detection of a dormant infection optionally comprises prediction from an indirect measurement of an antibody level.

During the life cycle of *P. vivax*, blood-stage forms of the parasite can initially be present at the same time as arrested liver forms, as described in the Background of the Invention. Even after the blood-stage infection has cleared, hypnozoites can still be present in the liver, and the parasite may still be indirectly detected via persisting antibody responses against the primary blood-stage infection. According to at least some embodiments, there is provided a system, method, apparatus and diagnostic test for detection of antibodies to malarial proteins that are present in the blood that indicate a high degree of probability of liver-stage infection.

According to at least some embodiments, there is provided a system, method, apparatus and diagnostic test for determination of the progression of infection by *P. vivax* in a population of a plurality of subjects. Optionally, it is possible to determine the rate of propagation of a particular *Plasmodium* species in a population not previously exposed to that species.

With regard to the diagnostic test, in at least some embodiments, there is provided a plurality of antibodies that bind to a plurality of antigens in a blood sample taken from the subject. Optionally any suitable tissue biological sample from a subject may be used for detecting a presence and/or level of a plurality of antibodies.

According to at least some embodiments, the dynamics of the measured antibodies preferably include a combination of short-lived and long-lived antibodies. Without wishing to be limited by a single hypothesis or a closed list, such a combination is useful to reduce measurement error.

Optionally the level of antibodies is measured at one time point or a plurality of time points.

Optionally, the presence of the actual antibodies in the blood of the subject is measured at a plurality of time points to determine decay in the level of the antibody in the blood. Such a decay in the level is then optionally and preferably fitted to a suitable model as described herein, in order to determine at least one of the infection parameters as described above. More preferably, decay of the level of a plurality of different antibodies is measured. Optionally and more preferably, the different antibodies are selected to have a range of different half-lives. Optionally, a maximum number of different antibodies is measured, which is optionally up to 20 or as few as two, or any integral number in between. According to at least some embodiments, the number of antibodies is preferably 4 or 8.

According to at least some embodiments, the level is measured of at least one antibody to a protein selected from the group consisting of: PVX_099980, PVX_112670, PVX 087885, PVX 082650, PVX_088860, PVX 112680, PVX 112675, PVX 092990, PVX_091710, PVX_117385, PVX_098915, PVX_088820, PVX_117880, PVX_121897, PVX 125728, PVX 001000, PVX_084340, PVX 090330, PVX_125738, PVX_096995, PVX_097715, PVX_094830, PVX_101530, PVX_090970, PVX_084720, PVX_003770, PVX 112690, PVX 003555, PVX_094255, PVX 090265, PVX_099930, PVX_123685, PVX_002550, PVX_082700, PVX_097680, PVX_097625, PVX_082670, PVX_082735, PVX 082645, PVX 097720, PVX 000930, PVX 094350, PVX 099930, PVX_114330, PVX_088820, PVX_080665, PVX_092995, PVX_087885, PVX_003795, PVX_087110, PVX_087670, PVX_081330, PVX_122805, RBP1b (P7), RBP2a (P9), RBP2b (P25), RBP2cNB (M5), RBP2-P2 (P55), PvDBP R3-5, PvGAMA, PvRipr, PvCYRPA, Pv DBPII (AH), PvEBP, RBP1a (P5) and Pv DBP (SacI).

Preferably, the level is measured of at least one antibody to a protein selected from the group consisting of PVX_099980, PVX_112670, PVX_087885, PVX_082650, PVX 088860, PVX 112680, PVX_112675, PVX_092990, PVX_091710, PVX_117385, PVX 098915, PVX 088820, PVX_117880, PVX_121897, PVX_125728, PVX_001000, PVX 084340, PVX 090330, PVX 125738, PVX_096995, PVX 097715, PVX_094830, PVX 101530, PVX_090970, PVX_084720, PVX_003770, PVX_112690, PVX_003555, PVX 094255, PVX_090265, PVX_099930 and PVX 123685.

More preferably, the level is measured of at least one antibody to a protein selected from the group consisting of PVX_099980, PVX_112670, PVX_087885, PVX 082650, PVX_096995, PVX 097715, PVX_094830, PVX_101530, PVX_090970, PVX 084720, PVX_003770, PVX_112690, PVX_003555, PVX_094255, PVX_090265, PVX 099930 and PVX 123685.

Most preferably, the level is measured of at least one antibody to a protein selected from the group consisting of PVX_099980, PVX_112670, PVX_087885 and PVX 082650.

According to at least some embodiments, preferably the level is measured of at least one antibody to a protein selected from the group consisting of RBP2b, L01, L31, X087885, PvEBP, L55, PvRipr, L54, L07, L30, PvDBPII, L34, X092995, L12, RBP1b, L23, L02, L32, L28, L19, L36, L41, X088820 and PvDBP . . . SacI.

More preferably the level is measured of at least one antibody to a protein selected from the group consisting of RBP2b, L01, L31, X087885, PvEBP, L55, PvRipr, L54, L07, L30, PvDBPII, L34, X092995, L12 and RBP1b.

Also more preferably the level is measured of at least one antibody to a protein selected from the group consisting of RBP2b, L01, L31, X087885, PvEBP, L55, PvRipr and L54.

Most preferably the level is measured of at least one antibody to a protein selected from the group consisting of RBP2b and L01.

A table containing additional proteins against which antibodies may optionally be measured is provided herein in Appendix I, as described in greater detail below, such that the level of one or more of these antibodies may optionally be measured.

Appendix II gives a list of preferred proteins against which antibodies may be measured, while Appendix III shows a complete set of data for antibodies against the proteins in Appendix II. Appendix III is given in two parts, due to the size of the table: Appendix IIIA and Appendix IIIB. The references to gene identifiers in Appendix II are the common ones used for *Plasmodium*—from PlasmoDB website: http://plasmodb.org/plasmo/.

For any protein described herein, optionally a fragment and/or variant may be used for detecting the presence and/or level of one or more antibodies in a biological sample taken from a subject.

According to at least some embodiments, a biologically-motivated model of the decay of antibody titers over time is used to determine a statistical inference of the time since last infection. The model preferably uses previously determined decay rates of a plurality of different antibodies to determine a likelihood that infection in the subject occurred within a particular time period. Optionally such previously determined decay rates may be achieved through estimation of antibody decay rates from longitudinal data, or estimation of decay rates from cross-sectional antibody measurements.

With regard to estimation of antibody decay rates from longitudinal data, preferably such an estimation is performed as described in equation (1), which is a mixed-effects linear regression model:

$$\log(A_{ijk}) \sim (\alpha_k^0 + \alpha_{ik}) + (r_k^0 + r_{ik})t_j + \varepsilon_k \qquad \text{Equation 1}$$

$$\alpha_{ik} \sim N(0, \sigma_{\alpha,k})$$

$$r_{ik} \sim N(0, \sigma_{r,k})$$

$$\varepsilon_{ik} \sim N(0, \sigma_{m,k})$$

For the above equation to be true, the following assumptions were made. We assume that for individual i we have measurements of antibody titer $A_{ijk}$ at time j to antigen k. We assume that at time 0, antibody titers are Normally distributed5 with mean $\alpha_k^0$ and standard deviation $\sigma_{\alpha,k}$ on a log-scale. We assume that an individual's rate of antibody decay is drawn from a Normal distribution with mean $r_k^0$ and standard deviation $\sigma_{r,k}$.

According to at least some embodiments, the plurality of different antibodies selected maximizes probability of determining at least one of the infection parameters as described above. A method for such a selection process is described below in Example 3. Optionally the plurality of antibodies is selected for determining an answer to a binary determinant, such as for example, whether an individual was infected before x months ago or after as previously described.

According to at least some embodiments, the model for determining at least one parameter about the infection in the subject may optionally comprise one or more of the following algorithms: linear discriminant analysis (LDA), quadratic discriminant analysis (QDA), combined antibody dynamics (CAD), decision trees, random forests, boosted trees and modified decision trees.

According to at least some embodiments, the levels of antibody in a blood-sample can be measured and summarized in a variety of ways, for input to the above described model.

a) Continuous Measurement

A continuous measurement that has a monotonic relationship with antibody titer. It can be compared with a titration curve to produce an estimate of antibody titer.

b) Binary Classification

Assesses whether antibody levels are greater or less than some threshold c) Categorical Classification Assigns antibody levels to one of a set of pre-defined categories, e.g. low, medium, high. A categorical classification can be generated via a series of binary classifications.

According to at least some embodiments, antibody levels may optionally be measured in a subject in a number of different ways, including but not limited to, bead-based assays (e.g. AlphaScreen® or Luminex® technology), the enzyme linked immunosorbent assay (ELISA), protein microarrays and the luminescence immunoprecipitation system (LIPS). All the aforementioned methods generate a continuous measurement of antibody.

BRIEF DESCRIPTION OF THE DRAWINGS

FIGS. 6B-6D show additional development and optimization of the Luminex bead-array assay for all 65 proteins assessed in the validation study as follows. FIG. 6B shows 40 down-selected proteins. FIG. 6C shows the remaining 25 proteins. Log-linear standard curves were achieved for all proteins. The amount of protein for one bulk reaction of 500 ul beads is shown in FIG. 6D, with the line indicating the median (1 and 1.08 ug, respectively).

FIG. 6E provides a key to FIG. 6B. FIG. 6F provides a key to FIG. 6C.

DESCRIPTION OF AT LEAST SOME EMBODIMENTS

Figure 1:
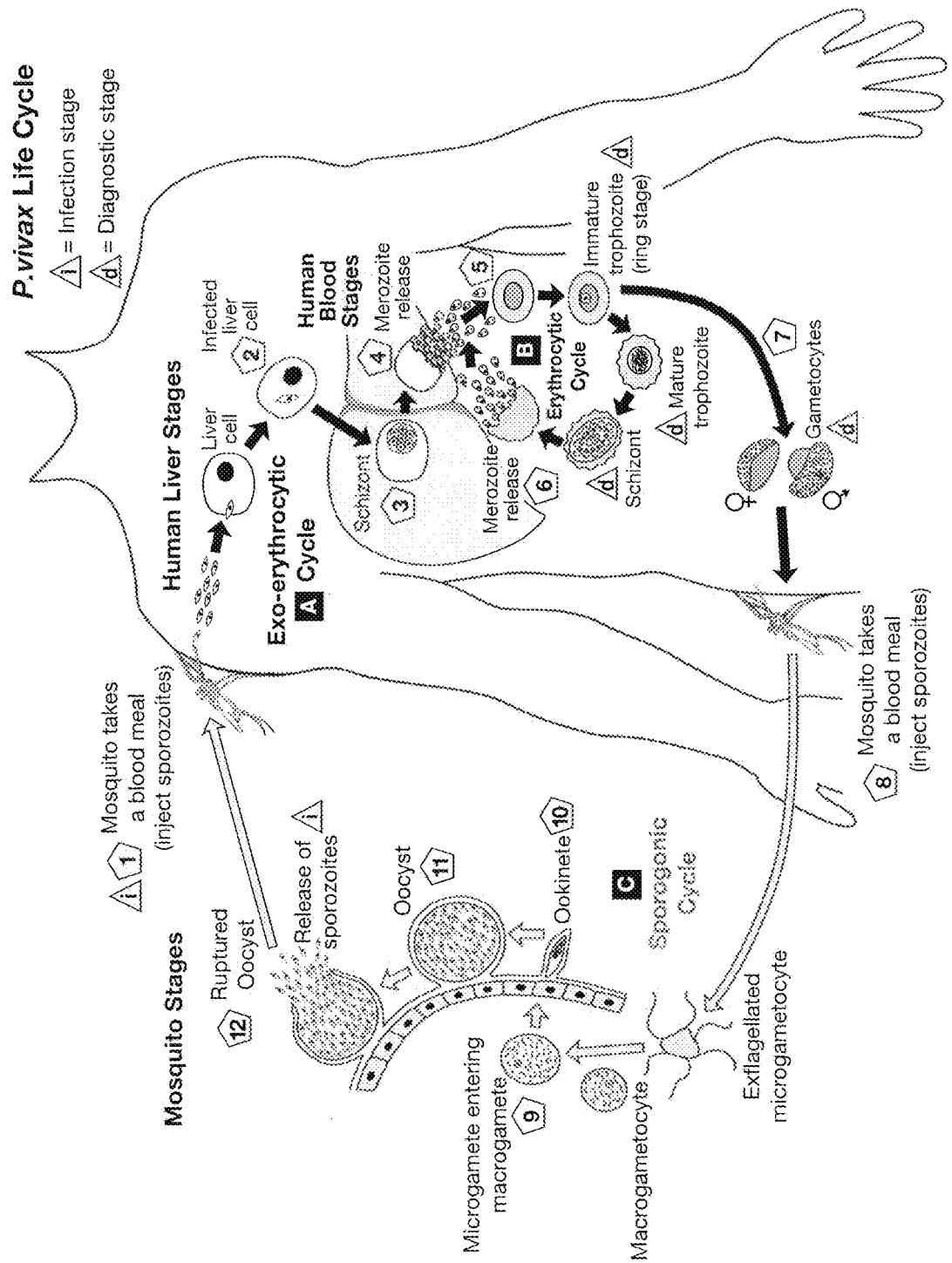
FIG. 1 shows a background art description of the lifecycle of *P. vivax* (see Mueller, I. et al. Key gaps in the knowledge of *Plasmodium vivax*, a neglected human malaria parasite. Lancet Infectious Diseases 9, 555-566 (2009)).

The present invention, in at least some embodiments, is of a system, method, apparatus and diagnostic test for at least *Plasmodium vivax*, and optionally other species such as *P. ovale*, to determine a likelihood of a concurrent or the specific timing of a recent past infection by *P. vivax* in a subject, and hence identify individuals with a high probability of being infected with otherwise undetectable liverstage hypnozoites. According to at least some embodiments, the system, method, apparatus and diagnostic test relate to the identification of hypnozoites ("dormant" liver-stages), or at least of the likelihood of the subject being so infected. Optionally and preferably, the specific timing relates to recent infections, for example within the last 9 months. Without wishing to be limited by a closed list, the present invention is able to identify such recent infections, and not just current infections.

According to at least some embodiments, the antibody measurements may optionally be used to provide an estimation of elapsed time since last infection. An estimate of the time since last *P. vivax* blood-stage infection-depending on the available calibration data, the time since last infection can be defined either as the time since last PCR-detectable blood-stage parasitemia, or as the time since last infected mosquito bite. Time since last infection can be estimated continuously or categorically. Concurrent estimation of uncertainty will be important.

According to at least some embodiments, the antibody measurements may optionally be used to provide a determination of medium-term serological exposure, for example a frequency of infections during a particular time period and/or time since last infection.

According to at least some embodiments, there is provided a system, method, apparatus and diagnostic test for detection of a "silent" (asymptomatic or presymptomatic) infection by *P. vivax*.

Protein Nomenclature

Throughout the below experiments, simplified names have been used for the proteins assessed. In the antigen discovery experiments using the AlphaScreen® assay, 342 proteins were assessed. These proteins were given codes consisting of single letters followed by 2 numbers in most instances, and on occasion 3 numbers.

In the validation experiments using the multiplexed assay (Luminex® technology), 40 proteins (out of the 53 potential candidates down-selected) were assessed. These proteins have been given codes beginning with 'L' followed by 2 numbers. These proteins were supplemented by an additional 25 proteins expressed in a variety of systems. These proteins have been given codes beginning with 'V' or 'X' followed by 2 numbers. The codes used for the tested candidates are outlined below, as well as in Appendix II, in reference to their PlasmoDB gene ID (plasmodb.org).

| PlasmoDB ID | AlphaScreen | Luminex |
|---|---|---|
| PVX_099980 | D10 | L01 |
| PVX_096995 | J12 | L02 |
| PVX_088860 | L19 | L03 |
| PVX_097715 | N17 | L07 |
| PVX_112680 | K21 | L06 |
| PVX_094830 | N13 | L10 |
| PVX_112675 | B19 | L11 |
| PVX_112670 | G21 | L12 |
| PVX_101530 | D21 | L05 |
| PVX_090970 | E10 | L14 |
| PVX_084720 | B8 | L18 |
| PVX_003770 | P17 | L19 |
| PVX_092990 | H14 | L20 |
| PVX_112690 | K10 | L21 |
| PVX_091710 | F13 | L22 |
| PVX_087885 | N9 | L23 |
| PVX_003555 | O21 | L24 |

A complete list of all sequences considered, plus the sequences themselves, may be found in Appendices I and II combined. These sequences include the reference to the amino acid and nucleic acid sequence records of the relevant antigens, plus actual sequences generated for testing. The actual amino acid sequences generated for testing include a methionine at the start (N-terminus) and a His-tag at the end (C-terminus) as non-limiting examples only. The nucleic acid sequences so generated correspond to these amino acid sequences. It should be noted that the sequences listed are intended as non-limiting examples only, as different sequences and/or different antigens may optionally be used with the present invention, additionally or alternatively. The amino acid sequences for the specific proteins referred to herein may optionally be obtained from Uniprot or another suitable protein database.

Example 1—Testing of Antigens

This non-limiting Example relates to testing of antibody responses to various *P. vivax* proteins, present in the blood, as potential antigens for a diagnostic test.

Materials and Methods

Ethics Statement.

The relevant local ethics committees approved all field studies and all patients gave informed consent or assent. The Ethics Committee of the Faculty of Tropical Medicine, Mahidol University, Thailand approved the Thai antigen discovery and validation studies (MUTM 2014-025-01 and 02, and MUTM 2013-027-01, respectively). The Ethics Review Board of the Fundação de Medicina Tropical Dr. Heitor Vieira Dourado (FMT-HVD) (957.875/2014) approved the Brazilian antigen discovery study. The samples used from Brazil for the validation study were approved by the FMT-HVD (51536/2012), by the Brazilian National Committee of Ethics (CONEP) (349.211/2013) and by the Ethics Committee of the Hospital Clinic, Barcelona, Spain (2012/7306). The National Health Research and Ethics Committee of the Solomon Islands Ministry of Health and Medical Services (HRC12/022) approved collection of the samples used from the Solomon Islands for the validation study. The Human Research Ethics Committee at WEHI approved samples for use in Melbourne (#14/02).

Field Sites and Sample Collection: Antigen Discovery Study.

Samples from two longitudinal cohorts, located in Thailand and Brazil, were used for the antigen discovery studies. The longitudinal study in Thailand was conducted from April 2014 to September 2015, as previously described (Longley et al., Am J Trop Med Hyg. 2016 Nov. 2; 95(5): 1086-1089). Briefly, 57 symptomatic *P. vivax* patients were enrolled from either the Tha Song Yang malaria clinic or hospital. Patients with glucose-6-phosphate dehydrogenase (G6PD) deficiency and those aged younger than 7 years or more than 80 years were excluded. Patients were treated with chloroquine (25 mg base/kg body weight, administered over 3 days) and primaquine (15 mg daily, for 14 days) according to the standard Thai treatment regimen. Antimalarial drugs were given under directly-observed treatment in order to reduce the likelihood of treatment failure and the presence of recurrent infections during follow-up. Volunteers were followed for 9-months following enrolment, with finger-prick blood samples collected at enrolment and week 1, then every 2 weeks for 6 months, then every month until the end of the study. Blood was separated into packed red cells and plasma at the field site. All blood samples were analysed by both light microscopy and quantitative PCR (qPCR) for the presence of blood-stage parasites. A sub-set of volunteers, n=32, were selected for use in the antigen discovery project. These volunteers had no detectable recurrent infections during 9-months follow-up, and were the first to complete follow-up.

The longitudinal study in Brazil followed the same format as in Thailand. The study was conducted from May 2014 to May 2015. 91 malaria patients at Fundação de Medicina Tropical Doutor Heitor Vieira Dourado in Manaus aged between 7 and 70 years were enrolled. Individuals with G6PD deficiency or chronic diseases were not enrolled. Patients were treated according to the guidelines of the Brazilian Ministry of Health (3 days chloroquine, 7 days primaquine). Follow-up intervals with finger-prick blood sample collection were as in the Thai study. A sub-set of volunteers, n=33, whom had no detectable recurrent infections during 9-months follow-up, were selected for use in the antigen discovery project.

Field Sites and Sample Collection: Validation Study.

For the validation studies, samples collected from four observational longitudinal cohort studies, conducted in Thailand, Brazil and the Solomon Islands, were used (data from the Solomon Islands not shown). Samples were collected from a cohort of volunteers every month for 1 year. Plasma samples from the final cohort time-point were used in the validation study, n=829 Thailand, n=925 Brazil, and n=751 Solomon Islands.

The Thailand observational cohort was conducted from May 2013 to June 2014 in the Kanchanaburi and Ratchaburi provinces of western Thailand. The design of this study has been published (Longley et al, Clin Vaccine Immunol. 2015 Dec. 9; 23(2): 117-24). Briefly, a total of 999 volunteers were enrolled (aged 1-82 years, median 23 years). Volunteers were sampled every month over the yearlong cohort, with 14 active case detection visits performed in total. A total of 609 volunteers attended all visits, with 829 attending the final visit. At each visit, volunteers completed a brief survey outlining their health over the past month (to determine the possibility of missed malarial infections), in addition to travel history and bed net usage. A finger-prick blood sample was also taken and axillary temperature recorded. Blood samples were separated into packed red blood cells, for detection of malaria parasites, and plasma, for antibody measurements, at the field sites. In addition to the monthly active case detection visits, passive case detection was also performed routinely by local malaria clinics.

The Brazilian observational cohort was conducted from April 2013 to April 2014 in three neighbouring communities located on the outskirts of Manaus, Amazonas State. Briefly, a total of 1274 residents of all age groups were enrolled (range 0-102 years, median 25 years). Volunteers were sampled every month over the yearlong period, with 13 active case detection visits performed in total. At each visit a finger-prick blood sample was collected, with the exception of children aged less than one in which blood was collected from the heel or big toe. As per the Thai cohort study, at each visit body temperature was also recorded and a questionnaire undertaken outlining the participants' health, bed net usage and travel history. Passive case detection was performed routinely by local health services. Blood samples were processed as per the Thai cohort. Plasma samples from 925 volunteers were available from the final visit.

The Solomon Islands observational cohort was conducted from May 2013 to May 2014 in 20 villages on the island of Ngella, Solomon Islands. 1111 children were initially enrolled, and after exclusion of children who withdrew, had inconsistent attendance or failed to meet other inclusion criteria, 860 remained (Quah & Waltmann, in preparation). The age of the children ranged from 6 months to 12 years, with a median age of 5.6 years. Over the yearlong cohort, children were visited approximately monthly, with 11 active case detection visits in total. Of the 860 children, 751 attended the final visit. At each visit, a brief survey was conducted as per the Thai cohort, temperature recorded and a finger-prick blood sample taken. Blood was separated into packed red cells for qPCR and plasma for antibody measurements. In addition to the monthly active case detection visits, local health clinics and centres also performed passive case detection routinely.

Negative Control Samples: Melbourne and Thai Red Cross, Melbourne Blood Donors

Three panels of control samples were collected from individuals with no known previous exposure to malaria. The first panel was collected from the Volunteer Blood Donor Registry (VBDR) at the Walter and Eliza Hall of Medical Research in Melbourne, Australia. These individuals are not screened for diseases but a record of their past travel, medical history and current drug use is recorded. 102 volunteers from the VBDR were utilized (median age 39 years, range 19-68). The second panel was collected from the Australian Red Cross (Melbourne, Australia). 100 samples were utilized (median age 52 years, range 18-77), and these individuals were screened as per the standard conditions of the Australian Red Cross. Finally, another control panel was collected from the Thai Red Cross (Bangkok, Thailand). Samples from 72 individuals were utilized, but no demographic data was available (hence the age range is unknown). Standard Thai Red Cross screening procedures exclude individuals from donating blood if they had a past malaria infection with symptoms within the last three years, and individuals who have travelled to malaria-endemic regions within the past year.

All studies (antigen discovery and validation) detected malaria parasites by quantitative PCR as previously described (2, 3).

Protein Expression.

Proteins were preferably expressed as full-length proteins, to ensure that any possible antibody recognition site was covered. For very large proteins, fragments were expressed that together cover the entire protein. These were treated as individual constructs in the down-selection process. The proteins were first produced at a small-scale with a biotin tag for the antigen discovery study, at Ehime University. A panel of 342 *P. vivax* proteins were assessed, including well-known *P. vivax* proteins such as potential vaccine candidates (i.e. MSP1, AMA1, CSP), orthologs of immunogenic *P. falciparum* proteins and proteins with a predicted signal peptide (SP) and/or 1-3 transmembrane domains (TM) (4). The genes were amplified by PCR and cloned into the pEU_E01 vector with N-terminal His-bls tag (CellFree Sciences, Matsuyama, Japan). *P. vivax* genes were obtained either from parent clones (4), using SAL-1 cDNA, or commercially synthesized from Genscript (Japan). The recombinant proteins were expressed without codon optimization using the wheat germ cell-free (WGCF) system as previously described (5). WGCF synthesis of the *P. vivax* protein library was based on the previously described bilayer diffusion system (6). For biotinylation of proteins, 500 nM D-biotin (Nacalai Tesque, Kyoto, Japan) was added to both the translation and substrate layers. Crude WGCF expressed BirA (1 µl) was added to the translation layer. In vitro transcription and cell-free protein synthesis for the *P. vivax* protein library were carried out using the GenDecoder 1000 robotic synthesizer (CellFree Sciences) as previously described (7, 8). Expression of the proteins was confirmed by western blot using HRP-conjugated streptavidin.

Large-scale protein expression for the down-selected candidates was then performed (CellFree Sciences Tokyo, Japan). Genes were synthesized by GenScript (Japan) and the products cloned into the pEU-E01-MCS expression vector. The sequence of all gene synthesis products and their correct insertion into the expression vector was confirmed by full-length sequencing of the vector inserts. Transcription was performed utilizing SP6 RNA polymerase (80 U/µl) and the SP6 promoter in the pEU-E01-MCS expression vector. For large-scale expression, a dialysis-based refeeding assay was used, with protein expression and solubility first tested on a 50 µl scale. The test results then enabled production on a 3 ml scale (maintained for up to 72 hours, 15° C.) to produce at least 300 µg of each target protein, using the wheat germ extract WEPRO7240H. The proteins were manually purified one-time on an affinity matrix (Ni Sepharose 6 Fast Flow from GE Healthcare, Chalfont, United Kingdom) using a batch method (all proteins were expressed with a His-tag at the C terminus). The purified proteins were stored and shipped in the following buffer: 20 mM Na-phosphate pH 7.5, 0.3 M NaCl, 500 mM imidazole and 10% (v/v) glycerol. Protein yields and purity were determined using 15% SDS page followed by Coomassie Brilliant Blue staining using standard laboratory methods. In addition, proteins were also analyzed by Western Blot using an anti-His-tag antibody.

An additional 25 proteins were also used in the validation study. 12 proteins were produced using the wheat-germ cell free system described above at Ehime University, and were selected based on associations with past exposure in preliminary work conducted in a PNG cohort. The remaining 13 proteins were produced using standard *E. coli* methods, and were selected based on their predicted high immunogenicity (due to their status as potential vaccine candidates). References can be found in Appendix II.

AlphaScreen® Assay for the Antigen Discovery Study.

The AlphaScreen® assay was used to measure antibody responses in the antigen discovery study. Plasma samples from the sub-set of volunteers (n=32 Thailand, n=33 Brazil) were used from four time-points, enrolment (week 0) and weeks 12, 24 and 36. Responses were measured against 342 *P. vivax* proteins. The assay was conducted as previously reported (9), with slight modifications. The protocol was automated by use of the JANUS Automated Workstation (PerkinElmer Life and Analytical Science, Boston, MA). Reactions were carried out in 25 μl of reaction volume per well in 384-well OptiPlate microtiter plates (PerkinElmer). First, 0.1 μl of the translation mixture containing a recombinant *P. vivax* biotinylated protein was diluted 50-fold (5 μl), mixed with 10 μl of 4000-fold diluted plasma in reaction buffer (100 mM Tris-HCL [pH 8.0], 0.01% [v/v] Tween-20 and 0.1% [w/v] bovine serum albumin), and incubated for 30 min at 26° C. to form an antigen-antibody complex. Subsequently, a 10 μl suspension of streptavidin-coated donor-beads and acceptor-beads (PerkinElmer) conjugated with protein G (Thermo Scientific, Waltham, MA) in the reaction buffer was added to a final concentration of 12 μg/ml of both beads. The mixture was incubated at 26° C. for one hour in the dark to allow the donor and acceptor-beads to optimally bind to biotin and human IgG, respectively. Upon illumination of this complex, a luminescence signal at 620 nm was detected by the En Vision plate reader (PerkinElmer) and the result was expressed as AlphaScreen counts. A translation mixture of WGCF without template mRNA was used as a negative control. Each assay plate contained a standard curve of total biotinylated rabbit IgG. This enabled standardisation between plates using a 5-parameter logistic standard curve. All samples were run in triplicate. Reading the plates was conducted in a randomized manner to avoid biases.

Multiplexed Bead-Based Assay for the Validation Study.

For validation of the down-selected candidate serological markers, IgG levels were measured in plasma collected from the last time-point of the longitudinal observation studies. IgG measurements were performed using a multiplexed bead-based assay as previously described (10). In brief, 2.5×10⁶ COOH microspheres (Bio-Rad, USA) were prepared for protein coupling by incubation for 20 minutes at room temperature in 100 mM monobasic sodium phosphate (pH 6.2), 50 mg/ml N-Hydroxysulfosuccinimide sodium salt and 50 mg/ml N-(3-Dimethylaminopropyl)-N'-ethylcarbodiimide hydrochloride. Proteins were then added and incubated overnight at 4° C. Optimal amounts of protein were determined experimentally, in order to achieve a log-linear standard curve when using a positive control plasma pool generated from hyper-immune PNG donors. Each assay plate subsequently included this 2-fold serial dilution standard curve (1/50 to 1/25600), to enable standardisation between plates.

The assay was run by incubating 50 μl of the protein-coupled microspheres (500 microspheres/well) with 50 μl test plasma (at 1/100 dilution) in 96-well multiscreen filter plates (Millipore, USA) for 30 minutes at room temperature, on a plate shaker. Plates were washed 3 times and then incubated for a further 15 minutes with the detector antibody, PE-conjugated anti-human IgG (1/100 dilution, Jackson ImmunoResearch, USA). The plates were once again washed and then assayed on a Luminex 200™ instrument. All median fluorescent intensity (MFI) values were converted to relative antibody unites using the plate-specific standard curve (five-parameter logistic function, as previously described in detail (10)).

Statistical Modelling.

The models are described in greater detail below (see Example 3).

Statistical Analysis.

All data manipulation and statistical analyses were performed in either R version 3.2.3 (11), Prism version 6 (GraphPad, USA) or Stata version 12.1 (StataCorp, USA).

Results

Down-Selection of Candidate Serological Markers.

Figure 2:
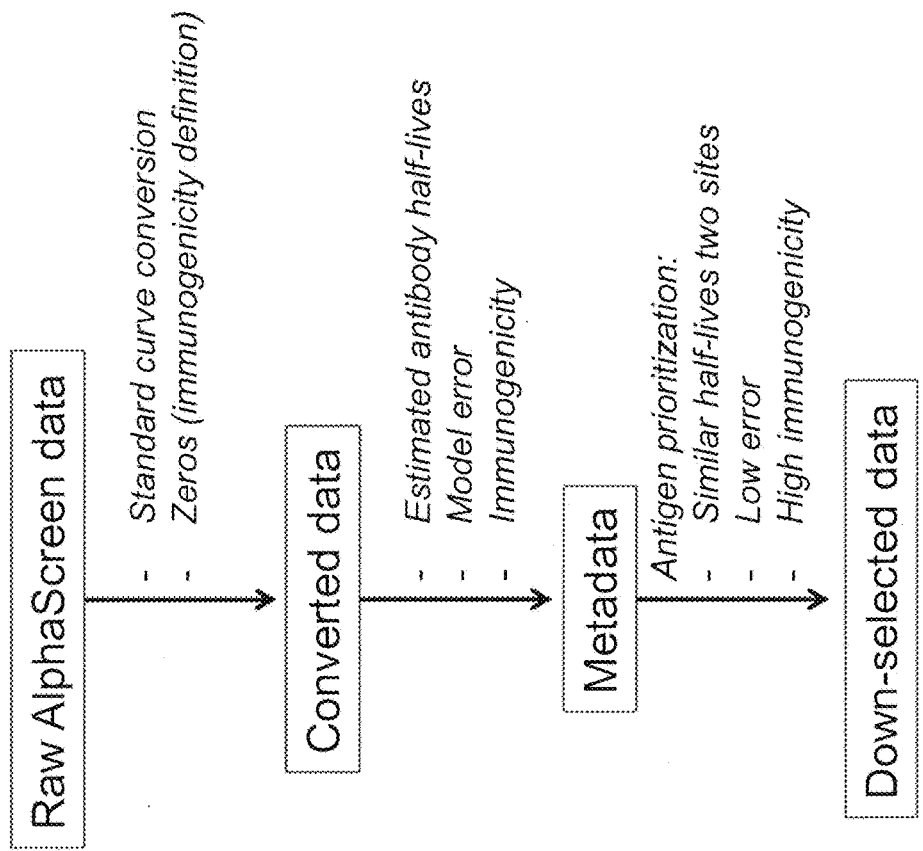
FIG. 2 shows a method for data processing and down-selection of candidate serological markers.
Figure 2:
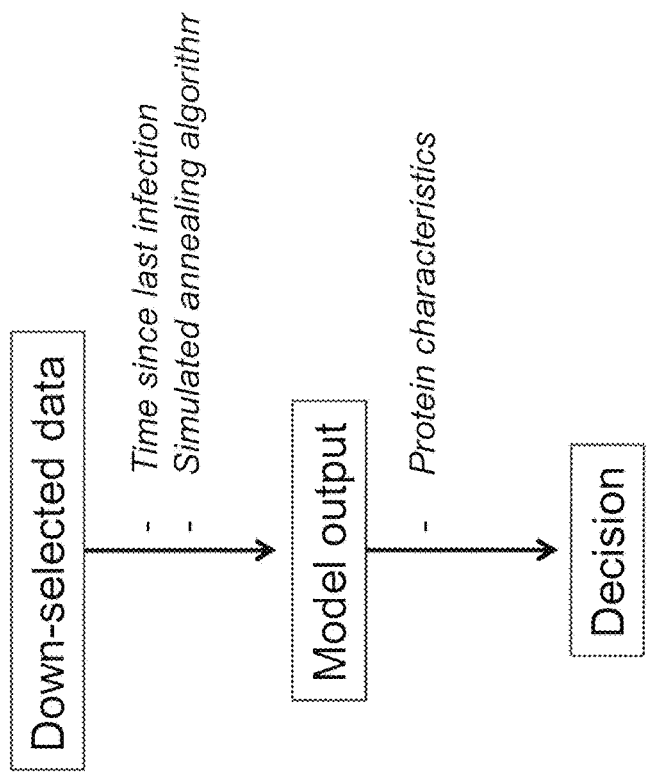

The data were processed and candidate serological markers down-selected following the pipeline shown in FIG. 2. The raw AlphaScreen data was converted based on the plate-specific standard curve, resulting in relative antibody units ranging from 0-400. Using the converted data, seropositivity was defined as a relative antibody unit greater than 0. For proteins that were defined as immunoreactive (more than 10% individuals seropositive at baseline, time of *P. vivax* infection), an estimated antibody half-life was determined using a mixed-effects linear regression model, described in detail below (see Statistical modelling). Using the metadata on immunoreactivity and half-life, an initial round of antigen down-selection was performed, with prioritisation of antigens that had similar estimated half-lives in both the Thai and Brazilian datasets (neither site more than double the other), high levels of seropositivity at baseline (more than 50% individuals seropositive, i.e. relative antibody units above 0), and low levels of error estimated in the model. Three rounds of initial down-selection were performed, resulting in approximately 100 antigens for the next round of model-based down-selection.

The model-based down-selection was performed in two stages: first, by calculating the estimated time since last infection based on antibody levels at 0, 3, 6 and 9 months (and comparing this with the known time since infection), and second, by determining the best combination of antigens for accurately detecting the time since last infection.

In more detail, FIG. 2 shows a pipeline for down-selection of candidate serological markers. As shown in the process of FIG. 2A, antigens were first down-selected based on prioritization of metadata characteristics such as similar levels of estimated antibody longevity in Thailand and Brazil, high levels of immunogenicity at the time of infection and low levels of error estimated in the model. As shown in the process of FIG. 2B, using the initial down-selected antigens, further modelling was performed to identify the optimal combination of antigens able to accurately estimate the time since last infection. A final decision on candidate serological markers was made using output from this modelling and other protein characteristics, as detailed above.

Figure 3:
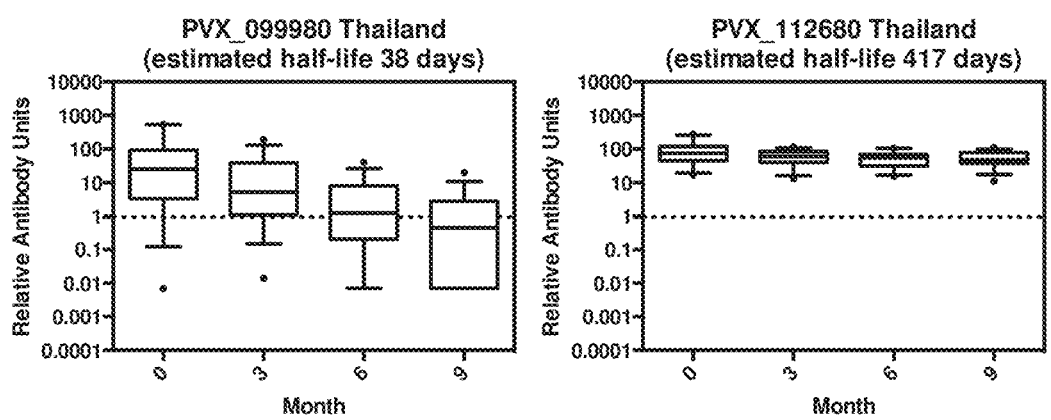
FIG. 3 shows an example of two differing antibody kinetic profiles. Antibody responses at the four time-points measured in the AlphaScreen® assay are shown for two proteins, PVX_099980 and PVX_122680. An arbitrary positivity cut-off is marked at 0.94 (the average of the wheat germ extract control well+6× standard deviation). Data is generated from 32 individuals in Thailand.
Figure 4:
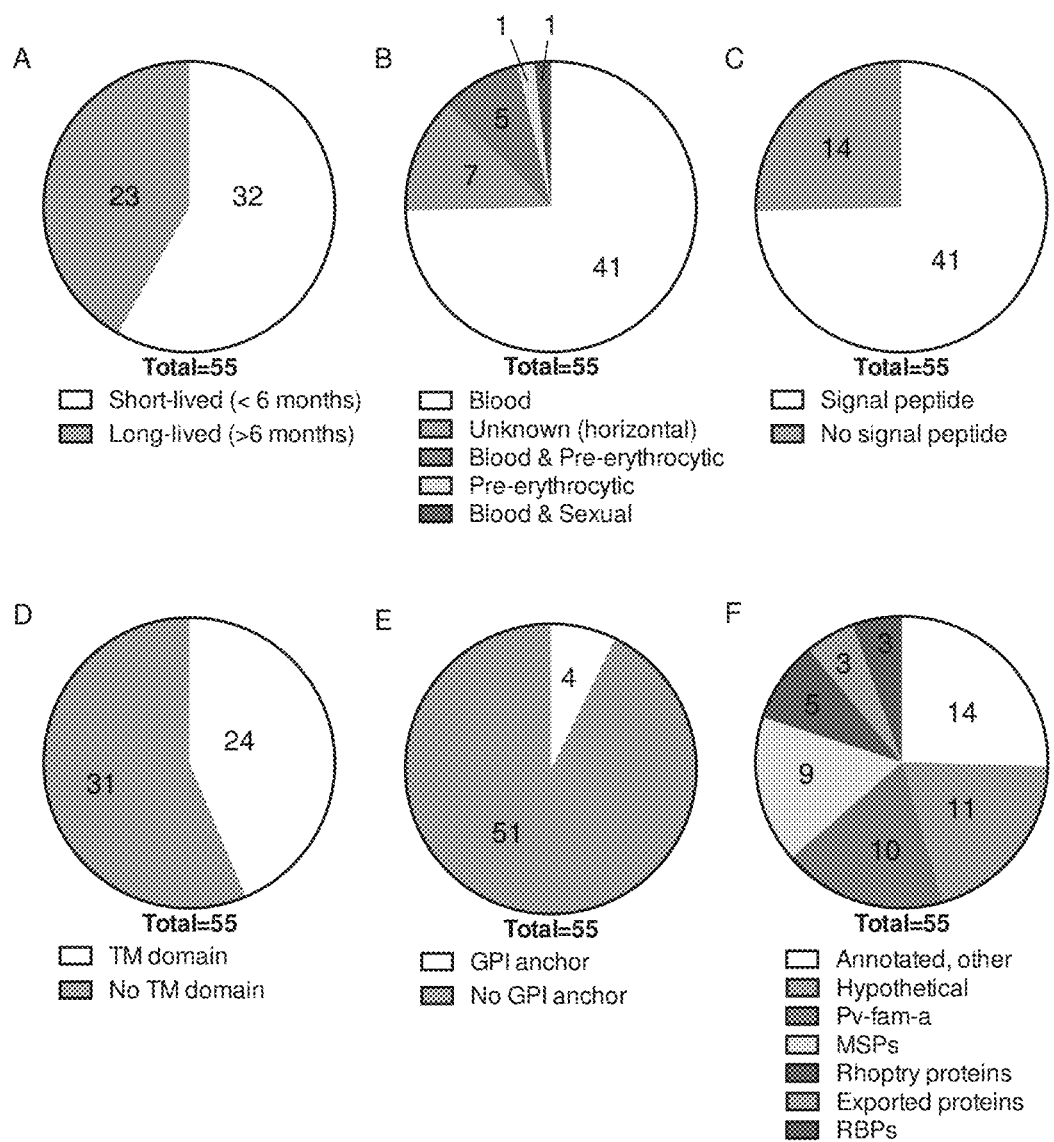
FIG. 4 shows characteristics of the top 55 protein constructs. (A) Length of the estimated antibody half-lives, note for 4 proteins the classification was different between Thailand and Brazil. (B)-(F) Details of protein characteristics as determined by PlasmoDB release 25 or published literature: (B) predicted expression stage, (C) presence of a signal peptide sequence, (D) presence of transmembrane domain/s, (E) presence of a GPI anchor, (F) annotation. TM=transmembrane domains, MSPs=merozoite surface proteins, RBPs=reticulocyte binding proteins.

As expected, different antibody kinetic profiles over 9-months were observed for different proteins (see FIG. 3 for an example). Antigen down-selection was performed as described in detail in the Materials and Methods, essentially by prioritizing antigens with high levels of immunogenicity, similar estimated half-lives between Thailand and Brazil and low levels of error estimated in the model. The initial down-selection was followed by further model-based down selection. The model-based down-selection was used to determine the ability of various proteins to predict the time since last infection, utilizing the same datasets from Thailand and Brazil, and to determine the best combination of proteins to do so successfully (see for example FIG. 20 and its accompanying description). Antigens were excluded from selection if they had less than a 40% probability of inclusion in a 40-antigen panel that was able to accurately determine the time since last infection. Remaining antigens were then ranked according to a high probability of inclusion in a successful 20-antigen panel. When required, ranking in 30 and 40-antigen panels was also considered. Antigens were excluded if they had unfavorable protein production characteristics, such as low-yield in the small-scale WGCF expression or presence of aggregates. Three rounds of selection were performed: the first resulted in 12 proteins, the second in a further 12, and the third in an additional 31 candidates. A final list of 55 protein constructs (53 unique proteins) representing candidate serological markers of recent exposure to *P. vivax* infection was generated (two fragments were included from two different antigens). Characteristics of these proteins are highlighted in FIG. 4.

Validation of Candidate Serological Markers.

Geographical validation (that is validation across different regions) was performed as follows.

Figure 5:
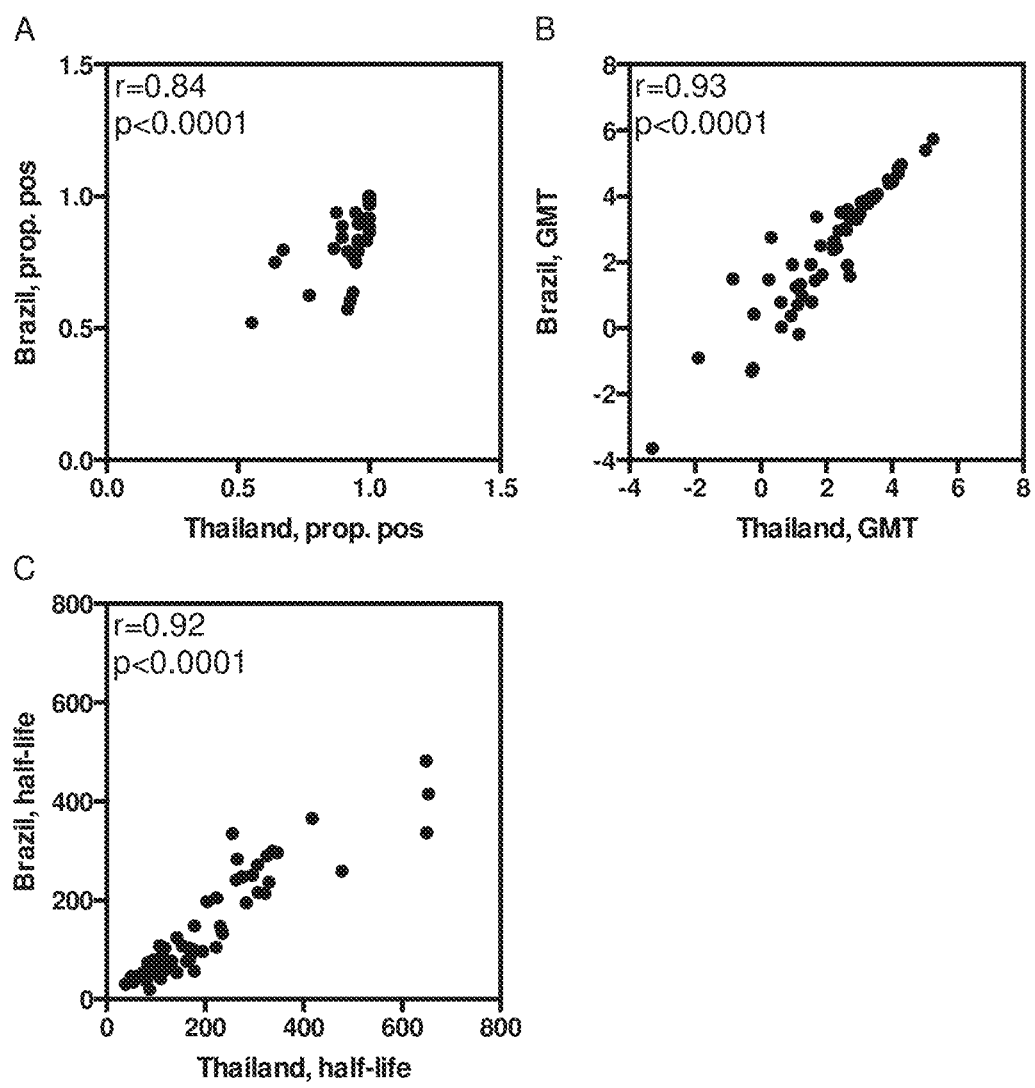
FIG. 5 shows correlation between antibody measurements in Thailand and Brazil. Correlation of data from the antigen discovery study generated using the AlphaScreen® assay. Correlations are shown for the 55 down-selected candidate serological markers. (A) Comparison of the proportion of individuals defined as positive at time of *P. vivax* infection (antibody value above the lower point of the standard curve, i.e. 0). (B) Comparison of the geometric mean antibody titers (GMT). (C) Comparison of the estimated antibody half-lives. Spearman correlation coefficients, r, are shown. Data was generated from 32 individuals in Thailand and 33 in Brazil.

The down-selected markers were chosen based on antibody data from individuals in Thailand, Brazil and the Solomon Islands, three discrete geographical areas. Despite this, there was a strong correlation between the antibody responses measured, in terms of both immunogenicity (sero-positivity rates) and antibody level at time of *P. vivax* infection, as well as the estimated antibody half-lives calculated from consecutive time-points. This is shown in FIG. 5.

Validation in association with recent and past infection was performed as well.

Figure 6A:
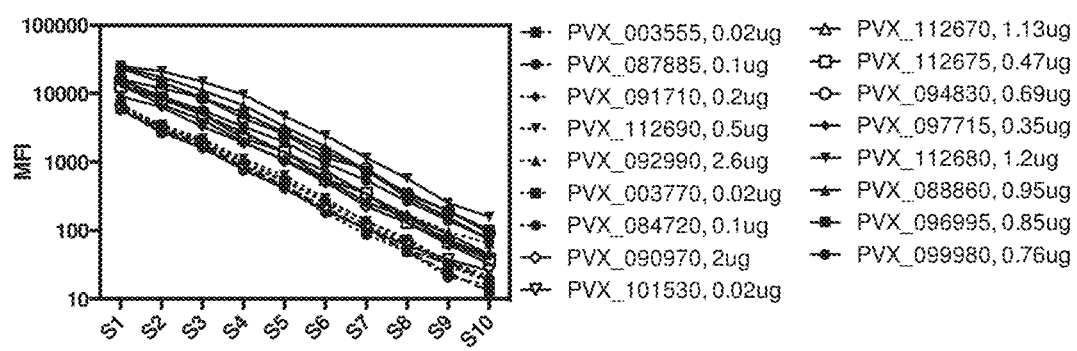
FIG. 6A shows optimization of Luminex® bead-array assay for the first 17 proteins. Log-linear standard curves were achieved for all proteins, using the amounts of protein shown for one bulk reaction of 500 µl beads.
Figure 22:
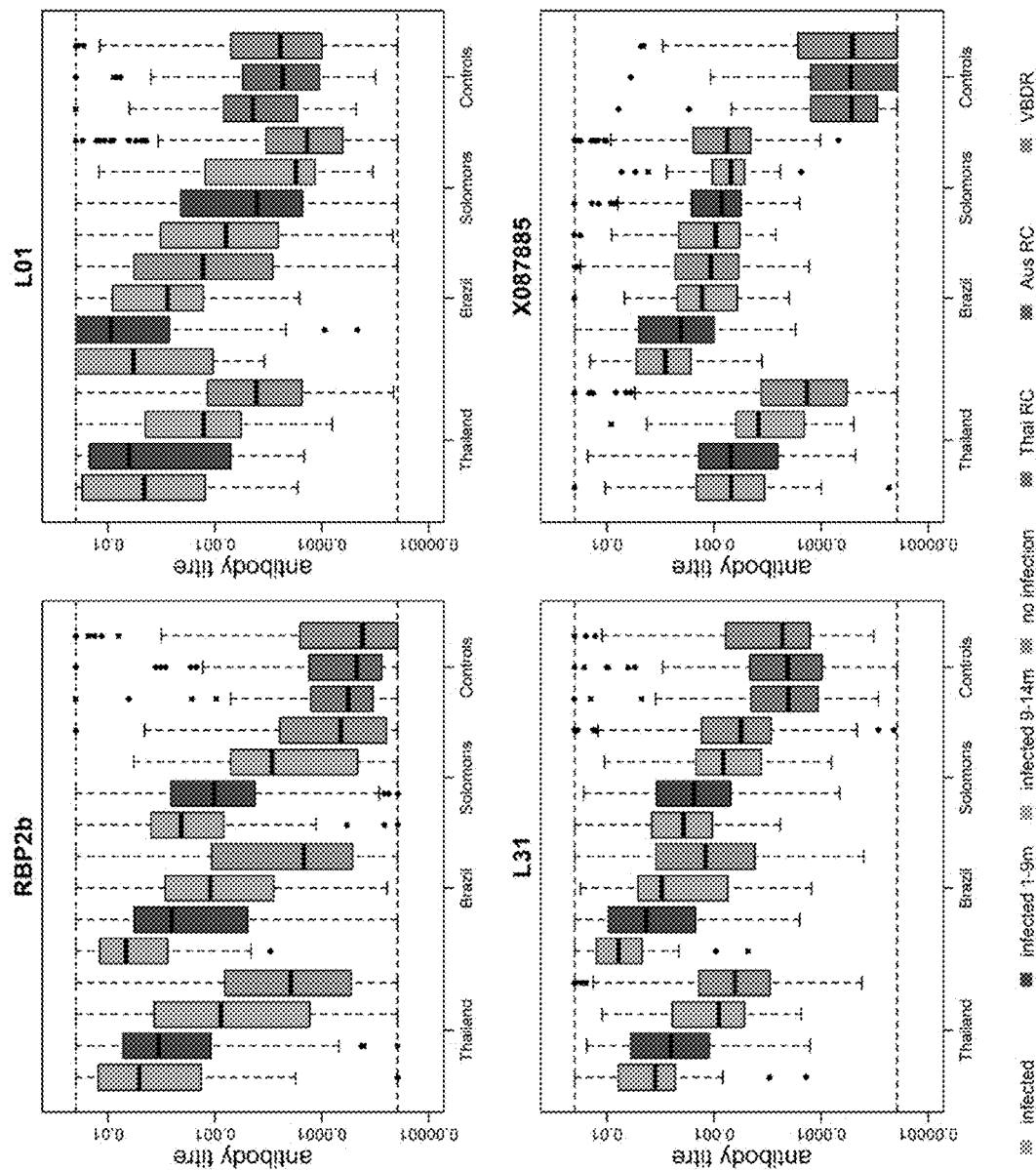
FIG. 22 shows measured antibody titers to four P. vivax antigens from Thailand, Brazil and the Solomon Islands, and from three panels of negative controls. The box plots show the median, interquartile range and 95% range of measured antibody titers. The horizontal dashed lines represent the lower and upper limits of detection.

The Luminex® bead-array assay has been successfully established for 40 of the 55 proteins identified in the antigen discovery study (FIG. 6) as well as for the additional 25 proteins (65 total). Plasma samples from three observational cohorts (final time-point) have been screened against these 65 proteins, Thai (n=829), Brazilian (n=925) and Solomon Islands (n=751), in addition to 3 sets of non-exposed (malaria) controls (two panels from Australia and one panel from Thailand). An example of the responses in these cohorts, with relation to time since last infection, to 4 of 65 proteins is shown in FIG. 22, described with regard to Example 4 below.

Figure 7:
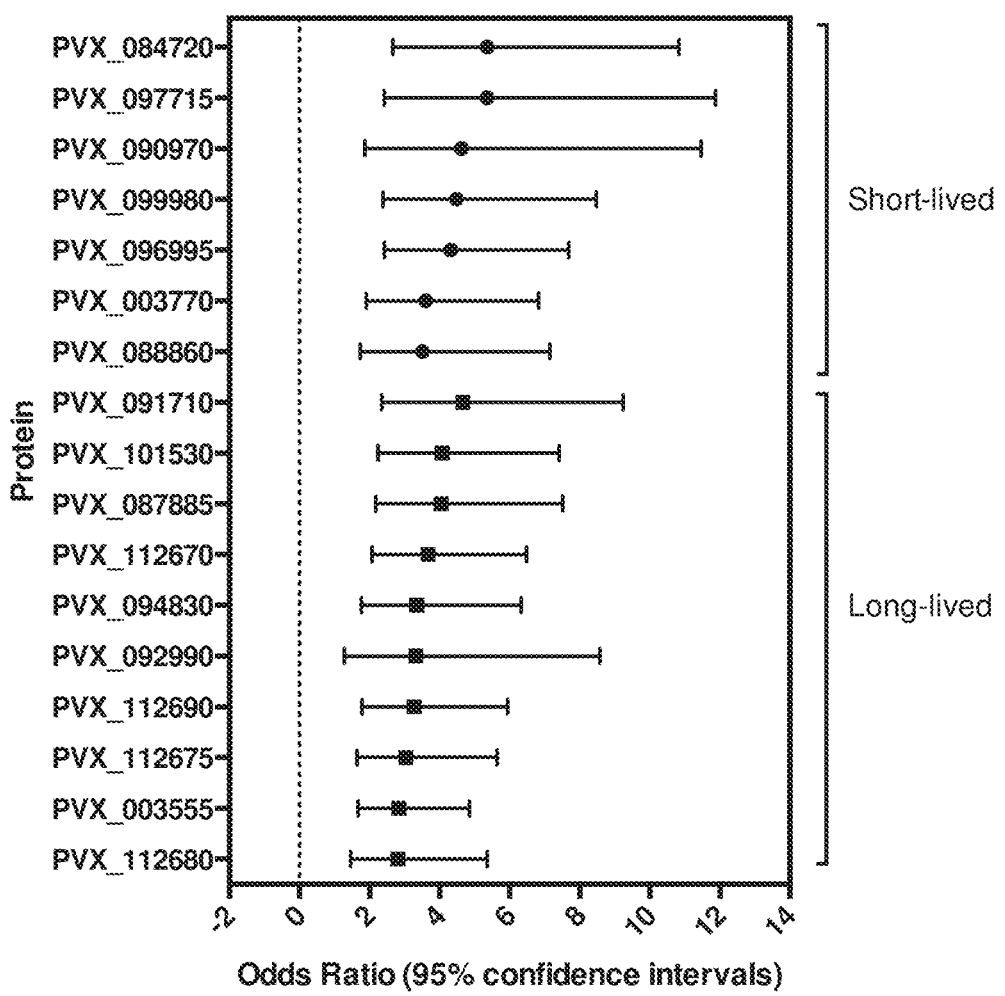
FIG. 7 shows the association of antibody levels with current *P. vivax* infections in the Thai validation cohort. Antibody responses were measured at the last time-point of the Thai cohort against the first 17 proteins assessed, using the Luminex® bead-array assay. The association between antibody responses and current infection was assessed using a logistic regression model, adjusting for age, sex and occupation. Odds ratios are shown, with 95% confidence intervals. Associations for all antibodies were significant (p<0.05). The estimate of antibody half-life shown is based on the antigen discovery dataset (AlphaScreen®).
Figure 8:
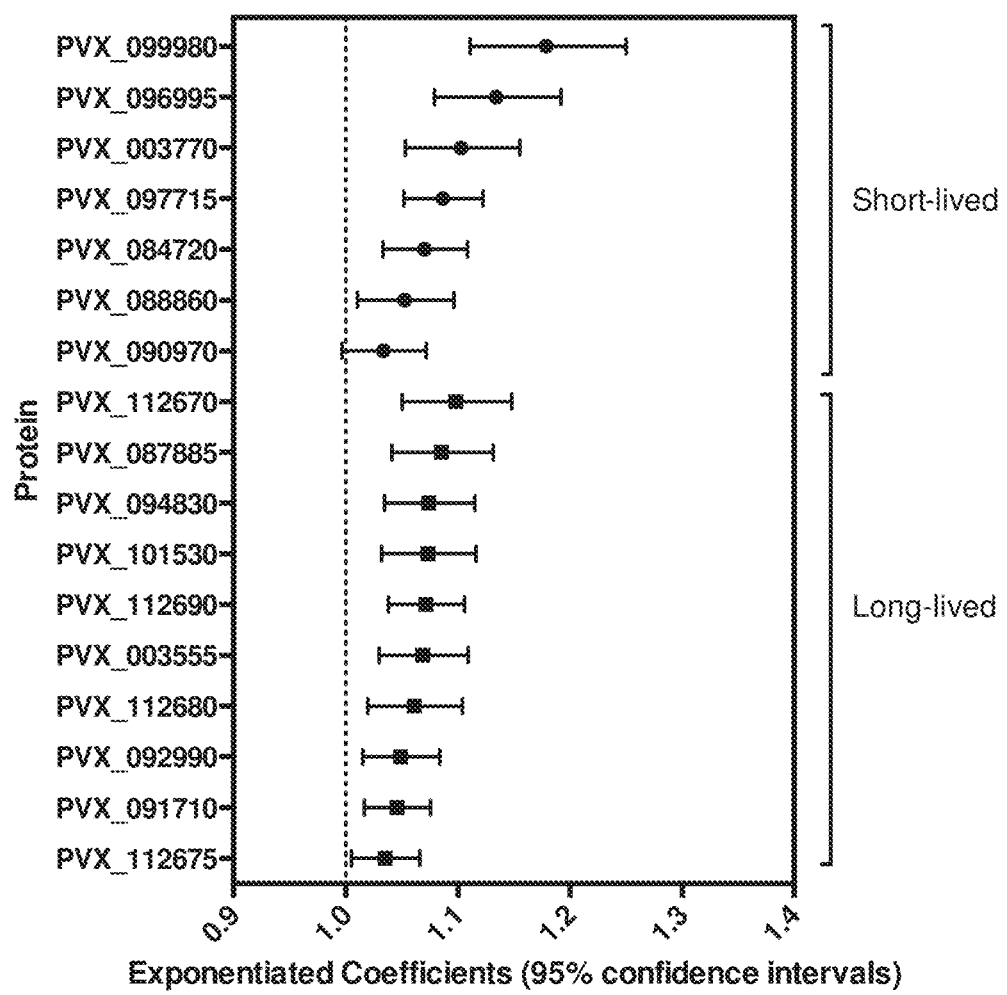
FIG. 8 shows association of antibody levels with past *P. vivax* exposure in the Thai validation cohort. Antibody responses were measured at the last time-point of the Thai cohort against the first 17 proteins assessed, using the Luminex® bead-array assay. The association between antibody responses and total exposure over the past year was assessed using a generalised linear model, adjusting for age, sex, occupation and current infection status. Exponentiated coefficients are shown, with 95% confidence intervals. Associations for all antibodies, except PVX_09070, were significant (p<0.05). The estimate of antibody half-life shown is based on the antigen discovery dataset (AlphaScreen®).

In the Thai cohort, antibody levels measured to all 17 proteins, selected for performing the first set of tests, were strongly associated with the presence of current *P. vivax* infections (logistic regression model, odds ratios of 2.8-5.4, p<0.05) (FIG. 7). In addition, antibody levels to 16 of 17 proteins at the last visit of the cohort study were positively and significantly associated with past exposure to *P. vivax* infections based on PCR results during the yearlong assessment period (measured as the molecular force of blood-stage infection, (molFOI) (generalised linear model, exponentiated coefficients of 1.03-1.18, p<0.05) (FIG. 8). The exception was for PVX_090970, exponentiated coefficient 1.03, p=0.073.

Figure 9:
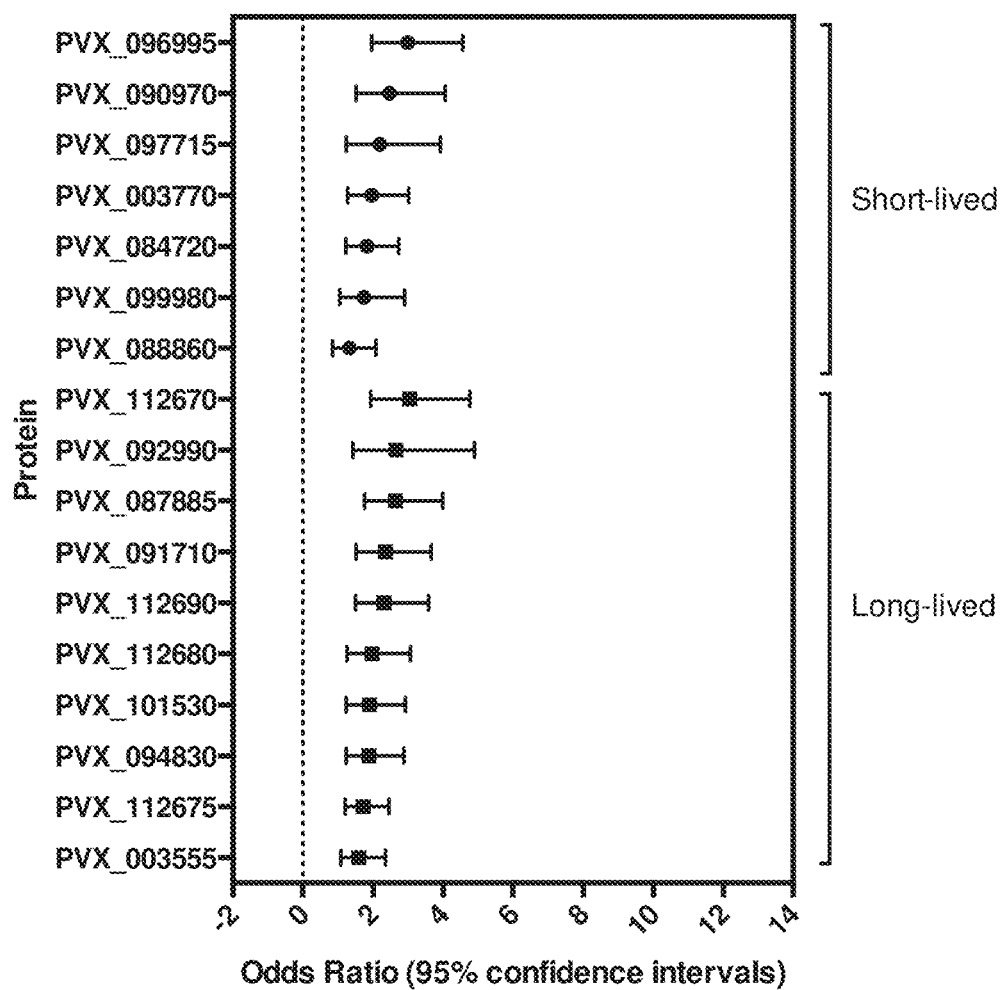
FIG. 9 shows the association of antibody levels with current *P. vivax* infections in the Brazilian validation cohort. Antibody responses were measured at the last time-point of the Brazilian cohort against the first 17 proteins assessed, using the Luminex® bead-array assay. The association between antibody responses and current infection was assessed using a logistic regression model, adjusting for age, sex and occupation. Odds ratios are shown, with 95% confidence intervals. Associations for all antibodies, except PVX_088860, were significant (p<0.05). The estimate of antibody half-life shown is based on the antigen discovery dataset (AlphaScreen®).
Figure 10:
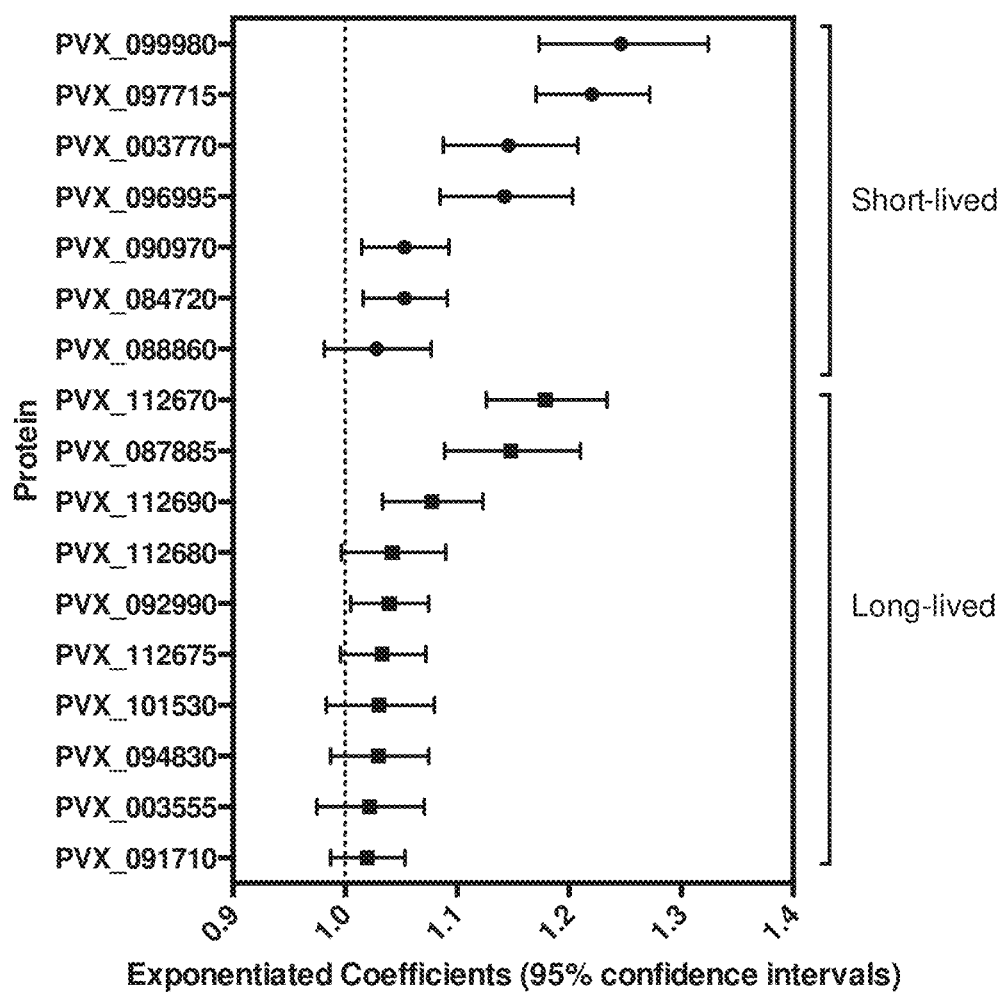
FIG. 10 shows the association of antibody levels with past *P. vivax* exposure in the Brazilian validation cohort. Antibody responses were measured at the last time-point of the Brazilian cohort against the first 17 proteins assessed, using the Luminex® bead-array assay. The association between antibody responses and total exposure over the past year was assessed using a generalised linear model, adjusting for age, sex, occupation and current infection status. Exponentiated coefficients are shown, with 95% confidence intervals. Associations for 10 of the 17 antibodies were significant (p<0.05). The estimate of antibody half-life shown is based on the antigen discovery dataset (AlphaScreen®).

In the Brazilian cohort, the effect size, overall, was not as great as for Thailand. Nevertheless, antibody levels to 16 of 17 proteins were strongly associated with the presence of current *P. vivax* infections (logistic regression model, odds ratios of 1.59-3.04, p<0.05) (FIG. 9). The exception was for PVX_088860, with an odds ratio of 1.33 (p=0.21). Antibody levels to 10 of 17 proteins at the last visit of the cohort were positively and significantly associated with past exposure to *P. vivax* (molFOI) (generalised linear model, exponentiated coefficients of 1.04-1.18, p<0.05) (FIG. 10). Of the antibodies with estimated 'short' half-lives (less than 6 months), there was one exception, PVX_088860, with an exponentiated coefficient of 1.03 (p=0.24). Of the antibodies with estimated 'long' half-lives (more than 6 months), 6 of 10 were not associated with past exposure (exponentiated coefficients of 1.02-1.04, p>0.05).

Various statistical methods can be used to test the association between antibody level to certain proteins and past (recent) or current exposure to *P. vivax* infections. For most proteins, there was a clear significant association with both past and current *P. vivax* infections, which is promising for the use of these antigens as serological markers. For others, there was a trend towards an association, which did not reach significance. In a final test, it will be an antibody signature that is used for classification of recent infection, made up of antibody responses to a multitude of proteins. Therefore the lack of significance for some individual proteins does not imply that they will not be useful in the final classification algorithm.

These analyses show that 16 of 17 proteins generate antibodies that are strongly associated with both current infections and 10 of 17 with past *P. vivax* exposure in both Thailand and Brazil, demonstrating that a majority of these antigens have the potential to detect both concurrent and recent past P: *vivax* infections.

REFERENCES

1. Longley R J, Reyes-Sandoval A, Montoya-Diaz E, Dunachie S, Kumpitak C, Nguitragool W, Mueller I, Sattabongkot J. 2015. Acquisition and longevity of antibodies to *Plasmodium vivax* pre-erythrocytic antigens in western Thailand. Clin Vaccine Immunol doi: 10.1128/cvi.00501-15.
2. Wampfler R, Mwingira F, Javati S, Robinson L, Betuela I, Siba P, Beck H P, Mueller I, Felger I. 2013. Strategies for detection of *Plasmodium* species gametocytes. PLOS One 8:e76316.
3. Rosanas-Urgell A, Mueller D, Betuela I, Barnadas C, Iga J, Zimmerman P A, del Portillo H A, Siba P, Mueller I, Felger I. 2010. Comparison of diagnostic methods for the detection and quantification of the four sympatric *Plasmodium* species in field samples from Papua New Guinea. Malar J 9:361.
4. Lu F, Li J, Wang B, Cheng Y, Kong D H, Cui L, Ha K S, Sattabongkot J, Tsuboi T, Han ET. 2014. Profiling the humoral immune responses to *Plasmodium vivax* infection and identification of candidate immunogenic rhoptry-associated membrane antigen (RAMA). J Proteomics 102:66-82.
5. Sawasaki T, Ogasawara T, Morishita R, Endo Y. 2002. A cell-free protein synthesis system for high-throughput proteomics. Proc Natl Acad Sci USA 99:14652-14657.
6. Sawasaki T, Hasegawa Y, Tsuchimochi M, Kamura N, Ogasawara T, Kuroita T, Endo Y. 2002. A bilayer cell-free protein synthesis system for high-throughput screening of gene products. FEBS Lett 514: 102-105.
7. Sawasaki T, Morishita R, Gouda M D, Endo Y. 2007. Methods for high-throughput materialization of genetic information based on wheat germ cell-free expression system. Methods Mol Biol 375:95-106.
8. Sawasaki T, Gouda M D, Kawasaki T, Tsuboi T, Tozawa Y, Takai K, Endo Y. 2005. The wheat germ cell-free expression system: methods for high-throughput materialization of genetic information. Methods Mol Biol 310: 131-144.

9. Matsuoka K, Komori H, Nose M, Endo Y, Sawasaki T. 2010. Simple screening method for autoantigen proteins using the N-terminal biotinylated protein library produced by wheat cell-free synthesis. J Proteome Res 9:4264-4273.
10. Franca C T, Hostetler J B, Sharma S, White M T, Lin E, Kiniboro B, Waltmann A, Darcy A W, Li Wai Suen C S, Siba P, King C L, Rayner J C, Fairhurst R M, Mueller I. 2016. An Antibody Screen of a *Plasmodium vivax* Antigen Library Identifies Novel Merozoite Proteins Associated with Clinical Protection. PLOS Negl Trop Dis 10:e0004639.
11. Team RC. 2015. R: A language and environment for statistical computing, R Foundation for Statistical Computing, Vienna, Austria. https://www R-project.org/.

Example 2—Illustrative Diagnostic Test

A diagnostic test according to at least some embodiments of the present invention could optionally include any of bead-based assays previously described (AlphaScreen® assay and multiplexed assay using Luminex® technology).

In addition to the ability to measure antibody responses using the bead-based assays previously described, other methods could also be used, including, but not limited to, the enzyme linked immunosorbent assay (ELISA) (1), protein microarray (2) and the luminescence immunoprecipitation system (LIPs) (3).

Antibody measurements via ELISA rely on coating of specialised plates with the required antigen, followed by incubation with the plasma sample of interest. IgG levels are detected by incubation with a conjugated secondary antibody followed by substrate, for example a horseradish peroxidase-conjugated anti-IgG and ABTS [2,2=-azinobis (3-ethylbenzothiazo-line-6-sulfonic acid)-diammonium salt].

Protein microarray platforms offer a high-throughput system for measuring antibody responses. Proteins of interest are spotted onto microarray chips then probed with plasma samples. The arrays are then further incubated with a labeled anti-immunoglobulin and analysed using a microarray scanner.

The LIPs assay utilizes cell lysate containing the expressed antigen fused to a *Renilla* luciferase reporter protein. Plasma samples are incubated with a defined amount of this lysate, with protein A/G beads used to capture the antibody. The amount of antibody-bound antigen-luciferase is measured by the addition of a coelenterazine substrate, and the light emitted measured using a luminometer.

Any of these assays may optionally be combined with a reader and if necessary, an analyzer device, to form an apparatus according to at least some embodiments of the present invention. The reader would read the test results and the analyzer would then analyze them according to any of the previously described algorithms and software.

REFERENCES

1. Longley R J, Reyes-Sandoval A, Montoya-Diaz E, Dunachie S, Kumpitak C, Nguitragool W, Mueller I, Sattabongkot J. 2015. Acquisition and longevity of antibodies to *Plasmodium vivax* pre-erythrocytic antigens in western Thailand. Clin Vaccine Immunol doi: 10.1128/cvi.00501-15.
2 Finney O C, Danziger S A, Molina D M, Vignali M, Takagi A, Ji M, Stanisic D I, Siba PM, Liang X, Aitchison J D, Mueller I, Gardner M J, Wang R. 2014. Predicting antidisease immunity using proteome arrays and sera from children naturally exposed to malaria. Mol Cell Proteomics doi:10.1074/mcp.M113.036632.
3. Longley R J, Salman A M, Cottingham M G, Ewer K, Janse C J, Khan S M, Spencer A J, Hill A V. 2015. Comparative assessment of vaccine vectors encoding ten malaria antigens identifies two protective liver-stage candidates. Sci Rep 5:11820.

Example 3—Illustrative Software Process for Diagnosis

This Examples relates to processes for estimation of time since last *P. vivax* infection using measurements of antibody titers, which may optionally be provided through software.

a. Section 1 relates to calibration and validation of the input data, as well as non-limiting examples of models and algorithms which may optionally be used to analyze the data. Section 2 provides additional information on the algorithms utilized.

Section 1—Overview of Calibration Data and Algorithms

Calibration and Validation Data

Both the down-selection of antigens for incorporation into a diagnostic test, and the calibration and validation of algorithms for providing classifications of recent *P. vivax* infection given blood samples, will depend on the available epidemiological data. Data will be required on the demography of the populations under investigation, serological measurements, and monitoring for parasitemia and clinical episodes. Table 1 provides an overview of the data sets that are used.

Algorithm Inputs and Outputs

A diagnostic test will take a blood sample as input and provide data to inform a decision making process as output. The type of data generated will depend on the technological specifications of the diagnostic platform. The outputted data can then be used as input for some algorithm to inform a decision making process. The following factors need to be taken into consideration when defining the inputs and outputs of a decision making algorithm:

1) Number of Antigens

The number of antigens to which antibodies can be measured will be restricted by the technological specifications of the diagnostic platform under consideration. Measurement of antigens to a greater number of antibodies will in theory provide more data as input for an algorithm, potentially increasing predictive power.

TABLE 1

Overview of data sets used for antigen down-selection and algorithm calibration and validation.

| demographic data | | | serological data | | | parasitological data | | |
|---|---|---|---|---|---|---|---|---|
| region | number | age | number of antigens | samples per person | platform | samples per person | PCR positive | clinical |
| Antigen down-selection | | | | | | | | |
| Thailand | 32 | 29 (7, 71) | 342 | 4 | AlphaScreen | 17 | enrolment | enrolment |
| Brazil | 33 | | 342 | 4 | AlphaScreen | 17 | enrolment | enrolment |
| Algorithm calibration and validation | | | | | | | | |
| Thailand | 829 | 25 (2, 79) | 65 | 1 | Luminex | 14 | 97/829 | 25/829 |
| Brazil | 928 | 25 (0, 102) | 65 | 1 | Luminex | 13 | 236/928 | 80/928 |
| Solomon Islands | 860 | 5.5 (0.5, 12.7) | 65 | 1 | Luminex | 11 | 294/860 | 35/860 |
| Negative controls | | | | | | | | |
| Australian Red Cross | 100 | 52 (18, 77) | 65 | 1 | Luminex | 1 | no | no |
| Thai Red Cross | 72 | | 65 | 1 | Luminex | 1 | no | no |
| Australian donors | 102 | 39 (19, 68) | 65 | 1 | Luminex | 1 | no | no |

2) Measurement of Antibody Levels

The levels of antibody in a blood-sample can be measured and summarised in a variety of ways.

a) Continuous Measurement

A continuous measurement that has a monotonic relationship with antibody titer. It can be compared with a titration curve to produce an estimate of antibody titer.

b) Binary Classification

Assesses whether antibody levels are greater or less than some threshold.

c) Categorical Classification

Assigns antibody levels to one of a set of pre-defined categories, e.g. low, medium, high. A categorical classification can be generated via a series of binary classifications.

3) Decision Making Requirements

The result of a diagnostic test and accompanying algorithm can be used to inform a decision on whether or not to treat, as well as to inform surveillance systems.

a) Classification of Recent Infection

A binary output corresponding to whether or not there was an infection with P. vivax blood-stage parasites in the past 9 months. This can be presented as a binary classification, or as a probabilistic classification. This can be adjusted for a range of different temporal thresholds: 3 months, 6 months, 12 months, 18 months.

b) Estimation of Time Since Last Infection

An estimate of the time since last P. vivax blood-stage infection-depending on the available calibration data the time since last infection can be defined either as the time since last PCR-detectable blood-stage parasitemia, or as the time since last mosquito bite. Time since last infection can be estimated continuously or categorically. Concurrent estimation of uncertainty will be important.

c) Medium-Term Serological Exposure

Given sufficient calibration data, the algorithms described here can be modified to provide extended measurements of an individual's recent to medium term P. vivax exposure, e.g. how many infections in the last 2 years?

4) Computational and Analytic Capabilities

An algorithm's complexity will be restricted by the analytic resources accompanying the diagnostic platform. In a low resource setting, we may require a decision to be made given a sequence of binary outputs from a rapid diagnostic test (sero-negative or sero-positive) without any access to computational devices. At the other extreme, in a high resource setting we may have continuous measurements of antibodies to multiple antigens accompanied with algorithms encoded in computational software.

a) No access to computational devices. Algorithms implemented via 'easy to follow' instructions on paper charts.

b) Algorithm implemented in software that can be installed on a portable computation device such as a smartphone or tablet. May require the manual entry of output from the diagnostic platform.

c) Computational software with encoded algorithms integrated within the diagnostic platform.

Algorithms

There is a wide range of algorithms for classification and regression in the statistical inference and machine learning literature (Hastie, Tibshirani & Friedman[3]). A classification algorithm can take a diverse range of input data and provide some binary or categorical classification as output. A regression algorithm can take similar input, but provides a continuous prediction as output. Table 2 provides an overview of some algorithms that can be used for classification problems. Four of these have been regularly described in the statistical learning literature: linear discriminant analysis (LDA); quadratic discriminant analysis (QDA); decision trees; and random forests. One of these has been specifically developed for the application at hand: combined antibody dynamics (CAD). The candidate algorithms are classified according to a number of factors. The degree of transparency describes the straightforwardness and reproducibility of an algorithm. A decision tree is considered very transparent as it can be followed by a moderately well-informed individual, as it requires answering a sequence of questions in response to measured data. This simple, logical structure makes decision trees particularly popular with doctors. Because of the transparency and ease of use, decision trees are sometimes referred to as glass box algorithms. At the other extreme, algorithms such as random forests are considered to be black box algorithms where there may be no obvious association between the inputs and outputs.

TABLE 2

Overview of algorithms suitable for classification of recent *P. vivax* infection or estimation of time since last *P. vivax* infection.

| algorithm | data needs | transparent | stochastic | time predicted | comments |
|---|---|---|---|---|---|
| linear discriminant analysis (LDA) | continuous | + | no | no | The assumption of common covariance for each category may be too restrictive. |
| quadratic discriminant analysis (QDA) | continuous | + | no | no; categorical estimation possible, incorporation of uncertainty challenging | There is an approximate equivalence between the QDA classification space and that predicted by the CAD algorithm. |
| decision trees | binary | +++ | no | no; possible via regression trees or categorical estimation | Very transparent and simple to implement in low technology settings. |
| random forests | continuous | — | yes | no; possible via regression trees or categorical estimation | Potentially very powerful but requires considerable computational resources. |
| combined antibody dynamics (CAD) | continuous | ++ | no | yes; with uncertainty | A biologically motivated representation of antibodies following infection; prior information on decay rates can be incorporated. |

Section 2—Expanded Details of Algorithms

Here we provide an overview of classification algorithms such as LDA, QDA, decision trees and random forests which have already been described extensively elsewhere (Hastie, Tibshirani & Friedman[3]). We also provide an extended description of the combined antibody dynamics (CAD) algorithm.

Linear and Quadratic Discriminant Analysis

The theory of linear discriminant analysis (LDA) and quadratic discriminant analysis (QDA) is described in detail in "The Elements of Statistical Learning: Data Mining, Inference and Prediction" by Hastie, Tibshirani & Friedman[6]. We provide a brief overview of how these methods may be applied. A key assumption for LDA and QDA classification algorithms is that individuals who have similar antibody titers are likely to have the same classification. It is convenient to compare individuals with different antibody profiles via Euclidean distance of log antibody titers. An LDA or QDA classifier can be implemented by fitting multivariate Gaussian distributions to the clusters of data points representing 'old' and 'new' infections. Assume we have measurements of p antibodies. Denote $k \in \{new, old\}$ to represent the classes of training individuals with new and old infections. These can be modelled as multivariate Gaussians:

$$f_k(x) = \frac{1}{(2\pi)^{p/2}|\Sigma_k|^{1/2}} e^{-\frac{1}{2}(x-\mu_k)^T \Sigma_k^{-1}(x-\mu_k)}$$

where $\mu_k$ and $\Sigma_k$ are the mean and p*p covariance matrix of the training data of each class.

In the case of LDA, all classes are assumed to have the same covariance matrix ($\Sigma_{new} = \Sigma_{old} = \Sigma$), and the classification between new and old infections can be evaluated via the log ratio:

$$\log\left(\frac{P(\text{new} \mid X = x)}{P(\text{old} \mid X = x)}\right) = \\ -\frac{1}{2}(\mu_{new} + \mu_{old})^T \sum\nolimits^{-1}(\mu_{new} + \mu_{old}) + x^T \sum\nolimits^{-1}(\mu_{new} + \mu_{old})$$

which is linear in x. The two categories are therefore separated by a hyperplane in p-dimensional space.

In QDA, the restriction that $\Sigma_{new} = \Sigma_{old} = \Sigma$ is relaxed and it can be shown that the classification boundary is described by a conic section in p-dimensional space.

LDA and QDA have consistently been shown to provide robust classification for a wide range of problems. The predictive power of these algorithms can be assessed through cross-validation whereby the data is split into training and testing data sets. The algorithm is calibrated using the training data set and subsequently validated using the test data set. An important method for assessing an algorithm's predictive power is to evaluate the sensitivity and specificity. In this context, we define sensitivity to be the proportion of recent infections correctly classified as recent infections, and we define specificity to be the proportion of old infections correctly classified as old infections.

Figure 25:
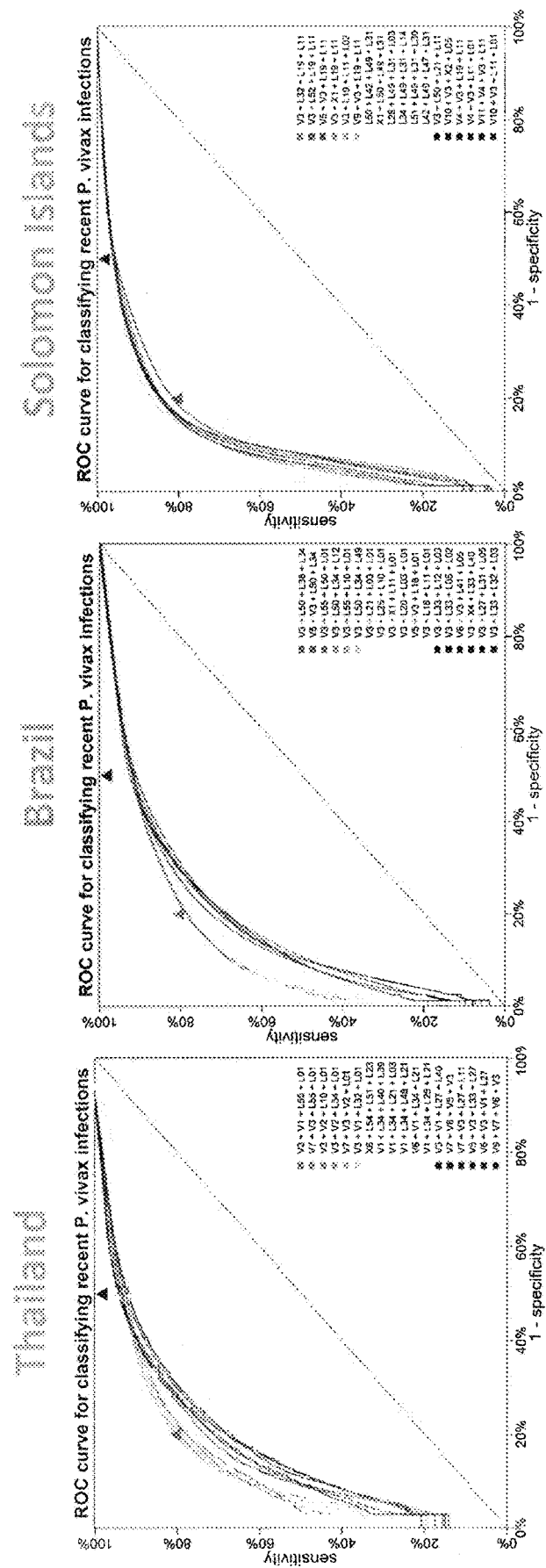
FIG. 25 shows cross-validated Receiver Operating Characteristic (ROC) curves from linear discriminant analysis (LDA) classifiers trained and tested using combinations of four antigens from Thailand, Brazil and The Solomon Islands.

A receiver operating characteristic (ROC) curve allows for detailed investigation of the association between sensitivity and specificity. At one extreme, we could obtain 100% sensitivity and 0% specificity by simply classifying all blood samples as new infections. At the other extreme, we could obtain 100% specificity and 0% sensitivity by classifying all blood samples as old infections. FIG. 25 shows ROC curves describing the classification performance of LDA algorithms for combinations of 4 antigens in Thailand, Brazil and the Solomon Islands.

Decision Trees and Random Forests

Tree-based algorithms partition the space spanned by the data into a set of rectangles with a unique classification applied to each rectangle. Similarly to the LDA and QDA classification algorithms, a great deal of theoretical information is supplied in the book "The Elements of Statistical Learning: Data Mining, Inference and Prediction".

There are several powerful methods for extending decision tree classifiers including bagging (bootstrapp aggregating), boosting and random forests[3]. These methods can lead to substantially improved classifiers but typically require more computation and more data. In addition to providing powerful classifiers, these algorithms can provide important diagnostics for investigating the association between the signal in the input and the output.

Figure 23A:
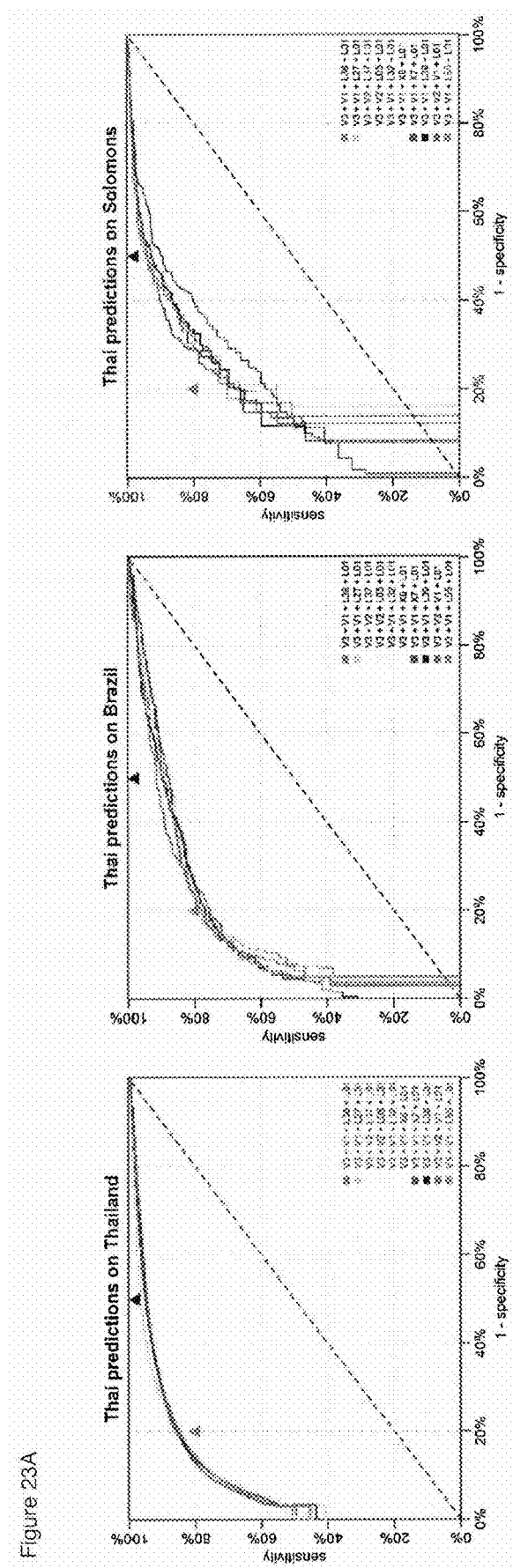
FIGS. 23A-23C show an overview of cross-validated random forests classification algorithms. The classifiers were trained on data from either Thailand, Brazil or The Solomon Islands.
Figure 23B:
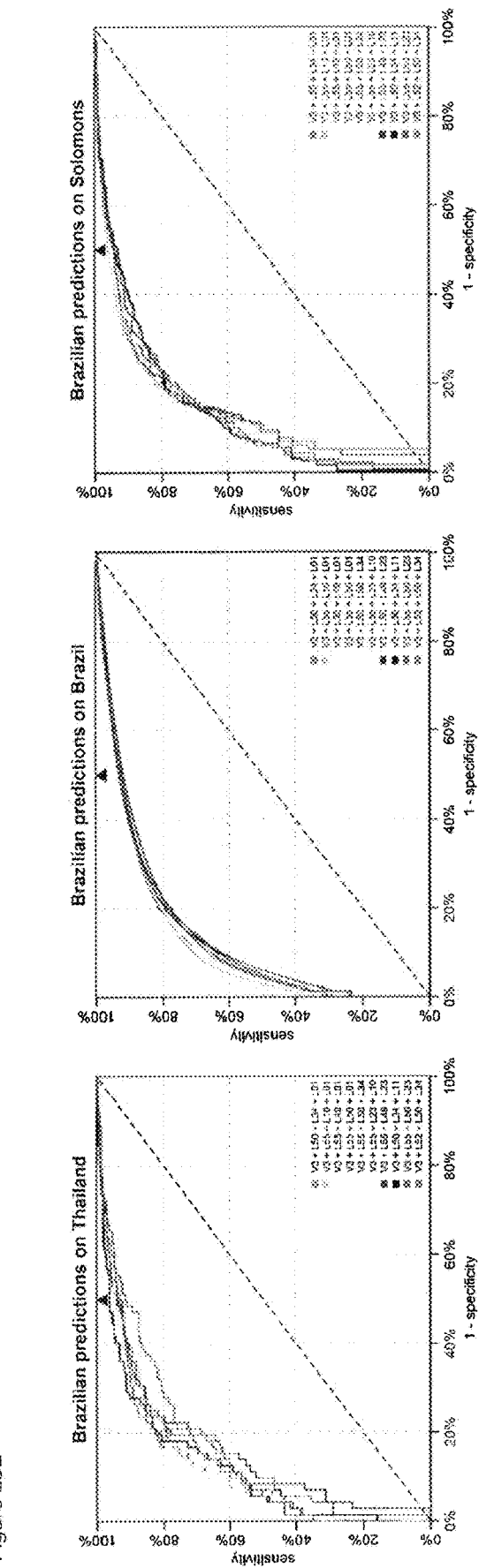
Figure 23C:
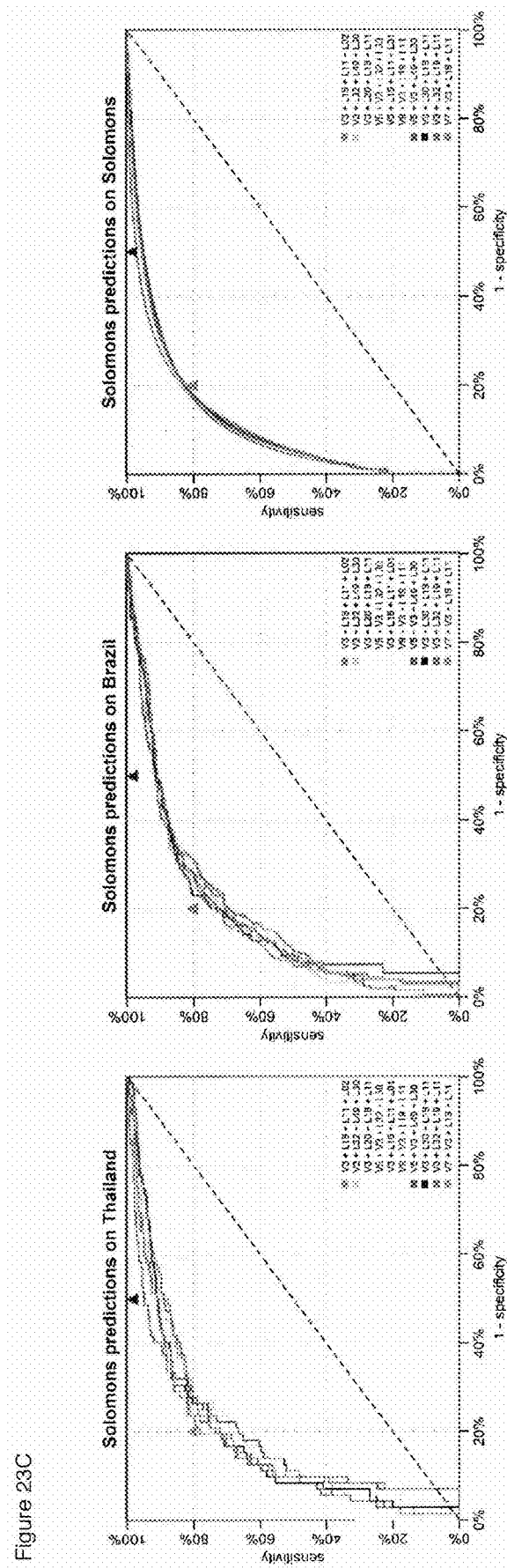

FIG. 23A-C shows the ROC curves for cross-validated random forests classifiers applied to data sets from Thailand, Brazil and Solomon Islands. Notably, when the training and testing data sets are from the same region, there are many combinations of four antigens that allow sensitivity >80% and specificity >80%. When training and testing data sets are from different regions, it was still possible to obtain combinations of four antigens with sensitivity >80% and specificity >80%.

Modelling of Antibody Dynamics

Figure 13:
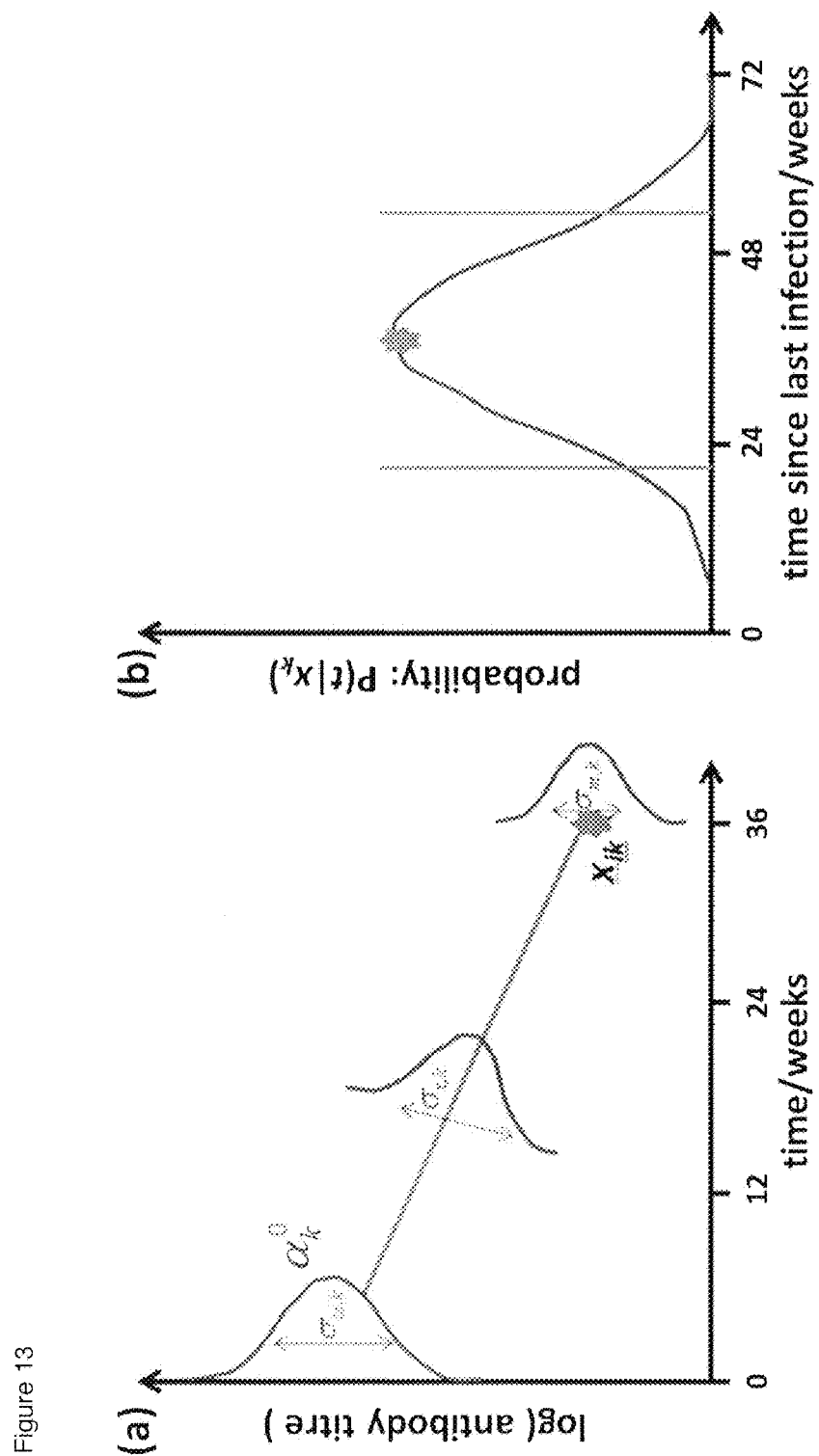
FIG. 13 presents the association between measured antibody titer $x_{ik}$ and time since infection t. (a) There are three sources of variation in the antibody titer $x_{ik}$ measured at time t since last infection: (i) variation in initial antibody titer; (ii) between individual variation in antibody decay rate; and (iii) measurement error. (b) Given estimates of the sources of variation, we can estimate the distribution of the time since last infection. The maximum likelihood estimate and the 95% confidence intervals of our estimate are indicated in blue.

A key premise of the proposed diagnostic test is that following infection with *P. vivax* blood-stage parasites, an antibody response will be generated that will change predictably over time (FIG. 13). Here we present a subset of the data that demonstrates how antibodies to *P. vivax* antigens change over time.

Longitudinal Antibody Titers Following Clinical *P. vivax*

Figure 11:
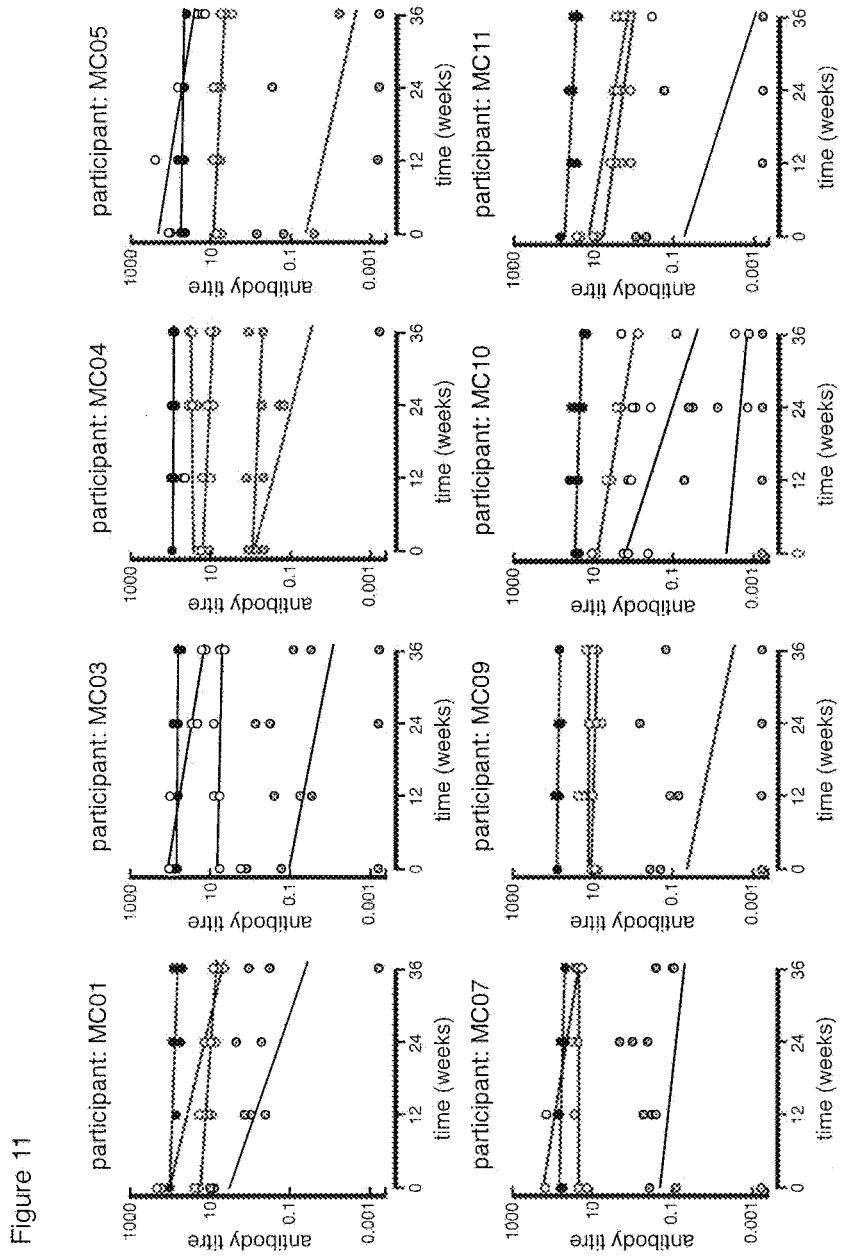
FIG. 11 shows longitudinal antibody dynamics of 4 antigens from 8 Thai participants in the antigen discovery cohort. For each blood sample antibody titers were measured in triplicate, using the AlphaScreen® assay. Each colour corresponds to antibodies to a different antigen. The lines represent the fit of the mixed-effects regression model described below.

We have data from longitudinal cohorts in Thailand and Brazil where participants were followed for up to 36 weeks after a symptomatic clinical episode of *P. vivax* (see also Table 1/Materials and Methods in Example 1, antigen discovery cohorts). Participants were treated with primaquine, and blood samples were frequently tested to ensure they remained free from reinfection. Antibody levels to a wide range of antigens were measured at 12 week intervals to investigate the changing antibody dynamics. The sample data in FIG. 11 illustrates that antibodies exhibit a range of different half-lives—a pattern consistent with the rest of the data (see also FIG. 3). Another important general feature of the data is exhibited here: rapidly decaying antibodies (short half-life) exhibit much more measurement error than slowly decaying antibodies (long-lived half-life).

The decay of anti-malaria antibodies following infection can be described by an exponential or a bi-phasic exponential distribution[4]. Because of the sampling frequency (every 12 weeks) we assume that antibodies decay exponentially. Exponential decay equates to linear decay on a log scale. Therefore we utilise linear regression models. In particular, we utilise a mixed-effects linear regression framework so that we can estimate both the mean rate of antibody decay as well as the standard deviation.

We assume that for individual i we have measurements of antibody titer $A_{ijk}$ at time j to antigen k. We assume that at time 0, antibody titers are Normally distributed[5] with mean $\alpha_k^0$ and standard deviation $\sigma_{\alpha,k}$ on a log-scale. We assume that an individual's rate of antibody decay is drawn from a Normal distribution with mean $r_k^0$ and standard deviation $\sigma_{r,k}$. The antibody dynamics in the population can therefore be described by the following mixed-effects linear regression model:

$$\log(A_{ijk}) \sim (\alpha_k^0 + \alpha_{ik}) + (r_k^0 + r_{ik})t_j + \varepsilon_k \quad (1)$$

$$\alpha_{ik} \sim N(0, \sigma_{\alpha,k})$$

$$r_{ik} \sim N(0, \sigma_{r,k})$$

$$\varepsilon_k \sim N(0, \sigma_{m,k})$$

This model can be fitted to data using the lmer package in R. FIG. 11 shows a sample of the fitted profiles of antibody dynamics.

Estimation Using Antibodies to a Single Antigen

Figure 12:
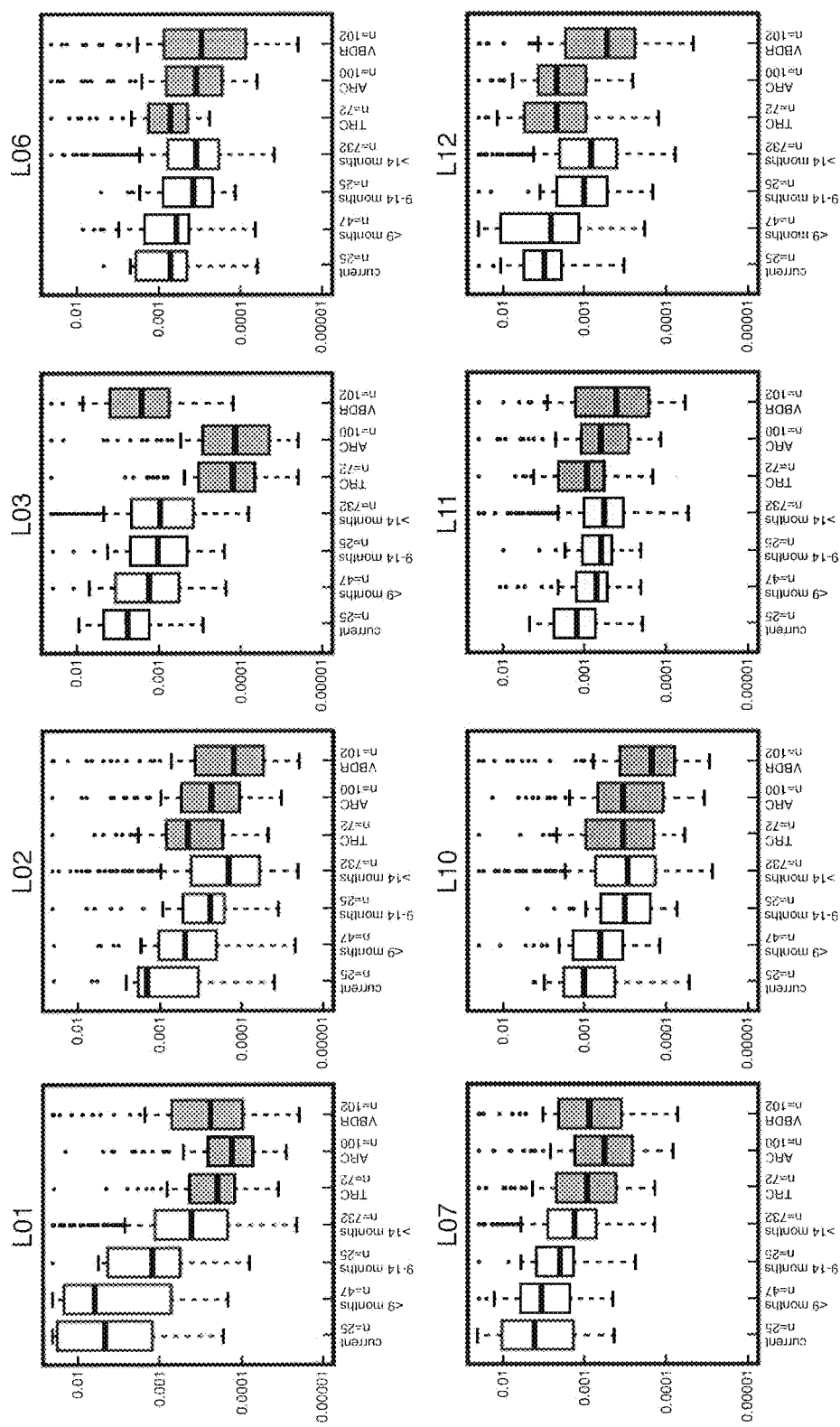
FIG. 12 shows the relationship between antibody titers to 8 *P. vivax* antigens and time since last PCR-detectable in individuals from a malaria-endemic region of Thailand (validation study, antibodies measured via Luminex® bead-array assay). The grey bars denote individuals with current infection (n=25); infection within the last 9 months (n=47); infection 9-14 months ago (n=25); and no infection detected within the last 14 months (n=732). The orange bars show the antibody titers from three different panels of negative controls.

Here we describe an algorithm that uses a biologically-motivated model of the decay of antibody titers over time to facilitate statistical inference of the time since last infection. A key requirement of this algorithm is that it requires some prior knowledge of the decay rates of antibodies. This can be achieved either through estimation of antibody decay rates from longitudinal data as described in equation (1), or estimation of decay rates from cross-sectional antibody measurements as presented in FIG. 12.

The linear regression model for the decay of antibody titers described in equation (1) has three sources of variation: (i) variation in initial antibody titer following infection; (ii) between individual variation in antibody decay rate; and (iii) measurement error. Notably, all these sources of variations are described by Normal distributions (FIG. 13a) so their combined variation will also be described by a Normal distribution. Therefore, the expected log antibody titer to antigen k in individual i at time t can be described by the following distribution.

$$x_{ik} \sim N(\alpha_k^0 + r_k t, \sigma_{\alpha,k}^2 + t^2 \sigma_{r,k}^2 + \sigma_{m,k}^2) \quad (2)$$

The probability distribution of the expected antibody titer to antigen k in individual i at time t is given by the following distribution:

$$P(x_{ik} \mid t) = \frac{1}{\sqrt{2\pi(\sigma_{\alpha,k}^2 + t^2 \sigma_{r,k}^2 + \sigma_{m,k}^2)}} e^{-\frac{(x_{ik} - \alpha_k^0 - r_k^0 t)^2}{2(\sigma_{\alpha,k}^2 + t^2 \sigma_{r,k}^2 + \sigma_{m,k}^2)}} \quad (3)$$

Note that we have $x_{ik} \in (-\infty, +\infty)$, as $x_{ik}$ denotes the log antibody titer and measurements of antibody titer are assumed to be positive. The probability distribution for the time since infection/given measured antibody titer $x_{ik}$ can be calculated by inverting equation (3) using Bayes rule[3].

$$P(t \mid x_{ik}) = \frac{P(x_{ik} \mid t) P(t)}{P(x_{ik})} \quad (4)$$

The time since last infection will have a lower bound of zero. We can choose to impose an upper bound of either the individual's age 'a' or positive infinity. Choosing positive infinity allows us to better handle the case where an individual was never infected—the low measured antibody titers will be consistent with a very large time since last infection, possibly greater than the age of the individual. Therefore we should only restrict t to the interval (0, a) if we know for certain that the individual has been infected. In practice, we choose some large time $t_{max}$ for our upper bound. We assume P(t) denotes a uniform distribution on the interval (0, $t_{max}$). $P(x_{ik})$ is a normalising constant which is calculated via numerical integration to ensure that $P(t|x_{ik})$ denotes a probability distribution.

Equation (4) provides a probability distribution for the time since last infection. For the purposes of a diagnostic test we may be more interested in obtaining a binary classification, e.g. was the individual infected within the last 9 months. It is usually not possible to definitively make such a categorisation, but we can instead calculate their probabilities as follows:

$$P_{0-9m}(x_{ik}) = \int_0^9 P(t \mid x_{ik}) dt \quad (5)$$

$$P_{9m+}(x_{ik}) = \int_9^{t_{max}} P(t \mid x_{ik}) dt$$

Combined Antibody Dynamics: Estimation Using Antibodies to Multiple Antigens

Previously, we described how the antibody titer to a single antigen can be used to estimate the time since last infection. However, in practice there is too much noise to make an accurate estimate of time since last infection with a single antigen. Increasing the number of measured antibodies can increase the information content in our data allowing us to obtain more accurate estimates of time since last infection. In particular, selecting antibodies with a range of half-lives may increase our power to resolve infection times more accurately.

Figure 14:
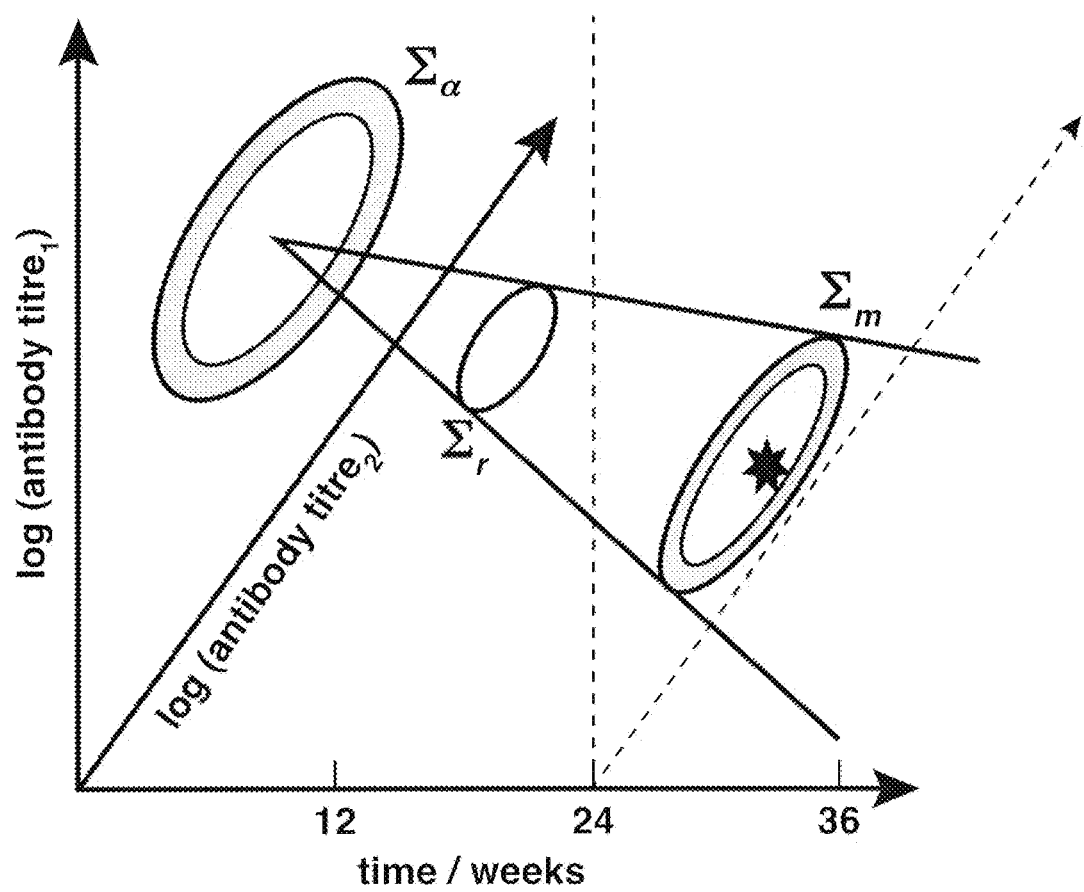
FIG. 14 shows the dynamics of multiple antibodies. The variance in initial antibody titer, antibody decay rates and measurement error are now described by covariance matrices, which account for the correlations between antibodies.
Figure 15:
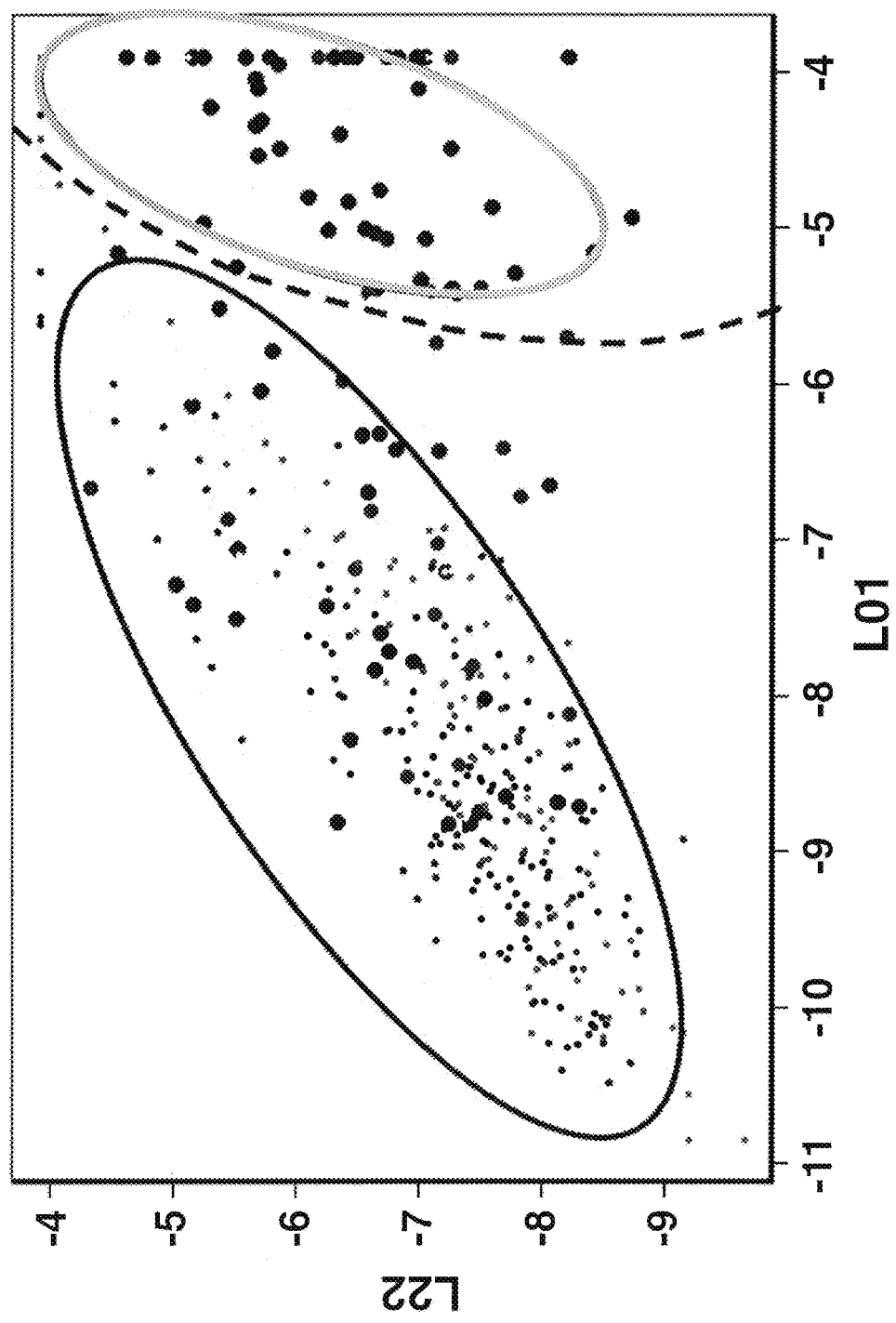
FIG. 15 shows an example of QDA classification for participants from the Thai validation cohort. Antibody measurements were made using the Luminex® bead-array assay. Each point corresponds to a measurement from a single individual with log(anti-L01 antibody titer) on the x-axis and log(anti-L22 antibody titer) on the y-axis. The blue ellipse represents the multivariate Gaussian fitted to data from individuals with 'old' infections and the red ellipse represents the multivariate Gaussian fitted to data from individuals with 'new' infections. The dashed lack line represents the boundary for classifying individuals according to whether or not they have had a recent infection.
Figure 16:
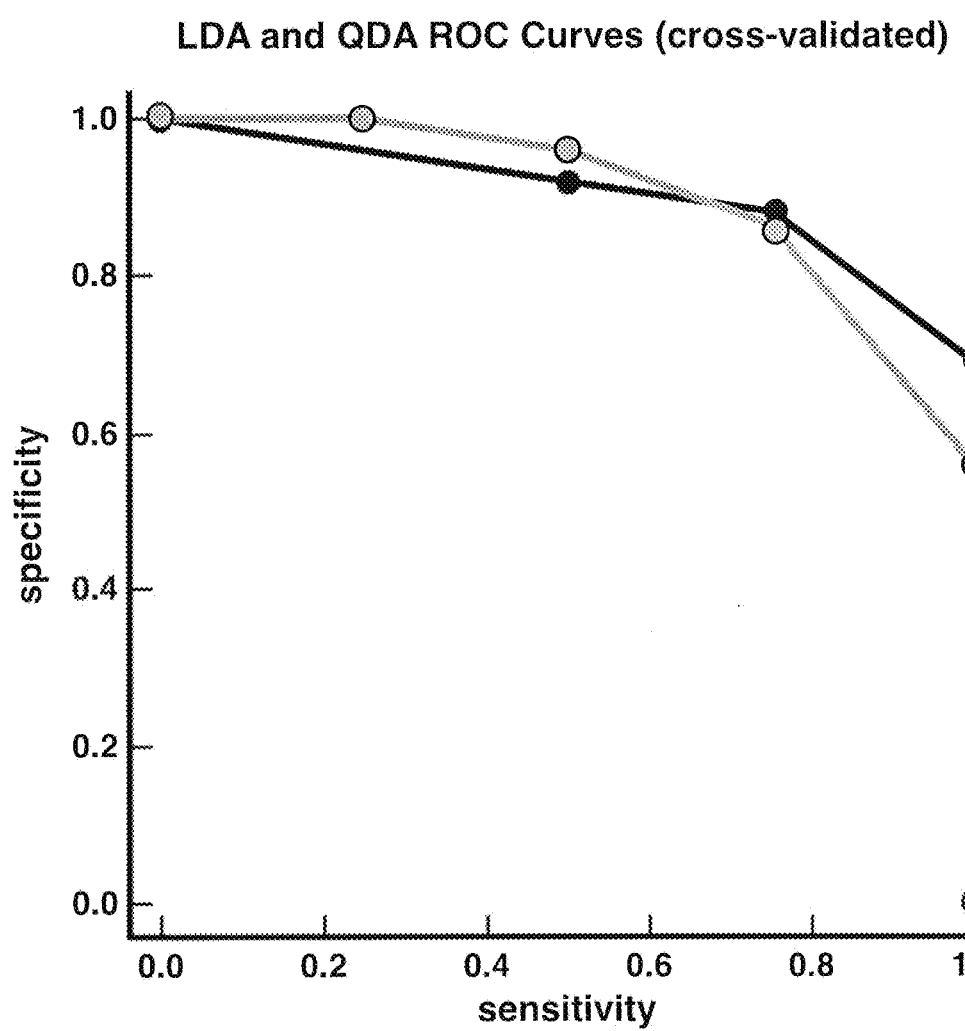
FIG. 16 shows receiver operator characteristic (ROC) curves estimated via cross-validation for LDA (blue) and QDA (black) classification algorithms, using the Thai validation data measured via the Luminex® bead-array assay.
Figure 17:
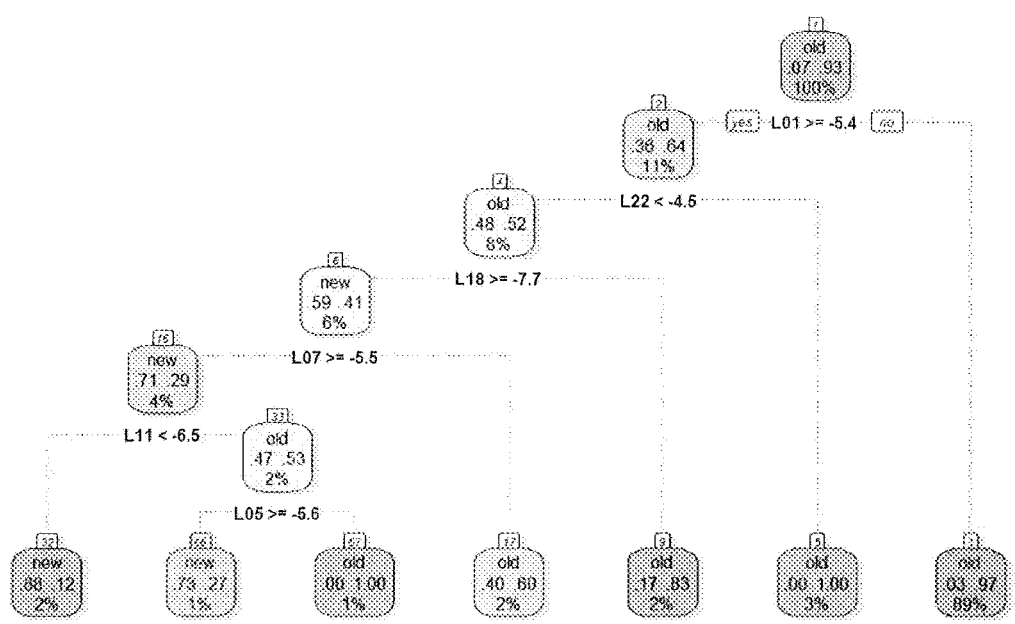
FIG. 17 shows an example of a decision tree for classifying old versus new infections using measurements of antibodies to 6 P. vivax antigens, using the Thai validation data measured via the Luminex® bead-array assay.
Figure 18:
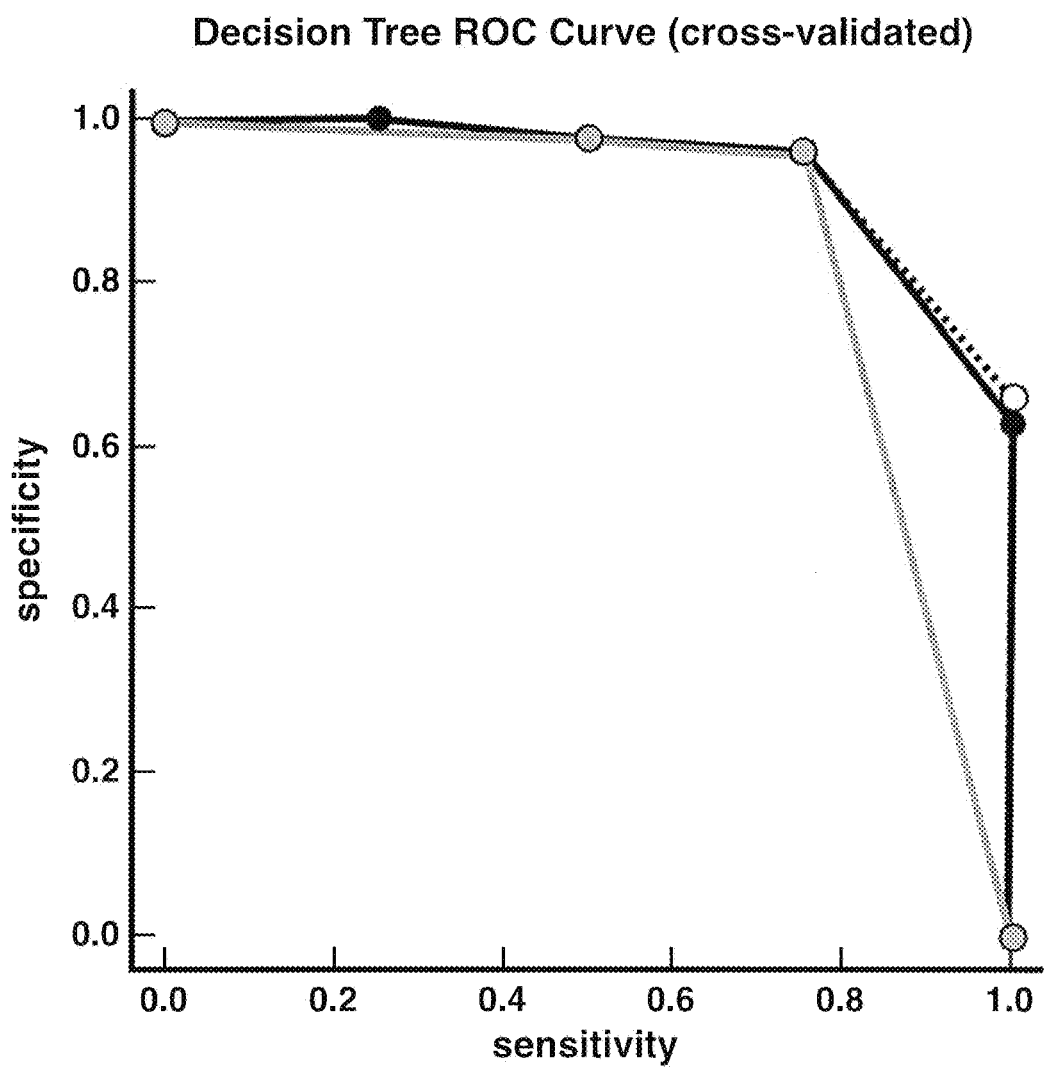
FIG. 18 shows ROC curve demonstrating the association between sensitivity and specificity for a decision tree algorithm, using the Thai validation data measured via the Luminex® bead-array assay. These curves have been generated through cross-validation by splitting the data into training and testing sets. The algorithm is formulated using the training data set and the sensitivity and specificity evaluated on the testing data set. The colours correspond to different subsets of antigens. Notably, we can obtain nearly 80% sensitivity with specificity >95%.
Figure 19:
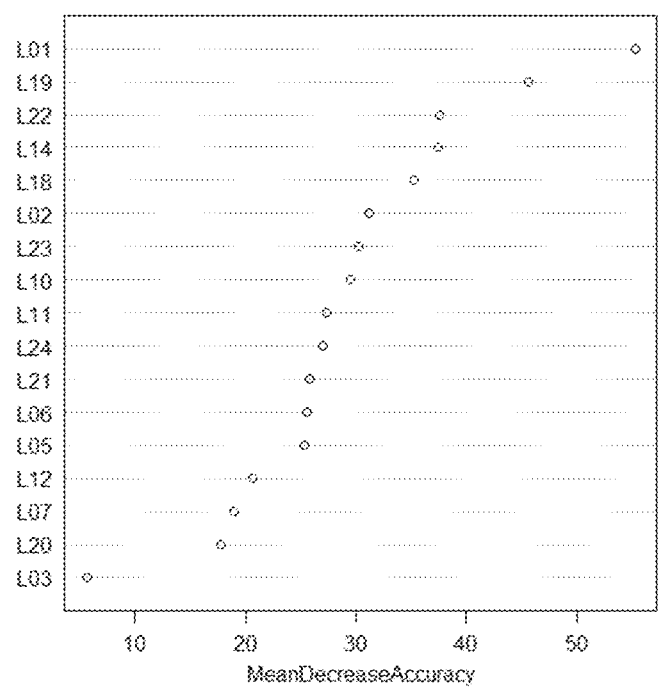
FIG. 19 shows a random forest variable importance plot of the contribution of antibodies to 17 antigens towards correct classification of infections into 'new' versus 'old', using the Thai validation data measured via the Luminex® bead-array assay. Antigens with greater values of 'MeanDecreaseAccuracy' are considered the most informative. Therefore L01 provides the most information for classification purposes.

FIG. 14 shows a schematic of the dynamics of antibodies to two antigens. We have rapidly decaying antibody 1 and slowly decaying antibody 2. At baseline, antibody titers are likely to be correlated, so we assume that initial titer following infection is described by a multivariate Normal distribution with covariance matrix $\Sigma_\alpha$. The between individual rates of antibody decay may also be correlated (i.e. all antibody titers may decay particularly quickly in some individuals) so we also assume that decay rates are described by a multivariate Normal distribution with covariance matrix $\Sigma_r$. Finally, there will be measurement error associated with each antibody. In particular, we assume the measurement errors between different antibodies are independent so that the total measurement error can be described by a multivariate Normal distribution with diagonal covariance matrix $\Sigma_m$.

$$P(x_i \mid t) = \quad (6)$$
$$(2\pi)^{-\frac{k}{2}} \left| \sum_\alpha + t^2 \sum_r + \sum_m \right|^{-\frac{1}{2}} e^{-\frac{1}{2}(x_i - \alpha^0 - r^0 t)^T (\Sigma_\alpha + t^2 \Sigma_r + \Sigma_m)^{-1}(x_i - \alpha^0 - r^0 t)}$$

The method for estimating the time since last infection given the multivariate probability distribution for the measured vector of antibody titers $x_i$ is the same as described in equation (4).

Selecting Optimal Combinations of Antigens

Machine learning algorithms take data from a large number of streams and identify which data streams have the most signal for classifying output. Such methods typically involve a greedy algorithm which will provide a good but not necessarily optimal solution. Greedy algorithms take the next best step, i.e. including the next antigen that gives the biggest increase in predictive power. As such they may provide a locally optimal solution but not necessarily a globally optimal solution. Simulated annealing algorithms provide an alternative to greedy algorithms that provide a higher likelihood of obtaining a globally optimal solution[7].

Here we describe how a simulated annealing algorithm can be applied to the combined antibody dynamics (CAD) classifier to select a combination of antigens that provides optimal predictive power. Assume that P measurements of antibodies are available. We want to select some subset of these that maximises predictive power. Denote y to be a vector of 0's and 1's indicating whether the $p^{th}$ antibody is included in our panel. Thus for example we may have $$y = (0, 0, 1, 1, 0, 1, 0, 0, 1) \quad (7)$$

The vector of binary states depicted in equation (7) will correspond to a vector of antibody measurements as follows:

$$x_i = (x_{i,1}, x_{i,2}, x_{i,3}, x_{i,4}) \quad (8)$$

Given data from I individuals on measured antibody responses, we can calculate the probability that the individual was infected within the last 9 months $P_{0-9 m}(x_i)$ or greater than 9 months ago $P_{9 m+}(x_i)$. Let $z_i$ be an indicator denoting whether individual I was infected in the last 9 months ($z_i=1$) or not ($z_i=0$). We can then write down the likelihood of the data as follows:

$$L(y) = \prod_{i=1}^{I} P_{0-9m}(x_i)^{z_i} P_{9m+}(x_i)^{1-z_i} \quad (9)$$

The challenge is to select a binary vector y corresponding to a combination of antigens that maximises the likelihood in equation (9) and thus has the highest likelihood of correctly classifying infections according to whether they occurred in the last 9 months.

Figure 20:
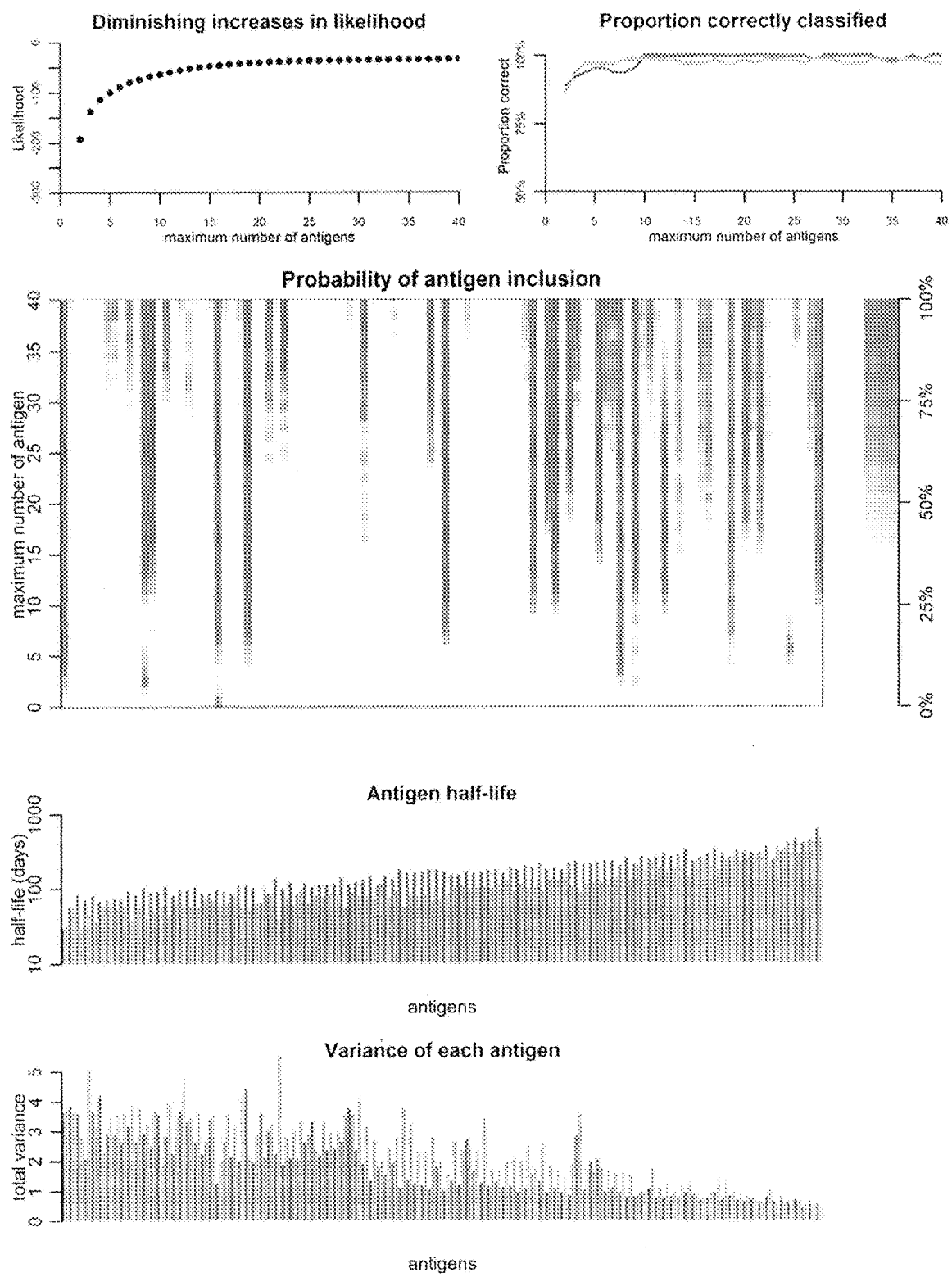
FIG. 20 shows an example of antigen down-selection using the simulated annealing algorithm. Data comes from the antigen discovery study using the AlphaScreen® assay. (A) Including additional antigens increases the likelihood that infection times will be correctly classified, but with diminishing returns. (B) Each column of the heatmap denotes one of K=98 antigens. The y-axis denotes the maximum number of antigens that can be included in a panel. Red antigens are more likely to be included in a panel of a given size. (C) Example of predicting time since last infection in 4 individuals using a panel of 15 antigens. The vertical dashed line at 6 months represents an infection occurring 6 months ago. The solid black curve denotes the estimated distribution of the time since last infection. The green point denotes the maximum likelihood estimate of the model, and the vertical green bars denote the 95% confidence intervals. The red, shaded area denotes infection within the last 9 months. If more than 50% of the probability mass of the distribution is in this region, then the infection will be classified as having occurred within the last 9 months.

If we have P antigens, there are $2^P$ combinations of antigens. For P >15 it is not computationally feasible to test all possible combinations. We therefore utilise a simulated annealing algorithm for exploring the state space of combinations and identifying the optimal combinations subject to various constraints (e.g. enforcing a maximum of 10 antigens to a panel). FIG. 20 shows the results, and this contributed to the initial down-selected of antigens as described in Example 1.

REFERENCES

1 White. N. J. Determinants of relapse periodicity in *Plasmodium vivax* malaria. *Malaria Journal* 10, doi: 29710.1186/1475-2875-10-297 (2011).
2 Mueller, I. et al. Key gaps in the knowledge of *Plasmodium vivax*, a neglected human malaria parasite. *Lancet Infectious Diseases* 9, 555-566 (2009).
3 Hastie. T., Tibshirani, R. & Friedman, J. *The elements of statistical learning: Data mining, inference, and prediction*. Second edn, (Springer, 2009).
4 White, M. T. et al. Dynamics of the Antibody Response to *Plasmodium falciparum* Infection in African Children. *Journal of Infectious Diseases* 210. 1115-1122, doi: 10.1093/infdis/jiu219 (2014).
5 Yman, V. et al. Antibody acquisition models: A new tool for serological surveillance of malaria transmission intensity. *Scientific Reports* 6. doi: 10.1038/srep19472 (2016).

6 The Elements of Statistical Learning: Data Mining, Inference and Prediction" by Hastie, Tibshirani & Friedman; 2001, Springer.
7 Kirkpatrick, S., Gelatt Jr, C. D. & Vecchi, M. P. Optimization by simulated annealing. Science 220, 671-680 (1983).

Example 4—Additional Testing of Antigens

This non-limiting Example relates to additional testing of antibody responses to various *P. vivax* proteins, present in the blood, as potential antigens for a diagnostic test. It further relates to selection of *Plasmodium vivax* antigens for classification of samples with past blood-stage infections.

The blood collection and laboratory work was generally performed according to the materials and methods described in Example 1.

Overview of Epidemiological Cohorts

Figure 21:
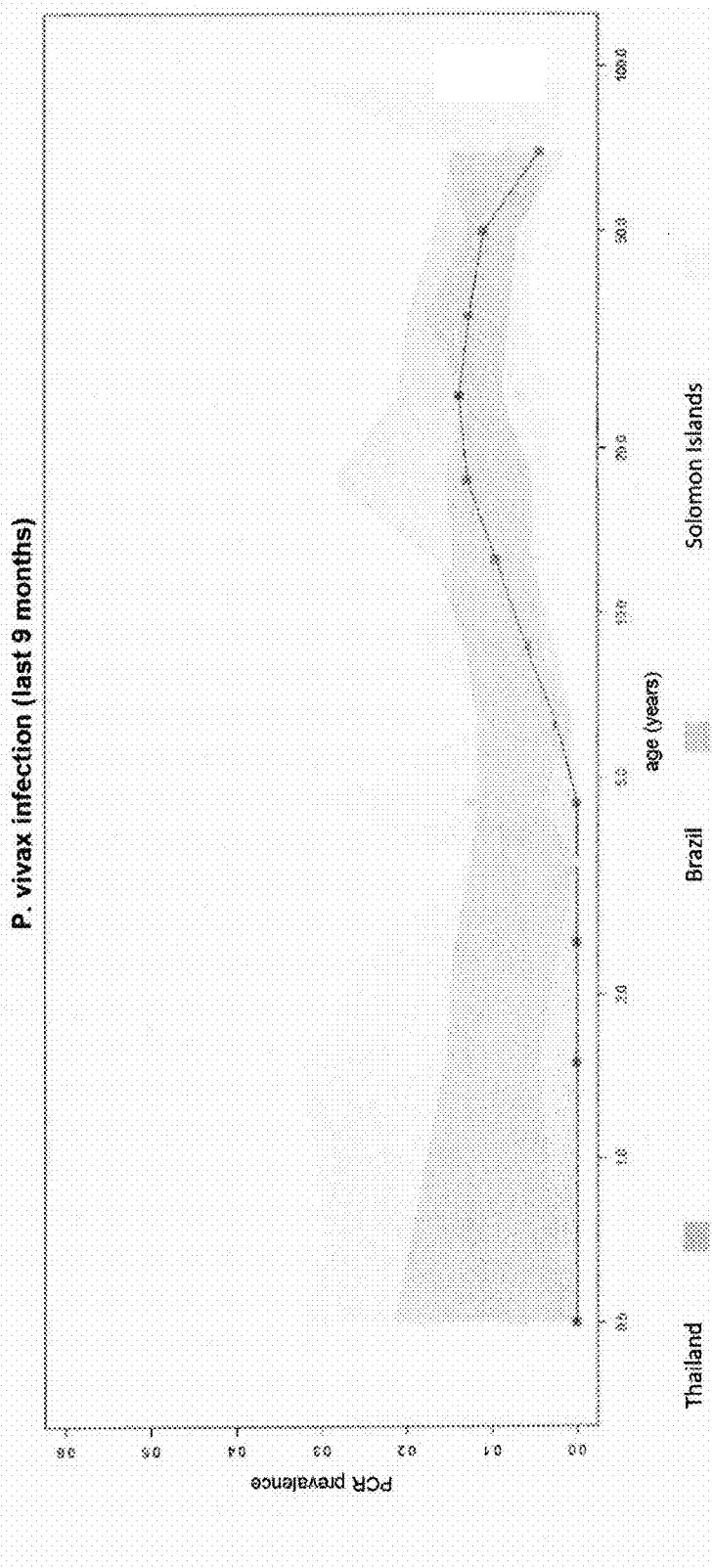
FIG. 21 shows comparison of age-stratified prevalence of PCR detectable blood-stage infection within the last 9 months.

Data was obtained from longitudinal cohorts in three different regions of the *P. vivax* endemic world. In each cohort, approximately 1,000 individuals were followed over time for approximately 1 year, with active case detection samples taken every month. These samples were supplemented by passive case detection samples from individuals experiencing clinical episodes of *P. vivax* or *P. falciparum*. An overview of the data collected is shown in Table 3, and age-stratified prevalence of PCR detectable blood-stage infection within the last 9 months is shown in FIG. 21.

In addition data was obtained from three cohorts of negative controls who were highly to have ever been exposed to malaria. These cohorts consisted of 102 individuals from the Victorian Blood Donor Registry (VBDR), 100 individuals from the Australian Red Cross, and 72 individuals from the Thai Red Cross (residents of Bangkok with no reported history of malaria).

TABLE 3

Epidemiological overview of cohorts analysed for the association between *P. vivax* antibody titers and time since last PCR detectable infection. Number of samples per individual and age are shown as median with range.

|  | Thailand | Brazil | Solomon Islands |
|---|---|---|---|
| number of individuals | 829 | 928 | 860 |
| samples per individual | 14 (4, 18) | 13 (4, 16) | 10 (6, 11) |
| Female | 454 (54.8%) | 471 (50.7%) | 416 (48.4%) |
| age (years) | 24 (1, 78) | 25 (0, 103) | 5.5 (0.5, 12.7) |
| PCR infection during study | 97 (11.7%) | 236 (25.4%) | 294 (34.2%) |
| PCR infection in last 9 months | 72 (8.7%) | 205 (22.1%) | 265 (30.8%) |
| PCR infection in last 3 months | 44 (5.3%) | 119 (12.8%) | 156 (18.1%) |
| PCR infection at last final time point | 25 (3.0%) | 40 (4.3%) | 93 (10.8%) |

Measured Antibody Responses

In each of the three longitudinal cohorts, antibody responses were measured at the final time point to allow investigation of the association between antibody response and time since last infection. The antibody responses to 65 antigens were measured. 40 of these antigens were selected following a previously published down-selection procedure from a starting panel of 342 wheat-germ expressed proteins. These 40 proteins were supplemented by another 25 purified *P. vivax* proteins obtained from collaborators. These *P. vivax* antigens were coupled to COOH micro-beads, and a multiplexed Luminex assay was used to measure Mean Fluorescence Intensity (MFI) for each antigen in each sample. MFI measurements were converted to antibody titers by calibrated to measurements from a hyper-immune pool of Papua New Guinean adults. FIG. 22 shows the measured response from 4 of the 65 antigens, and the variation with time since last infection.

Selection of Optimal Combinations of Antigens for Classification

Initial Investigation of Combinations of Parameters

Of the 65 *P. vivax* proteins considered, 5 were excluded because of poor immunogenicity which resulted in missing data from a large proportion of samples. This resulted in a panel of 60 antigens for detailed investigation and further down-selection. The aim is to identify combinations of up to 5 antigens that can provide accurate classification within a single cohort, and identify combinations of 8-15 antigens that can accurately across multiple cohorts with a wide range of transmission intensities and age ranges.

Without wishing to be limited by a single hypothesis, selection optimized for three classification targets:

1 Surveillance target. Select combinations of antigens such that both sensitivity and specificity are given equal weight in optimisation. This is done by maximising the area under the curve (AUC) of a receiver operating characteristic (ROC) curve.

2. Serological Screen and Treat (SSAT) target. Select combinations of antigens that maximise sensitivity (e.g. >95%) while enforcing a lower bound on specificity (e.g. >50%).

3 Surveillance target. Select combinations of antigens that maximise specificity (e.g. >95%) while enforcing a lower bound on sensitivity (e.g. >50%).

The first step is to identify combinations of antigens for which there is a strong signal enabling classification. This was done by using a linear discriminant analysis (LDA) classifier to test all combinations of antigen of size up to 5. Above size 5, it was not computationally feasible to evaluate all possible combinations. Therefore for n>5, combinations of size n+1 were evaluated by identifying the optimal 500 combinations of size n antigens and including all positive individually.

Optimisation of Algorithms Given Most Likely Parameter Combinations

Given a subset of n antigens, a range of classification algorithms were considered: LDA, quadratic discriminant analysis (QDA), decision trees, and random forests. For a given algorithm and subset of antigens classification performance was assessed through cross-validation. The key to cross-validation is to use disjoint training and testing data sets to assess classification of performance. For each cohort, this is done by randomly selecting ⅔ of the data as the training set and testing the algorithm on the remaining ⅓. This is repeated 200 times and the average of the cross-validated ROC curves is calculated.

FIGS. 23A-23C show cross-validated ROC curves for assessing the classification performance of random forests algorithms (determined according to the randomForests library in R). In cases where algorithms were trained and tested on data from the same region, many different combinations of 4 antigens resulted in sensitivity and specificity greater than 80%. Even when an algorithm was trained on data from one region and then tested on data from another region of the world, it was still possible to obtain combinations of antigens with both sensitivity and specificity greater than 80%, with the exception of algorithms trained on data from Thailand and tested on data from the Solomon Islands.

Ranking of Antigens

Figure 24:
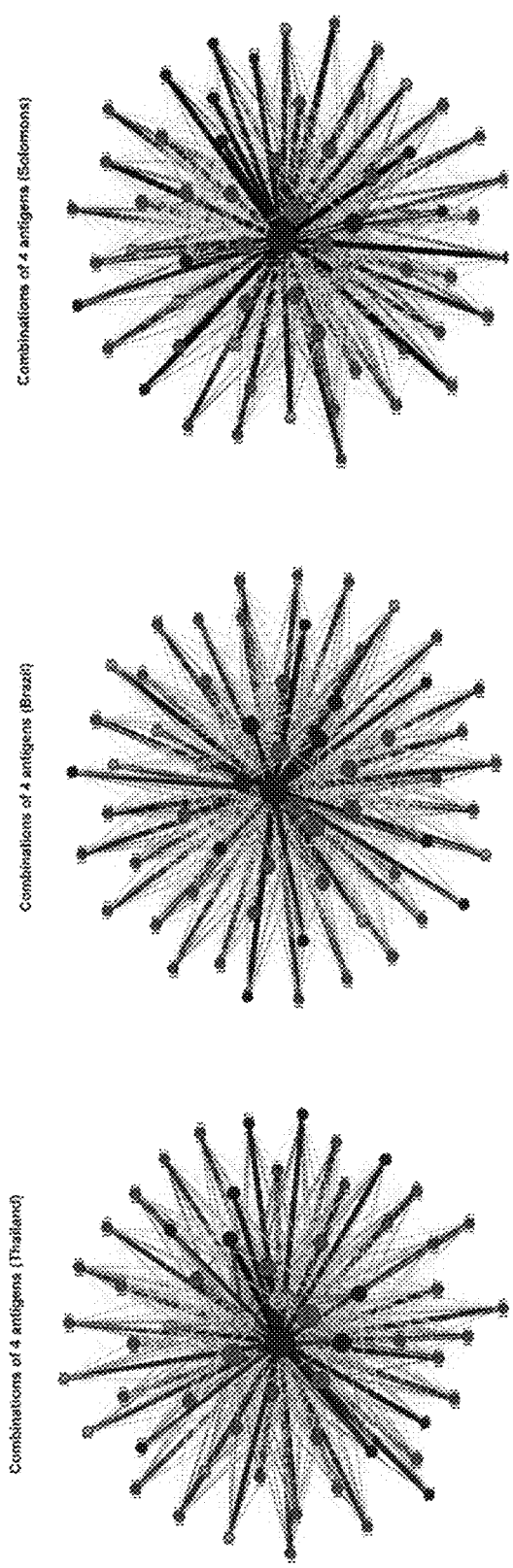
FIG. 24 shows an exemplary network visualization of combinations of 4 antigens. The size of the node represents the probability that an antigen appears in the best performing combinations. The width and darkness of the edges represents the probability that two antigens are selected together in the best performing combinations. Red denotes proteins purified at high yield by CellFree Sciences (the 40 down selected proteins, the results for which are shown in FIG. 6B). Blue denotes vaccine candidate antigens. Green denotes proteins expressed in wheat-germ by Ehime University. Blue and green proteins are the 25 additional proteins, the results for which are shown in FIG. 6C.

Multiple factors determine whether or not an antigen will contribute to classification of recent infection. These include but are not limited to: antibody dynamics; immunogenicity of recent infections compared to old infections and measurements from control samples; area under the ROC curve when considering one antigen at a time; frequency of selection in top combinations of antigens. FIG. 24 shows a network visualisation of how combinations of 4 antigens are selected. The size of each node represents the likelihood that an antigen is selected, and the width and colour of an edge represents the probability that a pair of antigens are selected in combination. Therefore, the most commonly selected antigens are biggest and cluster in the centre of the network. There was a high degree of consistency in the antigens that were selected in each of the three cohorts, with the most strongly identified antigens being RBP2b (V3), L01, L31, X087885 (X7), PvEBP (V11), L55, PvRipr (V8) and L54.

Table 4 shows a ranking of antigens according to a range of criteria. The top two antigens, RBP2b and L01, are preferred candidates. The next six antigens are likely candidates. The next seven antigens are possible candidates. Also included are an additional nine antigens worth further consideration.

TABLE 4

List of antigens ranked according to their contribution to classification of individuals with PCR detectable blood-stage *P. vivax* in the last 9 months. The area under the curve (AUC) is based on using antibody titers to a single antigen for classification. Combinations of antigens were investigated by assessing classification performance of linear discriminant analysis (LDA) for all combination of 4 antigens from the initial panel of 60 antigens. Recent infection sero-positivity shows the proportion of individuals with PCR detectable *P. vivax* in the last 9 months, with the threshold of sero-positivity defined as the geometric mean titer (GMT) plus two standard deviations of the negative controls.

| antigen | Area Under Curve (1 antigen) | | | Top 1% of combination (4 antigens) | | | Recent infection sero-positivity | | |
|---|---|---|---|---|---|---|---|---|---|
| | Thailand | Brazil | Solomons | Thailand | Brazil | Solomons | Thailand | Brazil | Solomons |
| RBP2b (V3) | 0.849 | 0.818 | 0.868 | 89.7% | 98.5% | 100.0% | 70.8% | 64.4% | 45.7% |
| L01 | 0.812 | 0.787 | 0.697 | 43.5% | 23.9% | 4.3% | 51.4% | 56.6% | 14.3% |
| L31 | 0.805 | 0.762 | 0.766 | 5.0% | 2.7% | 3.7% | 25.0% | 38.0% | 7.4% |
| X087885 (X7) | 0.807 | 0.748 | 0.697 | 20.3% | 9.2% | 14.6% | 41.7% | 81.0% | 50.9% |
| PvEBP (V11) | 0.794 | 0.739 | 0.707 | 5.0% | 2.4% | 3.1% | 55.6% | 41.0% | 7.8% |
| L55 | 0.79 | 0.781 | 0.643 | 17.2% | 20.9% | 2.6% | 38.9% | 29.8% | 3.5% |
| PvRipr (V8) | 0.754 | 0.772 | 0.646 | 3.0% | 9.1% | 3.1% | 31.9% | 29.3% | 4.8% |
| L54 | 0.79 | 0.727 | 0.654 | 5.6% | 4.4% | 3.1% | 26.4% | 19.0% | 2.2% |
| L07 | 0.747 | 0.765 | 0.599 | 3.1% | 5.3% | 2.8% | 27.8% | 41.5% | 3.9% |
| L30 | 0.732 | 0.61 | 0.609 | 2.3% | 3.8% | 5.4% | 47.2% | 11.7% | 9.6% |
| PvDBPII (V10) | 0.74 | 0.773 | 0.639 | 1.7% | 2.6% | 4.0% | 20.8% | 47.3% | 3.5% |
| L34 | 0.767 | 0.746 | 0.67 | 4.5% | 16.6% | 2.2% | 12.5% | 19.0% | 3.9% |
| X092995 (X6) | 0.792 | 0.703 | 0.642 | 11.5% | 1.9% | 5.6% | 15.3% | 34.1% | 10.0% |
| L12 | 0.755 | 0.731 | 0.637 | 3.5% | 6.1% | 2.9% | 16.7% | 15.1% | 3.0% |
| RBP1b (V1) | 0.533 | 0.578 | 0.525 | 24.1% | 4.7% | 2.5% | 0.0% | 0.0% | 0.0% |
| L23 | 0.759 | 0.753 | 0.658 | 4.0% | 14.8% | 2.9% | 12.5% | 19.5% | 5.7% |
| L02 | 0.746 | 0.724 | 0.677 | 2.7% | 3.7% | 3.9% | 15.3% | 13.7% | 2.6% |
| L32 | 0.705 | 0.651 | 0.493 | 3.7% | 1.9% | 30.2% | 4.2% | 3.9% | 0.4% |
| L28 | 0.759 | 0.744 | 0.667 | 3.8% | 2.5% | 2.4% | 45.8% | 33.2% | 9.1% |
| L19 | 0.753 | 0.67 | 0.664 | 2.6% | 2.3% | 6.5% | 33.3% | 19.5% | 10.9% |
| L36 | 0.727 | 0.698 | 0.662 | 3.2% | 1.8% | 2.8% | 36.1% | 22.0% | 10.4% |
| L41 | 0.702 | 0.66 | 0.636 | 2.55 | 1.7% | 3.3% | 29.2% | 17.6% | 8.3% |
| X088820 (X4) | 0.723 | 0.666 | 0.638 | 4.0% | 1.8% | 6.7% | 15.3% | 35.6% | 14.8% |
| PvDBP..SacI (V13) | 0.716 | 0.761 | 0.616 | 1.7% | 2.6% | 7.2% | 16.7% | 36.6% | 1.3% |

FIG. 25 shows Receiver Operating Characteristic (ROC) curves for assessing the trade-off between sensitivity and specificity for a cross-validated linear discriminant analysis (LDA) classifier applied to data from Thailand, Brazil and the Solomon Islands.

Appendix I

| No. | Protein Name | Protein Reference | Insert aa sequence (add M as start/His-tag at C-term) | Insert DNA sequence (Start from ATG to His-tag stop codon) |
|---|---|---|---|---|
| 1 | merozoite surface protein 1 (MSP1), MSP1-19 | PVX_099980 | MNESKEILSQLLNVQTQLLTMSSEH TCIDTNVPDNAACYRYLDGTEEWRC LLTFKEEGGKCVPASNVTCKDNNG GCAPEAECKMTDSNKIVCKCTKEGS EPLFEGVFCSHHHHHH (SEQ ID NO: 1) | ATGAACGAGTCCAAGGAGATCCTCAGCCAACTCCTGAACGTGCAAACC CAGCTCCTGACCATGTCCAGCGAGCACACCTGCATCGACACCAACGTCC CAGACAACGGCGCCTGCTACAGGTACCTGGACGGCACCGAGGAGTGG CGCTGCCTCCTGACCTTCAAGGAAGAGGGCGGCAAGTGCGTGCCAGCC TCCAACGTCACCTGCAAGGACAACAACGGCGGCTGCGCTCAGAGGCT GAGTGCAAGATGACCGACAGCAACAAGATCGTGTGCAAGTGCACCAA GGAAGGCTCCGAGCCACTCTTCGAGGGCGTCTTCTGCAGCCACCACCA CCACCACCACTGA (SEQ ID NO: 2) |
| 2 | trypto-phan-rich antigen (Pv-fam-a) | PVX_096995 | MKTETVTSRSNPHQAIEYANQGPS RDKVEEWKRNAWTDWMVQLDDD WKDFNAQIEEEKKAWIEEKEGDWV ILLKHLQNKWLHFNPNLDAEYQTD MLAKSETWDERQWKMWISTEGKQ LLEMDLKKWFTNNEMIYCKWTMDE WNEWKNEKIKEWVTSEWKESEDQ YWSKYDDATIQTLTVAERNQWFKW KERIYREGIEWKNWIAIKESKFVNA NWNSWSEWKNEKRLEFNDWIEAF VEKWIRQKQWLIWTDERKNFANRQ KAAPGGVAAAPGVFAPRPAFGAPS GFAPRPGFAAPSQPPRYSFAAASG YVAPSATSEAAPATSEAPASAEATT ALSSETTTPVNPEETAASPEAATPV NPEETAASSETTTVNPEATPVNPEA PVAEPEKKEEEPAAEPLLAIEPAQT EPAALEAAPSTSAHHHHHH (SEQ ID NO: 3) | ATGAAGACCGAGACGGTGACCTCCAGGAGCAACCCACACCAAGCCATC GAGTACGCCAACCAGGGCCCATCCAGGGACAAGGTGGAGGAGTGGAA GCGCAACGCCTGGACCGACTGGATGGTCCAGCTCGACGACGACTGGA AGGACTTCAACGCCCAGATCGAGGAAGAGAAGAAGGCCTGGATTGAG GAGAAGGAAGGCGACTGGGTCATCCTCCTGAAGCACCTCCAAAACAA GTGGCTGCACTTCAACCCAAACCTCGACGCCGAGTACCAGACCGACAT GCTGGCCAAGTCCGAGACGTGGGACGAGAGGCAGTGGAAGATGTGG ATCAGCACCGAGGGCAAGCAGCTCCTGGAGATGGACCTCAAGAAGTG GTTCACCAACAACGAGATGATCTACTGCAAGTGGACCATGGACGAGTG GAACGAGTGGAAGAACGAGAAGATCAAGGAGTGGGTGACCTCCGAGT GGAAGGAGAGCGAGGACCAATACTGGTCCAAGTACGACGCCACC ATCCAAACCCTGACCGTCGCCGAGCGCAACCAGTGGTTCAAGTGGAAG GAGAGGATCTACCGCGAGGGCATCGAGTGGAAGAACTGGATCGCCAT CAAGGAGAGCAAGTTCGTGAACGCCAACTGGAACTCCTGGTCTGAGTG GAAGAACGAGAAGAGGCTGGAGTTCAACGACTGGATCGAGGCCTTCG TCGAGAAGTGGATCCGCCAAAAGCAGTGGCTGATCTGGACCGACGAG AGGAAGAACTTCGCCAACCGCCAAAAGGCTGCTCAGGCGGCGTGGC TGCCGCCCCAGGCGTCTTCGCCCCACGCCCAGCCTTCGGCGCCCATCC GGCTTCGCCCCAAGGCCAGGCTTCGCTGCTCCAAGCCAGCCACCAGC TACTCCTTCGCTGCCGCCAGCGGCTACGTGGCTCCATCCGCTACCAGCG AGGCTGCTCCAGCCACCTCCGAGGCCCAGCCAGCGCCGAGGCTACCA CCGCTCTCTCCAGCGAGACGACCACCCCAGTCAACCCAGAGGAGACGG CTGCTAGCCCGGAGGCTGCTACCCCAGTGAACCCGGAGGAGACGGC TGCCTCCGAGACGACGGTCAACCCAGAGGCCACCCCGGTGAA CCCAGAGGCTCCAGTGGCTGAGCCAGAGAAGAAGGAAGAGGAGCCA GCTGCTGAGCCACTGCTCGCTATCGAGCCAGCTCAAACCGAGCCAGCT GCTCTGGAGGCTGCTCCATCCACCAGCGCCCACCACCACCACCACCACT GA (SEQ ID NO: 4) |
| 3 | sporozoite invasion-associated protein 2, putative (SIAP2) | PVX_088860 | MQLELEPAPDYESTSPTVPVRLLLH DDYAPNAEDMFGPEASQVMTNLYE TIDEDGTTTDGYQNGSDDDQSNQS DSNDDAVMLNYLSNETDSFDELIDEI DNHKKKKIYSPLRKPVLKRSDSSD SLSDYELDEVLRQTENEPEEDEDLD LSLEDSFEVINYPWKDILESSPYSTD HTNEEDFSSLEELELEDPVQEMNFG KLKFFEIGDPDLLIRKTPITPNTKTKS GLEKNGNNTEASNINQHEKEKMDK RKRRTHKQFKNPIENFSVTTTYDDF LKQNGLRDHPSKHQKDSSEPFVLD QYNYRNAKFKNVRFYILRMLYDNIK DIGLKEFQYLKSHKYEVEEFIKNILRN NLICLTFSQEDHLFNDAHLLIEKASIK SEHHHHHH (SEQ ID NO: 5) | ATGCAGCTGGAGCTGGAGCCAGCCCCAGACTACGAGTCCACCAGCCCA ACCGTGCCAGTCAGGCTCCTGCTCCACGACGACTACGCCCCAAACGCC GAGGACATGTTCGGCCCAGAGGCCTCCCAAGTGATGACCAACCTCTAC GAGACGATCGACGAGGACGGCACCACCACCGACGGCTACCAAAACGG CTCCGACGACGACCAAAGCAACCAGTCCGACAGCAACGACGACGCCGT CATGCTCAACTACCTGTCCAACGAGACGGACAGCTTCGACGAGCTCATC GACGAGATCGACAACCACAAGAAGAAGAAGATTTACTCCCCACTC AGGAAGCCAGTGCTGAAGCGCAGCGACTCCAGCGACTCCCTGAGCGA CTACGAGCTCGACGAGGTCCTGCGCCAGACCGAGAACGAGCCAGAGG AAGACGAGGACCTGGACCTCTCCCTGGAGGACAGCTTCGAGGTCATCA ACTACCCGTGGAAGGACATCCTGGAGTCCAGCCCATACAGCACCGACC ACACCAACGAGGAAGACTTCTCCAGCCTGGAGGAGCTGGAGCTGGAG GACCCAGTCCAAGAGATGAACTTCGGCAAGCTGAAGTTCTTCGAGATC GGCGACCCAGACCTGCTCATCAGGAAGACCCCAATCACCCCAAACACC AAGACCAAGTCCGGCCTGGAGAAGAACGGCAACAACACCGAGGCCAG CAACATCAACCAGCACGAGAAGGAGAAGATGGACAAGCGCAAGAGGC GCACCCACAAGCAATTCAAGAACCCAATCGAGAACTTCTCCGTGACCAC CACCTACGACGACTTCCTCAAGCAAAACGGCTGAGGGACCACCCAAG CAAGCACCAGAAGGACTCCAGCGAGCCATTCGTGCTCGACCAATACAA CTACCGCAACGCCAAGTTCAAGAACGTCAGGTTCTACATCCTCCGCATG CTGTACGACAACATCAAGGACATCGGCCTCAAGGAGTTCCAGTACCTG AAGTCCCACAAGTACGAGGTCGAGGAGTTCATCAAGAACATCCTCAGG AACAACCTCATCTGCCTGACCTTCAGCCAAGAGGACCACCTGTTCAACG ACGCCCATCTGCTCATCGAGAAGGCCTCCATCAAGAGCGAGCACCACC ACCACCACCACTGA (SEQ ID NO: 6) |
| 4 | rhoptry neck protein 2, putative (RON2) | PVX_117880 | MNAGDGQGVYGGNGINNPLVYHVQ HGVNIPNSNSDKKASDHTPDEDEDT YGRTRNKRYMHRNPGEKYKGSNSP HDSNDDSGDTEYELNEGDVKRLTP KNKKGATTEEVDTYPYGKKTNGSEF PRMNGSETGHYGYNNTGSGGHND ENGYTPIIVKYDNTHAKNRANEIEEN LNKGEYSRIKMAGKKGQKSGYE SDGEDSDVDSSNVFYVDNGQDMLI KEKMSRSEGPDEMSEEGLNVKYKA QRGPVNYHFSNYMNLDKRNTLSSN | ATGAACGCTGGCGACGGCCAAGGCGTGTACGGCGGAAACGGCATCAA CAACCCGCTCGTGTACCACGTCCAGCACGGCGTCAACATCCCAAACTCC AACAGCGACAAGAAGGCCAGCGACCACACCCCAGACGAGGACGAGGA CACCTACGGCAGGACCCGCAACAAGAGGTACATGCACCGCAACCCAG GCGAGAAGTACAAGGGCTCCAACAGCCCACACGACTCCAACGACGACA GCGGCGACACCGAGTACGAGCTGAACGAGGGCGACGTGAAGAGGCTC ACCCCAAAGAACAAGAAGGGCGCCACCACCGAGGAAGTGGACACCTA CCCATACGGCAAGAAGACCAACGGCAGCGAGTTCCCACGCATGAACG GCTCCGAGACGGGCCACTACGGCTACAACAACACCGGCAGCGGCGGC CACAACGACGAGAACGGCTACACCCCAATCATCGTGAAGTACGACAAC ACCCACGCCAAGAACAGGGCCAACGAGATCGAGGAGAACCTCAACAA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | EIELQKMIGPKFSEEVNKYCRLNEPS SKKGEFLNVSFEYSRALEELRSEMI NELQKRKAVGSNYYNNILNAIYTSM NRKNANFGRDAYEDKSFISEANSFR NEEMQPLSAKYNKILROYLCHVFVG NPGVNQLERLYFHNLALGELIEPIRR KYNKLASSSVGLNYEIYIASSSNIYLM GHLLMLSLAYLSYNSYFVQGLKPFY SLETMLMANSDYSFFMYNEVCNVY YHPKGTFNKDITFIPIESRPGRHSTY VGERKVTCDLLELILNAYTLINVHEIQ KVFNTSEAYGYENSISFGHNAVRIFS QVCPRDDAKNTFGCDFEKSTLYNS KVLLKMDEGDKENQRSLKRAFDMLR TFAEIESTSHLGDPSPNYISLIFEQNL YTDFYKYLFWYDNRELINVQIRNAG RRKKGKKVKFVYDEFVKRGKQLKD KLIKIDAKYNARSKALLVFYALVDKYA NIFRKSENVRKFFLNDVSSIRHHLYL NSVLTKSPKSNLDSMKKTLEELQSL TNAPLKFIVRGNNLKFLNNVAKFENL FYVNLFIMSSLSRKHHHHHH (SEQ ID NO: 7) | GGGCGAGTACTCCCGCATCAAGATGGCCAAGGGCAAGAAGGGCCAAA AGTCCGGCGGCTACGAGAGCGACGGCGAGGACTCCGACGTCGACTCC AGCAACGTGTTCTACGTCGACAACGGCCAGGACATGCTGATCAAGGAG AAGATGTCCAGGAGCGAGGGCCCAGACGAGATGAGCGAGGAAGGCC TCAACGTGAAGTACAAGGCCCAAAGGGGCCCAGTCAACTACCACTTCT CCAACTACATGAACCTGGACAAGCGCAACACCCTCTCCAGCAACGAGA TCGAGCTCCAGAAGATGATCGGCCCAAAGTTCAGCGAGGAAGTGAAC AAGTACTGCAGGCTGAACGAGCCATCCAGCAAGAAGGGCGAGTTCCTC AACGTCTCCTTCGAGTACAGCAGGGCCCTGGAGGAGCTGAGGTCCGA GATGATCAACGAGCTGCAAAAGCGCAAGGCCGTGGGCAGCAACTACT ACAACAACATCCTCAACGCCATCTACACCTCCATGAACAGGAAGAACGC CAACTTCGGCCGCGACGCCTACGAGGACAAGTCCTTCATCAGCGAGGC CAACAGCTTCAGGAACGAGGAGATGCAACCACTCTCCGCCAAGTACAA CAAGATCCTGCGCCAGTACCTCTGCCACGTGTTCGTCGGCAACCCAGGC GTGAACCAACTGGAGCGCCTGTACTTCCACAACCTCGCCCTGGGCGAG CTGATCGAGCCAATCAGGCGCAAGTACAACAAGCTGGCCTCCAGCTCC GTCGGCCTCAACTACGAGATCTACATCGCCAGCTCCAGCAACATCTACC TCATGGGCCACCTCCTGATGCTCAGCCTGGCCTACCTGTCCTACAACAG CTACTTCGTGCAGGGCCTCAAGCCATTCTACTCCCTCGAAACCATGCTC ATGGCCAACTCCGACTACAGCTTCTTCATGTACAACGAGGTGTGCAACG TCTACTACCACCCCAAAGGCACCTTCAACAAGGACATCACCTTCATCCC AATCGAGAGCAGGCCAGGCAGGCACTCCACCTACGTGGGCGAGAGGA AGGTCACCTGCGACCTCCTGGAGCTCATCCTGAACGCCTACACCCTGAT CAACGTGCACGAGATCCAAAAGGTCTTCAACACCAGCGAGGCCTACGG CTACGAGAACTCCATCAGCTTCGGCCACAACGCCGTGAGGATCTTCTCC CAGGTCTGCCCACGCGACGACGCCAAGAACACCTTCGGCTGCGACTTC GAGAAGAGCACCCTGTACAACTCCAAGGTGCTCAAGATGGACGAGGG CGACAAGGAGAACCAGAGGTCCCTGAAGCGCGCCTTCGACATGCTCCG CACCTTCGCCGAGATCGAGTCCACCAGCCACCTCGGCGACCCAAGCCC AAACTACATCTCCCTGATCTTCGAGCAAAACCTCTACACCGACTTCTACA AGTACCTGTTCTGGTACGACAACAGGGAGCTCATCAACGTGCAGATCC GCAACGCCGGCAGGCGCAAGAAGGGCAAGAAGGTGAAGTTCGTCTAC GACGAGTTCGTCAAGAGGGGCAAGCAACTGAAGGACAAGCTCATCAA GATCGACGCCAAGTACAACGCCCGCAGCAAGGCCCTCCTGGTGTTCTA CGCCCTGGTCGACAAGTACGCCAACATCTTCAGGAAGTCCGAGAACGT GCGCAAGTTCTTCCTCAACGACGTCTCCAGCATCAGGCACCACCTCTAC CTGAACAGCGTGCTGACCAAGTCCCCAAAGAGCAACCTCGACAGCATG AAGAAGACCCTGGAGGAGCTGCAGTCCCTCACCAACGCCCCACTGAAG TTCATCGTCAGGGGCAACAACCTGAAGTTCCTCAACAACGTGGCCAAG TTCGAGAACCTGTTCTACGTGAACCTCTTCATCATGTCCAGCCTCTCCCG CAAGCACCACCACCACCACCACTGA (SEQ ID NO: 8) |
| 5 | Plasmodium exported protein, unknown function | PVX_101530 | MNVNKKSSGEENNTKQALGLRVSR TLAKDGANENAEEGLSEEEEEAVEE GEEEAVEEGEEEVVEEEGEEVVEG EEEAVEEGEEEVVEDEEVVEGEEYA EGEEPVEGEEYAEGEEPVEGEEPV VEEYAEGEEPVEGEEYAEGEEPV EGEEVVEGEEYAEGGGEEGEEVA EGEEVAEGEEAVEGEEVAEGEEVA EGEEVAEGEEAAEEGAAEEGATEE GATEEGATKEEATEKAAEGEETAES EKPAEEQPTTFVETVEKKVEPVSKP PFKPLFPVDEKYLETLEDIAQSFLKE FQEAEGKRKQKKVKKRAKKITKKLA KEYAKKFKSKKKHHHHHH (SEQ ID NO: 9) | ATGAACGTCAACAAGAAGTCCAGCGGCGAGGAGAACAACACCAAGCA AGCTCTGGGCCTGAGGGTGTCCCGCACCCTCGCTAAGGACGGCGCCAA CGAGAACGCCGAGGAGGGCCTCAGCGAGGAAGAGGAAGAGGCCGTC GAGGAAGGCGAGGAAGAGGCCGTGGAGGAAGGCGAGGAAGAGGTG GTCGAGGAAGAGGGCGAGGAAGTGGTCGAGGGCGAGGAAGAGGAA GTGGTGGAGGGGGAGGAAGAGGTGGTGGAGGATGAGGAAGTGGTG GAGGGCGAGGAGTACGCTGAGGGCGAGGAGCCGGTGGAGGGGGAG GAGTACGCCGAGGGGGAGGAGCCAGTGGAGGGCGAGGAGCCAGTGG AGGTGGAGGAGTACGCGGAGGGGGAGGAGCCGGTGGAAGGTGAGG AGTACGCCGAGGGCGAGGAGCCTGTCGAGGGGGAGGAAGTGGTGGA AGGCGAGGAAGTGGTGGAAGGTGAGGAAGTGGCTGAGGGCGAGGA AGTGGCCGAGGGCGAGGAAGTCGAGGGCGAGGAAGCCGTGGA GGGCGAGGAAGTGGCGGAGGGGGAGGAAGTGGCGAAGGCGAGGA AGTGGCCGAAGGCGAGGAAGCCGCTGAGGAAGGCGCTGCCGAGGAA GGCGCCACGGAGGAAGGCGCTACCGAGGAAGGCGCCACCAAGGAAG AGGCCACCGAGAAGGCTGCTGAGGGCGAGGAGACGGCTGAGTCCGA GAAGCCAGCTGAGGAGCAACCAACCACCTTCGTGGAGACGGTCGAGA AGAAGGTGGAGCCAGTCAGCAAGCCACCATTCAAGCCACTCTTCCCAG TCGACGAGAAGTACCTCGAAACCCTGGAGGACATCGCCCAATCCTTCCT GAAGGAGTTCCAAGAGGCCGAGGGCAAGAGGAAGCAGAAGAAGGTG AAGAAGCGCGCCAAGAAGATCACCAAGAAGCTCGCCAAGGAGTACGC CAAGAAGTTCAAGTCCAAGAAGAAGCACCACCACCACCACCACTGA (SEQ ID NO: 10) |
| 6 | tryptophan/threonine-rich antigen | PVX_112680 | MPKPDQKNLKGGVKNAPLQQRKGS VPINPPKPVNDKLKDGSNKTETKNA KNTLSKPPMQVTDKSKDEAKKTPLQ STPKLTPKTKEVPKESNMEMWLKDT KDEYENLKCQYRTCLYDWFRKINDE YNELLNKLEEKWAKFPNDPKNKDVF DNLKTSSLKNDEKKAQWMRKNLKD LMREQVDEWLEGKKKIYEGMSPTY WDAWEKKIAKGLMGAAWYKMNSS | ATGCCAAAGCCAGACCAAAAGAACCTCAAGGGCGGCGTGAAGAACGC CCCACTGCAACAGAGGAAGGGCTCCGTGCCAATCAACCCACCAAAGCC AGTCAACGACAAGCTCAAGGACGGCAGCAACAAGACCGAGACGAAGA ACGCCAAGAACACCCTGTCCAAGCCACCAATGCAAGTGACCGACAAGA GCAAGGACGAGGCCAAGAAGACCCCACTCCAGTCCACCCCAAAGCTGA CCCCAAAGACCAAGGAAGTGCCAAAGGAGAGCAACATGGAGATGTGG CTCAAGGACACCAAGGACGAGTACGAGAACCTCAAGTGCCAGTACAG GACCTGCCTGTACGACTGGTTCCGCAAGATCAACGACGAGTACAACGA GCTCCTGAACAAGCTGGAGGAGAAGTGGGCCAAGTTCCCAAACGACC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | GRTKEWDKLRNELETRYNKKIKSLW GGFHRDVYFRFKEWIEEVFNKWIEN KQIDTWMNSGKKHHHHHH (SEQ ID NO: 11) | CAAAGAACAAGGACGTGTTCGACAACCTCAAGACCTCCAGCTGAAGA ACGACGAGAAGAAGGCCCAGTGGATGAGGAAGAACCTCAAGGACCTG ATGAGGGAGCAGGTGGACGAGTGGCTGGAGGGCAAGAAGAAGATCT ACGAGGGCATGTCCCCAACCTACTGGGACGCCTGGGAGAAGAAGATC GCTAAGGGCCTGATGGGCGCTGCTTGGTACAAGATGAACTCCTCCGGC AGGACCAAGGAGTGGGACAAGCTCAGGAACGAGCTCGAAACCCGCTA CAACAAGAAGATCAAGTCCCTCTGGGGCGGCTTCCACAGGGACGTGTA CTTCCGCTTCAAGGAGTGGATCGAGGAAGTGTTCAACAAGTGGATCGA GAACAAGCAAATCGACACCTGGATGAACAGCGGCAAGAAGCACCACC ACCACCACCACTGA (SEQ ID NO: 12) |
| 7 | hypothetical protein | PVX_097715 | MQYSIVKNEITKRRKPKIRNESPPDG NSPGGGKNNAAGNNGGGDNNAKN KAANKAANNAANNAANKAANNAAN NAANNAANNAANNAANNAANNAAN NAANNAANNANEQNGNKKKKGKPK KEEADLPVQAQNENDRNKIEDIADE AELFAEEAKMLADLASKRSKEVEQIL SSIPENKFGSEPKEDAIFAAKDAVRA SEDAMKAAQKARAAETVTQANEEK DKAKTAKELAERSAQIVKKNAVEALK EFGKIAEAAEMEAIKIPIPENLKPKKK VKQPRAAAQKVEPTQATAHKVVPP PAEPPRAPSPPPPPAKPEAAPPAKE VAPAVTTPEAPKEEAPKADAAPAAP QPAAESKVAKEPTDQSAENQSDSL YKETNIKEGTEEAGTGQEQKQEPEL QNLLEQQMNIFYILVQFFKSKIKALIK FLLILVSHHHHHH (SEQ ID NO: 13) | ATGCAATACTCCATCGTGAAGAACGAGATCACCAAGAGGCGCAAGCCA AAGATCAGGAACGAGTCCCCACCAGACGGCAACAGCCCAGGCGGCGG CAAGAACAACGCTGCTGGCAACAACGGCGGCGGCGACAACAACGCCA AGAACAAGGCTGCTAACAAGGCTGCTAACAACGCCGCCAACAAGGCC GCCAACAACGCTGCTAACAACGCCGCCAACAACGCCGCCAACAACGCC GCCAACAACGCAGCTAACAACGCCGCTAACAACGCGGCCAACAACGCC GCCAACAACGCGGCGAACAACGCTGCCAACAACGCCAACGAGCAAAA CGGCAACAAGAAGAAGAAGGGCAAGCCAAAGAAGGAAGAGGCCGAC CTCCCAGTGCAAGCCCAGAACGAGAACGACAGGAACAAGATCGAGGA CATCGCTGACGAGGCTGAGCTGTTCGCTGAGGAAGCCAAGATGCTCGC CGACCTGGCCTCCAAGCGCAGCAAGGAAGTGGAGCAGATCCTCTCCAG CATCCCAGAGAACAAGTTCGGCTCCGAGCCAAAGGAAGACGCCATCTT CGCTGCTAAGGACGCCGTGAGGGCTAGCGAGGACGAGTACAACAAGTC CGAGGACGCCATGAAGGCCGCCCAAAGGCTGACGCTGCTGAAACACACCC CTCAAAAGGCCAGGGCCGCTGAGACGGTCACCCAGGCCAACGAGGAG AAGGACAAGGCTAAGACCGCTAAGGAGCTGGCTGAGAGGTCCGCTCA AATCGTGAAGAAGAACGCCGTCGAGGCCCTGAAGGAGTTCGGCAAGA TCGCCGAGGCCGCCGAGATGGAGGCCATCAAGATCCCAATCCCAGAG AACCTGAAGCCAAAGAAGAAGGTGAAGCAACCAAGGGCCGCCCCA AAAGGTGGAGCCAACCCAAGCTACCGCTCACAAGGTGGTGCCACCACC AGCTGAGCCACCACGCGCCCCATCCCCACCACCACCACCAGCTAAGCCA GAGGCTGCCCCACCAGCTAAGGAAGTGGCTCCAGCTGTCACCACCCCA GAGGCTCCAAAGGAAGAGGCCCCAAAGGCTGACGCTGCTCCAGCTGC CCCACAGCCAGCCGCCGAGTCCAAGGTCGCCAAGGAGCCAACCGACCA GAGCGCCGAGAACCAATCCGACAGCCTCTACAAGGAGACGAACATCAA GGAAGGCACCGAGGAAGCCGGCACCGGCCAAGAGCAGAAGCAAGAG CCAGAGCTCCAAAACCTCCTGGAGCAACAGATGAACATCTTCTACATCC TGGTGCAGTTCTTCAAGTCCAAGATCAAGGCCCTCATCAAGTTCCTCCT GATCCTGGTCAGCCATCACCACCACCACCACTGA (SEQ ID NO: 14) |
| 8 | 41K blood stage antigen precursor 41-3, putative | PVX_084420 | MDENTGWPIDYEFNSKTLPSIEVKLS PPENPLPQVAAEIKLLESARLKLEEG MMQKLEDEYNKSLSSAKIKIQDTVE KSLSIFNDPNMLGSVISNSVKMLRSE NVKKRTENVQAKHNLKKMQTVNQA KSGPLPPPELRKHTSFLEQNYVNRV LPSVKISLSELTEPSVEIKEKIEEMEQ YRTDEEVAMFEMAISEFSILTDITILE LEKQIQLQLNPFLVDKKVVHRALTKE LKELEQREEKQKIKENFQRQSSFIEA GEDEDTGNILNVKISQTDYGYPTVD ELVMQMQKRRDISEKLERQKILDLQ MKLLKAQSEMIKDALHFALSKVIAQY SPLVETMKLESMRMLHHHHHH (SEQ ID NO: 15) | ATGGACGAGAACACCGGCTGGCCAATCGACTACGAGTTCAACTCCAAG ACCCTGCCAAGCATCGAGGTGAAGCTCTCCCCACCAGAGAACCCACTG CCACAAGTCGCCGCCGAGATCAAGCTCCTGGAGAGCGCCCGCCTCAAG CTCGAAGAGGGCATGATGCAGAAGCTGGAGGACGAGTACAACAAGTC CCTGTCCAGCGCCAAGATCAAGATCCAAGACACCGTGGAGAAGTCCCT CAGCATCTTCAACGACCCAAACATGCTGGGCTCCGTGATCTCCAACAGC GTCAAGATGCTCAGGAGCGAGAACGTGAAGAAGCGCACCGAGAACGT CCAGGCCAAGCACAACCTCAAGAAGATGCAGACCGTCAACCAAGCCAA GAGCGGCCCACTCCCACCACCAGAGCTGCGCAAGCACACCTCCTTCCTG GAGCAAAACTACGTGAACAGGGTCCTGCCATCCGTGAAGATCTCCCTC AGCGAGCTGACCGAGCCAAGCGTCGAGATCAAGGAGAAGATCGAGGA GATGGAGCAGTACGAGCGCACCGACGAGGAAGTGGCCATGTTCGAAATG GCCATCTCCGAGTTCAGCATCCTCACCGACATCACCATCCTGGAGCTGGA GAAGCAAATCCAGCTCCAACTGAACCCATTCCTCGTCGACAAGAAGGT GGTCCACAGGGCCCTGACCAAGGAGCTCAAGGAGCTGGAGCAGCGC AGGAGAAGCAAAGATCAAGGAGAACTTCCAGAGGCAATCCAGCTTC ATCGAGGCTGGCGAGGACGAGGACACCGGCAACATCCTCAACGTGAA GATCTCCCAGACCGACTACGGCTACCCAACCGTGGACGAGCTCGTCAT GCAGATGCAAAAGAGGCGCGACATCTCCGAGAAGCTGGAGCGCCAGA AGATCCTCGACCTGCAGATGAAGCTCCTGAAGGCCCAGAGCGAGATGA TCAAGGACGCCCTCCACTTCGCCCTGTCCAAGGTCATCGCCCAATACAG CCCACTCGTCGAGACGATGAAGCTGGAGAGCATGAGGATGCTCCACCA CCACCACCACCACTGA (SEQ ID NO: 16) |
| 9 | rhoptry-associated protein 1, putative (RAP1) | PVX_085930 | MSSDGKSSASAKSGSKSGSKYGGS SYSDYSAYDSGSASSVGSREFENE MYEFALQHPMEKLTKEMDILKNDYT KVKEEEGKILDEEHKEIEEKRKEERL KMLAEGDVEKNKGDEEINFIKHDYT DTRIRGGFTEFLSNLNPFKKEIKPMK KEISLITYIPDKIVNKEKIMRDLGISHK YEPYQQSILYTCPNSVFFFDSMENL RKELDKNHEKEAITNKILDHNKECLK NFGLFDFELPDNKTKLGNVIGSIGEY | ATGAGCAGCGACGGCAAGTCCAGCGCTTCCGCTAAGTCCGGCAGCAA GTCCGGCAGCAAGTACGGCGGCTCCAGCTACTCCGACTACAGCGCCTA CGACTCCGGCAGCGCCTCCAGCGTGGGCAGCCGCGAGTTCGAGAACG AGATGTACGAGTTCGCCCTGCAACACCCGATGGAGAAGCTCACCAAGG AGATGGACATCCTGAAGAACGACTACACCAAGGTGAAGGAGGAGGAA GGCAAGATCCTCGACGAGGAGCACAAGGAGATCGAGGAGAAGAGGA AGGAAGAGCGCCTCAAGATGCTGGCCGAGGGCGACGTGGAGAAGAA CAAGGGCGACGAGGAGATCAACTTCATCAAGCACGACTACACCGACAC CGGGATCCGCGGCGGCTTCACCGAGTTCCTCTCCAACCTGAACCCATTC AAGAAGGAGATCAAGCCGATGAAGAAGGAGATCTCCCTCATCACCTAC Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | HVRLYEIENDLLKYQPSLDYMTLAD DYKLVKNDVNTLENVNFCLLNPKTL EDFLKKKEIMELMGEDPIAYEEKFTK YMEESINCHLESLIYEDLDSSQDTKI VLKNVKSKLYLLONGLTYKSKKLINK LFNEIQKNPEPIFEKLTWIYENMYHL KRDYTFLAFKTVCDKYVSHNSIYTSL QGMTSYIIEYTRLYGACFKNITIYNAV ISGIHEQMKNLMKLMPRSGLLSDVH FEALLHKENKKITRTDYVLNDYDPSV KAYALTQVERLPMVSVINSFFEAKKK ALSKMLAQMKLDLFTLTNEDLKIPND KGANSKLTAKLISIYKAEIKKYFKEMR DDYVFLIKARYKGHYKNYLLYKRLE HHHHHH (SEQ ID NO: 17) | ATCCCAGACAAGATCGTCAACAAGGAGAAGATCATGCGCGACCTGGG CATCTCCCACAAGTACGAGCCATACCAACAGAGCATCCTCTACACCTGC CCAAACTGTGTTCTTCTTCGACGGCATGGAGAACCTCAGGAAGGAG CTGGACAAGAACCACGAGAAGGAAGCCATCACCAACAAGATCCTCGAC CACAACAAGGAGTGCCTCAAGAACTTCGGCCTGTTCGACTTCGAGCTCC CAGACAACAAGACCAAGCTGGGCAACGTCATCGGCTCCATCGGCGAGT ACCACGTGAGGCTCTACGAGATCGAGAACGACCTCCTGAAGTACCAAC CAAGCCTGGACTACATGACCCTCGCCGACGACTACAAGCTGGTGAAGA ACGACGTCAACACCCTGGAGAACGTGAACTTCTGCCTCCTGAACCCAA AGACCCTGGAGGACTTCCTCAAGAAGAAGGAGATCATGGAGCTGATG GGCGAGGACCCAATCGCCTACGAGGAGAAGTTCACCAAGTACATGGA GGAGTCCATCAACTGCCACCTGGAGAGCCTGATCTACGAGGACCTCGA CTCCAGCCAAGACACCAAGATCGTGCTCAAGAACGTCAAGTCCAAGCT GTACCTCCTGCAGAACGGCCTCACCTACAAGAGCAAGAAGCTCATCAA CAAGCTGTTCAACGAGATCCAGAAGAACCCAGAGCCAATCTTCGAGAA GCTCACCTGGATCTACGAGAACATGTACCACCTGAAGCGCGACTACAC CTTCCTCGCCTTCAAGACCGTGTGCGACAAGTATGTGTCCCACAACAGC ATCTACACCTCCCTGCAAGGCATGACCAGCTACATCATCGAGTACACCA GGCTCTACGGCGCCTGCTTCAAGAACATCACCATCTACAACGCCGTCAT CTCCGGCATCCACGAGCAGATGAAGAACCTCATGAAGCTGATGCCCAAG GTCCGGCCTCCTGAGCGACGTGCACTTCGAGGCCCTCCTGCACAAGGA GAACAAGAAGATCACCCGCACCGACTACGTGCTCAACGACTACGACCC ATCCGTCAAGGCCTACGCCCTGACCCAAGTGGAGAGGCTCCCAATGGT GTCCGTCATCAACAGCTTCTTCGAGGCCAAGAAGAAGGCCCTCAGCAA GATGCTGGCCCAGATGAAGCTCGACCTGTTCACCCTGACCAACGAGGA CCTCAAGATCCCAAACGACAAGGGCGCCAACTCCAAGCTCACCGCCAA GCTGATCAGCATCTACAAGGCCGAGATCAAGAAGTACTTCAAGGAGAT GAGGGACGACTACGTCTTCCTGATCAAGGCCCGCTACAAGGGGCACTA CAAGAAGAACTACCTCCTGTACAAGCGCCTGGAGCACCACCACCACCA CCACTGA (SEQ ID NO: 18) |
| 10 | hypothetical protein, conserved | PVX_094830 | MNTRASKFANSKRKRNGNAMRENK LNNDDVDHYSFLSLRTANEEKAATE NDSNNAKKEGEENTNGNEKKNEEN GSGNEKRNEENNANEKKNEQTNDQ SNGQSNSQTNIPKKNEAVPPEKKIN KENLLEYGTHDKDGHFIPSYKTLTDE ILSTNNSLERASSFLKIACSHIMKIVE FIPESKLSSQYIKVESKNVYIKDITSE CQNIFFSLEKLTMTMIVLNSKMNKLV YVQDKHHHHHH (SEQ ID NO: 19) | ATGAACACCAGGGCCTCCAAGTTCGCCAACAGCAAGAGGAAGCGCAA CGGCAACGCCATGCGCGAGAACAAGCTCAACAACGACGACGTGGACC ACTACTCCTTCCTCAGCCTGAGGACCGCTAACGAGGAGAAGGCTGCTA CCGAGAACGACTCCAACAACGCCAAGAAGGAAGGCGAGGAGAACACC AACGGCAACGAGAAGAAGAACGAGGAGAACGGCAGCGGCAACGAGA AGCGCAACGAGGAGAACAACGCCTAACGAGAAGAAGAACGAGCAAAC AACGACCAGTCCAACGGCCAATCCAACAGCCAGAACAACATCCCAAAG AAGAACGAGGCCGTCCCACCAGAGAAGAAGATCAACAAGGAGAACCT CCTGGAGTACGGCACCCACGACAAGGACGGCCACTTCATCCCAAGCTA CAAGACCCTCACCGACGAGATCCTGTCCACCAACAGCCTGGAGAGG GCCTCCAGCTTCCTGAAGATCGCCTGCTCCCACATCATGAAGATCGTG GAGTTCATCCCAGAGTCCAAGCTGTCCAGCCAATACATCAAGGTGGAG AGCAAGAACGTCTACATCAAGGACATCACCTCCGAGTGCCAGAACATC TTCTTCAGCCTGGAGAAGCTCACCATGACCATGATCGTCCTCAACAGCA AGATGAACAAGCTGGTCTACGTGCAAGACAAGCACCACCACCACCACC ACTGA (SEQ ID NO: 20) |
| 11 | tryptophan-rich antigen (Pv-fam-a) | PVX_112675 | MPKPAQNLKGGVKKPSLQQTKSPL PSKPPKPVNDKLKDDSNKTETKDAK NGLNKPPKNINDKVKDGENKTPSQD LNEPSFKLPMRQKASSWDAWLKGT KKDYENLKCFAKGNLYDWLCSVRD SFELYLOSLESKWTSCSDNTTTVFL CECLAESSGWGDPQWESWVKKEL KEQLKTEAQAWISTKKKDFDGLTSK YFSLWKDHRRKELEEEAWKTKASS GGLSEWEELTDKMNTRYTNNLDNM WSNYSGDLLFRFDEWSPEVLEKWI ESKQWNQWVKKVRKHHHHHH (SEQ ID NO: 21) | ATGCCAAAGCCAGCCCAAAACCTCAAGGGCGGCGTGAAGAAGCCATC CCTCCAACAGACCAAGTCCCCACTGCCAAGCAAGCCACCAAAGCCAGT CAACGACAAGCTCAAGGACGACAGCAACAAGACCGAGACGAAGGACG CCAAGAACGGCCTGAACAAGCCACCAAAGAACATCAACGACAAGGTG AAGGACGGCGAGAACAAGACCCCATCCCAAGACCTCAACGAGCCAAG CTTCAAGCTGCCAATGAGGCAAAAGGCCTCCAGCTGGGACGCTTGGCT CAAGGGCACCAAGAAGGACTACGAGAACCTGAAGTGCTTCGCCAAGG GCAACCTCTACGACTGGCTGTGCTCCGTCCGCGACAGCTTCGAGCTCTA CCTGCAATCCCTGGAGAGCAAGTGGACCTCCTGCAGCGACAACACCAC CACCGTGTTCCTCTGCGAGTGCCTCGCTGAGTCCAGCGGCTGGGGCGA CCCACAGTGGGAGTCCTGGGTCAAGAAGGAGCTCAAGGAGCAACTGA AGACCGAGGCCCAGGCCTGGATCAGCACCAAGAAGAAGGACTTCGAC GGCCTCACCTCCAAGTACTTCAGCCTGTGGAAGGACCACAGGCGCAAG GAGCTGGAGGAAGAGGCCTGGAAGACCAAGGCCTCCAGCGGCGGCCT CTCCGAGTGGGAGGAGCTGACCGACAAGATGAACACCAGGTACACCA ACAACCTCGACAACATGTGGTCCAACTACAGCGGCGACCTCCTGTTCCG CTTCGACGAGTGGTCCCCAGAGGTGCTGGAGAAGTGGATCGAGAGCA AGAGTGGAACCAGTGGGTGAAGAAGGTCAGGAAGCACCACCACCAC CACCACTGA (SEQ ID NO: 22) |
| 12 | tryptophan-rich antigen (Pv-fam-a) | PVX_112670 | MVTEGGDNLDDDLGGDLEGLLGDD AEGGAAGGEGAAAAASAEGLSGEV ENELLYVKEDDDDAPAATPDEKPST SGEETPAAFVDLVNETVPPPAKAPL PLQTKAPQGPKIKDWNQWMKQAKK DFSGYKGTMHTQRHEWTKEKEDEL QKFCKYLEKRWMNYTGNIDRECRS | ATGGTGACCGAGGGCGGCGACAACCTCGACGACGACCTCGGCGGCGA CCTGGAGGGCCTCCTGGGCGACGACGCTGAGGGCGGCGCCGCCGGCG GCGAGGGCGCTGCCGCCGCCGCTTCCGCCGAGGGCCTGAGCGGCGAG GTGGAGAACGAGCTCCTCTACGTGAAGGAGGACGACGACGACGCTCC AGCTGCTACCCCAGACGAGAAGCCATCCACCAGCGGCGAGGAGACGC CAGCTGCTTTCGTGGACCTCGTCAACGAGACGGTGCCACCACCAGCTA AGGCCCCACTCCCACTGCAAACCAAGGCCCCACAGGGCCCAAAGATCA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | DFLKSTQNWNESQWNKWVKSEGK HHMNKQFQKWLDYNKYKLQDWTN TEWNKWKTTVKEQLDDEEWKKKEA AGKTKEWIKCTDKMEKKCLKKTKKH CKNWEKKANSSFKKWEGDFTKKWT SNKQWNSWCKELEKHHHHHH (SEQ ID NO: 23) | AGGACTGGAACCAGTGGATGAAGCAGGCCAAGAAGGACTTCTCCGGC TACAAGGGCACCATGCACACCCAAAGGCACGAGTGGACCAAGGAGAA GGAAGACGAGCTGCAGAAGTTCTGCAAGTACCTGGAGAAGCGCTGGA TGAACTACACCGGCAACATCGACAGGGAGTGCCGCTCCGACTTCCTGA AGAGCACCCAAAACTGGAACGAGTCCCAGTGGAACAAGTGGGTGAAG AGCGAGGGCAAGCACCACATGAACAAGCAATTCCAGAAGTGGCTGGA CTACAACAAGTACAAGCTCAAGACTGGACCAACACCGAGTGGAACAA GTGGAAGACCACCGTCAAGGAGCAGCTGGACGACGAGGAGTGGAAG AAGAAGGAAGCCGCCGGCAAGACCAAGGAGTGGATCAAGTGCACCGA CAAGATGGAAGAAGTGCCTCAAGAAGACCAAGAAGCACTGCAAGA ACTGGGAGAAGAAGGCCAACTCCAGCTTCAAGAAGTGGGAGGGCGAC TTCACCAAGAAGTGGACCTCCAACAAGCAGTGGAACAGCTGGTGCAAG GAGCTGGAGAAGCACCACCACCACCACCACTGA (SEQ ID NO: 24) |
| 13 | Hyp, huge list of orthologs, paralogs, synteny with PyLSA3 (PyLSA3syn-2) | PVX_002550 | mAVEVVQEAADEVLEEEKIEEPLEIV EEEPVQVAAEEPVEEVLEEVVQEAA DEVMEEEKIEEPLEIVAEEPLEIVAEE PVQVAAEEPVLVEKEEVNENILNIVEEI KESIVDKLEANEEASEEGNEDLLESA EEAAEEVAEEEAVDTTTEADVVETVE EEAANATTEVSAEESLEVSTEAPEE TTESESHETFEEDILKNLEENKEANE NALEDIKEMKEEFLDYVEQRVEDNE NVLVDLLQHLERNAHVNESVLEDLE EIKEDLLANIQMAEETRKEVTDASAE SAEEVVEEPVEVSAEVAAEEPVEVAA EEPVEVTAEEPVEVTAEEPVEIPTEE NIFDVIEEIKEKVLENLEETTAESVAE SVGEGADENALDVLKEMQESLLENF GQKIEANENILASVLENIQEKVELNK SVLVDVLAELKEEAVSQRETAQEVA AELVEEAAEVPAVEPVEEEVVEPAV EVVEEPVEEEVVEPVVDVIEEPAVE VVEPVEETVEEPVEVTAEEPVEVT AEEPVEETVEEPVVEVVEEPVEEPV VEAIEEPVVEPVVEPAVEVIEDATEE PVEEAAEEPDVEVAEGSAIESVEEA FEQIIEDAAQVIAEESVEETAEQILEQ ATQAVTEEAADAADVADAEEAVGTA QVVTEESVAEAIEDTVEEISAEPIQAT IEGIVGEVVESVEENIEAVEEAIKDIV EGAVEGAPELSLEEMIEDVMVGTVA EEDSAKEAAEETVEEVVQEDAAEEE AAKEAAEETVEEAEREATQEAVEET VEDVVEEVSAEAVEEIVLETPEGTSD ESVETVVEHAVEDSLGETIATIVDDV AEETTEKSEESVVDNLGVKVEEVLD VDVEEVAQEAADDVIMRVSENESEG ESGAESGEEVEELESALFEVEKDIKK KVLDMFSGNVEFDEKESEKLALDLQ KNLLShhhhhh (SEQ ID NO: 25) | ATGGCTGTGGAGGTGGTCCAAGAGGCCGCTGACGAGGTGCTCGAAGA GGAGAAGATCGAGGAGCCACTGGAGATCGTGGAGGAAGAGCCAGTG CAAGTGGCCGCCGAGGAGCCAGTCGAGGAAGTGCTCGAAGAGGTGGT GCAAGAGGCCGCCGACGAGGTCATGGAGGAAGAGAAGATCGAGGAG CCTCTGGAGATCGTCGCTGAAGAACCTCTGGAGATCGTGGCTGAGGAG CCTGTGCAGGTGGCTGCCGAGGAAGTCGGTCGAGAAGGAAGAGGT GAACGAGAACATCCTCAACATCGTGGAGGAGATCAAGGAGAGCATCG TCGACAAGCTGGAGGCCAACGAGGAAGCCAGCGAGGAAGGCAACGA GGACCTCCTGGAGTCCGCTGAGGAAGCCGCTGAGGAAGTGGCTGAGG AAGCCGTGGACACCACCACCGAGGCTGACGTGGTGGAGACGGTGGAG GAAGAGGCCGCTAACGCTACCACCGAGGTGTCCGCTGAGGAGAGCCT GGAGGTGTCCACCGAGGCTCCAGAGGAGACGACCGAGTCCGAGAGCC ACGAGACGTTCGAGGAAGACATCCTGAAGAACCTGGAGGAGAACAAG GAAGCCAACGAGAACGCCCTGGAGGACATCAAGGAGATGAAGGAAG AGTTCCTCGACTACGTGGAGCAAAGGGTCGAGGACAACGAGAACGTG CTGGTCGACCTCCTGCAGCACCTGGAGCGCAACGCCCACGTGAACGAG AGCGTCCTGGAGGACCTGGAGGAGATCAAGGAAGACCTCCTGGCCAA CATCCAAATGGCCGAGGAGACGAGGAAGGAAGTGACCGACGCTTCCG CTGAGGAGGTCGTGGAGGAGCCCGTCGAGGTGTCCGCTGAGGTGGCC GCTGAGGTGGCCGCCGAGGAGCCAGTGGAGGTCACCGCTGAGGAGCC TGTTGAGGTGACGGCTGAGGAGCCAGTGGAGATCCCAACCGAGGAGA ACATCTTCGACGTGATCGAGGAGATCAAGGAGAAGGTCCTGGAGAAC CTGGAGGAGACGACCGCTGAGAGCGTGGCTGAGTCCGTGGGCGAGGG CGCTGACGAGAACGCCCTGGACGTGCTCAAGGAGATGCAAGAGAGCCTCCTGGAGAACTTCGGCCAGAAGATCGAGGCCAACGAGAACATCCTGGCCAGCGTGCTGGAGAACATCCAGGAGAAGGTCGAGCTGAACAAGTCCGTGCTCGTCGACGTGCTGGCCGAGCTCAAGGAAGAGGCCGTGTCCCAAAGGGAGACGGCTCAAGAGGTGGCTGCTGAGCTGGTCGAGGAAGCCGCTGAGGTCCCAGCTGTGGAGCCAGTCGAGGAAGAGGTGGTCGAGCCAGCTGTGGAGGTGGTGGAGGAGCCTGTGGAGGAAGAGGTGGTCGAGCCAGTGGTTGACGTGATCGAGGAGCCTGCCGTGGAGGTCGTGGAGGTCCCAGTGGAGGAGACGGTCGAGGAGCCTGTGGAGGTTACCGCGGAGGAGCCTGTGGAGGTCACGGCCGAGGAGCCTGTCGAGGAGACGGTGGAGGAGCCAGTGGTCGAGGTGGTCGAGGAGCCAGTTGAGGAGCCTGTGGTCGAGGCCATCGAGGAGCCCGTCGTCGAGCCAGTGGTCGAGCCAGCCGTCGAGGTCATCGAGGACGCTACGGAGGAGCCCGTGGAGGAAGCCGCCGAGGAGCCGGACGTGGAGGTGGCTGAGGGCAGCGCTATCGAGTCCGTGGAGGAAGCCTTCGAGCAAATCATCGAGGACGCCGCCCAAGTGATCGCTGAGGAGAGCGTGGAGGAGACGGCTGAGCAAATCCTGGAGCAAGCCACCCAGGCCGTGACCGAGGAAGCCGCTGACGCTGCTGACGTGGCTGACGCTGAGGAAGCCGTGGGCACCGCTCAAGTCGTCACCGAGGAGAGCGTGGCTGAGGCTATCGAGGACACCGTCGAGGAGATCTCCGCCGAGCCAATCCAGGCCACCATCGAGGGCATCGTGGGCGAGGTCGTCGAGTCCGTCGAGGAGAACATCGAGGCCGTGGAGGAAGCCATCAAGGACATCGTGGAGGGCGCTGTGGAGGGCGCTCCAGAGCTCAGCCTGGAGGAGATGATCGAGGACGTCATGGTGGGCACCGTGGCTGAGGAAGACTCCGCTAAGGAAGCCGCTGAGGAGACGGTGGAGGAAGTGGTGCAAGAGGACGCTGCTGAGGAAGAGGCCGCCAAGGAAGCCGCCGAAGAGACGGTGGAGGAAGCCGAGAGGGAGGCTACCCAAGAGGCCGTCGAGGAGACGGTTGAGGACGTGGTCGAGGAAGTGTCCGCTGAGGCTGTGGAGGAGATCGTCCTCGAAACCCCGGAGGGCACCTCCGACGAGAGCGTGGAGACGGTGGTGGAGCACGCTGTGGAGGACTCCCTGGGCGAGACGATCGCCACCATCGTGGACGACGTCGCCGAGGACGACCGAGAAGTCCGAGGAGAGCGTGGTCGACAACCTGGGCGTCAAGGTGGAGGAAGTGCTCGACGTCGACGTGGAGGAAGTGGCCCAAGAGGCCGCCGACGACGTGATCATGCGCGTCAGCGAGAACGAGTCCGAGGGCGAGAGCGGCGCTGAGTCCGGCGAGGAAGTGGAGGAGCTGGAGAGCGCCCTCTTCGAGGT |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GGAGAAGGACATCAAGAAGAAGGTCCTCGACATGTTCAGCGGCAACG TGGAGTTCGACGAGAAGGAGTCCGAGAAGCTCGCCCTGGACCTCCAG AAGAACCTCCTGTCCCACCACCACCACCACCACTGA (SEQ ID NO: 26) |
| 14 | conserved Plasmodium protein, unknown function | PVX_090970 | mTYMLMKDDDSHDDKDDENEEKKK KEGKTNKDTNKIIKGESMTREDLLQL LNEMLKLQTDMKNIVKDLIVVAKKNS YDFMSVYNVAKTYNTVDPLGKYQIE MPEFDKVVENYHFDPEVKETVSKLM SSQENYYANMSETATLNVDKIIEIHH FMLNELYKIDPEFKKIPNKHELDPKLI ALVIQSIVSAKVEEEFNLTSEDVEASI ANQQYALTSNMEFARVNIQMQTIMN KFMGDhhhhhh (SEQ ID NO: 27) | ATGACCTACATGCTCATGAAGGACGACGACTCCCACGACGACAAGGAC GACGAGAACGAGGAGAAGAAGAAGAAGGAAGGCAAGACCAACAAGG ACACCAACAAGATCATCAAGGGCGAGAGCATGACCAGGGAGGACCTC CTGCAACTCCTGAACGAGATGCTCAAGCTGCAGACCGACATGAAGAAC ATCGTCAAGGACCTCATCGTGGTCGCCAAGAAGAACTCCTACGACTTCA TGAGCGTGTACAACGTCGCCAAGACCTACAACACCGTGGACCCACTGG GCAAGTACCAAATCGAGATGCCAGAGTTCGACAAGGTGGTCGAGAAC TACCACTTCGACCCAGAGGTGAAGGAGACGGTGTCCAAGCTCATGTCC AGCCAGGAGAACTACTACGCCAACATGAGCGAGACGGCCACCCTGAA CGTCGACAAGATCATCGAGATCCACCACTTCATGCTCAACGAGCTGTAC AAGATCGACCCAGAGTTCAAGAAGATCCCAAACAAGCACGAGCTGGAC CCAAAGCTCATCGCCCTCGTGATCCAATCCATCGTGAGCGCCAAGGTCG AGGAAGAGTTCAACCTCACCTCCGAGGACGTCGAGGCCAGCATCGCCA ACCAACAGTACGCCCTGACCTCCAACATGGAGTTCGCCCGCGTGAACA TCCAAATGCAGACCATCATGAACAAGTTCATGGGCGACCACCACCACC ACCACCACTGA (SEQ ID NO: 28) |
| 15 | conserved Plasmodium protein, unknown function | PVX_084815 | mAGGVSEEAIKKLKEIKKLELDILKDF MKQDAGHADLYKKYHCIASDYISGN PKGSSAEGPNLAKKGEKSKKGEKH QNGEKPQNGEKPKKSFIEKIASFVSI FSYNNVSKIYSEHVQRIFPKARDHA GDGSAGDAIYPDDKIETGKKQNQSS YVQLSALNLMKRNMFLGGKDKSSE HFEVGNLGSFYMIFGARNTDYPWA CSCDPLQLIDYKEKKRNYVLCSNQV DMSIQNADLFCNPKhhhhhh (SEQ ID NO: 29) | ATGGCCGGCGGCGTCAGCGAGGAAGCCATCAAGAAGCTCAAGGAGAT CAAGAAGCTGGAGCTGGACATCCTGAAGGACTTCATGAAGCAAGACG CCGGCCACGCCGACCTCTACAAGAAGTACCACTGCATCGCCAGCGACT ACATCTCCGGCAACCCAAAGGGCTCCAGCGCTGAGGGCCCAAACCTGG CCAAGAAGGGCGAGAAGAGCAAGAAGGGCGAGAAGCACCAAAACGG CGAGAAGCCACAGAACGGCGAGAAGCCAAAGAAGTCCTTCATCGAGA AGATCGCCTCCTTCGTGAGCATCTTCTCCTACAACAACGTCAGCAAGAT CTACTCCGAGCACGTGCAAAGGATCTTCCCAAAGGCCCGCGACCACGC TGGCGACGGCAGCGCCGGCGACGCCATCTACCCAGACGACAAGATCG AGACGGGCAAGAAGCAAAACCAGTCCAGCTACGTCCAGCTCTCCGCCC TCAACCTGATGAAGCGCAACATGTTCCTGGGCGGCAAGGACAAGTCCA GCGAGCACTTCGAAGTGGGCAACCTCGGCAGCTTCTACATGATCTTCG GCGCCAGGAACACCGACTACCCATGGGCCTGCTCCTGCGACCCACTCC AGCTGATCGACTACAAGGAGAAGAAGCGCAACTACGTGCTCTGCAGCA ACCAAGTCGACATGTCCATCCAGAACGCCGACCTGTTCTGCAACCCAAA GCACCACCACCACCACCACTGA (SEQ ID NO: 30) |
| 16 | trypto- phan- rich antigen (Pv-fam-a) | PVX_090270 | mVSCTSLCLYIIYSLFLLNNVSLSIQV KTNEIKNGONGSVQLKEKGGGVNL APKVGTNITQKRDTKMAKKTVTKVA KKKVTKVAEKTGTKVADKTGTKVAD KTGTKVADKTGTKVAEKTGTKVADK TGTKVAEKTGTNISQKEDEKGPPKE DTQGTQKADAKAIQQADAQVSEKW KKKEWKEWIKKAESDLDIFNALMDN EKEKKWYSEKEKEWNKWIKGVEKK WMHYNKNIYVEYRSLVPWVGLKKWV ESQWEKWILSDGLEFLVMDWKKWI KENKSNPFDEWLKSEWDTWTNSQM EEWKSSNWKLNEDKRWEMWENDK KWIKWLYLKDWINCSKWKKRIQKES KEWLRWTKLKEEMYhhhhhh (SEQ ID NO: 31) | ATGGTGTCCTGCACCAGCCTCTGCCTGTACATCATCTACAGCCTCTTCCT CCTGAACAACGTGTCCCTGAGCATCCAAGTCAAGACCAACGAGATCAA GAACGGCCAAAACGGCTCCGTCAGCTCAAGGAGAAGGGCGGCGGCG TGAACCTGGCTCCAAAGGTCGGCACCAACATCACCCAGAAGAGGGACA CCAAGATGGCCAAGAAGACCGTGACCAAGGTCGCCAAGAAGAAGGTC ACGAAGGTCGCCGAGAAGACCGGCACCAAGGTGGCCGACAAGACCGG CACCAAGGTCGCTGATAAGACGGGGACGAAGGTCGCTGATAAGACCG GGACGAAGGTGGCTGAGAAGACGGGGACGAAGGTTGCTGATAAGAC GGGGACCAAGGTGGCTGAGAAGACCGGCACCAACATCAGCCAAAAGG AAGACGAGAAGGGCCCACCAAAGGAAGACACCCAAGGCACCCAGAAG GCCGACGCCAAGGCCATCCAACAGGCCGACGCCCAGGTGAGCGAGAA GTGGAAGAAGAAGGAGTGGAAGGAGTGGATCAAGAAGGCCGAGTCC GACCTCGACATCTTCAACGCCCTGATGGACAACGAGAAGGAGAAGAA GTGGTACAGCGAGAAGGAGAAGGAGTGGAACAAGTGGATCAAGGGC GTGGAGAAGAAGTGGATGCACTACAACAAGAACATCTACGTCGAGTA CAGGTCCCTCGTGTTCTGGGTCGGCCTGAAGTGGGTGGAGTCCCAATG GGAGAAGTGGATCCTCAGCGACGGCCTGGAGTTCCTGGTCATGGACTG GAAGAAGTGGATCAAGGAGAACAAGTCCAACTTCGACGAGTGGCTCA AGTCCGAGTGGGACACCTGGACCAACTCCCAGATGGAGGAGTGGAAG TCCAGCAACTGGAAGCTGAACGAGGACAAGCGCTGGGAGATGTGGGA GAACGACAAGAAGTGGATCAAGTGGCTCTACCTGAAGGACTGGATCA ACTGCAGCAAGTGGAAGAAGAGGATCCAAAAGGAGTCCAAGGAGTG GCTCCGCTGGACCAAGCTGAAGGAAGAGATGTACCACCACCACCACCA CCACTGA (SEQ ID NO: 32) |
| 17 | apical membrane antigen 1, AMA1 (Orthologs with Pf vaccine candidates) | PVX_092275 | mGEDAEVENAKYRIPAGRCPVFGK GIVIENSDVSFLRPVATGDQKLKDG GFAFPNANDHISPMTLANLKERYKD NVEMMKLNDIALCRTHAASFVMAGD QNSSYRHPAVYDEKEKTCHMLYLS AQENMGPRYCSPDAQNRDAVFCFK PDKNESFENLVYLSKNVRNDWDKK CPRKNLGNAKFGLWVDGNCEEIPY VKEVEAEDLRECNRIVFGASASDQP TQYEEEMTDYQKIQQGFRQNNREM IKSAFLPVGAFNSDNFKSKGRGFNW | ATGGGCGAGGACGCCGAGGTGGAGAACGCCAAGTACAGGATCCCAGC TGGCAGGTGCCCAGTGTTCGGCAAGGGCATCGTCATCGAGAACTCCGA CGTGAGCTTCCTCCGCCCAGTGGCTACCGGCGACCAAAAGCTGAAGGA CGGCGGATTCGCCTTCCCAAACGCCAACGACCACATCTCCCCAATGACC CTCGCCAACCTGAAGGAGAGGTACAAGGACAACGTGGAGATGATGAA GCTCAACGACATCGCTCTGTGCAGGACCCACGCTGCTAGCTTCGTGATG GCTGGCGACCAGAACTCCAGCTACAGGCACCCAGCCGTCTACGACGAG AAGGAGAAGACCTGCCACATGCTCTACCTGTCCGCCCAAGAGAACATG GGCCCAAGGTACTGCTCCCCAGACGCTCAGAACAGGGACGCTGTCTTC TGCTTCAAGCCAGACAAGAACGAGTCCTTCGAGAACCTCGTGTACCTG AGCAAGAACGTCAGGAACGACTGGGACAAGAAGTGCCCACGCAAGAA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | ANFDSVKKKCYIFNTKPTCLINDKNFI ATTALSHPQEVDLEFPCSIYKDEIER EIKKQSRNMNLYSVDGERIVLPRIFIS NDKESIKCPCEPERISNSTCNFYVC NCVEKRAEIKENNQVVIKEEFRDYY ENGEEKSNKQhhhhhh (SEQ ID NO: 33) | CCTCGGCAACGCCAAGTTCGGCCTGTGGGTGGACGGCAACTGCGAGG AGATCCCATACGTGAAGGAAGTGGAGGCCGAGGACCTCAGGGAGTGC AACAGGATCCTCTTCGGCGCTTCCGCTAGCGACCAACCAACCCAGTAC GAGGAAGAGATGACCGACTACCAAAAGATCCAACAGGGCTTCAGGCA GAACAACCGCGAGATGATCAAGTCCGCCTTCCTCCCAGTGGGCGCCTT CAACTCCGACAACTTCAAGAGCAAGGGCCGCGGCTTCAACTGGGCCAA CTTCGACAGCGTGAAGAAGAAGTGCTACATCTTCAACACCAAGCCAAC CTGCCTGATCAACGACAAGAACTTCATCGCCACCACCGCCCTCTCCCAC CCACAAGAGGTCGACCTGGAGTTCCCATGCAGCATCTACAAGGACGAG ATCGAGAGGGAGATCAAGAAGCAGTCCCGCAACATGAACCTCTACAGC GTGGACGGCGAGAGGATCGTCCTGCCACGCATCTTCATCTCCAACGAC AAGGAGAGCATCAAGTGCCCATGCGAGCCAGAGAGGATCTCCAACAG CACCTGCAACTTCTACGTGTGCAACTGCGTCGAGAAGAGGGCCGAGAT CAAGGAGAACAACCAAGTGGTCATCAAGGAAGAGTTCAGGGACTACT ACGAGAACGGCGAGGAGAAGTCCAACAAGCAGCACCACCACCACCAC CACTGA (SEQ ID NO: 34) |
| 18 | hypothetical protein | PVX_084720 | mNGNRNLNIKPTCHKSGKNDKANG SDNIANKGGAQHAANGATGTPSGS SNGKKGATTTSASAGQAGASGGMA APGMNPNFEQMMKPLNDMFKGNG EGLNIENIMNSDMFQNFFNSLMGGN PHDGAGGGQEILFKDMLNAMNAQG GGAPGAAATSGGANKDPNISVSPE QLNKINQLKDKLENVLKNVGVDVEQ LKENMQNENIMQNKDALRDLLANLP MNPGMMQNMMAGKDGNMFNMDP NQMMNMFNQLSQGKMNMKDFGM GDFMPPPVHANDQDAEDDSRGKAF VTNSSNNDINFAHKLNAFEYSNGPS EGMFQLYGMNNDDGVIDDGMSDSV GKNSALDVSGGSINRNLSDGDSAKE DSDESNANATSNSNATVPNKGGHE GGSANEVYSNEEELITSSGSKGDAN KLAGTGGYKNNNAFLDLNNLKKDAS AAKYGKDNSGDKSNGGNSNGGNN KVMNKRIGGKKKKTFKKKKNPGQIP FKMETLQKLVKEYTNTSNQKIMEKII KKYVSMSNQSARGNSEEEDDEEEA EDEKSAKDKNSEKEAELNMNEFSVK DIKKLISEGILTYEDLTEEELKKLAKP DDMFYELSPYANEEKDLSLNETSGV SNEQLNAFLRKNGSYHMSYDSKAID YLKQKKAEKKEEEQEDDNFYDAYK QIKNSYEGIPSNYYHDAPQLIGENYV FTSVYDKKKELIDFLKRSNGATDSSN SSAGKDKGNSAESGTYKSKYYDKY MKKLSEYRRREAFKILKKRRAQEKK MQKKQEMQNNSSNEVDYSEYFKKN GFINSSNGTVKTFSKDQLDNMVKQF NSDGDDIPSSSGAGADLGDNYSGV SGGGQFSPSGGSGNNPSGYVTFD GQNIVGPNENEEEEPTEDVLNEDDD NADDDDhhhhhh (SEQ ID NO: 35) | ATGAACGGCAACAGGAACCTGAACATCAAGCCAACCTGCCACAAGAGC GGCAAGAACGACAAGGCCAACGGCTCCGACAACATCGCTAACAAGGG CGGCGCCCAACACGCTGCTAACGGCGCCACCGGCACCCCAAGCGGCTC CAGCAACGGCAAGAAGGGCGCTACGACCACCAGCGCTTCCGCTGGCC AAGCTGGCGCTTCCGGCGGCATGGCCGCCCCAGGCATGAACCCAAACT TCGAGCAGATGATGAAGCCACTGAACGACATGTTCAAGGGCAACGGC GAGGGCCTCAACATCGAGAACATCATGAACAGCGACATGTTCCAGAAC TTCTTCAACTCCCTGATGGGCGGCAACCCACACGACGGCGCTGGCGGC GGCCAAGAGATCCTGTTCAAGGACATGCTCAACGCCATGAACGCCCAA GGCGGCGGCGCCCCAGGCGCTGCCGCCACCTCCGGCGGCGCCAACAA GGACCCAAACATCAGCGTCTCCCCAGAGCAGCTGAACAAGATCAACCA ACTCAAGGACAAGCTGGAGAACGTGCTCAAGAACGTGGGCGTCGACG TGGAGCAGCTCAAGGAGAACATGCAAAACGAGAACATCATGCAGAAC AAGGACGCTCTGAGGGACCTCCTGGCTAACCTCCCGATGAACCCAGGC ATGATGCAAAACATGATGGCCGGCAAGGACGGCAACATGTTCAACATG GACCCAAACCAGATGATGAACATGTTCAACCAACTCAGCCAAGGCAAG ATGAACATGAAGGACTTCGGCATGGGCGACTTCATGCCACCACCAGTC CACGCCAACGACCAAGACGCTGAGGACGACTCCCGCGGCAAGGCTTTC GTGACCAACTCCAGCAACAACGACATCAACTTCGCCCACAAGCTGAAC GCCTTCGAGTACAGCAACGGCCCATCCGAGGGCATGTTCCAGCTCTAC GGCATGAACAACGACGACGGCGTCATCGACGACGGCATGAGCGACTC CGTCGGCAAGAACAGCGCTCTGGACGTGAGCGGCGGCTCCATCAACA GGAACCTCAGCGACGGCGACTCCGCCAAGGAAGACAGCGACGAGTCC AACGCCAACGCCACCAGCAACTCCAACGCCACCGTCCCAAACAAGGGC GGCCACGAGGGCGGCAGCGCTAACGAGGTGTACTCCAACGAGGAAGA GCTGATCACCTCCAGCGGCTCCAAGGGCGACGCTAACAAGCTGGCTGG CACCGGCGGCTACAAGAACAACAACGCCTTCCTCGACCTGAACAACCT GAAGAAGGACGCCAGCGCCGCCAAGTACGGCAAGGACAACAGCGGC GACAAGTCCAACGGCGGCAACTCCAACGGCGGCAACAACAAGGTCAT GAACAAGCGCATCGGCGGCAAGAAGAAGAAGACCTTCAAGAAGAAGA AGAACCCAGGCCAAATCCCATTCAAGATGGAGACGCTCCAGAAGCTGG TCAAGGAGTACACCAACACCAGCAACCACCGTCCACCGGCATGAAGATCA TCAAGAAGTATGTGTCCATGTCCAACCAGAGCGCCAGGGGCAACTCCG AGGAAGAGGACGACGAGGAAGAGGCCGAGGACGAGAAGAGCGCCAA GGACAAGAACTCCGAGAAGGAAGCCGAGCTGAACATGAACGAGTTCA GCGTCAAGGACATCAAGAAGCTCATCTCCGAGGGCATCCTGACCTACG AGGACCTCACCGAGGAAGAGCTCAAGAAGCTGGCCAAGCCAGACGAC ATGTTCTACGAGCTCAGCCCATACGCCAACGAGGAGAAGGACCTCTCC CTGAACGAGACGAGCGGCGTGTCCAACGAGCAACTGAACGCCTTCCTC CGCAAGAACGGCTCCTACCACATGAGCTACGACTCCAAGGCCATCGAC TACCTGAAGCAAAAGAAGGCCGAGAAGAAGGAAGAGGAGCAAGAGG ACGACAACTTCTACGACGCCTACAAGCAAATCAAGAACAGCTACGAGG GCATCCCATCCAACTACTACCACGACGCCCCACAGCTCATCGGCGAGAA CTACGTCTTCACCAGCGTGTACGACAAGAAGAAGGAGCTGATCGACTT CCTCAAGAGGTCCAACGGCGCTACCGACTCCAGCAACTCCAGCGCTGG CAAGGACAAGGGCAACAGCGCTGAGTCCGGCACCTACAAGAGCAAGT ACTACGACAAGTACATGAAGAAGCTGTCCGAGTACAGGCGCAGGGAG GCCTTCAAGATCCTCAAGAAGCGCAGGGCCCAGGAGAAGAAGATGCA AAAGAAGCAGGAGATGCAAAACAACTCCAGCAACGAGGTGGACTACT CCGAGTACTTCAAGAAGAACGGCTTCATCAACTCCAGCAACGGCACCG TCAAGACCTTCAGCAAGGACCAACTGGACAACATGGTGAAGCAGTTCA ACTCCGACGGCGACGACATCCCATCCAGCTCCGGCGCTGGCGCTGACC TCGGCGACAACTACAGCGGCGTGTCCGGCGGCCAATTCAGCCCAT CCGGCGGCAGCGGCAACAACCCATCCGGCTACGTCACCTTCGACGGCC AGAACATCGTGGGCCCAAACGAGAACGAGGAAGAGGAGCCAACCGA GGACGTGCTCAACGAGGACGACGACAACGCCGACGACGACGACCACC ACCACCACCACCACTGA (SEQ ID NO: 36) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 19 | merozoite surface protein 5 | PVX_003770 | mPLEVSLWGQGNAHLGTQTSRLLR ESGRNGQANRVNQADQADQVASP PISGKERRRGIGMTSNLQLLSGEDE KDSTSEEAPNLEGKDNADAGKDGE KEPSEKQSGDVDPTVTDAERAKDE NASVSEEEQMKTLDSGEDHTDDGN ADGGQGGGDGNDENQKGDGKEKE GGEEKKEDGKDDHEKGEKGSEGES GEKDEAAPKGDAAEKDKKLESKTAD AKVSEHKADDANPGGNKDSPEGES PKEGNPDDPSQKNPEAAGDDDSRL HLDNLDDKVPHYSALRNNRVEKGVT DTMVLNDIIGENAKSCSVDNGGCAD DQICIRIDNIGIKCICKEGHLFGDKCIL TKhhhhhh (SEQ ID NO: 37) | ATGCCGCTGGAGGTGTCCCTGTGGGGCCAGGGCAACGCTCACCTCGGC ACCCAAACCTCCCGCCTGCTCAGGGAGTCCGGCAGGAACGGCCAGGCC AACAGGGTGAACCAGGCTGACCAGGCTGACCAAGTGGCTTCCCCACCA ATCTCCGGCAAGGAGAGGCGCAGGGGCATCGGCATGACCTCCAACCTC CAACTCCTGAGCGGCGAGGACGAGAAGGACTCCACCAGCGAGGAAGC CCCAAACCTGGAGGGCAAGGACAACGCTGACGCTGGCAAGGATGGCG AGAAGGAGCCATCCGAGAAGCAGAGCGGCGACGTGGACCCAACCGTC ACCGACGTGGACGAGGGCTAAGGACGAGAACGCTTCCGTCAGCGAGGA AGAGCAGATGAAGACCCTGGACAGCGGCGAGGACCACACCGACGACG GCAACGCTGACGGCGGACAAGGCGGCGGCGACGGCAACGACGAGAA CCAAAAGGGCGACGGCAAGGAGAAGGAAGGCGGCGAGGAGAAGAA GGAAGACGGCAAGGACGACCACGAGAAGGGCGAGAAGGGCTCCGAG GGCGAGAGCGGCGAGAAGGACGAGGCTGCTCAAAGGGCGACGCTG CCGAGAAGGACAAGAAGCTGGAGTCCAAGACCGCCGACGCCAAGGTG AGCGAGCACAAGGCTGACGACGCTAACCCAGGCGGCAACAAGGACTC CCCAGGGCGAGAGCCCAAAGGAAGGCAACCCAGACGACCCATCCC AGAAGAACCCGGAGGCTGCTGGCGACGACGCAGCCGCCTCCACCCTG ACACCTCGACGACAAGGTCCCACACTACTCCGCCCTGCGCAACAAC AGGGTGGAGAAGGGCGTCACCGACACCATGGTGCTGAACGACATCAT CGGCGAGAACGCCAAGTCCTGCAGCGTGGACAACGGCGGCTGCGCTG ACGACCAAATCTGCATCAGGATCGACAACATCGGCATCAAGTGCATCT GCAAGGAAGGCCACCTCTTCGGCGACAAGTGCATCCTGACCAAGCACC ACCACCACCACCACTGA (SEQ ID NO: 38) |
| 20 | TRAg (Pv-fam-a) | PVX_092990 | mDVLQLVIPSEEDIQLDKPKKDELGS GILSILDVHYQDVPKEFMEEEEETAV YPLKPEDFAKEDSQSTEWLTFIQGL EGDWERLEVSLNKARERWMEQRN KEWAGWLRLIENKWSEYSQISTKGK DPAGLRKREWSDEKWKKWFKAEV KSQIDSHLKKWMNDTHSNLFKILVK DMSQFENKKTKEWLMNHWKKNER GYGSESFEVMTTSKLLNVAKSREW YRANPNINRERRELMKWFLLKENY LGQEWKKWTHWKKVKFFVFNSMC TTFSGKRLTKEEWNQFVNEIKVhhhh hh (SEQ ID NO: 39) | ATGGACGTGCTCCAACTGGTCATCCCAAGCGAGGAAGACATCCAGCTC GACAAGCCAAAGAAGGACGAGCTGGGCAGCGGCATCCTCTCCATCCTG GACGTGCACTACCAAGACGTCCCAAAGGAGTTCATGGAGGAAGAGGA AGAGACGGCCGTGTACCCACTCAAGCCAGAGGACTTCGCCAAGGAAG ACTCCCAAAGCACCGAGTGGCTCACCTTCATCCAAGGCCTGGAGGGCG ACTGGGAGAGGCTGGAGGTGTCCCTGAACAAGGCCAGGGAGCGCTGG ATGGAGCAAAGGAACAAGGAGTGGGCTGGCTGGCTCAGGCTGATCGA GAACAAGTGGTCCGAGTACCAGCAGATCTCCACCAAGGGCAAGGACC CGGCTGGCCTCAGGAAGCGCGAGTGGTCCGACGAAAAGTGGAAGAAG TGGTTCAAGGCCGAGGTGAAGAGCCAAATCGACTCCCACCTGAAGAA GTGGATGAACGACACCCACAGCAACCTCTTCAAGATCCTGGTCAAGGA CATGTCCCAGTTCGAGAACAAGAAGACCAAGGAGTGGCTCATGAACCA CTGGAAGAAGAACGAGAGGGGCTACGGCTCCGAGAGCTTCGAGGTCA TGACCACCAGCAAGCTCCTGAACGTCGCCAAGTCCAGGGAGTGGTACC GCGCCAACCCAAACATCAACCGCGAGAGGCGCGAGCTCATGAAGTGG TTCCTCCTGAAGGAGAACGAGTACCTGGGCCAAGAGTGGAAGAAGTG GACCCACTGGAAGAAGGTGAAGTTCTTCGTCTTCAACAGCATGTGCAC CACCTTCTCCGGCAAGCGCCTGACCAAGGAAGAGTGGAACCAGTTCGT GAACGAGATCAAGGTCCACCACCACCACCACCACTGA (SEQ ID NO: 40) |
| 21 | unspecified product | PVX_112690 | mEAMPKFPQNNLKGGLKDSPLKQP KSPLINGPPKPVNDKLKDDSNKTET KDAKNGLNKPPKNINDKVKDGENKT PSQDLNEPSFKLPMRQKESSWYTW LKGTKKDYETLKCFAKGNLYDWLCN VRESFDLYLQSLEKKWTTCSDSATT LFLCECFAESSGWNDSQWGNWMN NQLKEQLKTEAEAWISTKKKDFDGL TSKYFSLWKDHRRKELDADEWKNK VSSGGLSEWEELTNKMNTRYRNNL DNMWSHFSRDLFFNFDEWAPQVLE KWIENKQWNRWVKKVRKhhhhhh (SEQ ID NO: 41) | ATGGAGGCCATGCCAAAGTTCCCACAAAACAACCTCAAGGGCGGCCTG AAGGACTCCCCACTCAAGCAGCCAAAGAGCCCACTGATCAACGGCCCA CCAAAGCCAGTGAACGACAAGCTCAAGGACGACTCCAACAAGACCGA GACGAAGGACGCCAAGAACGGCCTGAACAAGCCACCAAAGAACATCA ACGACAAGGTCAAGGACGGCGAGAACAAGACCCCATCCCAAGACCTC AACGAGCCAAGCTTCAAGCTGCCAATGAGGCAGAAGGAGTCCAGCTG GTACACCTGGCTCAAGGGCACCAAGAAGGACTACGAGACGCTGAAGT GCTTCGCCAAGGGCAACCTCTACGACTGGCTGTGCAACGTGCGCGAGT CCTTCGACCTCTACCTGCAAAGCCTGGAGAAGAAGTGGACCACCTGCT CCGACAGCGCTACCACCCTCTTCCTGTGCGAGTGCTTCGCCGAGTCCAG CGGCTGGAACGACTCCCAGTGGGGCAACTGGATGAACAACCAACTCAA GGAGCAGCTGAAGACCGAGGCCGAGGCCTGGATCAGCACCAAGAAGA AGGACTTCGACGGCCTCACCTCCAAGTACTTCAGCCTGCTGGAAGGACC ACAGGCGCAAGGAGCTCGACGCCGACGAGTGGAAGAACAAGGTGTCC AGCGGCGGCCTCAGCGAGTGGGAGGAGCTGACCAACAAGATGAACAC CAGGTACCGCAACAACCTCGACAACATGTGGTCCCACTTCAGCAGGGA CCTGTTCTTCAACTTCGACGAGTGGGCCCCACAAGTCCTGGAGAAGTG GATCGAGAACAAGCAGTGGAACCGCTGGGTGAAGAAGGTCCGCAAGC ACCACCACCACCACCACTGA (SEQ ID NO: 42) |
| 22 | petidase, M16 family | PVX_091710 | mQKAPNNGKNNYGLNDDELGAILF GLNYDSIAKNKDNLEKRKNVENESIF LRNFANEDTSKNTQSEKAQKEIKIET ETESVNSNEKEVATSQKSDTSNKNS SVENEKIELKNDELLGKNFEKDKVN KKGDNTTTNNHDLTNSSEKQGVDI RGSKNMNNYLQKTGDTNIEKSESLQ KDVNIKNHNEEANDAKRLDSAQTNN EKSKISKDTIDKDVQSNELTNLASNR SNKKSQGLAKKENELKSANLEENHN | ATGCAAAAGGCCCCAAACAACGGCAAGAACAACTACGGCCTCAACGAC GACGAGCTGGGCGCCATCCTCTTCGGCCTGAACTACGACAGCATCGCC AAGAACAAGGACAACCTGGAGAAGAGGAAGAACGTCGAGAACGAGT CCATCTTCCTGCGCAACTTCGCCAACGAGGACACCAGCAAGAACACCC AATCCGAAAGGCCCAGAAGGAGATCAAGATCGAGACAGAGACGGA GTCCGTCAACTCCAACGAGAAGGAAGTGGCCACCTCCCAGAAGAGCG ACACCTCCAACAAGAACTCCAGCGTCGAGAACGAGAAGATCGAGCTGA AGAACGACGAGCTCCTGGGCAAGAACTTCGAGAAGGACAAGGTGAAC AAGAAGGGCGACAACACCAACACCACCAACAACCACGACCTCACCAAC TCCAGCGAGAAGCAAGGCGTCGACATCAGGGGCAGCAAGAACATGAA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | AKKDLLKKDQKREDGKKITHPENSN SDQYGVQVSLNDEEKNTNTKSVSH SEDHSASYSGEKFGTHVSNSQKDM LKNIRPVQFDESAYGKLNGGSPEND ENEILNKINKNNENNFSEKVALRKGT KDRNEYEYFKLKSNDFKVLGIINKYS SRGGFSISVDCGGYDDFDEVPGVS NLLQHAIFYKSEKRNTTLLSELGKYS SEYNSCTSESSTSYYATAHSEDIYHL LNLFAENLFYPVFSEEHIQNEVKEIN NKYISIENNLESCLKIASQYITNFKYS KFFVNGNYTTLCENVLKNRLSIKNIL TEFHKKCYQPRNMSLTILLGNKVNT ADHYNMKDVENMVVHIFGKIKNESY PIDGDVIGKRINRMESERVNLYGKK DSYNDANFIHIEGRNEKEAAFLQSM NELHYALDLNOKSRYVEIIKKEEWG DQLYLYWSSKTNAELCKKIEEFGSM TFLREIFSDFRRNGLYYKISVENKYV YDLEVTSICNKYYLNFGILVKLTQRG RTNLAHLIHICNVFVNEIGKLFDRDSL DKGISKYILDYREKALVTDLKFNSD NVNVSLDDLVIYSKRLLVHADDPSSL LTIHSLIEDKHKNDFRNHIKIThhhhhh (SEQ ID NO: 43) | CAACTACCTCCAAAAGACCGGCGACACCAACATCGAGAAGTCCGAGAG CCTGCAGAAGGACGTGAACATCAAGAACCACAACGAGGAAGCCAACG ACGCCAAGAGGCTGGACAGCGCCCAGACCAACAACGAGAAGAGCAAG ATCTCCAAGGACACCATCGACAAGGACGTGAATCCAACGAGCTCACC AACCTGGCCAGCAACCGCTCCAACAAGAAGAGCCAGGGCCTCGCCAA GAAGGAGAACGAGCTCAAGTCCGCCAACCTGGAGGAGAACCACAACG CCAAGAGGACCTCCTGAAGAAGGACCAAAAGAGGGAGGACGGCAA GAAGATCACCCACCCAGAGAACTCCAACAGCGACCAATACGGCGTGCA AGTGTCCCTGAACGACGAGGAGAAGAACACCAACACCAAGTCCGTCA GCCACTCCGAGGACCACAGCGCTTCCTACAGCGGCGAGAAGTTCGGCA CCCACGTCTCCAACAGCCAAAAGGACATGCTCAAGAACATCCGCCCAG TGCAGTTCGACGAGAGCGCTTACGGCAAGCTCAACGGCGGCTCCCCAG AGAACGACGAGAACGAGATCCTGAACAAGATCAACAAGAACAACGAG AACAACTTCAGCGAGAAGGTGGCCCTCAGGAAGGGCACCAAGGACCG CAACGAGTACGAGTACTTCAAGCTCAAGTCCAACGACTTCAAGGTCCT GGGCATCATCAACAAGTACTCCAGCAGGGGCGGCTTCTCCATCAGCGT GGACTGCGGCGGATACGACGACTTCGACGAGGTGCCAGGCGTCTCCA ACCTCCTGCAACACGCCATCTTCTACAAGAGCGAGAAGCGCAACACCA CCCTCCTGTCCGAGCTCGGCAAGTACTCCAGCGAGTACAACAGCTGCA CCTCCGAGTCCAGCACCAGCTACTACGCCACCGCCCACTCCGAGGACAT CTACCACCTCCTGAACCTCTTCGCCGAGAACCTGTTCTACCCAGTCTTCA GCGAGGAGCACATCCAAACGAGGTGAAGGAGATCAACAACAAGTAC ATCTCCATCGAGAACAACCTGGAGAGCTGCCTGAAGATCGCCTCCCAG TACATCACCAACTTCAAGTACAGCAAGTTCTTCGTCAACGGCAACTACA CCACCCTCTGCGAGAACGTGCTCAAGAACAGGCTGAGCATCAAGAACA TCCTGACCGAGTTCCACAAGAAGTGCTACCAGCCACGCAACATGTCCCT CACCATCCTCCTGGGCAACAAGGTCAACACCGCCGACCACTACAACAT GAAGGACGTGGAGAACATGGTGGTCCACATCTTCGGCAAGATCAAGA ACGAGTCCTACCCAATCGACGGCGACGTCATCGGCAAGAGGATCAACC GCATGGAGAGCGAGAGGGTCAACCTCTACGGCAAGAAGGACTCCTAC AACGACGCCAACTTCATCCACATCGAGGGCCGCAACGAGAAGGAAGC CGCCTTCCTCCAAAGCATGAACGAGCTGCACTACGCCCTCGACCTGAAC CAGAAGTCCCGCTACGTGGAGATCATCAAGAAGGAAGAGTGGGGCGA CCAACTCTACCTGTACTGGTCCAGCAAGACCAACGCCGAGCTCTGCAA GAAGATCGAGGAGTTCGGCAGCATGACCTTCCTCCGCGAGATCTTCTC CGACTTCAGGCGCAACGGCCTGTACTACAAGATCAGCGTGGAGAACAA GTATGTGACGACCTGGAGGTGACCTCCATCTGCAACAAGTACTACCTG AACTTCGGCATCCTCGTCAAGCTGACCCAAAGGGGCCGCACCAACCTC GCTCACCTGATCCACATCTGCAACGTGTTCGTCAACGAGATCGGCAAGC TCTTCGACAGGGACAGCCTGGACAAGGGCATCTCCAAGTACATCCTCG ACTACTACCGCGAGAAGGCCCTCGTGACCGACCTGAAGTTCAACAGCG ACAACGTGAACGTCTCCCTCGATGACCTGGTCATCTACAGCAAGAGGC TCCTGGTGCACGCCGACGACCCATCCAGCCTCCTGACCATCCACTCCCT CATCGAGGACAAGCATAAGAACGACTTCCGCAACCACATCAAGATCAC CCACCACCACCACCACTGA (SEQ ID NO: 44) |
| 23 | rhoptry-associated membrane antigen, RAMA | PVX_087885 | mKEAVKKGSKKAMKQPMHKPNLLE EEDFEEKESFSDDEMNGFMEESMD ASKLDAKKATTLRSSEKKKTPTSG MSGMSGSGATSAATEAATNMATA MNAAAKGNSEASKKQTDLSNEDLF NDELTEEVIADSYEEGGNVGSEEAE SLTNAFDDKLLDQGVNENTLLNDNM IYNVNMVPHKKRELYISPHKHTSAAS SKNGKHHAADADALDKKLRAHELLE LENGEGSNSVIVETEEVDVDLNGGK SSGSVSFLSSVVFLLIGLLCFTNhhhh hh (SEQ ID NO: 45) | ATGAAGGAAGCCGTGAAGAAGGGCTCCAAGAAGGCCATGAAGCAACC AATGCACAAGCCAAACCTCCTGGAGGAAGAGGACTTCGAGGAGAAGG AGTCCTTCAGCGACGACGAGATGAACGGCTTCATGGAGGAGTCCATGG ACGCCAGCAAGCTGGACGCCAAGAAGGCCAAGACCACCCTCAGGTCC AGCGAGAAGAAGAAGACCCCAACCTCCGGCATGAGCGGCATGTCCGG CAGCGGCGCTACCAGCGCTGCTACCGAGGCCGCCACCAACATGAACGC TACCGCCATGAACGCTGCCGCCAAGGGCAACTCCGAGGCTAGCAAGAA GCAAACCGACCTCTCCAACGAGGACCTGTTCAACGACGAGCTCACCGA GGAAGTGATCGCCGACAGCTACGAGGAAGGCGGCAACGTGGGCTCCG AGGAAGCCGAGAGCCTGACCAACGCCTTCGACGACAAGCTCCTGGACC AGGGCGTGAACGAGAACACCCTCCTGAACGACAACATGATCTACAACG TGAACATGGTCCCACACAAGAAGAGGGAGCTCTACATCTCCCCACACA AGCACACCAGCGCCGCCTCCAGCAAGAACGGCAAGCACCACGCTGCTG ACGCTGACGCTCTGGACAAGAAGCTCAGGGCTCACGAGCTCCTGGAGC TGGAGAACGGCGAGGGCTCCAACAGCGTGATCGTCGAGACGGAGGAA GTGGACGTGGACCTGAACGGCGGCAAGTCCTCCGGCTCCGTCAGCTTC CTCTCCAGCGTGGTCTTCCTCCTGATCGGCCTCCTGTGCTTCACCAACCA CCACCACCACCACCACTGA (SEQ ID NO: 46) |
| 24 | HP, conserved | PVX_003555 | mDDNGRRLPRKAAPPVDKAKQDVM KDIVNYLSKNMLAFVRQKRNVSGKE GEAPTGPSGAQGGDSSQYASKFTF TDHSVDFSKYNKLDKEKFAAKDDLK SRLKNEVVASMLDTEGDILTEEFGYL LRNYFDKVKLEEKKSQEAESAKPAE QEEEAEEEAPEQKEEATAEKATEETT EAATEETTEAATEETTEAATEETTEA ATEETTEAATEETTEAATEETTEAAT EETTEAATEEATEGATEEGAEETTE | ATGGACGACAACGGCAGGCGCCTCCCAAGGAAGGCTGCCCCACCAGT GGACAAGGCCAAGCAGGACGTGATGAAGGACATCGTCAACTACCTCTC CAAGAACATGCTGGCCTTCGTGAGGCAAAAGCGCAACGTCTCCGGCAA GGAAGGCGAGGCTCCAACCGGCCCAAGCGGCGCTCAAGGCGGCGACT CCAGCCAGTACGCCAGCAAGTTCACCTTCACCGACCACTCCGTGGACTT CAGCAAGTACAACAAGCTCGACAAGGAGAAGTTCGCCGCCAAGGACG ACCTCAAGTCCAGGCTGAAGAACGAGGTGGTCGCCAGCATGCTCGACA CCGAGGGCGACATCCTGACCGAGGAGTTCGGCTACCTCCTGCGCAACT ACTTCGACAAGGTCAAGCTGGAGGAGAAGAAGTCCCAAGAGGCCGAG AGCGCTAAGCCAGCTGAGCAAGAGGAAGAGGCCGAGGAAGCCCCAG |

| No. | Protein Name | Protein Reference | Insert aa sequence (add M as start/His-tag at C-term) | Insert DNA sequence (Start from ATG to His-tag stop codon) |
|---|---|---|---|---|
| | | | EATEEGAEEATEEGAEEEATEEGAEE TTEEATEEGAEETTEETTEEGAEEE ATEEGAEETTEEGAEEAAEEGAEEG AEAATEEATEEATEEATEEATEEAT EEATEEATAEVAEAATPEKVTEEAT EEATEEGDNEPAEQAAEKEEDVKG GLMDNETYYNTLQELYEEIENDDKK EKEKIQKAKEQEELEKKLFKESKKG KKKEKKRRKKLCKMAKIVEKYAEEIP KDSERSLRYDKEEHIDDPDEMDDLL FGEFKTLEKYGTHKTSTFYYEMTCF DERLRDFEINTKLKEMEEVPEKWEL LSLYWQSYRNERHKYLAVKKYLLEK FLELKTNQSTEALPKYNKKWKQCEE IVDNNFTKQHEHVNDVFYTFVAKEN LSRDEFKEILNDVRASWhhhhhh (SEQ ID NO: 47) | AGCAAAAGGAAGAGGCCACCGCTGAGAAGGCTACCGAGGAGACGACC GAGGCTGCCACGGAGGAGACGACGGAGGCCGCCACGGAGGAGACGA CCGAGGCCGCCACCGAGGAGACGACGGAGGCTGCCACTGAAGAGACG ACCGAGGCTGCCACGGAGGAGACGACCGAGGCCGCGACGGAAGAGA CGACTGAGGCTGCCACTGAGGAGACGACGGAAGCTGCTACCGAGGAA GCCACCGAGGGCGCTACCGAGGAAGGCGCTGAGGAGACGACGGAGG AAGCCACGGAGGAAGGCGCTGAGGAAGCCACCGAGGAAGGCGCCGA GGAAGCCACGGAGGAAGGCGCACAGGAGGACGACAGGAGGAAGCCACG GAGGAAGGCGCCGAAGAGACGACCGAAGAGACGACCGAGGAAGGCG CGGAGGAAGAGGCCACTGAGGAAGGCGCCGAGGAGACGACTGAGGA AGGCGCAGAGGAAGCCGCTGAGGAAGGCGCTGAGGAAGGCGCTGAG GCCGCCACGGAGGAAGCCACCGAGGAAGGCGCCACGGAGGAAGCCACG AGGAAGCCACAGAGGAAGCCACTGAGGAAGCCACAGAGGAAGCCAC AGCTGAGGTGGCTGAGGCTGCTACCCCAGAGAAGGTCACAGAGGAAG CCACAGAGGAAGCCACCGAGGAAGGCGACAACGAGCCAGCTGAGCAG GCTGCTGAGAAGGAAGAGGACGTGAAGGGCGGCCTCATGGACAACG AGACGTACTACAACACCCTCCAAGAGCTGTACGAGGAGATCGAGACG ACGACAAGAAGGAGAAGGAGAAGATCCAAAAGGCCAAGGAGCAAGA GGAGCTGGAGAAGAAGCTGTTCAAGGAGTCCAAGAAGGGCAAGAAG AAGGAGAAGAAGAGGCGCAAGAAGCTCTGCAAGATGGCCAAGATCGT CGAGAAGTACGCCGAGGAGATCCCAAAGGACTCCGAGAGGAGCCTGC GCTACGACAAGGAAGAGCACATCGACGACCCAGACGAGATGGACGAC CTCCTGTTCGGCGAGTTCAAGACCCTGGAGAAGTACGGCACCCACAAG ACCTCCACCTTCTACTACGAGATGACCTGCTTCGACGAGAGGCTCCGCG ACTTCGAGATCAACACCAAGCTGAAGGAGATGGAGGAAGTGCCAGAG AAGTGGGAGCTCCTGTCCCTCTACTGGCAGAGCTACAGGAACGAGCGC CACAAGTACCTGGCCGTCAAGAAGTACCTCCTGGAGAAGTTCCTGGAG CTGAAGACCAACCAAAGCACCGAGGCCCTGCCAAAGTACAACAAGAA GTGGAAGCAGTGCGAGGAGATCGTCGACAACAACTTCACCAAGCAAC ACGAGCACGTGAACGACGTCTTCTACACCTTCGTGGCCAAGGAGAACC TCTCCAGGGACGAGTTCAAGGAGATCCTGAACGACGTCCGCGCCAGCT GGCACCACCACCACCACCACTGA (SEQ ID NO: 48) |
| 25 | phosphatidylinositol-4-phosphate-5-kinase, putative | PVX_117385 | MRCCTKDAVNVESPKKVVVGETEE DTREEENPYEDLPTVTVTLSDGSVY TGTTKDNRVHGRGVLKYVNGDQYE GEFVDGKKEGKGKWTDKENNTYEG DWVKDKRHGHGVYKTAEGFIFEGE FANNKREGKGTIITPEKTKYVCSFQD DEEVGEVEFFFANGDHALGYIKDGY LCQNGRYEFKNGDIYVGNFEKGLFH GEGYYKWNNDANYTIYEGNYSEGK KHGKGQLINKDGRILCGMFRDNNM DGEFLEISPQGNQTKVLYDKGFFVK VLDKIEENLDVQEFLKDSIIHTTIFSD PTTYKKLYEITEKKKPQFRLNLKRTQ PTShhhhhh (SEQ ID NO: 49) | ATGAGGTGCTGCACCAAGGACGCCGTCAACGTGGAGTCCCCAAAGAA GGTGGTCGTGGGCGAGACGGAGGAAGACACCAGGGAGGAAGAGAAC CCATACGAGGACCTCCCAACCGTCACCGTGACCCTGTCCGACGGCAGC GTCTACACCGGCACCACCAAGGACAACAGGGTGCACGGCCGCGGCGT CCTCAAGTATGTGAACGGCGACCAATACGAGGGCGAGTTCGTCGACG GCAAGAAGGAAGGCAAGGGCAAGTGGACCGACAAGGAGAACAACAC CTACGAGGGCGACTGGGTCAAGGACAAGAGGCACGGCCACGGCGTGT ACAAGACCGCTGAGGGCTTCATCTTCGAGGGCGAGTTCGCCAACAACA AGCGCGAGGGCAAGGGCACCATCATCACCCCAGAGAAGACCAAGTAT GTGTGCAGCTTCCAAGACGACGAGGAAGTGGGCGAGGTGGAGTTCTT CTTCGCCAACGGCGACCACGCCCTCGGCTACATCAAGGACGGCTACCT GTGCCAGAACGGCCGCTACGAGTTCAAGAACGGCGACATCTACGTGG GCAACTTCGAGAAGGGCCTGTTCCACGGCGAGGGCTACTACAAGTGG AACAACGACGCCAACTACACCATCTACGAGGGCAACTACTCCGAGGGC AAGAAGCACGGCAAGGGCCAACTCATCAACAAGGACGGCAGGATCCT GTGCGGCATGTTCCGCGACAACAACATGGACGGCGAGTTCCTGGAGAT CAGCCCACAAGGCAACCAGACCAAGGTCCTCTACGACAAGGGCTTCTT CGTCAAGGTGCTGGACAAGATCGAGGAGAACCTCGACGTGCAGGAGT TCCTGAAGGACTCCATCATCCACACCACCATCTTCAGCGACCCAACCAC CTACAAGAAGCTGTACGAGATCACCGAGAAGAAGAAGCCACAATTCAG GCTCAACCTGAAGCGCACCCAGCCAACCTCCCACCACCACCACCACCAC TGA (SEQ ID NO: 50) |
| 26 | Plasmodium exported protein, unknown function | PVX_113225 | mNKLGTSLVEDATANGEFGLRVQRL LGGSRSSRDSIFADSFYDDDDDDDD NNDKLFDYDSDHKSRREVKDRHHR HRHSHSRHKRRHSHKRRTSSRSR REKEESSTTNDDDDDEVLSLSRPFDVD DDKDDRSHSRYSVDYDDENDDEPS SSRPASTDYDDIIDLTNARRSGSKYR ISSMDIELYPEHEDEYLFEGKRRSG GVLKKADNYCENKIFDALSALDKYK EYYGEERRVMKQAAYRKATKVFAIP GAAALSPLIITLFLTTSNVVALPLAAS AVILGGILYKKSKDKSDYGRPHLKSI TYhhhhhh (SEQ ID NO: 51) | ATGAACAAGCTGGGCACCAGCCTCGTGGAGGACGCTACCGCTAACGG CGAGTTCGGCCTCCGCGTCCAAAGGCTGCTGGGCGGCTCCAGGTCCAG CCGCGACAGCATCTTCGCCGACTCCTTCTACGATGATGACGACGACGAC GACGACAACAACGACAAGCTGTTCGACTACGACAGCGACCACAAGTCC AGGCGCGAGGTGAAGGACAGGCACCACAGGCACAGGCACAGCCACTC CCACCGCCACAAGAGGCGCCACAGCCACAAGAGGACCTCCAGCC CTCCAGGCGCGAGAAGGAAGAGTCCAGCACCACCAACGACGACGACG ACGAGGTGCTCAGCCTGTCCAGGTTCGACGTCGACGACGACAAGGAC GACAGGAGCCACTCCCGCTACAGCGTGGACTACGACGACGAGAACGA CGACGAGCCATCCAGCTCCAGGCCAGCCTCCACCGACTACGACGACAT CATCGACCTCACCAACGCTAGGCGCAGCGGCTCCAAGTACCGCATCAG CTCCATGGACATCGAGCTCTACCCAGAGCACGAGGACGAGTACCTGTT CGAGGGCAAGAGGCGCAGCGGCGGCGTCCTGAAGAAGGCTGACAACT ACTGCGAGAACAAGATCTTCGACGCCCTCTCCGCCCTGGACAAGTACA AGGAGTACTACGGCGAGGAGAGGCGCGTGATGAAGCAGGCCGCCTAC AGGAAGGCCACCAAGGTCTTCGCTATCCCAGGCGCTGCCGCCCTCAGC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | CCACTGATCATCACCCTCTTCCTGACCACCAGCAACGTGGTGGCTCTCC CACTGGCTGCTTCCGCCGTCATCCTCGGCGGCATCCTGTACAAGAAGA GCAAGGACAAGTCCGACTACGCCGCCCACACCTCAAGTCCATCACCT ACCACCACCACCACCACTGA (SEQ ID NO: 52) |
| 27 | trypto-phan-rich antigen (Pv-fam-a) | PVX_090265 | MEAARGVSGLVPSSNSLQEITLRYK DKLLNMDKEQMILTLGVTMIAITSAV AFGVLATHGDINDFLGVESDEESEK KKEIVEKSEEWKRKEWSNWLKKLE QDWKVFNEKLQNEKKTFLEEKEED WNTWIKSVEKKWTHFNPNMDKEFH TNMMRRSINWTESQWREWIQTEGR LYLDIEWKKWFFENQSRLDELIVKK WIQWKKDKIINWLMSDWKRAEQEH WEEFEEKSWSSKFFQIFEKRNYEDF KDRVSDEWEDWFEWVKRKDNIFIT NVLDQWIKWKEEKNLLYNNWADAF VTNWINKKQWVVWVNERRNLAAKA KAALNKKKhhhhhh (SEQ ID NO: 53) | ATGGAGGCTGCCAGGGGCGTGTCCGGCCTCGTCCCATCCAGCAACAGC CTCCAAGAGATCACCCTGCGCTACAAGGACAAGCTCCTGAACATGGAC AAGGAGCAGATGATCCTCACCCTGGGCGTCACCATGATCGCTATCACCT CCGCTGTGGCTTTCGGCGTCCTGGCTACCCACGGCGACATCAACGACTT CCTGGGCGTCGAGTCCGACGAGGAGAGCGAGAAGAAGAAGGAGATC GTGGAGAAGTCCGAGGAGTGGAAGAGGAAGGAGTGGAGCAACTGGC TCAAGAAGCTGGAGCAAGACTGGAAGGTCTTCAACGAGAAGCTCCAG AACGAGAAGAAGACCTTCCTGGAGGAGAAGGAAGAGGACTGGAACAC CTGGATCAAGTCCGTGGAGAAGAAGTGGACCCACTTCAACCCAAACAT GGACAAGGAGTTCCACACCAACATGATGAGGCGCTCCATCAACTGGAC CGAGAGCCAATGGCGCGAGTGGATCCAGACCGAGGGCAGGCTCTACC TGGACATCGAGTGGAAGAAGTGGTTCTTCGAGAACCAAAGCAGGCTC GACGAGCTGATCGTGAAGAAGTGGATCCAGTGGAAGAAGGACAAGAT CATCAACTGGCTCATGTCCGACTGGAAGCGCGCCGAGCAAGAGCACTG GGAGGAGTTCGAGGAGAAGAGCTGGTCCAGCAAGTTCTTCCAGATCTT CGAGAAGCGCAACTACGAGGACTTCAAGGACCGCGTGAGCGACGAGT GGGAGGACTGGTTCGAGTGGGTCAAGCGCAAGGACAACATCTTCATC ACCAACGTGCTGGACCAGTGGATCAAGTGGAAGGAAGAGAAGAACCT CCTGTACAACAACTGGGCCGACGCCTTCGTCACCAACTGGATCAACAA GAAGCAGTGGGTGGTCTGGGTGAACGAGAGGCGCAACCTCGCTGCTA AGGCTAAGGCTGCCCTGAACAAGAAGAAGCACCACCACCACCACCACT GA (SEQ ID NO: 54) |
| 28 | MSP7 family | PVX_082700 | mTKGPSGPPPNKKLNANALHFLRG KLELLNKISEEQVVSPDFKKNVELLK KKIEELQGKAEKDKSKTDGEDTTPK EQQEDQNVSQNGLEEQAPSDSNEG EAQEENTQVKNVIFTEKEEAVDEEA EKEDTAVISEKANFPNEESQGNDET QTQESIEGEASPGVVVDETDDSPEG EPLSGLETEGNSSAESAPNEPDVNT THTAVDTHMPADANIGVDTNMPFDT PPHPSGENPGAPQETHLPSIDENAN RRASRMKHMSSFLNGLLTNQSNNK KEIFFHPYYGPYFNHGGYYNYDPYY NYAPAYNPFVSQARDYEVIKKLLDA CFNKGEGADPNVPCIIDIFKKVLDDE RFRNELKTFMYDLYEFLKKNDVLSD DEKKNELMRFFFDNAFQLVNPMFYY hhhhhh (SEQ ID NO: 55) | ATGACCAAGGGCCCATCCGGCCCACCACCAAACAAGAAGCTCAACGCC AACGCCCTCCACTTCCTGAGGGGCAAGCTGGAGCTCCTGAACAAGATC TCCGAGGAGCAAGTGGTCAGCCCAGACTTCAAGAAGAACGTCGAGCTC CTCAAGAAGAAGATCGAGGAGCTCCAGGGCAAGGCCGAGAAGGACAA GTCCAAGACCGACGGCGAGGACACCACCCCAAAGGAGCAAGAGGAG ACCAAAACGTGAGCCAGAACGGCCTGGAGGAGCAAGCTCCGTCCGAC AGCAACGAGGGCGAGGCTCAAGAGGAGAACACCCAGGTCAAGAACGT GATCTTCACCGAGAAGGAAGAGGCCGTCGACGAGGAAGCCGAGAAG GAAGACACCGCCGTGATCTCCGAGAAGGCCAACTTCCCAAACGAGGA GAGCCAGGGCAACGACGAGACGCAAACCCAAGAGTCCATCGAGGGCG AGGCTAGCCCCGGCGTGGTGGTGGACGAGACGGACGACTCCCCGGAG GGCGAGCCACTCAGCGGCCTCGAAACCGAGGGCAACTCCAGCGCTGA GTCCGCTCCAAACGAGCCAGACGTCAACACCACCCACACCGCTGTGGA CACCCACATGCCAGCTGACGCCAACATCGGCGTCGACACCAACATGCC ATTCGACACCCCACCACACCCAAGCGGCGAGAACCCGGGCGCCCCACA AGAGACGCACCTCCCATCCATCGACGAGAACGCCAACAGGCGCGCCAG CAGGATGAAGCACATGTCCAGCTTCCTGAACGGCCTCCTGACCAACCA GTCCAACAACAAGAAGGAGATCTTCTTCCACCCATACTACGGCCCATAC TTCAACCACGGCGGATACTACAACTACGACCCATACTACAACTACGCCC CAGCCTACAACCCATTCGTCAGCCAAGCCCGCGACTACGAGGTCATCA AGAAGCTCCTGGACGCCTGCTTCAACAAGGGCGAGGGCGCTGACCCA AACGTCCCATGCATCATCGACATCTTCAAGAAGGTGCTCGACGACGAG AGGTTCCGCAACGAGCTGAAGACCTTCATGTACGACCTCTACGAGTTCC TGAAGAAGAACGACGTCCTCAGCGACGACGAGAAGAAGAACGAGCTG ATGAGGTTCTTCTTCGACAACGCCTTCCAGCTCGTGAACCCAATGTTCT ACTACCACCACCACCACCACCACTGA (SEQ ID NO: 56) |
| 29 | Hyp, huge list of orthologs, paralogs, synteny with Py LSA3 (PyLSA3syn-3) | PVX_002550 | mFSGGVGDDEEEEEEEGEEGESE RDDSERDYAGRDDAGRDDAERND AERDDAERNDAERDDAERDHAERD HADKAESDRESSLEANENRLVKLSE GGESEPALLEVEEDIKQTVLGMFSL KGEFDEAESEKLALDLQKNLLSMLS GNMEDNDDEYEDIDEEYEEVEEDY EEEKLGKPVEVVVEDATEEAVDEVV GVVQEPEEEGAEESDKDTGEVSEE EVAKEAADEVMEEEKKEEAGEPSV VVEEPSVVVEKEPSVVVEEPSVVVEE PSVVVEEPSVVVEEPSVVVEEPAFT VEEPAFTVEEPAITVEEPAITVEEPVF TVEEPVFTVEEPAFTVEEPAFTVEEP AFTVEEPATTVEELVEEVLKVAEEEV ATEAVEKDGEEAEEQVTEESVEEDE EESGEEEGEESEEETEESAEEVA KESVEEEVAKEAEESEESGEESAEE EKEKAEEEPVAPVDEVLKEGMQKIEE SVKEALGVVQEAVDKVAEEEQTEQ | ATGTTCAGCGGCGGCGTGGGCGACGACGAGGAAGAGGAAGAGGAAG AGGAAGGCGAGGAAGGCGAGAGCGAGAGGGACGACTCCGAGAGGG ACTACGCTGGCAGGGACGATGCCGGCAGGGACGACGCCGAGAGGAA CGACGCCGAGCGCGATGATGCTGAGCGCAACGACGCCGAGCGCGACG ACGCCGAGAGGGACCACGCCGAGCGCGACCACGCCGACAAGGCCGAG TCCGACAGGGAGTCCAGCCTGGAGGCCAACGAGAACAGGCTGGTGAA GCTCAGCGAGGGCGGCGAGTCCGAGCCTCTCTTGGAGGTGGAGG AAGACATCAAGCAAACCGTCCTGGGCATGTTCAGCCTCAAGGGCGAGT TCGACGAGGCCGAGTCCGAGAGCTCGCCCTGGACCTCCAGAAGAACC TCCTGTCCATGCTCAGCGGCAACATGGAGGACAACGACGACGAGTACG AGGACATCGACGAGGAGTACGAGGAAGTGGAGGAAGACTACGAGGA AGAGAAGCTCGGCAAGCCAGTGGAGGTGGTCGTGGAGGACGCCACCG AGGAAGCCGTGGACGAGGTGGTGGGCGTCGTGCAAGAGCCAGAGGA AGAGGGCGCTGAGGAGAGCGACAAGGACACCGGCGAGGTGTCCGAG GAAGAGGTGGCCAAGGAAGCCGCCGACGAGGTCATGGAGGAAGAGA AGAAGGAAGAGGCCGGCGAGCCATCCGTGGTGGTGGAGGAGCCAAG CGTGGTCGTGGAGGAGCCATCCGTCGTGGTCAAGGAGCCTTCCGTGGT CGTGGAGGAGCCTAGCGTCGTCGTCGAGGAGCCTTCCGTCGTGGTGGA AGGAGCCAGCGTGGTCGTCGAGGAGCCAGCCTTCACCGTGGAGGAG CCTGCCTTCACCGTCGAGGAGCCAGCCATCACCGTGGAGGAGCCCGCT |

| No. | Protein Name | Protein Reference | Insert aa sequence (add M as start/His-tag at C-term) | Insert DNA sequence (Start from ATG to His-tag stop codon) |
|---|---|---|---|---|
| | | | AQGPAEAGPVGVVKEPEEEEESEE EGEEGEAGESEAGKSDAAESEVAE SEAGEPAEDQAGMDAKMKDELLGM LSEKMKAEGKDLDKLPPEVKNLLD MLAGNMEMDDEEEGEEGEDLG NEELDLQKNLLEMLSGKGGFNPNM LGNLKELEALQKSVPGLMGKAQGIS PAEIESLKSMFSGAFDSRGFKGMPQ MKLPAELQSIMMPKKEEKGKPQGA QAKAKVPAKAGVQKPKAQDIMPS RRIRDLFVLPKEIFGSLKNFKESALKF ANHIGLNLETIKKHLTTVKNFLLRVDA VVDKEIGNIIEAGKSPQNVVQANEGF LDKMKRLVNKYKIFSIPFFAGMGSFG Fhhhhhh (SEQ ID NO: 57) | ATCACGGTGGAGGAGCCAGTGTTCACCGTGGAAGAACCCGTGTTCACC GTGGAAGAGCCCGCCTTCACCGTTGAGGAGCCCGCCTTCACCGTAGAA GAGCCTGCCTTCACCGTTGAAGAACCAGCTACCACCGTGGAGGAGCTG GTGGAGGAAGTGCTCAAGGTGGCTGAGGAAGAGGTGGCTACCGAGG CTGTGGAGAAGGACGGCGAGGAAGCCGAGGAGCAAGTCACCGAGGA GAGCGTCGAGGAAGACGAGGAAGAGTCCGGCGAGGAAGAGGGCGA GGAGAGCGAGGAAGAGGAGACCGAGGAGTCCGCTGAGGAAGAGGTG GCGAAGGAGAGCGTGGAGGAAGAGGTGGCTAAGGAAGCCGAGGAGT CCGAGGAGAGCGGGGAGGAGAGCGCTGAGGAAGAGAAGGAGAAGG CCGAGGAGCCAGTGGCTCCAGTGGACGAGGTCCTGAAGGAAGGCATG CAGAAGATCGAGGAGAGCGTGAAGGAAGCCCTGGGCGTGGTCCAAG AGGCCGTGGACAAGGTCGCCGAGGAAGAGCAGACCGAGCAGGCTCA GGGCCCAGCTGAGGCTGGCCCAGTCGGCGTGGTCAAGGAGCCTGAGG AAGAGGAAGAGTCTGAGGAAGAGGGCGAGGAAGGCGAGGAAGGCG AGGAAGGCGAGGAAGAGGAAGAGGAAGAGAGTGAGGAAGAGGAGT CTGAGGAAGGCGAGTCCGAGGCTGGGGAGAGCGAGGCTGGCAAGAG CGACGCCGCCGAGTCCGAGGTGGCCGAGAGCGAGGCCGGCGAGCCG GCTGAGGACCAAGCTGGCATGGACGCCAAGATGAAGGACGAGCTCCT GGGCATGCTGAGCGAGAAGATGAAGGCCGAGGGCAAGGACCTGGAC AAGCTCCCACCAGAGGTCAAGAAGAACCTCCTGGACATGCTCGCCGGC AACATGGAGATGGACGATGAGGAAGAGGGAAGGCGAGGAAGAGGGC GAAGACCTGGGCAACGAGGAGCTCGACCTCCAGAAGAACCTCCTGGA GATGCTCTCCGGCAAGGGCGGCTTCAACCCAAACATGCTGGGCAACCT CAAGGAGCTGGAGGCCCTCCAAAAGAGCGTGCCAGGCCTGATGGGCA AGGCTCAGGGCATCTCCCCAGCTGAGATCGAGTCCCTCAAGAGCATGT TCTCCGGCGCCTTCGACAGCAGGGGCTTCAAGGGCATGCCACAGATGA AGCTGCCAGCCGAGCTCCAGTCCATCATGATGCCAAAGAAGGAAGAG AAGGGCAAGCCACAAGGCGCTCAAGCTAAGGCTAAGGTGCCAGCTAA GGCTGGCCAAGTCCAGAAGCCAAAGGCCCAGGACATCATGCCAAGCA GGCGCATCCGCGACCTGTTCGTGCTCCCAAAGGAGATCTTCGGCAGCC TGAAGAACTTCAAGGAGTCCGCCCTCAAGTTCGCCAACCACATCGGCCT GAACCTGGAGACCATCAAGAAGCACCTCACCACCGTGAAGAACTTCCT CCTGAGGGTCGACGCCGTGGTCGACAAGGAGATCGGCAACATCATCG AGGCCGGCAAGTCCCCACAAAACGTGGTCCAGGCCAACGAGGGCTTCC TGGACAAGATGAAGCGCCTCGTGAACAAGTACAAGATCTTCAGCATCC CATTCTTCGCCGGCATGGGCTCCTTCGGCTTCCACCATCACCACCATCAC TGA (SEQ ID NO: 58) |
| 30 | MSP7-like protein | PVX_082650 | mQLGIQKKKKNLEQDAMHALMKKLE SLYKLSATDNGEIFNKEIDALKKQID QLHQHGGGNEGESLGHLLESEAAD DSGKKTIFGVDEDDLDNYDADFIGQ SKGKIKGQADTTAVAKPPTGSGAGA HGSHSPPKPSVLVVPGKSGKEDSV ATLENGYESIHGEDEPREDSTSHDS PPALPVGRSEGDSSASGGGTEGQQ PDPASARGSQASGGRGGGDQTNT TQPAGGQQSSSAARSLQAPHAGDS QLPNAGGDPQSPAAAGHQQPPTSP PANNEGTTVTQESALAATPPKGTAD SNDAKIKYLDKLYDEVLTTSDNTSGI HVPDYHSKYNTIRQKYEYSMNPVEY EIVKNLFNVGFKNDGAASSDATPLV DVFKKALADEKFQAEFDNFVHGLYG FAKRHSYLSEARMKDNKLYSDLLKN AISLMSTLQVShhhhhh (SEQ ID NO: 59) | ATGCAGCTCGGCATCCAAAAGAAGAAGAAGAACCTGGAGCAGGACGC CATGCACGCCCTCATGAAGAAGCTGGAGAGCCTGTACAAGCTCTCCGC CACCGACAACGGCGAGATCTTCAACAAGGAGATCGACGCCCTGAAGA AGCAAATCGACCAGCTCCACCAACACGGCGGCGGAAACGAGGGCGAG AGCCTGGGCCACCTCCTGGAGAGCGAGGCTGCTGACGACTCCGGCAA GAAGACCATCTTCGGCGTGGACGAGGACGACCTGGACAACTACGACG CCGACTTCATCGGCCAGTCCAAGGGCAAGATCAAGGGCCAGGCTGACA CCACCGCTGTGGCTAAGCCACCAACCGGCAGCGGCGCTGGCGCTCACG GCAGCCACTCCCCACCAAAGCCATCCGTGCTCGTGGTCCCAGGCAAGA GCGGCAAGGAAGACTCCGTCGCCACCCTGGAGAACGGCTACGAGAGC ATCCACGGCGAGGACGAGCCCAGGGAGGACAGCACCTCCCACGACTC CCCACCAGCTCTCCCAGTGGGCCGCAGCGAGGGCGACTCCAGCGCTTC CGGCGGCGGCACCGAGGGCCAACAGCCAGACCCAGCTAGCGCCAGGG GCAGCCAGGCTTCCGGCGGCAGGGGCGGCGGCGACCAAACCAACACC ACCCAACCAGCTGGCGGCCAACAGTCCAGCTCCGCTGCTAGGAGCCTG CAGGCCCCACACGCTGGCGACAGCCAGCTCCCAAACGCCGGCGGCGA CCCACAATCCCCAGCTGCCGCCGGCCACCAACAGCCACCAACCTCCCCA CCAGCCAACAACGAGGGCACCACCGTGACCCAAGAGTCCGCTCTGGCT GCTACCCCACCAAAGGGCACCGCCGACTCCAACGACGCCAAGATCAAG TACCTGGACAAGCTCTACGACGAGGTGCTGACCACCAGCGACAACACC TCCGGCATCCACGTCCCAGACTACCACAGCAAGTACAACACCATCCGCC AAAAGTACGAGTACTCCATGAACCCAGTGGAGTACGAGATCGTCAAGA ACCTCTTCAACGTGGGCTTCAAGAACGACGGCGCTGCCAGCTCCGACG CTACCCCACTGGTGGACGTCTTCAAGAAGGCCCTCGCCGACGAGAAGT TCCAGGCCGAGTTCGACAACTTCGTCCACGGCCTGTACGGCTTCGCCAA GGAGCACAGCTACCTCTCCGAGGCCCGCATGAAGGACAACAAGCTGTA CAGCGACCTCCTGAAGAACGCCATCAGCCTGATGTCCACCCTCCAAGTG TCCCACCACCACCACCACCACTGA (SEQ ID NO: 60) |
| 31 | reticulocyte binding protein 2b (RBP2b) | PVX_094255 | mAAYNTVLQIYKYSDDIVRKQEKCE QLVKDGKDICLKFKSINEIKVMIQNSK GKESTLSAKVSHSFNKLSELNKIKCN DESYDAILETPSREELNKLRSTFKQE KDTIANQAKLSGYKTDFETHIGKLND LAKIVDNLKASETLPKNIEEKKTSINLI STKLETIEKEIESINSSFDQLLEKGKK CEMTKYKLVRDSLSTKINDHSAIIKD | ATGGCCGCCTACAACACCGTGCTCCAAATCTACAAGTACTCCGACGACA TCGTGAGGAAGCAAGAGAAGTGCGAGCAGCTGGTCAAGGACGGCAA GGACATCTGCCTGAAGTTCAAGTCCATCAACGAGATCAAGGTCATGATC CAGAACAGCAAGGGCAAGGAGTCCACCCTCAGCGCTAAGGTGTCCCA CAGCTTCAACAAGCTCAGCGAGCTGAACAAGATCAAGTGCAACGACGA GAGCTACGACGCCATCCTCGAAACCCCATCCAGGGAGGAGCTAAACAA GCTGCGCAGCACCTTCAAGCAAGAAGGACACCATCGCCAACCAGGC CAAGCTCTCCGGCTACAAGACCGACTTCGAGACGCACATCGGCAAGCT |

Appendix I-continued

| No. | Protein Name | Protein Reference | Insert aa sequence (add M as start/His-tag at C-term) | Insert DNA sequence (Start from ATG to His-tag stop codon) |
| --- | --- | --- | --- | --- |
| | | | NQKKATEYLTYIQNNHISIFKDIDMLN ENLGEKSVSRYAIAKIEEANDLSAQL TAAVSEYEAIANSIRKEFTNISDHTE MDTLENEAKMLKEHYDNLINKKNIIT ELHNKINLIKLLEIRATSDKYVDIAELL GEVVKDQKKKLQEAKNKLDTLKDHI AVKEKELINHDSSFTLVSIKAFDEIYD DIKYNVGQLHTLEVTNPDELKKGKT YEENVTHLLNRRETLONDLHNYEEK DKLKNTNIEMSNEENNQIRQTSEVIK KLESEFQNLLKIIQQSNTLCSNDNIK QFISDILKKVETIRERFVKNFPEREKY HQIEINYNEIKGIVKEVDTNPEISIFTE KINTYIRQKIRSAHHLEDAQKIKDIIED VTSNYRKIKSKLSQVNNALDRIKIKK SEMDTLFESLSKENANNYNSAKYFL VDSDKIIKHLEDQVSKMSSLISYAER EIKELEEKVYShhhhhh (SEQ ID NO: 61) | CAACGACCTGGCCAAGATCGTGGACAACCTCAAGGCCAGCGAGACGCT GCCAAAGAACATCGAGGAGAAGAAGACCTCCATCAACCTCATCAGCAC CAAGCTCGAAACCATCGAGAAGGAGATCGAGTCCATCAACTCCAGCTT CGACCAACTCCTGGAGAAGGGCAAGAAGTGCGAGATGACCAAGTACA AGCTCGTCAGGGACTCCCTGAGCACCAAGATCAACGACCACTCCGCCA TCATCAAGGACAACCAAAAGAAGGCCACCGAGTACCTCACCTACATCC AGAACAACCACATCAGCATCTTCAAGGACATCGACATGCTCAACGAGA ACCTGGGCGAGAAGTCCGTGAGCAGGTACGCCATCGCCAAGATCGAG GAAGCCAACGACCTCTCCGCTCAACTCACCGCTGCCGTCAGCGAGTAC GAGGCTATCGCCAACTCCATCCGCAAGGAGTTCACCAACATCTCCGACC ACACCGAGATGGACACCCTGGAGAACGAGGCCAAGATGCTGAAGGAG CACTACGACAACCTCATCAACAAGAAGAACATCATCACCGAGCTCCACA ACAAGATCAACCTGATCAAGCTCCTGGAGATCCGCGCCACCAGCGACA AGTATGTGGACATCGCCGAGCTCCTCGGGCGAGGTGGTCAAGGACCAA AAGAAGAAGCTGCAAGAGGCCAAGAACAAGCTCGACACCCTGAAGGA CCACATCGCCGTGAAGGAGAAGGAGCTGATCAACCACGACTCCAGCTT CACCCTCGTCAGCATCAAGGCCTTCGACGAGATCTACGACGACATCAA GTACAACGTGGGCCAACTCCACACCCTGGAGGTCACCAACTTCGACGA GCTCAAGAAGGGCAAGACCTACGAGGAGAAGGATAAGCTGAAGAACA CAGGCGCGAGACGCTCCAGAACGACCTGCACAACTACGAGGAGAAG GACAAGCTCAAGAACACCAACATCGAGATGTCCAACGAGGAGAACAA CCAAATCAGGCAGACCAGCGAGGTCATCAAGAAGCTGGAGTCCGAGT TCCAAAACCTCCTGAAGATCATCCAACAGTCCAACACCCTCTGCAGCAA CGATAACATCAAGCAGTTCATCAGCGACATCCTGAAGAAGGTGGAGAC GATCAGGGAGCGCTTCGTCAAGAACTTCCCAGAGCGCGAGAAGTACCA CCAAATCGAGATCAACTACAACGAGATCAAGGGCATCGTGAAGGAAG TGGACACCAACCCAGAGATCTCCATCTTCACCGAGAAGATCAACACCTA CATCAGGCAAAAGATCAGGAGCGCTCACCACCTGGAGGACGCTCAGA AGATCAAGGACATCATCGAGGACGTGACCTCCAACTACAGGAAGATCA AGTCCAAGCTGAGCCAAGTCAACAACGCCCTCGACCGCATCAAGATCA AGAAGAGCGAGATGGACACCCTCTTCGAGTCCCTGAGCAAGGAGAAC GCCAACAACTACAACAGCGCCAAGTACTTCCTGGTGGACTCCGACAAG ATCATCAAGCACCTGGAGGACCAAGTGTCCAAGATGTCCAGCCTGATC AGCTACGCCGAGCGCGAGATCAAGGAGCTGGAGGAGAAGGTCTACTC CCACCACCACCACCACCACTGA (SEQ ID NO: 62) |
| 32 | MSP3.3 [merozoite surface protein 3 beta (MSP3b)] | PVX_097680 | mNVATRGEIVNLKNPNLRNGWSMK NLSAQNEENIVHSDGSDDVTDKEED GEVLEGQKGSPKKSAEQKVHAQEE VNKESLKSKAQNAKAEAEKAAKAE SAKENTLDALEKVNVPTELNNEKNF AESAATEAKKQEKISTEAAEEVKEIE VDGQLEKLKNEEEKTAKKARKQEIK TEIAEQAAKAQAAKTEAETAQKDAT TAKDEAIKETGKPKSQNTTKAVTMA TEEEKKTKDEAQTASEKAGKTAEEA QKEVGKETADDDKEVSQLEEEIKEL ERILKIVKDLASEASSASDNAKKAKL KTQIAAEVVKAEKARIEAEEAEKEAG EAKTKTEATEKEVLKISDESKAAKVK KAVEKAKEAEKQAKSEAEKAKGMA DDAGGKGTTNLEDVLTKLSEVLTSV KSLASNAEVASKNAKKEMTKAQIAA EVAKAEKAKIEAENAKLLADTASKAA ENIAKSSKAAKIANNVSTIAAEKSKVA TEAADEAAKALDETENPESKIAEVTE KATKATKAVNAAEEAKKEKAKAEVAVEV AHAEVAKEKAKQEAKEAAKQVADKS KLEKAIQAADKASEKANEASKLAEEA LSNLESLEKETGEIVEKVNAIEQKVQ TAKNAAIEAHKEKTKAEIAVEVAKAE EAKKEADNAKVAAEKAKETAEKIAKT SKSTEKITEEVRKATEFAKTAGDETT LAATKAESEIPSEEKNQKELLDSIKQ KAESAFQASQEAIKAKTEAENFLEIA KEVPKAEAAKEEAQKAATAAEEAKT EVLKIAEEVNKSDASESEKKKIETAA NETAGEEAKKAATFAKEAADAAKDTN KAVTLAVAKEKVEKALKAAKEAAKKA NEKASYALIRTKKQYALEPLEITSEA GYNITEKEEQVKEEIEEQDDKASEE | ATGAACGTCGCCACCAGGGGCGAGATCGTGAACCTGAAGAACCCCAA CCTCCGCAACGGCTGGAGCATGAAGAACCTGTCCGCCCAAAACGAGGA GAACATCGTCCACTCCGACGGCAGCGACGACGTGACCGACAAGGAAG AGGACGGCGAGGTGCTGGAGGGCCAGAAGGGCAGCCCCAAAGAAGTC GCCGAGCAAAAGGTCCACGCCCAAGAGGAAGTGAACAAGGAGTCCC TCAAGAGCAAGGCCCAAAACGCCAAGGCTGAGGCTGAGAAGGCTGCT AAGGCTGCCGAGTCCGCCAAGGAGAACACCCTCGACGCCCTGGAGAA GGTGAACGTCCCAACCGAGCTCAACAACGAGAAGAACTTCGCTGAGA GCGCTGCTACCGAGGCCAAGAAGCAGGAGAAGATCTCCACCGAGGCC GCCGAGGAAGTGAAGGAGATCGAGGTGGACGGCCAACTGGAGAAGC TGAAGAACGAGGAAGAGAAGACCGCCAAGAAGGCCAGGAAGCAGGA GATCAAGACCGAGATCGCTGAGCAAGCTGCTAAGGCTCAGGCTGCTAA GACCGAGGCCGAGACGGCCCAAAAGGACGCCACCACCGCCAAGGACG AGGCCATCAAGGAGACGGGCAAGCCCAAGAGCCAGAACACCACCAAG GCCGTCACCATGGCCACCGAGGAAGAAGAAGACCAAGGACGAGGC TCAAACCGCTTCCGAGAAGGCTGGCAAGACCGCTGAGGAAGCCCAGA AGGAAGTGGGCAAGGAGACGGCCGACGACGACAAGGAAGTGTCCCA ACTCGAAGAGGAGATCAAGGAGCTGGAGAGGATCCTCAAGATCGTGA AGGACCTGGCTAGCGAGGCCTCCAGCGCTTCCGACAACGCCAAGAAG GCCAAGCTCAAGACCCAAATCGCTGCTGAGGTGGTCAAGGCTGAGAA GGCTAGGATCGAGGCTGAGGAAGCCGAGAAGGAAGCCGGCGAGGCT AAGACCAAGACCGAGGCTACCGAGAAGGAAGTGCTGAAGATCTCCGA CGAGAGCAAGGCCGCCAAGGTCAAGAAGGCCGTGGAGAAGGCCAAG GAAGCCGAGAAGCAAGCCAAGTCCGAGGCTGAGAAGGCTAAGGGCAT GGCTGACGACGCCGGCGGCAAGGGCACCACCAACCTGGAGGACGTGC TCACCAAGCTGAGCGAGGTCCTGACCTCCGTGAAGTCCCTGGCTTCAA CGCTGAGGTGGCTTCCAAGAACGCCAAGAAGGAGATGACCAAGGCTC AGATCGCTGCTGAGGTGGCTAAGGCTGAGAAGGCCAAGATCGAGGCC GAGAACGCCAAGCTGCTGGCTGACACCGCTAGCAAGGCTGCCGAGAA CATCGCCAAGTCCAGCAAGGCCGCCAAGATCGCCAACAACGTCAGCAC CATCGCCGCCGAGAAGTCCAAGGTGGCTACCGAGGCTGCTGACGAGG CTGCCAAGGCCCTCGACGAGACGGAGAACCCAGAGTCCAAGATCGCC GAGGTGACCGAGAAGGCTACCAAGGCTGTGAACGCTGCTGAGGAAGC CAAGAAGGAAGGCAAGGCTGAGGTGGCTGTGGAGGTGGCTCAC GCTGAGGTGGCTAAGGAGAAGGCCAAGAGGGCCAAGGAAGCCGCCA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | EEEDTQQIDQTQIDEVDISVDNEEEE EGAAEEQIEGEKDTPTKEAKEEQTS GEKILDDKEAHKTLAEKFKDSNTAKT GGVEFLETLISDVGEDTLKNLQQDL HQYFKGKhhhhhh (SEQ ID NO: 63) | AGCAGGTGGCCGACAAGAGCAAGCTGGAGAAGGCCATCCAAGCCGCC GACAAGGCCAGCGAGAAGGCCAACGAGGCCTCCAAGCTCGCCGAGGA AGCCCTCAGCAACCTGGAGTCCCTGGAGAAGGAGACGGGCGAGATCG TCGAGAAGGTGAACGCCATCGAGCAAAAGGTGCAGACCGCCAAGAAC GCCGCCATCGAGGCCCACAAGGAGAAGACCAAGGCTGAGATCGCTGT GGAGGTCGCCAAGGCCGAGGAAGCCAAGAAGGAAGCCGACAACGCC AAGGTGGCTGCTGAGAAGGCTAAGGAGACGGCCGAGAAGATCGCCAA GACCTCCAAGAGCACCGAGAAGATCACCGAGGAAGTGAGGAAGGCTA CCGAGTTCGCTAAGACCGCTGGCGACGAGACGACCCTGGCTGCTACCA AGGCTGAGAGCGAGATCCCATCCGAGGAGAAGAACCAAAAGGAGCTC CTGGACAGCATCAAGCAGAAGGCCGAGAGCGCCTTCCAAGCCTCCCAA GAGGCCATCAAGGCCAAGACCGAGGCCGAGAACTTCCTGGAGATCGC CAAGGAAGTGCCAAAGGCCGAGGCCGCCAAGGAAGAGGCCCAAAAG GCTGCTACGGCCGCTGAGGAAGCCAAGACCGAGGTCCTCAAGATCGCC GAGGAAGTGAACAAGTCCGACGCCTCCGAGAGCGAGAAGAAGAAGAT CGAGACGGCTGCTAACGACGGCTGGCGAGGCCGAGAAGGCCGCTA CCTTCGCTAAGGAAGCCGCTGACGCTGCTAAGGACACCAACAAGGCCG TCACCCTGGCCGTGGCCAAGGAGAAGGTCGAGAAGGCCCTCAAGGCC GCCAAGGAAGCCAAGAAGGCCAACGAGAAGGCCAGCTACGCCCTGAT CCGCACCAAGAAGCAGTACGCCCTGGAGCCACTGGAGATCACCTCCGA GGCCGGCTACAACATCACCGAGAAGGAAGAGCAAGTGAAGGAAGAG ATCGAGGAGCAGGACGACAAGGCCAGCGAGGAAGAGGAAGAGGACA CCCAACAGATCGACCAAACCCAGATCGACGAGGTCGACATCTCCGTGG ACAACGAGGAAGAGGAAGAGGGCGCTGCTGAGGAGCAAATCGAGGG CGAGAAGGACACCCCAACCAAGGAAGCCAAGGAAGAGCAGACCTCCG GCGAGAAGATCCTGGACGACAAGGAAGCCCACAAGACCCTCGCCGAG AAGTTCAAGGACAGCAACACCGCTAAGACCGGCGGCGTCGAGTTCCTC GAAACCCTCATCTCCGACGTGGGCGAGGACACCCTGAAGAACCTCCAA CAGGACCTCCACCAGTACTTCAAGGGCAAGCACCACCACCACCACACT GA (SEQ ID NO: 64) |
| 33 | hypothetical protein, conserved | PVX_001000 | mNNYGKLKHGKWDDGSYSERTRW RMLSGDDHDDLLPSCDSPGGRNDE HQVNKEVSRTAPSEKVKVVDKETG ESMLVDVGESGGKSSPGVAEESGP SLRGRDVRDVRVDQETRETLQGGA TNRRDLTQHGEEETGDDSKRAKQD DEAGVRSMLNDTVTAIKDNGSNLLR SVIGQINFVQGSAELLKVANEEERQ PSGGSVLSKEGEEATPGDFLGGNN PNGGEKGELPNGTKNDVMIKGYAN VLLNEGKHVLVGNVRNFLSRVFNLIV REKIMTRMCHRGGEASIERSGEPVG ERSGEPTGERSGDPTGERSGDPTG ERSGEPTGERSGEPTGERSGEPTA ERSGEPTAERSDEPTAERSDEPTAD PKGDPTNCRLPKRSATKFYQSEDLY NYYSSLEEMLKGRGIRWKTDRVSR YFTFSPSKKIKDNFEEVMNNKVFIES VRSILFDSHKKNKKAVFSSFAVVVET LFSLIKEEKVIADMYSYVKLFFQDLDI LNLKVLHFLSSSSTENTQFVGPPDL SLTNFEYILAKIYSRSVLANILSPKMN HSDSKKLSKLLTRRENNLKFSFLEG VKMVHSAIPSEGVSAVVLGNAGGQ VNVPIPGADDTLCKFIPIRKKLLYERL SVTRKVAEEVILDYLFRLLLRKVHEY VLEhhhhhh (SEQ ID NO: 65) | ATGAACAACTACGGCAAGCTCAAGCACGGCAAGTGGGACGACGGCTC CTACAGCGAGAGGACCAGGTGGAGGATGCTGTCCGGCGACGACCACG ACGACCTCCTCCCATCCTGCGACAGCCCAGGCGGCAGGAACGACGAGC ACCAAGTCAACAAGGAAGTGTCCAGGACCGCCCCAAGCGAGAAGGTG AAGGTGGTCGACAAGGAGACCGGCGAGTCCATGCTGGTGGACGTGGG CGAGAGCGGCGGCAAGTCCTCCCCAGGCGTGGCTGAGGAGTCCGGCC CAAGCCTCGCCGGCAGGGACGTGCGCGACGTCAGGGTGGACCAAGAG ACCCGCGAGACCCTGCAGGGCGGCGCCACCAACAGGCGCGACCTCAC CCAACACGGCGAGGAAGAGACCGGCGACGACAGCAAGCGCGCTAAGC AGGACGAGGCTGGCGTCAGGTCCATGCTCAACGACACCGTGACC GCCATCAAGGACAACGGCTCCAACCTCCTGCGCAGCGTCATCGGCCAA ATCAACTTCGTGCAAGGCAGCGCTGAGCTCCTGAAGGTCGCCAACGAG GAAGAGCGCCAGCCATCCGGCGGCAGCGTGCTGTCCAAGGAAGGCGA GGAAGCCACCCCAGGCGACTTCCTCGGCGGCAACAACCCGAACGGCC AGCGAAAGGGCGAGCTGCCAAACGGCACCAAGAACGACGTCATGATC AAGGGCTACGCCAACGTCCTCCTGAACGAGGGCAAGCACGTCCTCGTG GGCAACGTCCGCAACTTCCTGTCCAGGGTGTTCAACCTCATCGTCAGGG AGAAGATCATGACCAGGATGTGCCACAGGGGCGGCGAGGCTAGCATC GAGAGGTCCGGCGAGCCAGTGGGGGAGCGCTCCGGCGAGCCAACCG GCGAGAGGAGCGGCGACCCAACCGGCGAGAGGTCTGGCGACCCTACG GGGGAGAGGAGCGGGGAGCCTACCGGCGAGCGCAGCGGGGAGCCTA CGGGCGAGAGGTCCGGGGAGCCTACCGCTGAGAGAAGCGGCGAGCC AACCGCTGAGAGGAGCGATGAGCCTACCGCTGAGAGGTCCGACGAGC CAACCGCTGACCCAAAGGGCGACCCAACCAACTGCCGCCTCCCAAAGA GGTCCGCCACCAAGTTCTACCAAAGCGAGGACCTGTACAACTACTACTC CAGCCTGGAGGAGATGCTCAAGGGCAGGGGCATCAGGTGGAAGACC GACCGCGTCAGCAGGTACTTCACCTTCTCCCCAAGCAAGAAGATCAAG GACAACTTCGAGGAAGTGATGAACAACAAGGTCTTCATCGAGAGCGTG CGCTCCATCCTCTTCGACTCCCACAAGAAGAACAAGAAGGCCGTGTTCT CCAGCTTCGCCGTGGTCGTGGAGACCCTGTTCAGCCTCATCAAGGAAG AGAAGGTCATCGCCGACATGTACTCCTACGTGAAGCTGTTCTTCCAAGA CCTCGACATCCTGAACCTCAAGGTCCTGCACTTCCTCTCCAGCTCCAGCA CCGAGAACACCCAGTTCGTGGGCCCACCAGACCTGAGCCTCACCAACT TCGAGTACATCCTCGCCAAGATCTACTCCCGCAGCGTCCTGGCCAACAT CCTCAGCCCAAAGATGAACCACTCCGACAGCAAGAAGCTGTCCAAGCT CCTGACCCGCCGCGAGAACAACCTGAAGTTCTCCTTCCTGGAGGGCGT CAAGATGGTGCACAGCGCTATCCCATCCGAGGGCGTGAGCGCTGTGGT GCTGGGCAACGCTGGCGGCCAGGTCAACGTGCCAATCCCAGGCGCCG ACGACACCCTCTGCAAGTTCATCCCAATCAGGAAGAAGCTCCTGTACGA GCGCCTGTCCGTCACCAGGAAGGTGGCCGAGGAAGTGATCCTGGACT ACCTCTTCCGCCTCCTGCTCAGGAAGGTGCACGAGTATGTGCTGGAGC ACCATCACCACCATCACTGA (SEQ ID NO: 66) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 34 | merozoite surface protein 8 (GPI-anchored, C24) | PVX_097625 | mGNVSPPNFNDNRVGNNGNKGN GNDNDVPSFIGGNNNNVNGNNDDN IFNKNGKDVTRNDGDAKDGENRNN KKNENGSGSNENNSIANADNGSGK SDANANQIDEDGNKMDEASLKKILKI VDEMENIQGLLDGDYSILDKYSVKLV DEDDGETNKRKIIGEYDLKMLKNILL FREKISRVCENKYNKNLPVLLKKCS NVDDPKLSKSREKIKKGLAKNNMSIE DFVVGLLEDLFEKINEHFIKDDSFDL SDYLADFELINYIIMHETSELIDELLNII ESMNFRLESGSLEKMVKSAESGMN LNCKMKEDIIHLLKKSSAKFFKIEIDR KTKMIYPVQATHKGANMKQLALSFL QKNNVCEHKKCPLNSNCYVINGEEV CRCLPGFSDVKIDNVMNCVRDDTLD CSNNNGGCDVNATCTLIDKKIVCEC KDNFEGDGIYChhhhhh (SEQ ID NO: 67) | ATGGGCAACGTGTCCCCACCAAACTTCAACGACAACAGGGTCAACGGC AACAACGGCAACAAGGGCAACGGCAACGACAACGACGTGCCAAGCTT CATCGGCGGCAACAACAACAACGTCAACGGCAACAACGACGACAACAT CTTCAACAAGAACGGCAAGGACGTGACCCGCAACGACGGCGACGCTA AGGACGGCGAGAACCGCAACAACAAGAAGAACGAGAACGGCTCCGGC AGCAACGAGAACAACTCCATCGCCAACGCTGACAACGGCTCCGGCAG AGCGACGCCAACGCCAACCAAATCGACGAGGACGGCAACAAGATGGA CGAGGCCAGCCTCAAGAAGATCCTGAAGATCGTGGACGAGATGGAGA ACATCCAGGGCCTCCTGGACGGCGACTACTCCATCCTCGACAAGTACA GCGTGAAGCTGGTCGACGAGGACGACGGCGAGACGAACAAGAGGAA GATCATCGGCGAGTACGACCTCAAGATGCTGAAGAACATCCTCCTGTTC AGGGAGAAGATCTCCCGCGTCTGCGAGAACAAGTACAACAAGAACCTC CCAGTGCTCCTGAAGAAGTGCAGCAACGTCGACGACCCAAAGCTCTCC AAGAGCCGCGAGAAGATCAAGAAGGGCCTGGCTAAGAACAACATGTC CATCGAGGACTTCGTGGTCGGCCTCCTGGAGGACCTGTTCGAGAAGAT CAACGAGCACTTCATCAAGGACGACTCCTTCGACCTCAGCGACTACCTG GCCGACTTCGAGCTCATCAACTACATCATCATGCACGAGACCGTCCGAGC TGATCGACGAGCTCCTGAACATCATCGAGAGCATGAACTTCAGGCTGG AGTCCGGCAGCCTGGAGAAGATGGTGAAGTCCGCCGAGAGCGGCATG AACCTCAACTGCAAGATGAAGGAAGACATCATCCACCTCCTGAAGAAG TCCAGCGCCAAGTTCTTCAAGATCGAGATCGACCGCAAGACCAAGATG ATCTACCCAGTGCAAGCCACCCACAAGGGCGCCAACATGAAGCAACTC GCCCTGTCCTTCCTCCAGAAGAACAACGTCTGCGAGCACAAGAAGTGC CCACTGAACAGCAACTGCTACGTGATCAACGGCGAGGAAGTGTGCAG GTGCCTCCCAGGCTTCTCCGACGTCAAGATCGACAACGTGATGAACTG CGTCCGCGACGACACCCTCGACTGCAGCAACAACAACGGCGGCTGCGA CGTGAACGCTACCTGCACCCTGATCGACAAGAAGATCGTCTGCGAGTG CAAGGACAACTTCGAGGGCGACGGCATCTACTGCCACCACCACCACCA CCACTGA (SEQ ID NO: 68) |
| 35 | adenylate kinase-like protein 2, putative (AKLP2) | PVX_087110 | METLLDSETLKNYEKETNEYIRKKKV EKLFDVILKNVLVNKPENVYLYIYKNI YSFLLNKIFVIGPPLLKITPTLCSAIAS CFSYYHLSASHMIESYTTGEVDDAA ESSTSKKLVSDDLICSIVKSNINQLNA KQKRGYVVEGFPGTNLQADSCLRH LPSYVFVLYADEEYIYDKYEQENNV KIRSDMNSQTFDENTQLFEVAEFNT NPLKDEVKVYLRNhhhhhh (SEQ ID NO: 69) | ATGGAGACGCTCCTGGACTCCGAGACGCTCAAGAACTACGAGAAGGA GACGAACGAGTACATCAGGAAGAAGAAGGTGGAGAAGCTCTTCGACG TCATCCTCAAGAACGTGCTGGTCAACAAGCCAGAGAACGTGTACCTGT ACATCTACAAGAACATCTACAGCTTCCTCCTGAACAAGATCTTCGTCATC GGCCCACCACTCCTGAAGATCACCCCAACCCTCTGCTCCGCCATCGCCT CCTGCTTCAGCTACTACCACCTGTCCGCGAGCCACATGATCGAGAGTA CACCACCGGCGAGGTGGACGACGCTGCTGAGTCCAGCACCTCCAAGAA GCTCGTGAGCGACGACCTGATCTGCTCCATCGTCAAGAGCAACATCAA CCAACTCAACGCCAAGCAGAAGAGGGGCTACGTGGTCGAGGGCTTCC CAGGCACCAACCTCCAGGCTGACTCCTGCCTCAGGCACCTGCCAAGCTA CGTGTTCGTCCTGTACGCCGACGAGGAGTACATCTACGACAAGTACGA GCAGGAGAACAACGTGAAGATCAGGTCCGACATGAACAGCCAAACCT TCGACGAGAACACCCAGCTGTTCGAGGTCGCCGAGTTCAACACCAACC CACTCAAGGACGAGGTGAAGGTCTACCTGCGCAACCACCACCACCACC ACCACTGA (SEQ ID NO: 70) |
| 36 | MSP7-like protein | PVX_082670 | mKPGVEKKKKLEEDVIGILRRKLESL QKRSLTNSDGKLKKEIELVKKQIQEL QKYEKGEAGKKVDATLGEEPGVES AEEQPLSVEEAGDTQDEDRLDELE GVEDFEEENLEQSEQVEEAEVVEEA EEEEAGDAEEEQPAEAEEDGSLLEEA PNSVERKAEGAIAEFEEADVEEGAE ADEGVETDEGADADEASLGSFDLE GELIEEDLQESFDLEGEQEEEDLQE GFKSEEEANQGGQLPREIPPHGEEA VEPPLRGNKPSMEYVGNLHSDVGP TEGSANQISPPSVDEKGKEDGDKYK SASQDGGNSVGINNFGGCFQGGNS NGICPLDIFKKVLEDENFLQEFDSFIH NLYGSSKNNTPWGGDKMGNENLY MDLFTNALSFLNTIEVIhhhhhh (SEQ ID NO: 71) | ATGAAGCCAGGCGTGGAGAAGAAGAAGAAGCTCGAAGAGGACGTCA TCGGCATCCTGCGCAGGAAGCTGGAGTCCCTGCAAAAGAGGTCCCTCA CCAACAGCGACGGCAAGCTCAAGAAGGAGATCGAGCTGGTCAAGAAG CAAATCCAGGAGCTGCAGAAGTACGAGAAGGGCGAGGCTGGCAAGA AGGTGGACGCTACCCTGGGCGAGGAGCCGGGCGTGGAGTCCGCTGAG GAGCAACCACTGAGCGTGGAGGAAGCCGGCGACACCCAGGACGAGG ACAGGCTCGACGAGCTGGAGGGCGTCGAGGACTTCGAGGAAGAGAAC CTGGAGCAAAGCGAGCAGGTGGAGGAAGCCGAGGTGGTGGAGGAAG CCGAGGAAGAGGCCGGCGACGCTGAGGAAGAGCAACCGGCTGAGGC TGAGGAAGAGCAACCGGCTGAGGCCGAGGAAGACGGCTCCCTCCTGG AGGAAGCGCCTAACTCCGTAGAGCGCAAGGCCGAGGGCGCCATAGCT GAGTTCGAGGAAGCCGACGTCGAG GAAGGCGCCGAGGCCGACGAGGGCGTGGAGCGGACGAGGGCGCTG ACGCTGACGAGGCTTCCCTGGGCAGCTTCGACCTGGAGGGCGAGCTG ATCGAGGAAGACCTCCAGGAGTCTTTCGACCTGGAGGGGGAGCAAGA GGAAGAGGACCTCCAAGAGGGCTTCAAGAGCGAGGAAGAGGCCAAC CAAGGCGGCCAGCTGCCAAGGGAGATCCCACCACACGGCGAGGAAGC CGTGGAGCCACCACTCCGCGGCAACAAGCCATCCATGGAGTATGTGGG CAACCTGCACAGCGACGTGGGCCCAACCGAGGGCAGCGCCAACCAAA TCTCCCCACCAAGCGTCGACGAGAAGGGCAAGGAAGACGGCGACAAG TACAAGTCCGCCGCCAGCCAAGACGGCGGAAACTCCGTGGGCATCAACAAC TTCGGCGGATGCTTCCAGGGCGGCAACAGCAACGGCATCTGCCCACTC GACATCTTCAAGAAGGTCCTGGAGGACGAGAACTTCCTGCAGGAGTTC GACTCCTTCATCCACAACCTGTACGGCTCCAGCAAGAACAACACCCCAT GGGGCGGCGACAAGATGGGCAACGAGAACCTCTACATGGACCTGTTC ACCAACGCCCTCAGCTTCCTGAACACCATCGAGGTCATCCACCACCACC ACCACCACTGA (SEQ ID NO: 72) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 37 | high molecular weight rhoptry protein-2, putative | PVX_099930 | mELSHSLSVKNAPDASALNIEVEKD KKKICKNAFQYINVAELLSPREEETY VQKCEEVLDTIKNDSPDESAEAEINE FILSLLHARSKYTIINDSDEEVLSKLL RSINGSISEEAALKRAKQLITFNRFIK DKAKVKNVQEMLVISSKADDFMNEP KQKMLQKIIDSFELYNDYLVILGSNIN IAKRYSSETFLSIKNEKFCSDHIHLCQ KFYEQSIIYYRLKVIFDNLVTYVDQNS KHFKKEKLLELLNMDYRVNRESKVH ENYVLEDETVIPTMRITDIYDQDRLIV EVVQDGNSKLMHGRDIEKREISERYI VTVKNLRKDLNDEGLYADLMKTVKN YVLSITQIDNDISNLVRELDHEDVEKh hhhhh (SEQ ID NO: 73) | ATGGAGCTCTCCCACAGCCTGTCCGTGAAGAACGCTCCAGACGCTAGC GCTCTCAACATCGAGGTCGAGAAGGACAAGAAGAAGATCTGCAAGAA CGCCTTCCAATACATCAACGTCGCCGAGCTCCTGTCCCCAAGGGAGGA AGAGACTTACGTGCAGAAGTGCGAGGAAGTGCTGGACACCATCAAGA ACGACAGCCCAGACGAGTCCGCTGAGGCTGAGATCAACGAGTTCATCC TCAGCCTTCCTGCACGCCCGCTCCAAGTACACCATCATCAACGACAGCGA CGAGGAAGTGCTGAGCAAGCTCCTGAGGTCCATCAACGGCAGCATCTC CGAGGAAGCCGCTCTCAAGAGGGCTAAGCAACTGATCACCTTCAACAG GTTCATCAAGGACAAGGCCAAGGTGAAGAACGTCCAGGAGATGCTCG TCATCTCCAGCAAGGCCGACGACTTCATGAACGAGCCAAAGCAAAAGA TGCTCCAGAAGATCATCGACAGCTTCGAGCTGTACAACGACTACCTCGT GATCCTGGGCTCCAACATCAACATCGCCAAGCGCTACTCCAGCGAGAC GTTCCTCAGCATCAAGAACGAGAAGTTCTGCTCCGACCACATCCACCTG TGCCAAAGTTCTACGAGCAGAGCATCATCTACTACAGGCTCAAGGTC ATCTTCGACAACCTGGTGACCTACGTCGACCAAAACTCCAAGCACTTCA AGAAGGAGAAGCTCCTGGAGCTCCTGAACATGGACTACAGGGTGAAC CGCGAGTCCAAGGTGCACGAGAACTACGTCCTGGAGGACGAGACTGT GATCCCAACCATGCGCATCACCGACATCTACGACCAAGACAGGCTCATC GTGGAGGTGGTCCAGGACGGCAACAGCAAGCTGATGCACGGCAGGG ACATCGAGAAGCGCGAGATCTCCGAGAGGTACATCGTGACCGTCAAG AACCTCCGCAAGGACCTGAACGACGAGGGCCTCTACGCCGACCTGATG AAGACCGTGAAGAACTACGTCCTCAGCATCACCCAGATCGACAACGAC ATCTCCAACCTCGTGAGGGAGCTGGACCACGAGGACGTCGAGAAGCA CCACCACCACCACCACTGA (SEQ ID NO: 74) |
| 38 | IMP-specific 5'-nucleotidase | PVX_084340 | MEKLDIPPHEMYEDMQQAFREQDK YDFLAISDGSVINSYMKKNVVDWNN RYSYNQLKNKDSLIMFLVDIFRSLFL SNCIDKNIDNVLSSIEEMFTDHYYNP MHSRLKYLIDDVGIFFTKLPITKAFHT YNKKYRITKRLYAPPTFNEVRHILNL AQILSLEDGLDLLTFDADETLYPDGY DFHDEVLASYISSLLKKMNIAIVTAAS YSNDAEKYQKRLENLLRYFSKHNIE DGSYENFYVMGGESNYLFKCNEDA NLYSVPEEEWYHYKKYVNKETVEQI LDISQKCLQQVITDFKLCAQIQRKEK SIGLVPNKIPSANNQKEQKNYMIKYE VLEEAVIRVKKEIVKNKITAPYCAFNG GQDLWVDIGNKAEGLIILQKLLKIEKK KCCHIGDQFLHSGNDFPTRFCSLTL WISNPQETKACLKSIMNLNMKSFIPE VLYENEhhhhhh (SEQ ID NO: 75) | ATGGAGAAGCTCGACATCCCACCACACGAGATGTACGAGGACATGCAA CAGGCCTTCAGGGAGCAAGACAAGTACGACTTCCTGGCCATCTCCGAC GGCAGCGTGATCAACTCCTACATGAAGAAGAACGTGGTCGACTGGAAC AACAGGTACTCCTACAACCAGCTCAAGAACAAGGACAGCCTCATCATG TTCCTGGTGGACATCTTCCGCTCCCTCTTCCTGAGCAACTGCATCGACA AGAACATCGACAACGTCCTCTCCAGCATCGAGGAGATGTTCACCGACC ACTACTACAACCCAATGCACAGCAGGCTCAAGTACCTGATCGACGACG TGGGCATCTTCTTCACCAAGCTCCCAATCACCAAGGCCTTCCACACCTAC AACAAGAAGTACAGGATCACCAAGCGCCTGTACGCCCCACCAACCTTC AACGAGGTCCGCCACATCCTCAACCTGGCCCAAATCCTCTCCCTGGAGG ACGGCCTCGACCTCCTGACCTTCGACGCCGACGAGACGCTGTACCCAG ACGGCTACGACTTCCACGACGAGGTGCTCGCCAGCTACATCTCCAGCCT CCTGAAGAAGATGAACATCGCCATCGTCACCGCCGCCTCCTACAGCAA CGACGCCGAGAAGTACCAGAAGAGGCTGGAGAACCTCCTGCGCTACTT CTCCAAGCACAACATCGAGGACGGCAGCTACGAGAACTTCTACGTGAT GGGCGGCGAGTCCAACTACCTCTTCAAGTGCAACGAGGACGCCAACCT GTACAGCGTCCCAGAGGAAGAGTGGTACCACTACAAGAAGTATGTGA ACAAGGAGACGGTCGAGCAAATCCTCGACATCTCCCAGAAGTGCCTGC AACAAGTGATCACCGACTTCAAGCTCTGCGCCCAAATCCAGAGGAAGG AGAAGTCCATCGGCCTGGTCCCAAACAAGATCCCAAGCGCCAACAACC AAAAGGAGCAGAAGAACTACATGATCAAGTACGAGGTGCTCGAAGAG GCCGTGATCCGCGTCAAGAAGGAGATCGTCAAGAACAAGATCACCGCT CCATACTGCGCCTTCAACGGCGGCCAAGACCTGTGGGTGGACATCGGC AACAAGGCCGAGGGCCTCATCATCCTGCAAAAGCTCCTGAAGATCGAG AAGAAGTGCTGCCACATCGGCGACCAGTTCCTCCACAGCGGCAAC GACTTCCCAACCCGCTTCTGCTCCCTCACCCTGTGGATCAGCAACCCAC AGGAGACGAAGGCCTGCCTCAAGTCCATCATGAACCTGAACATGAAGA GCTTCATCCCAGAGGTCCTCTACGAGAACGAGCACCACCACCACCACCA CTGA (SEQ ID NO: 76) |
| 39 | subpellicular microtubule protein 1, putative (SPM1) | PVX_098915 | MEIIAEKPKVKFNFASEEYKNCDSSD YSECAEDYGRPNGKDYFYANRILSL DRNSEQRRKESPSKRPGLCVDEICT CGFHRCPKIVKSLPFDGESNYRSEF GPKPLPELPPRQEAKLTRSLPFEGE SNYRSEFGPKPLPELPPRVEQKPPK SLPFDGESNYRSEFGPKPLPELPPR VEQKPPKSLPFDGESNYRSEFGPKP LPELPPRVEQKPPKSLPFEGESNYR SEFGPKPLPELPPRVEQKPPKSLPF EGESNYRSEFGPKALPELPPRVEQK PPKSLPEGESNYRSEFGPKPLPAL PPRVETKLVKSLPFEGESNYRSEFG PKPLPELPPRVEQKPPKSLPFEGES NYRSEFGPKPLPALPPRVVTKLVKS LPFEGESNYRSEFGPKPLPEIPPRV EQKPPKSLPFEGESNYRSEFGPKPL PELPPRVEQKPPKSLPFEGESNYRS EFGPKQLPELPPRQEAKLTRSLPFE | ATGGAGATCATCGCCGAGAAGCCAAAGGTCAAGTTCAACTTCGCCTCC GAGGAGTACAAGAACTGCGACTCCAGCGACTACTCCGAGTGCGCTGA GGACTACGGCAGGCCAAACGGCAAGGACTACTTCTACGCCAACAGGAT CCTCTCCCTGGACCGCAACAGCGAGCAGAGGCGCAAGGAGTCCCCAA GCAAGAGGCCAGGCCTCTGCGTGGACGAGATCTGCACCTGCGGCTTCC ACCGCTGCCCAAAGATCGTCAAGTCCCTGCCATTCGACGGCGAGTCCA ACTACCGCAGCGAGTTCGGCCCAAAGCCACTCCCAGAGCTGCCACCA GGCAAGAGGCCAAGCTCACCCGCAGCCTGCCATTCGAGGGCGAGTCC AACTACAGGTCCGAGTTCGGGCCTAAGCCTCTGCCTGAGCTGCCACCA CGCGTGGAGCAAAAGCCACCAAAGTCCCTCCCTTTCGATGGCGAGAGC AACTACAGGAGTGAATTCGGGCCTAAGCCTGCTGCCTGAGCTGCCACCA CGCGTCGAGCAGAAGCCACCAAAGAGCCTCCCTTTCGATGGCGAGAGC AACTACAGGAGCGAATTTGGGCCTAAGCCGCTGCCGGAACTGCCACCA CGCGTGGAACAGAAGCCACCAAAGTCCCTTCCGTTTGAGGGGGAGTC CAACTACAGGAGTGAGTTTGGGCCTAAGCCGTTGCCTGAACTGCCACC ACGCGTCGAACAGAAACACCAAAAGCCTCCCTTTCGAGGGCGAGAG CAACTACCGCTCCGAGTTCGGCCCAAAGCCTCTGCCGGAGCTGCCACC ACGCGTGGAACAGAAACCACCAAAGAGCCTCCCCTTCGAGGGGGAGA GCAATTATCGCTCTGAGTTCGGGCCAAAGCCGCTGCCGGCTCTGCCACC |

Appendix I-continued

| No. | Protein Name | Protein Reference | Insert aa sequence (add M as start/His-tag at C-term) | Insert DNA sequence (Start from ATG to His-tag stop codon) |
|-----|-----|-----|-----|-----|
| | | | GESSYRSEYVRKAIPICPVNLLPKYP APTYPSEHVFWDSACKRWYhhhhhh (SEQ ID NO: 77) | ACGCGTGGAGACGAAGCTCGTCAAGAGCCTCCCGTTCGAGGGGGAGA GCAACTATCGCTCCGAATTTGGGCCTAAACCACTGCCTGAACTGCCACC ACGCGTGGAACAGAAGCCACCAAAAAGCCTCCCCTTTGAAGGGGAGA GCAATTACCGCTCCGAGTTCGGGCCCAAGCCGCTGCCGGCCCTGCCAC CACGCGTGGTCACCAAGCTCGTGAAGTCCCTCCCCTTTGAAGGCGAGA GCAACTACAGATCTGAGTTCGGGCCTAAGCCACTCCCAGAGATCCCAC CACGCGTCGAGCAAAAACCACCAAAATCTCTCCCCTTTGAGGGTGAGA GCAATTATCGCTCAGAGTTCGGGCCCAAGCCTCTGCCGGAGCTGCCAC CACGCGTCGAACAGAAGCCACCAAAGAGCTTACCTTTTGAAGGGGAGA GCAACTACCGCAGTGAATTCGGCCCAAAGCAGCTGCCAGAACTGCCAC CAAGGCAAGAGGCCAAACTCACCCGCTCCCTGCCTTTCGAGGGCGAGT CCAGCTACAGGAGCGAGTATGTGAGGAAGGCCATCCCAATCTGCCCAG TCAACCTCCTGCCAAAGTACCCAGCCCCAACCTACCCATCCGAGCACGT GTTCTGGGACAGCGCCTGCAAGCGCTGGTACCACCACCACCACCACCA CTGA (SEQ ID NO: 78) |
| 40 | trypto-phan-rich antigen (Pv-fam-a) | PVX_088820 | mAAANRPNANGFVSPTLIGFGELSI QESEEFKRMAWNNWMLRLESDWK HFNDSVEEAKTKWLHERDSAWSD WLRSLQSKWSHYSEKMLKEHKSNV MEKSANWNDTQWGNWIKTEGRKIL EAQWEKWIKKGDDQLQKLILDKWV QWKNDKIRSWLSSEWKTEEDYYWA NVERATTAKWLQEAEKMHWLKWKE RINRESEQWVNWVOMKESVYINVE WKKWPKWKNDKKILFNKWSTNLVY KWTLKKQWNVWIKEANTAPQVhhhh hh (SEQ ID NO: 79) | ATGGCTGCCGCCAACAGGCCAAACGCCAACGGCTTCGTCTCCCCAACC CTCATCGGCTTCGGCGAGCTGTCCATCCAAGAGAGCGAGGAGTTCAAG AGGATGGCCTGGAACAACTGGATGCTCCGCCTGGAGTCCGACTGGAA GCACTTCAACGACAGCGTGGAGGAAGCCAAGACCAAGTGGCTGCACG AGAGGGACTCCGCTTGGAGCGACTGGCTCCGCTCCCTGCAGAGCAAGT GGTCCCACTACAGCGAGAAGATGCTGAAGGAGCACAAGTCCAACGTC ATGGAGAAGAGCGCCAACTGGAACGACACCCAATGGGGCAACTGGAT CAAGACCGAGGGCCGCAAGATCCTGGAGGCCCAGTGGGAGAAGTGG ATCAAGAAGGGCGACGACCAACTGCAGAAGCTCATCCTGGACAAGTG GGTCCAGTGGAAGAACGACAAGATCAGGTCCTGGCTCTCCAGCGAGT GGAAGACCGAGGAAGACTACTACTGGGCTAACGTGGAGAGGGCTACC ACCGCTAAGTGGCTCCAAGAGGCCGAGAAGATGCACTGGCTGAAGTG GAAGGAGAGGATCAACCGCGAGTCCGAGCAATGGGTGAACTGGGTCC AGATGAAGGAGAGCGTGTACATCAACGTCGAGTGGAAGAAGTGGCCA AAGTGGAAGAACGATAAGAAGATCCTGTTCAACAAGTGGAGCACCAA CCTCGTGTACAAGTGGACCCTGAAGAAGCAGTGGAACGTCTGGATCAA GGAAGCCAACACCGCCCCACAGGTGCACCACCACCACCACCACTGA (SEQ ID NO: 80) |
| 41 | PvTRAP/ SSP2 | PVX_082735 | mEKVVDEVKYSEEVCNESVDLYLLV DGSGSIGYPNWITKVIPMLNGLINSL SLSRDTINLYMNLFGNYTTELIRLGS GQSIDKRQALSKVTELRKTYTPYGT TNMTAALDEVQKHLNDRVNREKAIQ LVILMTDGVPNSKYRALEVANKLKQ RNVSLAVIGVGQGINHQFNRLIAGC RPREPNCKFYSYADWNEAVALIKPFI AKVCTEVERVANCGPWDPWTACSV TCGRGTHSRSRPSLHEKCTTHMVS ECEEGECPVEPEPLPVPAPLPTVPE DVNPRDTDDENENPNFNKGLDVPD EDDDEVPPANEGADGNPVEENVFP PADDSVPDESNVLPLPPAVPGGSSE EFPADVQNNPDSPEELPMEQEVPQ DNNVNEPERSDSNGYGVNEKVIPN PLDNERDMANKNKTVHPGRKDSAR DRYARPHGSTHVNNNRANENSDIP NNPVPSDYEQPEDKAKKSSNNGYK hhhhhh (SEQ ID NO: 81) | ATGGAGAAGGTGGTCGACGAGGTGAAGTACAGCGAGGAAGTGTGCA ACGAGTCCGTCGACCTCTACCTCCTGGTGGACGGCTCCGGCAGCATCG GCTACCCAAACTGGATCACCAAGGTCATCCCAATGCTCAACGGCCTGAT CAACTCCCTCAGCCTGTCCCGCGACACCATCAACCTCTACATGAACCTG TTCGGCAACTACACCACCGAGCTCATCAGGCTGGGCAGCGGCCAATCC ATCGACAAGCGCCAGGCCCTCAGCAAGGTGACCGAGCTGAGGAAGAC CTACACCCCATACGGCACCACCAACATGACCGCCGCCCTCGACGAGGT GCAAAAGCACCTGAACGACAGGGTCAACCGCGAGAAGGCCATCCAGC TCGTGATCCTGATGACCGACGGCGTCCCAAACAGCAAGTACCGCGCCC TGGAGGTGGCCAACAAGCTGAAGCAAAGGAACGTCTCCCTGGCCGTG ATCGGCGTGGGCCAAGGCATCAACCACCAGTTCAACAGGCTGATCGCT GGCTGCAGGCCACGCGAGCCAAACTGCAAGTTCTACAGCTACGCTGAC TGGAACGAGGCTGTGGCTCTCATCAAGCCATTCATCGCCAAGGTCTGC ACCGAGGTGGAGAGGGTGGCTAACTGCGGCCCATGGGACCCGTGGAC CGCTTGCTCCGTGACCTGCGGCAGGGGCACCCACAGCAGGTCCCGCCC AAGCCTGCACGAGAAGTGCACCACCCACATGGTGTCCGAGTGCGAGG AAGGCGAGTGCCCAGTGGAGCCAGAGCCACTGCCGGTCCCAGCCCCA CTGCCAACCGTGCCAGAGGACGTCAACCCAAGAGACACCGACGACGA GAACGAGAACCCAAACTTCAACAAGGGCCTCGACGTGCCAGACGAGG ACGACGACGAGGTCCCACCAGCTAACGAGGGCGCTGACGGCAACCCA GTGGAGGAGAACGTCTTCCCACCAGCCGACGACAGCGTGCCAGACGA GTCCAACGTGCTGCCACTGCCACCAGCTGTGCCAGGCGGCTCCAGCGA GGAGTTCCCAGCTGACGTCCAAAACAACCCAGACTCCCCAGAGGAGCT CCCGATGGAGCAAGAGGTGCCACAGGACAACAACCCTAACGAGCCAG AGCGCAGCGACTCCAACGGCTACGGCGTGAACGAGAAGGTCATCCCA AACCCACTGGACAACGAGAGGGACATGGCCAACAAGAACAAGACCGT GCACCCGGGCAGGAAGGACAGCGCCAGGGACCGCTACGCCAGGCCAC ACGGCTCCACCCACGTGAACAACAACAGGGCCAACGAGAACAGCGAC ATCCCAAACAACCCAGTCCCATCCGACTACGAGCAGCCAGGAGACAAG GCCAAGAAGTCCAGCAACAACGGCTACAAGCACCACCACCACCACCAC TGA (SEQ ID NO: 82) |
| 42 | MSP7-like protein | PVX_082645 | mDDKKDKENEHKEDADKKNNDELK TLKGKLQKIRVQIKDDKLPQKISEEQI SVLKKKLEDFKNLKSEHEAKLASEK GDTSAGGEGELGLSDKEFVGQNVK ANGDAAGVSGEQGASGGSGQGEA GPSSPADEQDDDNEAVQWGPATEE VVAEAMSDEGPQEQGAEGGPSNPT DDQAEEATPGPSKPASGASGSQGA | ATGGACGACAAGAAGGACAAGGAGAACGAGCACAAGGAAGACGCCG ATAAGAAGAACAACGACGAGCTCAAGACCCTGAAGGGCAAGCTCCAA AAGATCAGGGTGCAGATCAAGGACGACAAGCTGCCACAAAAGATCTC CGAGGAGCAGATCAGCGTGCTCAAGAAGAAGCTGGAGGACTTCAAGA ACCTCAAGTCCGAGCACGAGGCCAAGCTGGCCTCCGAGAAGGGCGAC ACCTCCGCCGGCGGCGAGGGCGAGCTGGGCCTGTCCGACAAGGAGTT CGTGGGCCAAAACGTCAAGGCCAACGGCGACGCCGCCGGCGTGAGCG GCGAGCAAGGCGCCTCCGGCGGCAGCGGCCAGGGCGAGGCTGGGCCC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | SDSSNDSAEPTSAAAAAAPAGPTAA AASPQVKHVDTLCDELLAGENKKNV LDEGEDHSQYNIFRKQYDKMVLNKT EYNISLKLLDTMLTNGQVEREKKNTL IKTFKKALYDKQYSEKLRNLISGVYA FAKRNNFIDGDKVKEGDYSKLFEYIG CMMNTLELhhhhhh (SEQ ID NO: 83) | ATCCAGCCCAGCCGACGAGCAAGACGACGACAACGAGGCTGTCCAGT GGGGCCCAGCTACCGAGGAAGTGTGGCTGAGGCTATGTCCGACGAG GGGCCCACAAGAGCAGGGCGCTGAGGGCGGCCCAAGCAACCCAACCGA CGACCAAGCTGAGGAAGCCACCCCAGGCCCATCCAAGCCAGCTTCCGG CGCTTCCGGCAGCCAGGGCGCTTCCGACTCCAGCAACGACTCCGCCGA GCCAACCAGCGCTGCCGCCGCCGCCGCCCAGCTGGCCCAACCGCTGC CGCCGCCAGCCCACAGGTGAAGCACGTGGACACCCTCTGCGACGAGCT CCTGGCTGGCGAGAACAAGAAGAACGTGCTGGACGAGGGCGAGGAC CACTCCCAATACAACATCTTCAGGAAGCAGTACGACAAGATGGTCCTCA ACAAGACCGAGTACAACATCAGCCTCAAGCTCCTGGACACCATGCTGA CCAACGGCCAAGTGGAGCGCGAGAAGAAGAACACCCTCATCAAGACC TTCAAGAAGGCCCTGTACGACAAGCAGTACTCCGAGAAGCTCAGGAAC CTGATCAGCGGCGTGTACGCCTTCGCCAAGCGCAACAACTTCATCGAC GGCGACAAGGTGAAGGAAGGCGACTACAGCAAGCTCTTCGAGTACAT CGGCTGCATGATGAACACCCTGGAGCTGCACCACCACCACCACCACTG A (SEQ ID NO: 84) |
| 43 | early transcribed membrane protein (etramp 10.2) | PVX_111065 | mKRHATRGALHSLKSIEHEVQRKKN KKKKIILYSIGSILALAAVIATGVGIGM YIKKKKKNSLEKLQQIEPQKLESKTD ESDPLLGKSEAAKVEVKGDSEEVPQ EVSSPSEALDVEPPVSEALNMEPAV GESANFEDSAKGEVDIEPVSEVESIE PVSEVESIESPVSEVESIEPSVDEVMD AAEPISTEPVNVEPAGNETENIVPTS FEQVNIEPAVSEAFSQERSGEETAD FEDSVKEDVIPESPPVESVTIEAENI QPMNVEQMNVDPTVSDAESIEPTPV EAVDIEPVNVEPVNVEPAVSETMSQ EPSLDEVENVESAVNEMMSQEPSA EETANFAHSIKEDVSPESTSVESLDV ESSVSEPMSTDPSPVESVSMESVD SETVNVESIDSETVNVEPSDETSKV EADVQQFTDEELSTIGNVADKASDG PAPEASDFPDSIFEENLDNANPPLKL EDALVDPPASDEAQPEPSHPNEAV GAAKSAESAEADQISHSGSGDASPS APSSSDDTSGSKNSGTSGKDRLFKT YDSDVEPPIVPEKYPTVGVKEAPKM GFAEMAFKNIFDTFSKVADASKVLTP EKQSAPEKQSAPEKQSAPEKQSAP EKHSTPPKQSTSPKESTSPKQPAPP KPSTSPKQSAPAKQSAPPKQSAPAK QSAPAKNAAPPQSASSSRFFSSSSN GNKGFGLRLFSDASSSNNKKRAG NPIIRFKRRANhhhhhh (SEQ ID NO: 85) | ATGAAGAGGCACGCTACCCGCGGCGCCCTCCACTCCCTGAAGAGCATC GAGCACGAGGTGCAAAGGAAGAAGAACAAGAAGAAGAAGATCATCCT CTACTCCATCGGCAGCATCCTGGCTCTGGCTGCCGTGATCGCTACCGGC GTCGGCATCGGCATGTACATCAAGAAGAAGAAGAACAGCCTGGA GAAGCTGCAACAGATCGAGCCACAAAAGCTGGAGTCCAAGACCGACG AGAGCGACCCACTCCTGGGCAAGAGCGAGGCTGCTAAGGTGGAGGTC AAGGGCGACTCCGAGGAAGTGCCACAAGAGGTGTCCTCCCCGAGCGA GGCTCTGGACGTGGAGCCACCAGTCTCCGAGGCCCTGAACATGGAGCC AGCCGTGGGCGAGTCCGCCAACTTCGAGGACAGCGCCAAGGGCGAGG TCGACATCGAGCCAGTGTCCGAGGTCGAGTCTATTGAACCAGTGTCCG AGGTGGAGTCTATTGAGCCAGTGTCCGAAGTCGAGAGCATCGAGCCAT CCGTGGACGAGGTCATGGACGCTGCTGAGCCAATCAGCACCGAGCCA GTGAACGTCGAGCCAGCCGGCAACGAGACGGAGAACATCGTGCCAAC CTCCTTCGAGCAAGTGAACATCGAGCCAGCCGTCAGCGAGGCCTTCTC CCAAGAGAGGAGCGGCGAGGAGACGGCTGACTTCGAGGACTCCGTGA AGGAAGACGTCATCCCAGAGTCCCCACCAGTGGAGAGCGTCACCATCG AGGCCGAGAACATCCAACCGATGAACGTGGAGCAGATGAACGTGGAC CCAACCGTCTCCGACGCCGAGAGCATCGAGCCAACCCCAGTGGAGGCC GTGGATATCGAGCCTGTCAACGTGGAGCCTGTCAACGTTGAGCCAGCC GTGTCCGAGACGATGAGCCAGGAACCCATCCCTCGACGAGGTGGAGAA CGTCGAGAGCGCCGTCAACGAGATGATGTCCCAGGAGCCCATCCGCTGA GGAGACGGCCAACTTCGCCCACTCCATCAAGGAAGACGTGAGCCCAGA GAGCACCTCCGTCGAGTCCCTGGACGTGGAGTCCAGCGTCAGCGAGCC AATGTCCACCGACCCAAGCCCAGTGGAGAGCGTCTCCATGGAGTCCGT GGACAGCGAGACGGTGAACGTCGAGTCCATCGATTCCGAGACGGTCA ACGTGGAGCCATCCGACGAGACGAGCAAGGTGGAGGCCGACGTCCAA CAGTTCACCGACGAGGAGCTCAGCACCATCGGCAACGTGGCTGACAAG GCTTCCGACGGCCCAGCTCCAGAGGCCTCCGACTTCCCAGACAGCATCT TCGAGGAGAACCTCGACAACGCCAACCCACCCACTCAAGCTGGAGGACG CTCTGGTGGACCCACCAGCTAGCGACGAGGCTCAACCAGAGCCATCCC ACCCAAACGAGGCTGTGGGCGCTGCTAAGTCCGCTGAGAGCGCTGAG GCTGACCAAATCAGCCACTCCGGCAGCGGCGACGCTTCCCCAAGCGCT CCATCCAGCTCCGACGACACCTCCGGCAGCAAGAACTCCGGCACCAGC GGCAAGGACAGGCTCTTCAAGACCTACGACTCCGACGTGGAGCCACCA ATCGTCCCAGAGAAGTACCCAACCGTGGGCGTGAAGGAAGCCCCAAA GATGGGCTTCGCCGAGATGGCCTTCAAGAACATCTTCGACACCTTCTCC AAGGTGGCTGACGCTAGCAAGGTCCTGACCCCAGAGAAGCAATCCGCC CCAGAGAAGCAGAGCGCTCCTGAGAAGCAGAGCGCTCCCGAGAAGCA GAGCGCCCCAGAGAAGCACTCCACCCCACCAAAGCAATCCACCAGCCC AAAGGAGTCCACCAGCCCAAAGCAGCCAGCCCCACCAAAGCCATCCAC CAGCCCTAAGCAGTCCGCTCCAGCTAAGCAGTCCGCCCCACCAAAGCA GAGCGCTCCAGCTAAGCAATCCGCTCCAGCTAAGAACGCTGCCCCACC ACAGAGCGCCAGCTCCAGCAGGTTCTTCTCCAGCTCCAGCAACGGCAA CAAGGGCTTCGGCCTCAGGCTGTTCTCCGACGCCTCCAGCTCCAACAAC AAGAAGGGCAGGGCCGGCAACCCAATCATCCGCTTCAAGAGGCGCGC CAACCACCACCACCACCACTGA (SEQ ID NO: 86) |
| 44 | hypothetical protein, conserved | PVX_091500 | MNNPAEVVAAHLRRTGNSNEIRQAS HVESVGGSANSSLDDDDGGGYDSA APPGELHTTGDAPPGEFRTTGVVPP GRQKGGKKRMFKIKKKKSLTPLHID DGGFTQGGEAKGPDVALESFAITRK RRRPPLLGRGVVESSNIELTSKLGG KLGSKLGGKLNPTLSLVASRAVDGL LGGVHKHMQGPFSLDLDGTNNSPL ATPIVTPNLYSNISTPFNMHNGIPPS APAPMALPPQGVQVPLPNAQPQPP PSVATTATAAPAATSPMASPTTPTP | ATGAACAACCCAGCTGAGGTGGTGGCTGCTCACCTGAGGCGCACCGGC AACTCCAACGAGATCAGGCAGGCTAGCCACGTGGAGAGCGTCGGCGGC TCCGCTAACTCCAGCCTCGACGACGACGACGGCGGCGGATACGACAG CGCTGCCCCACCAGGCGAGCTCCACACCACCGGCGACGCCCCACCAGG CGAGTTCCGCACCACCGGCGTGGTCCCACCAGGCAGGCAAAAGGGCG GCAAGAAGCGCATGTTCAAGATCAAGAAGAAGAAGTCCCTCACCCCAC TGCACATCGACGACGGCGGCTTCACCCAGGGCGGCGAGGCTAAGGGC CCAGACGTGGCTCTGGAGTCCTTCGCCATCACCAGGAAGAGGCGCAGG CCACCACTCCTGGGCCGCGGCGTGGTCGAGTCCAGCAACATCGAGCTC ACCAGCAAGCTGGGCGGCAAGCTCGGCTCCAAGCTGGGCGGCAAGCT CAACCCGACCCTCAGCCTGGTGGCCTCCAGGGCCGTGGACGGCCTCCT |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | AASTGVPPPPGIQLATNAMTYPQMN MQNVMTANQMAQNPAFNIHPTATN LRDDPGNVNYNEVVTITIGIVICLFLF CFVFGCIVKMCKPAKRRRhhhhhh (SEQ ID NO: 87) | GGGCGGCGTGCACAAGCACATGCAAGGCCCATTCAGCCTCGACCTGGA CGGCACCAACAACTCCCCACTGGCCACCCCAATCGTCACCCCAAACCTC TACTCCAACATCAGCACCCCATTCAACATGCACAACGGCATCCCACCAA GCGTCCAGCTCCAATGCTCTGCCACCACAAGGCGTGCAGGTCCCAC TCCCAAACGCCCAACCACAACCACCACCATCCGTGGCTACCACCGCTAC CGCTGCTCCAGCTGCTACCAGCCCAATGGCTTCCCCAACCACCCCAACC CCAGCTGCTAGCACCGGCGTGCCACCACCACCAGGCATCCAGCTGGCC ACCAACGCCATGACCTACCCACAGATGAACATGCAGAACGTCATGACC GCCAACCAAATGGCCCAGAACCCAGCCTTCAACATCCACCCGACCGCTA CCAACCTCAGGGACGACCCAGGCAACGTGAACTACAACGAGGTGGTC ACCATCACCATCGGCATCGTCATCTGCCTCTTCCTGTTCTGCTTCGTGTT CGGCTGCATCGTCAAGATGTGCAAGCCGGCTAAGCGCAGGCGCCATCA CCACCACCACCACTGA (SEQ ID NO: 88) |
| 45 | hypothetical protein, conserved | PVX_090145 | mSKTGNNNRNAKNAKGGGGGKR GNNEANKNDGMSGKGSQKGKKKD PGGGGTPKGQGKGPEQGKQKNKK GEDSHFDEYIKDMKNSQDEDNFMD ELNRFEKNFHDEDFESDENLFNYGK GGTHSGEFNKIGELNSGNYNEMKP DANDYQYFDNEDILEGDEDLTNIWN KNMQNFEPSTLLTFEIQGNSEEYLF EEVTSLNTYFRGVFYSNNESDDNKI LFFITDPDGEVIYKKEASEGIFYFYTQ KIGVYTITLKNSKWMGKKLTTVALGL GESPSLKSEHIKDFTNYIDKIVAETKR LKNELKYLSSKHMTHIEKMKKITNKA FLYCFIKLFVLVFLSLFTIYYIKNLVSN KRVLhhhhhh (SEQ ID NO: 89) | ATGTCCAAGACCGGCAACAACAACAGGAACGCCAAGAACGCTAAGGG CGGCGGCGGCGGCGGCAAGAGGGGCAACAACGAGGCCAACAAGAAC GACGGCATGTCCGGCAAGGGCAGCCAAAAGGGCAAGAAGAAGGACC CAGGCGGCGGCGGCACCCCGAAGGGCAGGGCAAGGGCCCAGAGCA AGGCAAGCAGAAGAACAAGAAGGGCGAGGACTCCCACTTCGACGAGT ACATCAAGGACATGAAGAACAGCCAAGACGAGGACAACTTCATGGAC GAGCTCAACAGGTTCGAGAAGAACTTCCACGACGAGGACTTCGAGTCC GACGAGAACCTGTTCAACTACGGCAAGGGCGGCACCCACTCCGGCGA GTTCAACAAGATCGGCGAGCTCAACAGCGGCAACTACAACGAGATGA AGCCAGACGCCAACGACTACCAGTACTTCGACAACGAGGACATCCTGG AGGGCGACGAGGACCTGACCAACATCTGGAACAAGAACATGCAAAAC TTCGAGCCAAGCACCCTCCTGACCTTCGAGATCCAGGGCAACTCCGAG GAGTACCTCTTCGAGGAAGTGACCAGCCTGAACACCTACTTCCGCGGC GTCTTCTACTCCAACAACGAGAGCGACGACAACAAGATCCTGTTCTTCA TCACCGACCCAGACGGCGAGGTCATCTACAAGAAGGAAGCCTCCGAG GGCATCTTCTACTTCTACACCCAAAAGATCGGCGTGTACACCATCACCC TCAAGAACAGCAAGTGGATGGGCAAGAAGCTGACCACCGTGGCTCTG GGCCTGGGCGAGTCCCCAAGCCTCAAGAGCGAGCACATCAAGGACTTC ACCAACTACATCGACAAGATCGTCGCCGAGACGAAGAGGCTGAAGAA CGAGCTCAAGTACCTGTCCAGCAAGCACATGACCCACATCGAGAAGAT GAAGAAGATCACCAACAAGGCCTTCCTCTACTGCTTCATCAAGCTCTTC GTGCTGGTCTTCCTCTCCCTGTTCACCATCTACTACATCAAGAACCTCGT GAGCAACAAGCGCGTCCTGCACCACCACCACCACCACTGA (SEQ ID NO: 90) |
| 46 | hypothetical protein, conserved | PVX_119265 | MNNHQAVKQQMNPKGSKEQNRMV APNSNMPGGMRDLAYHRNNGNNE MGKMNMNANGGQQHNAGSSNTYNS NSINNNNYSLGLYIDNPQNAFVFDE NDLKTLFSHYKGAKNIRILNDKAAAQ ITFNDKNMIQQVRKDINGLTITDGTI RCIILNEGKIVEQFLPFSANDPASAQ QKGGSNQSGDSTVDMLKKLANLLQ PERAMDSSMAPKMGDNGGLSATG SVNMGASIATNVGMGGNMPTNANM GGVITTNANVSANVSANVSANPMPG KNQVKNKMGNHAIYNNGGSHFNQA HMNKGEPGENNPYATKRLSRIELIDI FGFPVEFDVMKKILGKNNSNISYIKE QTNNSVSIEIKGKPFNEAPIVERMHV SVSSDDLIGYKKATELIVKLLNSIFEE FYDFCYEKNYPVPENLSFKRHEYMY NPDGSTKYVGFKDKWHVMKDSYRT DYSFRKNKGLQKNDKDKRMHGGAF GGHPNLSIGYANQNAPQGDFKEMN hhhhhh (SEQ ID NO: 91) | ATGAACAACCACCAAGCCGTCAAGCAACAGATGAACCCAAAGGGCTCC AAGGAGCAGAACAGGATGGTGGCCCCAAACAGCAACATGCCAGGCGG CATGAGGGACCTCGCTTACCACAGGAACAACGGCAACAACGAGATGG GCAAGATGAACATGAACGCCAACGGCCAACAGCACAACGCCGGCTCCA GCAACACCTACAACTCCAACTCCATCAACAACAACAACTACTCCCTCGG CCTGTACATCGACAACCCACAAAACGCCTTCGTCTTCGACGAGAACGAC CTCAAGACCCTGTTCAGCCACTACAAGGGCGCCAAGAACATCAGGATC CTCAACGACAAGGCTGCCGCCCAGATCACCTTCAACGACAAGAACATG ATCCAACAGGTCAGGAAGGACATCAACGGCCTGACCATCACCGACATC GGCACCATCCGCTGCATCATCCTCAACGAGGGCAAGATCGTGGAGCAA TTCCTGCCATTCTCCGCCAACGACCCAGCGTCAGCACAGCAACAGAAGGGC GGCTCCAACCAAAGCGGCGACTCCACCGTGGACATGCTCAAGAAGCTC GCTAACCTCCTGCAGCCAGAGAGGGCCATGGACTCCAGCATGGCCCCA AAGATGGGCGACAACGGCGGCCTCTCCGCTACCGGCTCCGTCAACATG GGCGCCTCCATCGCCACCAACGTGGGCATGGGCGGCAACATGCCAACC AACGCCAACATGGGCGGCGTCATCACCACCAACGCCAACGTGAGCGCT AACGTCTCCGCTAACGTGAGCGCTAACCCAATGCCAGGCAAGAACCAA GTGAAGAACAAGATGGGCAACCACGCCATCTACAACAACGGCGGCTCC CACTTCAACCAGGCCCACATGAACAAGGGCGAGCCAGGCGAGAACAA CCCATACGCCACCAAGAGGCTCAGCCGCATCGAGCTGATCGACATCTTC GGCTTCCCAGTCGAGTTCGACGTGATGAAGAAGATCCTCGGCAAGAAC AACAGCAACATCTCCTACATCAAGGAGCAAACCAACAACTCCGTCAGC ATCGAGATCAAGGGCAAGCCATTCAACGAGGCCCCAATCGTGGAGCG CATGCACGTGTCCGTCTCCAGCGACGACCTCATCGGCTACAAGAAGGC CACCGAGCTGATCGTCAAGCTCCTGAACAGCATCTTCGAGGAGTTCTAC GACTTCTGCTACGAGAAGAACTACCCAGTGCCAGAGAACCTGTCCTTCA AGAGGCACGAGTACATGTACAACCCAGACGGCAGCACCAAGTATGTG GGCTTCAAGGACAAGTGGCACGTGATGAAGGACTCCTACAGGACCGA CTACAGCTTCCGCAAGAACAAGGGCCTCCAGAAGAACGACAAGGACA AGAGGATGCACGGCGGCGCTTTCGGCGGACACCCAAACCTGAGCATC GGCTACGCCAACCAAAACGCCCCACAGGGCGACTTCAAGGAGATGAA CCACCACCACCACCACCACTGA (SEQ ID NO: 92) |

| No. | Protein Name | Protein Reference | Insert aa sequence (add M as start/His-tag at C-term) | Insert DNA sequence (Start from ATG to His-tag stop codon) |
|---|---|---|---|---|
| 47 | rhoptry neck protein 2, putative (RON2) | PVX_117880 | mREAKGSVRDGKQYVKTKSPTYTP QKKTKVIFYMPGQEQEEEEDDNDP NGSKKNGKSDTGANKGTHMGSKTD AGNSPSGLNKGSGVGSGSRPASNN YKGNAGGGINIDMSPHGDNSNKGQ QGNAGLNKNQEDTLRDEYEKIRKQE EEEEERINNORRADMKRAQRGKNK FGDDKGVQDShhhhhh (SEQ ID NO: 93) | ATGCGCGAGGCTAAGGGCTCCGTGCGCGACGGCAAGCAATACGTCAA GACCAAGAGCCCAACCTACACCCCACAGAAGAAGACCAAGGTCATCTT CTACATGCCAGGCCAAGAGCAAGAGGAAGAGGAAGACGACAACGACA CAAACGGCTCCAAGAAGAACGGCAAGAGCGACACCGGCGCCAACAAG GGCACCCACATGGGCTCCAAGACCGACGCTGGCAACTCCCCGAGCGGC CTCAACAAGGGCTCCGGCGTGGGCTCCGGCAGCAGGCCAGCCAGCAA CAACTACAAGGGCAACGCCGGCGGCGGCATCAACATCGACATGTCCCC ACACGGCGACAACAGCAACAAGGGCCAACAGGGCAACGCCGGCCTCA ACAAGAACCAAGAGGACACCCTGAGGGACGAGTACGAGAAGATCCGC AAACAAGAGGAAGAGGAAGAGGAGCGCATCAACAACCAAAGGCGCG CTGACATGAAGAGGGCTCAGAGGGGCAAGAACAAGTTCGGCGACGAC AAGGGCGTGCAAGACAGCCACCACCACCACCACCACTGA (SEQ ID NO: 94) |
| 48 | tryptophan-rich antigen (Pv-fam-a) | PVX_121897 | mSSQSAVDYIEQEPLDILNLEEGDLE VTEQWKDNEWHNWKLKLEEDWDS FSTSLIRDKKDFMKIKTDELNGWLNL EENKWNNFSGYLSDGYKNYLLKKS EKWNDADWENWANTEMVAHLDKD YHLWSLNTERSVNALVRGEWNQW QHDKMSSWLSSDWKKVGAMYWDL QESRNWASYSHTDDMKEHWIKWN DRNARENIEWSKWVQNKEYFIMYA RHSDIEQWKYDNYALYSTWRNDFIN RWVSEKKWNSILNhhhhhh (SEQ ID NO: 95) | ATGTCCAGCCAAAGCGCCGTGGACTACATCGAGCAGGAGCCACTCGAC ATCCTCAACCTCGAAGAGGGCGACCTGGAGGTCACCGAGCAGTGGAA GGACAACGAGTGGCACAACTGGAAGCTCAAGCTCGAAGAGGACTGGG ACTCCTTCAGCACCTCCCTCATCAGGGACAAGAAGGACTTCATGAAGAT CAAGACCGACGAGCTGAACGGCTGGCTCAACCTGGAGGAGAACAAGT GGAACAACTTCAGCGGCTACCTCTCCGACGGCTACAAGAACTACCTCCT GAAGAAGTCCGAGAAGTGGAACGACGCCGACTGGGAGAACTGGGCC AACACCGAGATGGTGGCCCACCTCGACAAGGACTACCACCTCTGGAGC CTGAACACCGAGAGCGTCAACGCCCTCGTGCGCGGCGAGTGGAA CCAATGGCAGCACGACAAGATGTCCAGCTGGCTCTCCAGCGACTGGAA GAAGGTCGGCGCCATGTACTGGGACCTGCAGGAGAGCAGGAACTGGG CCAGCTACTCCCACACCGACGACATGAAGGAGCACTGGATCAAGTGGA ACGACAGGAACGCCCGCGAGAACATCGAGTGGTCAAGTGGGTGCAA AACAAGGAGTACTTCATCATGTACGCCCGCCACAGCGACATCGAGCAG TGGAAGTACGACAACTACGCCCTCTACTCCACCTGGAGGAACGACTTC ATCAACCGCTGGGTCAGCGAGAAGAAGTGGAACTCCATCCTGAACCAC CACCACCACCACCACTGA (SEQ ID NO: 96) |
| 49 | tryptophan-rich antigen (Pv-fam-a) | PVX_125728 | mKSSNEIERLTHVKLKDTSEWTENV EEWVKDEWHEWMDEVQMDWKEF NSSLESEKNKWFGKKEKEMMELIKS IEDKWLDFNENMHEVLNYAILKISLM WSFSEWQKWINKDGKRIIENQWER WTISNKNLYYKIIMKEWFKWNKKIK QWLKRNWLHHEGRILENWERLPYT KILAMSEKKPWFNSNAQVINERDYF LIWIKKKEDFLVNEERDKWENWEYY KNDFFQTWMDSFLSHWLNIKKRDIL HSQShhhhhh (SEQ ID NO: 97) | ATGAAGTCCAGCAACGAGATCGAGAGGCTCACCCACGTGAAGCTGAA GGACACCTCCGAGTGGACCGAGAACGTGGAGGAGTGGGTCAAGGAC GAGTGGCACGAGTGGATGGACGAGGTCCAGATGGACTGGAAGGAGTT CAACTCCAGCCTGGAGTCCGAGAAGAACAAGTGGTTCGGCAAGAAGG AGAAGGAGATGATGGAGCTGATCAAGAGCATCGAGGACAAGTGGCTC GACTTCAACGAGAACATGCACGAGGTGCTCAACTACGCCATCCTCAAG ATCTCCCTGATGTGGTCCTTCAGCGAGTGGCAAAAGTGGATCAACAAG GACGGCAAGAGGATCATCGAGAACCAGTGGGAGCGCTGGACCATCAG CAACAAGAACCTGTACTACAAGATCATCATGAAGGAGTGGTTCAAGTG GAACAAGAAGATCAAGCAATGGCTCAAGAGGAACTGGCTGCACC ACGAGGGCAGGATCCTGGAGAACTGGGAGCGCCTGCCATACACCAAG ATCCTGGCCATGTCCGAGAAGAAGCCATGGTTCAACAGCAACGCCCAA GTGATCAACGAGGGACTACTTCCTGATCTGGATCAAGAAGAAGGA AGACTTCCTCGTCAACGAGGAGCGCGACAAGTGGGAGAACTGGGAGT ACTACAAGAACGACTTCTTCCAAACCTGGATGGACTCCTTCCTCAGCCA CTGGCTGAACATCAAGAAGCGCGACATCCTCCACTCCCAGAGCCACCA CCACCACCACCACTGA (SEQ ID NO: 98) |
| 50 | reticulocyte binding protein 2 precursor (PvRBP-2), putative | PVX_090330 | mRLKHDHNLLPNYANLMRDDQNGQ NSENRGDNINNHNKHNDQNNHNG NNDNSINSEYLKTSHLQNSSAMVHL NDHKITTKPARYSYIQRSKIYAFNPN NKKIENINNELHShhhhhh (SEQ ID NO: 99) | ATGAGGCTCAAGCACGACCACAACCTCCTGCCAAACTACGCCAACCTG ATGAGGGACGACCAAAACGGCCAGAACTCCGAGAACCGCGGCGACAA CATCAACAACCACAACAAGAACCACAACGACCAAAACAACCACAACGG CAACAACGACAACTCCATCAACAGCGAGTACCTCAAGACCAGCCACCT GCAGAACTCCAGCGCCATGGTGCACCTCAACGACCACAAGATCACCAC CAAGCCAGCCAGGTACTCCTACATCCAACGCAGCAAGATCTACGCCTTC AACCCAAACAACAAGAAGATCGAGAACATCAACAACGAGCTGCACTCC CACCACCACCACCACCACTGA (SEQ ID NO: 100) |
| 51 | histone-lysine N-methyltransferase, H3 lysine-4 specific, putative (SET10) | PVX_123685 | mSMEQGTPIVFPHKEGTILTKGTNN LAVAHKEEVHRSEEETTLKGLKEEL PHEHTLAIQKYDPSFGRGGSPGSGS TEHTNGSFSNSYETILYNKSNDVVK NLKEIKKGAPFGGVISDAVSCPASSS SNTGGNKNLCFSNMMKLSKKILGFP LLTDFERGMSTNQPCLPLSDHLKRL SVCTVCYSKHNDLAKAIICRVTKMHF EANYNDGLGDEDMFKTSSECIQSVI RELANTIKEYRKRELSGAYVQELAR SGSSSYRSCSSSSYSSRGGSCAGS RGDGLAGSHGEIHAVIAGPPLTDDH NDIGAEAHSPSSSLKLPPQKPFYGM MSDPPCSDRRPGDTNNPFENNTPP LLWDNKVNYTDDYTCKRGEVNSTL | ATGTCCATGGAGCAAGGCACCCCAATCGTGTTCCCACACAAGGAAGGC ACCATCCTCACCAAGGGCACCAACAACCTGGCCGTGGCCCACAAGGAA GAGGTGCACAGGAGCGAGGAAGAGACGACCCTCAAGGGCCTGAAGG AAGAGCTCCCACACGAGCACACCCTGGCCATCCAGAAGTACGACCCAA GCTTCGGCCGCGGCGGCTCCCCAGGCAGCGGCAGCACCGAGCACACC AACGGCTCCTTCAGCAACTCCTACGAGACGATCCTCTACAACAAGTCCA ACGACGTGGTCAAGAACCTGAAGGAGATCAAGAAGGGCGCTCCATTC GGCGGCGTGATCTCCGACGCCGTCTCCTGCCCGGCCTCCAGCTCCAGC AACACCGGCGGCAACAAGAACCTCTGCTTCAGCAACATGATGAAGCTC TCCAAGAAGATCCTGGGCTTCCCACTCCTGACCGACTTCGAGAGGGGC ATGAGCACCAACCAACATGCCTCCCATGCCTGAGCGACCACCTCAAGCGC CTCAGCGTGTGCACCGTCTGCTACAGCAAGCACAACGACCTGGCCAAG GCCATCATCTGCAGGGTGACCAAGATGCACTTCGAGGCCAACTACAAC GACGGCCTCGGCGACGAGGACATGTTCAAGACCTCCAGCGAGTGCATC CAATCCGTGATCCGCGAGCTGGCCAACACCATCAAGGAGTACAGGAAG |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | GKRPHEEDNKGSSQKKSKLRTKPS NDTIGGENGDSLKGGTDEGKTHEG GGNVGSCTAQGGADQLPRSDLCRD PRGDPCVDPLPEQHAHRSKDENQK GDKNDIHFAGEKLDEIEAPGDQKGN YVTLENISKASNFIPLLGVELGSTKIQ REFTNGTYVGTVTEQIKDEHGNPFF VVTYEDGDAEWMTPCFLFQELLKQ STNSVDYPLATTFKEVFNPEFKKDL KLSNCSLELKIERRKRKSNCESASN NNSVSKRQKHAQEENSSRKKKQRF hhhhhh (SEQ ID NO: 101) | CGCGAGCTGTCCGGCGCCTACGTCCAAGAGCTCGCTAGGTCCGGCTCC AGCTCCTACAGGAGCTGCAGCTCCAGCTCCTACAGCTCCAGGGGCGGC AGCTGCGCTGGCTCCCGCGGCGACGGCCTCGCCGGCTCCCACGGCGGA ATCCACGCCGTCATCGCTGGCCCACCACTGACCGACGACCACAACGAC ATCGGCGCTGAGGCTCACAGCCCAAGCTCCAGCCTCAAGCTGCCACCA CAAAAGCCATTCTACGGCATGATGTCCGACCCACCATGCTCCGACAGG CGCCAGGCGACACCAACAACCCATTCGAGAACAACACCCCACCACTCC TGTGGGACAACAAGGTGAACTACACCGACGACTACACCTGCAAGAGG GGCGAGGTCAACTCCACCCTCGGCAAGCGCCCACACGAGGAAGACAA CAAGGGCTCCAGCCAGAAGAAGTCCAAGCTCAGGACCAAGCCAAGCA ACGACACCATCGGCGGCGAGAACGGCGACAGCCTGAAGGGCGGCACC GACGAGGGCAAGACCCACGAGGGCGGCGGCAACGTGGGCTCCTGCAC CGCCCAAGGCGGCGCCGACCAGCTCCCAAGGTCCGACCTGTGCAGGG ACCCACGCGGCGACCCATGCGTCGACCCACTCCCAGAGCAACACGCCC ACCGCTCCAAGGACGAGAACCAGAAGGGCGACAAGAACGACATCCAC TTCGCCGGCGAGAAGCTCGACGAGATCGAGGCCCCAGGCGACCAAAA GGGCAACTACGTGACCCTGGAGAACATCAGCAAGGCCTCCAACTTCAT CCCGCTCCTGGGCGTGGAGCTGGGCAGCACCAAGATCCAACGCGAGTT CACCAACGGCACCTACGTGGGCACCGTCACCGAGCAGATCAAGGACG AGCACGGCAACCCATTCTTCGTGGTCACCTACGAGGACGGCGACGCTG AGTGGATGACCCCATGCTTCCTCTTCCAAGAGCTCCTGAAGCAGAGCAC CAACTCCGTGGACTACCCACTGGCCACCACCTTCAAGGAAGTGTTCAAC CCAGAGTTCAAGAAGGACCTCAAGCTGAGCAACTGCTCCCTGGAGCTG AAGATCGAGAGGCGCAAGAGGAAGTCCAACTGCGAGAGCGCCTCCAA CAACAACAGCGTGTCCAAGCGCCAAAAGCACGCCCAAGAGGAGAACT CCTCAGGAAGAAGAAGCAGCGCTTCCACCACCACCACCACCACTGA (SEQ ID NO: 102) |
| 52 | reticulocyte binding protein 1 precursor, putative | PVX_ 125738 | mTFNDGSDEISTAQKYKTDVEGIIDK LNVIDETINGINSTLDELLELGNNCQL HRTFLISSSLNNKIAKFLVEIREQKEN TKKCFQYVKRNHQHLANFVSELHKT QGGIFENVNLVDNTPDADKYYHEFM EIEQEATKIVKDIKKEIYHLNDDVDEP VLEKRIKDVINTYNKLKTKKVQMDQS YKNMYITKLREVEGSHDLFNQVAQLI RGETDKKGKALSERENNLHSIYNFV GTTCATGGAGATCGAGCAAGAGGCCACCAAGATCGTCAAGGACATCA KLHETELHNLYAKYTPEYMEKINKIF DDINARMIAVDLNDDHSSEYSDVKR HEHEAMLLMDATNNLSKEVEMMQN ESGGKNDGINGGKSQLVEDYTNTM SEFTEQAKTVAKKIHDSKGDYANMF DHIRENEAMLERIDLKKKDIKEILAHL NRMKEYLLKKLSEEEKLHHMREKLE EVNTSTDEIVKKFRTYDQMVDISQNI DIKNVQSKRYDSVDEIDKEMSYIKTH NKDLIDSKFIVERALENDKRKKSEMA QIFSTISRDNSSMYEYAKSFFDSVLK EIEKLTQMIRNMDKLINENEAVMEKL KDQRRELQNVENASTDLGKLEEVD KMAQTKSETELSERNDSRNAKDGA TYSTLMDDKETDSVNGEETKQENV VVKKGLPPQTDIYTSVVLKNDRNDQ KSEKIGEKKSNKPVGTEENIQHSSYL NNDNSNNDIDVGTLYTLGGYNAPND NYNTNESGDDINEEAKKKRNAVLFV YVGGLFSALFICIGAVFYLLHRKIGIE GVGKSDHEKKPTIEDTKIEVFEETNG SKRNVKDEVIDVPFVDMEDNLhhhhh h (SEQ ID NO: 103) | ATGACCTTCAACGACGGCAGCGACGAGATCTCCACCGCCCAAAAGTAC AAGACCGACGTGGAGGGCATCATCGACAAGCTGAACGTCATCGACGA GACGATCAACGGCATCAACAGCACCCTGGACGAGCTCCTGGAGCTCGG CAACAACTGCCAACTCCACAGGACCTTCCTGATCTCCAGCTCCCTCAAC AACAAGATCGCCAAGTTCCTCGTGGAGATCAGGGAGCAGAAGGAGAA CACCAAGAAGTGCTTCCAATACGTGAAGCGCAACCACCAGCACCTGGC CAACTTCGTCTCCGAGCTCCACAAGACCCAAGGCGGCATCTTCGAGAA CGTCAACCTGGTGGACAACACCCCAGACGCCGACAAGTACTACCACGA AGAAGGAGATCTACCACCTGAACGACGACGTGGACGAGCCAGTCCTG GAGAAGAGGATCAAGGACGTGATCAACACCTACAACAAGCTGAAGAC CAAGAAGGTCCAGATGGACCAGTCCTACAAGAACATGTACATCACCAA GCTGAGGGAGGTGGAGGGCAGCCACGACCTGTTCAACCAAGTCGCCC AGCTCATCAGGGGCGAGACTGGACAAGAAGGGCAAGGCCTCGTCCGAG CGCGAGAACAACCTCCACAGCATCTACAACTTCGTGAAGCTGCACGAG ACGGAGCTCCACAACCTGTACGCCAAGTACACCCCAGAGTACATGGAG AAGATCAACAAGATCTTCGACGACATCAACGCCAAGATGATCGCCGTG GACCTCAACGACGACCACAGCTCCGAGTACAGCGACGTCAAGCGCCAC GAGCACGAGGCCATGCTCCTGATGGACGCCACCAACAACCTGTCCAAG GAAGTGGAGATGATGCAGAACGAGAGCGGCGGCAAGAACGACGGCA TCAACGGCATCAACGGCAAGTCCCAACTCGTGGAGGACTACACCAACACATGA GCGAGTTCACCGAGCAGGCCAAGACCGTCGCCAAGAAGATCCACGACT CCAAGGGCGACTACGCCAACATGTTCGACCACATCAGGGAGAACGAG GCCATGCTGGAGCGCATCGACCTCAAGAAGAAGGACATCAAGGAGAT CCTCGCCCACCTGAACAGGATGAAGGAGTACCTCCTGAAGAAGCTGTC CGAGGAAGAGAAGCTCCACCATGCGCGAGAAGCTCGAAGAGGTGA ACGAGCACCGACGAGATCGTCAAGAAGTTCCGCACCTACGACCAAA TGGTGGACATCTCCCAGAACATCGACATCAAGAACGTGCAAAGCAAGC GCTACGACTCCGTCGACGAGATCGACAAGGAGATGTCCTACATCAAGA CCCACAACAAGGACCTGATCGACAGCAAGTTCATCGTCGAGAGGGCCC TGGAGAACGACAAGCGCAAGAAGAGCGAGATGGCCCAAATCTTCAGC ACCATCTCCAGGGACAACAGCTCCATGTACGAGTACGCCAAGAGCTTC TTCGACTCCGTGCTGAAGGAGATCGAGAAGCTCACCCAGATGATCCGC AACATGGACAAGCTCATCAACGAGAACGAGGCCGTCATGGAGAAGCT GAAGGACCAAAGGCGCGAGCTCCAGAACGTGGAGAACGCCTCCACCG ACCTCGGCAAGCTCGAAGAGGTGGACAAGATGGCCCAGACCAAGAGC GAGACGGAGCTGTCCGAGAGGAACGACAGCCGCAACGCTAAGGACG GCGCTACCTACTCCACCCTCATGGACGACAAGGAGACGGACAGCGTGA ACGGCGAGGAGACGAAGCAAGAGAACGTGGTCGTGAAGAAGGGCCT GCCACCACAGACCGACATCTACACCAGCGTCGTGCTCAAGAACGACAG GAACGACCAAAAGTCCGAGAAGATCGGCGAGAAGAAGAGCAACAAGC CAGTGGGCACCGAGGAGAACATCCAGCACAGCTCCTACCTCAACAACG ACAACTCCAACAACGACATCGACGTGGGCACCCTCTACACCCTGGGCG GCTACAACGCCCCAAACGACAACTACAACACCAACGAGAGCGGCGACG ACATCAACGAGGAAGCCAAGAAGAAGAGGAACGCCGTGCTCTTCGTCT ACGTGGGCGGCCTCTTCTCCGCCCTGTTCATCTGCATCGGCGCCGTGTT CTACCTCCTGCACCGCAAGATCGGCATCGAGGGCGTCGGCAAGAGCGA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | CCACGAGAAGAAGCCAACCATCGAGGACACCAAGATCGAGGTGTTCG AGGAGACGAACGGCTCCAAGCGCAACGTCAAGGACGAGGTCATCGAC GTGCCATTCGTCGACATGGAGGACAACCTCCACCACCACCACCACCACT GA (SEQ ID NO: 104) |
| 53 | PvDBP (region II); Duffy receptor precursor (DBP) | PVX_110810 | mGEHKTDSKTDNGKGANNLVMLDY ETSSNGQPAGTLDNVLEFVTGHEG NSRKNSSNGGNPYDIDHKKTISSAII NHAFLQNTVMKNCNYKRKRRERDW DCNTKKDVCIPDRRYQLCMKELTNL VNNTDTNFHRDITFRKLYLKRKLIYD AAVEGDLLLKLNNYRYNKDFCKDIR WSLGDFGDIIMGTDMEGIGYSKVVE NNLRSIFGTDEKAQQRRKQWWNES KAQIWTAMMYSVKKRLKGNFIWICK LNVAVNIEPQIYRWIREWGRDYVSE LPTEVQKLKEKCDGKINYTDKKVCK VPPCQNACKSYDQWITRKKNQWDV LSNKFISVKNAEKVQTAGIVTPYDILK QELDEFNEVAFENEINKRDGAYIELC VCSVEEAKKNTQEVVhhhhhh (SEQ ID NO: 105) | ATGGGCGAGCACAAGACCGACTCCAAGACCGACAACGGCAAGGGCGC CAACAACCTGGTCATGCTCGACTACGAGACGTCCTCCAACGGCCAGCC AGCTGGCACCCTGGACAACGTGCTGGAGTTCGTCACCGGCCACGAGG GCAACAGCAGGAAGAACTCCAGCAACGGCGGCAACCCATACGACATC GACCACAAGAAGACCATCTCCAGCGCCATCATCAACCACGCCTTCCTGC AGAACACCGTGATGAAGAACTGCAACTACAAGAGGAAGAGGCGCGAG CGCGACTGGGACTGCAACACCAAGAAGGACGTCTGCATCCCAGACAG AGCGCTACCAACTCTGCATGAAGGAGCTGACCAACCTCGTGAACAACAC CGACACCAACTTCCACAGGGACATCACCTTCCGCAAGCTGTACCTCAAG AGGAAGCTGATCTACGACGCTGCTGTGGAGGGCGACCTCCTGCTCAAG CTCAACAACTACAGGTACAACAAGGACTTCTGCAAGGACATCCGCTGG TCCCTGGGCGACTTCGGCGACATCATCATGGGCACCGACATGGAGGGC ATCGGCTACTCCAAGGTGGTCGAGAACAACCTCCGCAGCATCTTCGGC ACCGACGAGAAGGCCCAACAGAGGCGCAAGCAATGGTGGAACGAGTC CAAGGCCCAGATCTGGACCGCCATGATGTACAGCGTGAAGAAGAGGC TGAAGGGCAACTTCATCTGGATCTGCAAGCTCAACGTGGCCGTCAACA TCGAGCCACAGATCTACAGGTGGATCAGGGAGTGGGGCAGGGACTAC GTCTCCGAGCTGCCAACCGAGGTGCAAAAGCTCAAGGAGAAGTGCGA CGGCAAGATCAACTACACCGACAAGAAGGTGTGCAAGGTCCCACCATG CCAAAACGCCTGCAAGAGCTACGACCAGTGGATCACCAGGAAGAAGA ACCAATGGGACGTCCTGTCCAACAAGTTCATCAGCGTGAAGAACGCCG AGAAGGTCCAGACCGCCGGCATCGTGACCCCATACGACATCCTGAAGC AAGAGCTCGACGAGTTCAACGAGGTGGCCTTCGAGAACGAGATCAAC AAGCGCGACGGCGCCTACATCGAGCTCTGCGTGTGCAGCGTCGAGGA AGCCAAGAAGAACACCCAAGAGGTGGTCCACCACCACCACCACCACTG A (SEQ ID NO: 106) |
| 54 | MSP3.10 [merozoite surface protein 3 alpha (MSP3a)] | PVX_097720 | mVIGGSPNNEAPNSSRHHLRNGFP GKNDSLPHEEPNNLEGKNESSDQC DTINLGOVTEKEKKTIEQASVQAQD ATKPEANNAEQIQAELQKVKTAKDE SATAAKDAETAKKNAVDAGKGLDAA KGAIKKAEEAAAEAKKQAGIAEKAEK DAEAAGKKDKLEDVNSQVQIAVEAS TKAKDKKTEAEIAVEIVKAVVAKEEA QKASDEAQKACEKAQKAHAKAQKA SDTTKTVETFKTNAEAAAKNAKEKA GNANKAATEAESANELSVAKQKAKD AEEAAKEAKKEQVKAEIAAEVAKAK VAKEEADAAQKKAEAAKKIVDKIAQD TKVPEAQREAKLATQTASKATEAAT EAGKKAQEAEESSKEAEEKAETSDA VKGKADAAEKAAGEAKKASIETEIAI EVAKAEVLNAEVKKTAQEAEKDATE AKEQAEKAKAAAEEAKTHGEKAEKV GESTKAHSDEAQQENKNAKDASEE AENRAVDALEEAYAVEAHLARTKNA AESAKSATDMSELEKAKEEAIDAANI AHQKWLKATQAATIAKEKKEAAKVA AEKAQTAANVVKDKAAKAEAAKKAET EAVKAAVEARAAAEEEAKQEAAKVGA SKEPQETKNKANVEAEATGNEAKKA EDAAEEAKEAAKKANEATDANVARS EADKAIAAAKKAKKAREKAAYGLLKT KNQYVLEPLDISPESADNITSKEEQV KEEMEDQGDEDSNEAEVEEALPNG SGAQEEDVNLEMDDEEEVEEVEEN VATNQQTGGKREKRNTNDTVDDTN ADKQFGDEFDTYNDIKKVTEALVKS MTSLVSDDPSVGDTINEFLSDMNHL FLSWhhhhhh (SEQ ID NO: 107) | ATGGTCATCGGCGGCTCCCCAAACAACGAGGCCCCAAACTCCAGCAGG CACCACCTCCGCAACGGCTTCCCAGGCAAGAACGACTCCCTCCCACACG AGGAGCCAAACAACCTGGAGGGCAAGAACGAGTCCAGCGACCAATGC GACACCATCAACCTGGGCCAGGTGACCGAGAAGGAGAAGAAGACCAT CGAGCAAGCTAGCGTCCAAGCTCAGGACGCTACCAAGCCAGAGGCCA ACAACGCCGAGCAAATCCAGGCCGAGCTCCAAAAGGTGAAGACCGCT AAGGACGAGTCCGCTACCGCTGCTAAGGACGCTGAGACGGCCAAGAA GAACGCTGTGGACGCTGGCAAGGGCCTGGACGCCGCCAAGGGCGCCA TCAAGAAGGCTGAGGAAGCCGCCGAGGCCAAGAAGCAGGCTGGC ATCGCCGAGAAGGCTGAGAAGGACGCTGAGGCTGCTGGCAAGAAGG ACAAGCTGGAGGACGTGAACAGCCAAGTCCAGATCGCCGTGGAGGCC TCCACCAAGGCCAAGGACAAGAAGACCGAGGCCGAGATCGCCGTGGA GATCGTCAAGGCCGTGGTCGCCAAGGAAGAGGCCCAAAAGGCTAGCG ACGAGGCTCAGAAGGCTTGCGAGAAGGCCCAAAAGGCTCACGCTAAG GCTCAGAAGGCTTCCGACACCACCAAGACCGTGGAGACGTTCAAGACC AACGCCGAGGCTGCCGCCAAGAACGCCAAGGAGAAGGCTGGCAACGC TAACAAGGCTGCTACCGAGGCTGAGAAGCGCTAACAGCTCTCCGTGGC CAAGCAGAAGGCCAAGGACGCCGAGGAAGCCGCCAAGGAAGCCAAG AAGGAGCAAGTCAAGGCTGAGATCGCTGCTGAGGTGGCTAAGGCTAA GGTGGCTAAGGAAGAGGCCGACGCTGCTCAGAAGAAGGCTGAGGCC GCCAAGAAGATCGTGGACAAGATCGCCCAAGACACCAAGGTGCCGGA GGCTCAGAGGGAGGCTAAGCTGGCTACCCAGACCGCTAGCAAGGCTA CCGAGGCCGCCACCGAGGCTGGCAAGAAGGCTCAAGAGGCCGAGGA GTCCAGCAAGGAAGCCGAGGAGAAGGCTGAGACGAGCGACGCTGTG AAGGGCAAGGCTGACGCTGCTGAGAAGGCTGCTGGCGAGGCCAAGAA GGCTTCCATCGAGACGGAGATCGCCATCGAGGTGCCCAAGGCCGAGG TGCTCAACGCCGAGGTCAAGAAGACCGCTCAAGAGGCCGAGAAGGAC GCTACCGAGGCCAAGGAGCAAGCCGAGAAGGCCAAGGCTGCCGCCGA GGAAGCCAAGACCCACGGCGAGAAGGCCGAGAAGGTGGGCGAGAGC ACCAAGGCCCACTCCGACGAGGCCCAACAGGAGAACAAGAACGCCAA GGACGCCAGCGAGGAAGCCGAGAACAGGGCTGTGGACGCTCTCGAAG AGGCCTACGCTGTGGAGGCTCACCTGGCTAGGACCAAGAACGCTGCTG AGTCCGCTAAGAGCGCTACCGACATGTCCGAGCTGGAGAAGGCCAAG GAAGAGGCCATCGACGCCGCCAACATCGCCCACCAAAAGTGGCTGAAG GCTACCCAGGCTACCATCGCTAAGGAGAAGAAGGAAGCCGCCAA GGTGGCTGCTGAGAAGGCTCAGACCGCTGCCAACGTGGTCAAGGACA AGGCTGCTAAGGCTGAGGCCAAGAAGGCTGAGACGGAGGCCGTCAAG GCTGCTGTGGAGGCCAGGGCCGCCGCCGAGGAAGAACAAGGAGCA CGCTAAGGTCGGCGCTAGCAAGGAGCCACAAGAGACGAAGAACAAGG CTAACGTGGAGGCTGAGGCTACCGGCAACGAGGCCAAGAAGGCCGAG GACGCTGCTGAGGAAGCCAAGGAAGCCGCCAAGAAGGCTAACGAGGC TACCGACGCTAACGTGGCTAGGTCCGAGGCTGACAAGGCTATCGCCGC CGCCAAGAAGGCCAAGAAGGCCCGCGAGAAGGCTGCTTACGGCCTCC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | TGAAGACCAAGAACCAATACGTGCTGGAGCCACTGGACATCTCCCCAG AGAGCGCCGACAACATCACCTCCAAGGAAGAGCAGGTGAAGGAAGAG ATGGAGGACCAAGGCGACGAGGACAGCAACGAGGCCGAGGTGGAGG AAGCCCTGCCAAACGGCTCCGGCGCTCAAGAGGAAGACGTCAACCTG GAGATGGACGACGAGGAAGAGGTGGAGGAAGTGGAGGAGAACGTG GCCACCAACCAACAGACCGGCGGCAAGAGGGAGAAGCGCAACACCAA CGACACCGTCGACGACACCAACGCCGACAAGCAATTCGGCGACGAGTT CGACACCTACAACGACATCAAGAAGGTGACCGAGGCCCTCGTCAAGTC CATGACCAGCCTGGTGTCCGACGACCCATCCGTGGGCGACACCATCAA CGAGTTCCTCAGCGACATGAACCACCTCTTCCTGTCCTGGCACCACCA CCACCACCACTGA (SEQ ID NO: 108) |
| 55 | sexual stage antigen s16, putative | PVX_ 000930 | mENNKIKGGKVPPPSVPTGNNSDN NVPKKDGGENNPPPDAENALQELK NFTKNLEKKTTTNRNIIISTTVINMVLL VLLSGLIGYNTKKGFKKGQMGSVKE VTPEAQKGKLhhhhhh (SEQ ID NO: 109) | ATGGAGAACAACAAGATCAAGGGCGGCAAGGTGCCACCACCATCCGT CCCAACCGGCAACAACTCCGACAACAACGTGCCAAAGAAGGACGGCG GCGAGAACAACCCACCACCAGACGCCGAGAACGCCCTCCAAGAGCTGA AGAACTTCACCAAGAACCTGGAGAAGAAGACCACCACCAACAGGAAC ATCATCATCTCCACCACCGTCATCAACATGGTGCTCCTGGTCCTCCTGA GCGGCCTGATCGGCTACAACACCAAGAAGGGCTTCAAGAAGGGCCAAA TGGGCTCCGTGAAGGAAGTGACCCCAGAGGCCCAGAAGGGCAAGCTC CACCACCACCACCACCACTGA (SEQ ID NO: 110) |
| 56 | | Positive Control? | | |
| 57 | | Negative Control? | | |

TABLE 5 list of protein references for additional 25 proteins

| Protein Code | Protein Name | Protein Reference | Source |
|---|---|---|---|
| X1 | PVX_094350 | PVX_094350 | Ehime University |
| X2 | PVX_099930 | PVX_099930 | Ehime University |
| X3 | PVX_114330 | PVX_114330 | Ehime University |
| X4 | PVX_088820 | PVX_088820 | Ehime University |
| X5 | PVX_080665 | PVX_080665 | Ehime University |
| X6 | PVX_092995 | PVX_092995 | Ehime University |
| X7 | PVX_087885 | PVX_087885 | Ehime University |
| X8 | PVX_003795 | PVX_003795 | Ehime University |
| X9 | PVX_087110 | PVX_087110 | Ehime University |
| X10 | PVX_087670 | PVX_087670 | Ehime University |
| X11 | PVX_081330 | PVX_081330 | Ehime University |
| X12 | PVX_122805 | PVX_122805 | Ehime University |
| V1 | RBP1b (P7) | PVX_098582 | WEHI |

TABLE 5-continued list of protein references for additional 25 proteins

| Protein Code | Protein Name | Protein Reference | Source |
|---|---|---|---|
| V2 | RBP2a (P9) | PVX_121920 | WEHI |
| V3 | RBP2b (P25) | PVX_094255 | WEHI |
| V4 | RBP2cNB (M5) | PVX_090325 | WEHI |
| V12 | RBP1a (P5) | PVX_098585 | WEHI |
| V5 | RBP2-P2 (P55) | PVX_101590 | WEHI |
| V11 | PvEBP | KMZ83376.1 | IPP |
| V10 | Pv DBPII (AH) | AAY34130.1 | IPP |
| V13 | Pv DBPII (SalI) | PVX_110810 | IPP |
| V6 | PvDBP R3-5 | PVX_110810 | WEHI |
| V7 | PvGAMA | PVX_088910 | WEHI |
| V8 | PvRipr | PVX_095055 | WEHI |
| V9 | PvCYRPA | PVX_090240 | WEHI |

List of protein sequences (insert aa sequence)

X1:

(SEQ ID NO: 111)

ENPVRHSVDIKSEDFVVLISLQNLQTFIMIGYTAVNKDHLNFDFSYLWALCIGTGLFIYSL

ISFVLIRSLALSKIDIGKYVLELLFSLSIIATCSLSIIDSFKIANMQLLFFSFALTGYAYYNL

MSLFFFCTLVGMTIQYNLSFTGFRAHSTSFFFLDMLSYLVQMIGGNILYFRMYELCTLIVI

SKRNPCKYVVASKEVKQVEKQIFSSLFNSYMCIKSKTYSDLTCTNDLLNKDSQSVVGRD

TNPKWNSPIGTSYQDKVNHTKKLLLRRGKRDKRYPKGGGGARLTCAKHSAYHNSRSL

ANCASKNTPICTTNFRISNTLSLKNHFNPNLTLEASPPVCKKCVSEKNSHKDNEYKNGEE

RKKAKRGIKSGTANKSNQLGNHGGDATQVANPTYRTTSHGGDATQVAYPTYRTTSHG

GDATQVDSPTHPTTSHGGNNSSSGHPQDDEVLIPIRGTNATNDAAATYNSNASWIKTAA

```
VIDVSVEGKQKKGGHQTFAGNPVNSSANFPSDKKPSYNSHRNGGTPPPNEQLRYYACPC

YQTHSSGSSLSEVPSGQTTKRKNSAHNSVEGGNPKMDNQQSRRVSNKRVDGATGEEHD

HPSDPPADNPNGNSNTYHC

X2
                                                  (SEQ ID NO: 112)
ELSHSLSVKNAPDASALNIEVEKDKKKICKNAFQYINVAELLSPREEETYVQKCEEVLDT

IKNDSPDESAEAEINEFILSLLHARSKYTIINDSDEEVLSKLLRSINGSISEEAALKRAKQLI

TFNRFIKDKAKVKNVQEMLVISSKADDFMNEPKQKMLQKIIDSFELYNDYLVILGSNINI

AKRYSSETFLSIKNEKFCSDHIHLCQKFYEQSIIYYRLKVIFDNLVTYVDQNSKHFKKEKL

LELLNMDYRVNRESKVHENYVLEDETVIPTMRITDIYDQDRLIVEVVQDGNSKLMHGR

DIEKREISERYIVTVKNLRKDLNDEGLYADLMKTVKNYVLSITQIDNDISNLVRELDHED

VEK

X3
                                                  (SEQ ID NO: 113)
LPWTKKRKAVNQMGIIKDMSQELRTKAEQLPTPEDISAKIHRVDKEVIDKLNKDIIEEEN

LDKHKPHVCQEPAYERDYSYLCPEDWVKNSNDQCWGIDYDGHCEALKYFQDYSVEEK

KEFEMNCCVLWPKLKNEGMKGAHKKDLLRGSISSNNGLIIKPKYL

X4
                                                  (SEQ ID NO: 114)
ELKKNNAALTSQRSSSRTTSTRSYKNAPKNSTSFLSRLSILIFALSCAIFVNTASGAAANR

PNANGFVSPTLIGFGELSIQESEEFKRMAWNNWMLRLESDWKHFNDSVEEAKTKWLHE

RDSAWSDWLRSLQSKWSHYSEKMLKEHKSNVMEKSANWNDTQWGNWIKTEGRKILE

AQWEKWIKKGDDQLQKLILDKWVQWKNDKIRSWLSSEWKTEEDYYWANVERATTAK

WLQEAEKMHWLKWKERINRESEQWVNWVQMKESVYINVEWKKWPKWKNDKKILFN

KWSTNLVYKWTLKKQWNVWIKEANTAPQV

X5
                                                  (SEQ ID NO: 115)
KGVTLSCVFSHASEEREGGTGTFALSNEPIYYAPSGGLAPCALISRGLSGDEEGSGEDGG

EDGDGDGGEDSAEDNAEDGDDDGGEDGGLPGGRFPYEEGKKSSLVSDAPSDLLDGDA

DEHAAEDGGAKRKMSKKEEEAEDNKIDKLVNAEMKKLEAGEEANKDPDAEPEKEDQG

SGQGQRAKLRCSNKLNYIQVTANGQREGDLFGENDGESAPAFVEIPHEVEEESGGVPTK

HDEAGEAAAAEEPHNRVDRAEKENNAKDLKFVEGERERQRSSPPSNGYSQNSFVELKG

VPDKLPPNFTNSLGSSPTHSNLEKPVYKHLPWSILASDSGSNTGSWADVNSSTYNVSPFS

FTSIRSGNSLHLLPMNFQIQNSIVKVTDEEYDKLKLKNSVKVYDKNALVDYKYEIFEVKE

GEEYNDGNDPYEERNGEEGDAGGEGGSDGEGDADSKSYQNNKSDGRGFFDGTLVTYTI

IILAGVIILLLSFVIYYYDIINKVKRRMSAKRKNNKSMAIANDTSAGMYMGDTYMENPH

V

X6
                                                  (SEQ ID NO: 116)
SQGCSGYRLPPPKRWFTFTSRPYCKTAAYYELKHMPYYVDAVSASENVKHEKWNNWL

KEMKISLTEKLEKESQEYMEKLEQQWDEFMKNSEDKWRHYNPQMEEEYQCSVYPLGL

KWDDEKWTAWFYEKGLWCLKKSFKTWLTDSKKGYNTYMKNLLQEFGKQFYEDWCR

RPEKRREDKICKRWGQKGLRNDNYYSLKWMQWRNWKNRNHDQKHVWVTLMKDAL

KEYTGPEFKLWTEFRKEKIDFYKQWMQAFAEQWTQDKQWNTWTEERNEYMKKKKEE

EAKKKAASKKKAASKKGGAAKKAPAKKAPTKKAAPGTKAPAKKAAPKKVAAPNAA

X7
```

-continued (SEQ ID NO: 117)
KEAVKKGSKKAMKQPMHKPNLLEEEDFEEKESFSDDEMNGFMEESMDASKLDAKKAK

TTLRSSEKKKTPTSGMSGMSGSGATSAATEAATNMNATAMNAAAKGNSEASKKQTDL

SNEDLFNDELTEEVIADSYEEGGNVGSEEAESLTNAFDDKLLDQGVNENTLLNDNMIYN

VNMVPHKKRELYISPHKHTSAASSKNGKHHAADADALDKKLRAHELLELENGEGSNSV

IVETEEVDVDLNGGKSSGSVSFLSSVVFLLIGLLCFTN

X8

(SEQ ID NO: 118)
NLSNDCKKGANNSFKLIVHTSDDILTLKWKVTGEGAAPGNKADVKKYKLPTLERPFTSV

QVHSANAKSKIIESKFYDIGSGMPAQCSAIATNCFLSGSLEIEHCYHCTLLEKKLAQDSEC

FKYVSSEAKELIEKDTPIKAQEEDANSADHKLIESIDVILKAVYKSDKDEEKKELITPEEV

DENLKKELANYCTLLKEVDTSGTLNNHQMANEEETFRNLTRLLRMHSEENVVTLQDKL

RNAAICIKHIDKWILNKRGLTLPEEGYPSEGYPPEEYPPEELLKEIEKEKSALNDEAFAKD

TNGVIHLDKPPNEMKFKSPYFKKSKYCNNEYCDRWKDKTSCMSNIEVEEQGDCGLCWI

FASKLHLETIRCMRGYGHFRSSALFVANCSKRKPEDRCNVGSNPTEFLQIVKDTGFLPLE

SDLPYSYSDAGNSCPNKRNKWTNLWGDTKLLYHKRPNQFAQTLGYVSYESSRFEHSID

LFIDILKREIQNKGSVIIYIKTNNVIDYDENGRVVHSLCGHKDADHAANLIGYGNYISAGG

EKRSYWIVRNSWGYYWGDEGNFKVDMYGPEGCKRNFIHTAVVFKIDLGIVEVPKKDEG

SIYSYFVQYVPNFLHSLFYVSYGKGADKGAAVVTGQAGGAVVTGQTETPTPEAAKNGD

QPGAQGSEAEVAEGGQAGNEAPGGLQESAVSSQTSEVTPQSSITAPQIGAVAPQIGAAAP

QIDVAAPQIDVVAPQTRSVDAPQTSSVAAHPPNVTPQNVTLGEGQHAGGVGSLIPADN

X9

(SEQ ID NO: 119)
ETLLDSETLKNYEKETNEYIRKKKVEKLFDVILKNVLVNKPENVYLYIYKNIYSFLLNKIF

VIGPPLLKITPTLCSAIASCFSYYHLSASHMIESYTTGEVDDAAESSTSKKLVSDDLICSIV

KSNINQLNAKQKRGYVVEGFPGTNLQADSCLRHLPSYVFVLYADEEYIYDKYEQENNV

KIRSDMNSQTFDENTQLFEVAEFNTNPLKDEVKVYLRN

X10

(SEQ ID NO: 120)
YPKKNFDKPDPTSPYQGQYGESEEQRQGYGIPPNPIMINLIGNQDQRPNVLQQFGINNK

NVMQFLINMFVYVAAILVSLKIWDYMSYSKCDYYKDLLLRIVRYQSHMNDGKMA

X11

(SEQ ID NO: 121)
SRIDKQPIQSSYLFQDNAVPPVRFSAVDADLFSIGVVHTEEQIFMDDANWVISSVPSKYL

NLHLLKTGSRPHFSHFSVSMNTGCNLFIASPVGETFPLSPSKDGATWKAFETDDSVEVIH

RETKEKRIYKLKFIPLKSGALLKVDVLKGIPFWVISQGRKILPTICSGDEEVLSNPQNEVF

KECTSSSSLSPEFDCLAGLSTYHRDKKNHTWKTSSGSIGQFIKIFFNKPVQITKFRFKPRD

DLLSWPSEVALQFDTDEEVIIPILHTHNMGQNTTRLEHPIITTSVKVEVRDMYERASENT

GGSFEVIGSTCOMMEDDYMTHHAVIDITECDRRLESLPDVMPLTKGSKFLAICPRPCLSS

SNGGVIYGSDVYSTDSAVCGAAVHAGVCSREGEGSCHFLVVRGGRANFVGALQNNV

LSLSRGGGGSGSGSSTSSDGDGDSDSSTSRANFSFSLSSASGFGGGPRGAHAEAAPSSYSI

VFKPRDHLAPTNGFLVDSGREFTSYGSVAYGWKREVSPSSSFSSPSPSYTSPPLEEPTLLR

GDSSSFNGIYSGGIEFPPASASQNCISQLDCQTNFWKFQMQENGTYFVQVLVGNKTSPEK

QKAFVELNGVPIIKGVDLGPDEVFVATDRVQVTNRALVLTSTCLGGESACSRARVSIMA

VQIVKT

X12

(SEQ ID NO: 122)

NGMNKDKDAEITPPPFIVLPGGKKIHMLQSEYEYDVLRDMYRTDEANGGSGEKESHPSG

DGAIRRNEFFKLFHHREGHYKFVIKNVPTKLSDLLQKGGNEQETDLFPLLYRSLQFACSA

DGTWPYARREVAFFKNGSVHCEAEFQNELSVRRTPRSGKKSFGRFPRGTLIKSSDLRSKI

VEGNSYDKRAAPLKSEKKKKALFLHPESVLYKMEEIFFYENPSVKSEIVGFVLFHDVCT

VTSLGHGAHPVNSPFLGSDLLEMIFGYCILHGFKKIRVKSESLNYETGIRTSFIEILLNGKT

ALEHLGLRLTNVAKFSKELYYVITGYTWKSDLVLSPIVRFEHDLYVHHDIEERFFLYVNK

MYRNMLHDLSFSCDENYYPYKNCYDIYPSVRRSQNNLCLFELNPIYEELKELFPDSCNIG

QRVRKCYEEIKKNVVCTHNGEGGEDGCKYYQFIVNTFIKPRRKTSFFIYHNMYVQEYLS

KKSYPYYLLLSEVIKNEENNFLEKGNYDLVADAQTHLFLNYVLQNSTFFIFWNFSTEFW

KRFRYIQAGPTGATSTPQKGQAVFCPMAYAYEFVEHLDTFYVRG

V6

(SEQ ID NO: 123)

SVEEAKKNTQEVVTNVDNAAKSQATNSNPISQPVDSSKAEKVPGDSTHGNVNSG

QDSSTTGKAVTGDGQNGNQTPAESDVQRSDIAESVSAKNVDPQKSVSKRSDDTASVTGI

AEAGKENLGASNSRPSESTVEANSPGDDTVNSASIPVVSGENPLVTPYNGLRHSKDNSDS

DGPAESMANPDSNSKGETGKGQDNDMAKATKDSSNSSDGTSSATGDTTDAVDREINKG

VPEDRDKTVGSKDGGGEDNSANKDAATVVGEDRIRENSAGGSTNDRSKNDTEKNGAS

TPDSKQSEDATALSKTESLESTESGDRTTNDTTNSLENKNGGKEKDLQKHDFKSNDTPN

EEPNSDQTTDAEGHDRDSIKNDKAERRKHMNKDTFTKNTNSHHLN

V7

(SEQ ID NO: 124)

IRNGNNPQALVPEKGADPSGGQNNRSGENQDTCEIQKMAEEMMEKMMKEKDV

FSSIMEPLQSKLTDDHLCSKMKYTNICLHEKDKTPLTFPCTSPQYEQLIHRFTYKKLCNS

KVAFSNVLLKSFIDKKNEENTFNTIIQNYKVLSTCIDDDLKDIYNASIELFSDIRTSVTEITE

KLWSKNMIEVLKTREQTIAGILCELRNGNNSPLVSNSFSYENFGILKVNYEGLLNQAYAA

FSDYYSYFPAFAISMLEKGGLVDRLVAIHESLTNYRTRNILKKINEKSKNEVLNNEEIMH

SLSSYKHHAGGTRGAFLQSRDVREVTQGDVSVDEKGDRATTAGGNQSASVAAAAPKD

AGPTVAAPNTAATLKTAASPNAAATNTAAPPNMGATSPLSNPLYGTSSLQPKDVAVLV

RDLLKNTNIIKFENNEPTSQMDDEEIKKLIESSFFDLSDNTMLMRLLIKPQAAILLIIESFIM

MTPSPTRDAKTYCKKALVNGQLIETSDLNAATEEDDLINEFSSRYNLFYERLKLEEL

V8

(SEQ ID NO: 125)

KEYCDQLSFCDVGLTHHFDTYCKNDQYLFVHYTCEDLCKTCGPNSSCYGNKYK

HKCLCNSPFESKKNHSICEARGSCDAQVCGKNQICKMVDAKATCTCADKYQNVNGVC

LPEDKCDLLCPSNKSCLLENGKKICKCINGLTLQNGECVCSDSSQIEEGHLCVPKNKCKR

KEYQQLCTNEKEHCVYDEQTDIVRCDCVDHFKRNERGICIPVDYCKNVTCKENEICKVV

NNTPTCECKENLKRNSNNECVFNNMCLVNKGNCPIDSECIYHEKKRHQCLCHKKGLVA

INGKCVMQDMCRSDQNKCSENSICVNQVNKEPLCICLFNYVKSRSGDSPEGGQTCVVD

NPCLAHNGGCSPNEVCTFKNGKVSCACGENYRPRGKDSPTGQAVKRGEATKRGDAGQ

PGQAHSANENACLPKTSEADQTFTFQYNDDAAIILGSCGIIQFVQKSDQVIWKINSNNHF

YIFNYDYPSEGQLSAQVVNKQESSILYLKKTHAGKVFYADFELGHQGCSYGNMFLYAH

REEA

V9
(SEQ ID NO: 126)
SKNIIILNDEITTIKSPIHCITDIYFLFRNELYKTCIQHVIKGRTEIHVLVQKKINSAW

ETQTTLFKDHMWFELPSVFNFIHNDEIIIVICRYKQRSKREGTICKRWNSVTGTIYQKEDV

QIDKEAFANKNLESYQSVPLTVKNKKFLLICGILSYEYKTANKDNFISCVASEDKGRTWG

TKILINYEELQKGVPYFYLRPIIFGDEFGFYFYSRISTNNTARGGNYMTCTLDVTNEGKKE

YKFKCKHVSLIKPDKSLQNVAKLNGYYITSYVKKDNFNECYLYYTEQNAIVVKPKVQN

DDLNGCYGGSFVKLDESKALFIYSTGYGVQNIHTLYYTRYD

List of polynucleotide sequences (insert bp sequence)
X1
(SEQ ID NO: 127)
GAGAACCCCGTGAGGCACTCGGTGGACATAAAGTCGGAAGACTTCGTCGTCC

TGATTTCGCTCCAAAACCTGCAGACCTTCATCATGATAGGGTACACAGCCGTGAACA

AAGACCACCTGAATTTCGACTTCTCCTACTTATGGGCCCTCTGCATCGGGACGGGCC

TCTTCATATACTCCCTCATCAGCTTTGTACTCATAAGATCCCTAGCACTGTCAAAAAT

AGACATAGGCAAATACGTCCTGGAGCTGCTATTCAGTTTGAGTATAATCGCCACATG

TTCACTCTCCATAATAATTGACTCTTTCAAAATAGCCAACATGCAGTTGCTTTTTTTT

TCGTTCGCTTTAACGGGCTATGCCTACTACAATTTGATGAGCCTCTTCTTTTTCTGCA

CACTGGTAGGAATGACCATTCAGTACAATTTAAGTTTCACTGGGTTCAGAGCGCATT

CGACTTCTTTCTTCTTTTTAGATATGCTATCTTACCTAGTGCAAATGATAGGAGGGAA

CATCCTCTACTTTCGCATGTACGAGCTGTGTACCCTAATCGTCATTTCGAAGAGGAA

CCCCTGCAAGTATGTTGTCGCATCGAAGGAAGTGAAACAAGTGGAGAAGCAAATTT

TCTCTTCTTTATTTAATTCTTACATGTGCATCAAGTCCAAAACTTATTCAGATTTAAC

CTGCACTAATGATCTGTTAAATAAAGACAGTCAATCTGTTGTCGGTAGGGATACGAA

CCCTAAGTGGAACTCCCCCATTGGTACTTCCTACCAGGATAAGGTCAATCATACGAA

GAAGTTACTCCTTCGGAGGGGAAAACGGGACAAACGCTACCCCAAAGGGGGAGGG

GGAGCTCGACTAACATGTGCAAAACATAGTGCCTACCATAATAGCCGAAGTCTTGCC

AACTGTGCCAGTAAGAATACCCCCATTTGCACAACTAACTTTAGGATATCTAACACC

CTTTCACTTAAAAATCATTTCAACCCTAACCTAACCTTAGAAGCGTCTCCCCCCGTTT

GTAAAAAATGCGTTTCGGAAAAGAATAGCCATAAGGATAATGAGTACAAAAACGGG

GAAGAGAGAAAAAAAGCAAAACGTGGTATCAAGTCGGGCACTGCAAACAAGTCTA

ACCAGTTGGGCAACCACGGGGGGGACGCTACGCAGGTGGCTAATCCTACCTACAGA

ACTACTTCCCACGGGGGGGACGCAACCCAGGTGGCTTATCCTACCTACAGAACTACT

TCCCACGGGGGGGACGCAACGCAGGTGGATAGTCCTACCCACCCAACTACCTCCCA

TGGGGGGAACAACTCGTCGAGCGGGCACCCCCAAGACGACGAAGTGCTCATCCCCA

TTAGGGGAACCAACGCCACTAACGATGCAGCCGCCACCTACAACTCGAACGCTAGT

TGGATCAAAACCGCTGCGGTTATTGACGTGTCTGTGGAGGGGAAGCAGAAAAAGGG

GGGACATCAAACGTTCGCGGGCAATCCCGTAAATTCATCCGCTAATTTCCCATCGGA

CAAGAAACCTTCCTACAACTCGCACCGCAACGGAGGTACTCCCCCCCCCAAATGAAC

AACTCAGGTACTACGCCTGCCCCTGCTACCAGACCCACTCCAGCGGATCGTCCCTCA

GTGAGGTGCCCTCGGGACAAACGACGAAGCGGAAAAATAGTGCGCACAACTCGGTT

-continued

```
GAAGGGGGAAACCCCAAAATGGATAATCAGCAAAGTCGCCGCGTGAGTAACAAGC

GGGTAGATGGCGCAACGGGTGAGGAACATGACCACCCAAGTGACCCCCCCGCAGAT

AACCCAAATGGAAACTCCAACACCTACCACTGC
```

X2
(SEQ ID NO: 128)
```
GAGCTGAGCCACAGCTTGTCCGTGAAGAACGCGCCGGACGCGAGCGCGCTG

AACATCGAGGTGGAGAAGGACAAAAAGAAGATCTGCAAAAACGCATTCCAATACAT

AAACGTAGCTGAGCTGTTGTCCCCAAGGGAGGAAGAAACCTACGTGCAGAAATGTG

AAGAGGTCCTAGACACAATAAAGAATGACAGTCCAGATGAATCGGCAGAAGCAGA

GATAAACGAATTTATACTGAGCTTACTGCACGCTCGTTCTAAGTATACCATAATAAA

TGACTCAGATGAGGAGGTACTGAGCAAGCTCCTGAGGAGTATCAACGGATCGATAA

GTGAAGAGGCAGCGTTGAAGAGAGCCAAACAGCTAATCACATTCAATCGGTTTATA

AAAGACAAAGCGAAGGTAAAAAATGTGCAAGAGATGCTAGTAATAAGTAGCAAAG

CAGATGACTTCATGAATGAGCCGAAGCAAAAAATGCTCCAAAAAATTATAGATTCG

TTTGAACTGTATAATGATTACCTAGTCATTTTAGGGTCAAATATTAACATCGCCAAG

AGGTACTCCTCAGAAACGTTTCTTTCTATTAAAAATGAAAAGTTCTGCTCAGACCAC

ATCCACTTATGCCAGAAGTTCTACGAGCAGTCTATCATTTACTACAGATTGAAGGTT

ATTTTTGATAACCTGGTGACTTATGTAGATCAAAATTCCAAGCATTTTAAAAAGGAA

AAGTTGCTGGAGCTTCTAAATATGGATTATAGGGTCAATCGAGAGTCGAAGGTGCAT

GAAAATTACGTGCTGGAGGATGAGACGGTCATCCCCACGATGCGCATTACAGACAT

TTACGATCAAGATAGGCTAATTGTTGAGGTCGTTCAGGATGGAAATAGCAAGCTGAT

GCACGGCAGGGATATTGAGAAGAGGGAAATCAGCGAGAGGTACATCGTCACCGTGA

AGAACCTGCGCAAGGACCTCAACGACGAGGGGCTCTACGCCGACTTGATGAAGACC

GTCAAGAACTACGTGCTCTCCATCACGCAGATCGACAACGACATTTCCAACCTCGTG

CGCGAGCTCGACCACGAGGATGTGGAGAAG
```

X3
(SEQ ID NO: 129)
```
CTACCATGGACGAAGAAAAGAAAGGCGGTGAACCAAATGGGCATCATAAAA

GATATGTCGCAGGAGCTTAGGACTAAGGCCGAACAGCTTCCAACCCCCGAGGATAT

ATCAGCCAAAATTCACAGAGTAGATAAAGAGGTCATCGATAAGTTAAACAAAGACA

TCATAGAGGAAGAAAATTTAGACAAGCACAAACCGCACGTCTGCCAGGAGCCAGCA

TACGAGAGGGACTATTCGTACCTATGTCCCGAAGACTGGGTGAAGAACTCCAACGA

TCAGTGCTGGGGCATAGACTACGATGGTCACTGTGAAGCGCTAAAATATTTCCAAGA

TTATTCTGTAGAGGAGAAAAAAGAATTTGAAATGAACTGCTGCGTCTTGTGGCCTAA

GCTAAAAAATGAAGGCATGAAAGGAGCGCACAAGAAGGACCTCCTAAGGGGATCG

ATAAGTTCAAACAATGGGTTAATAATAAAGCCGAAATATTTG
```

X4
(SEQ ID NO: 130)
```
GAATTGAAGAAGAACAATGCCGCGTTGACCTCACAAAGGTCATCTTCTAGAA

CCACATCCACAAGGAGCTACAAAAATGCCCCAAAAAATTCCACTTCATTCCTTTCTC

GTTTATCTATTCTGATATTTGCCTTATCATGTGCTATTTTTGTAAATACTGCATCAGG

GGCGGCAGCTAATAGACCAAACGCGAATGGCTTTGTGTCACCTACTTTAATAGGATT

TGGCGAATTAAGCATCCAAGAATCAGAAGAATTCAAAAGAATGGCTTGGAATAATT
```

-continued

```
GGATGTTGCGATTGGAGTCCGACTGGAAACATTTTAACGATTCTGTTGAAGAAGCCA

AAACCAAATGGCTTCATGAAAGAGACTCAGCTTGGTCTGATTGGCTTCGTTCCTTGC

AAAGTAAATGGTCTCACTATAGTGAAAAAATGCTTAAAGAACACAAAAGTAATGTT

ATGGAAAAATCAGCCAACTGGAATGACACGCAATGGGGAAATTGGATAAAAACTGA

AGGAAGAAAAATTCTAGAAGCGCAATGGGAAAAATGGATTAAAAAAGGTGATGAC

CAATTACAAAAGTTAATTTTAGATAAATGGGTTCAATGGAAAAATGATAAGATCCG

ATCCTGGTTATCCAGTGAATGGAAAACCGAAGAAGATTACTACTGGGCAAATGTAG

AGCGCGCTACAACAGCAAAATGGTTGCAAGAAGCAGAGAAAATGCATTGGCTTAAA

TGGAAAGAAAGAATTAACAGAGAGTCTGAACAATGGGTGAACTGGGTCCAAATGAA

AGAAAGCGTTTACATCAATGTAGAATGGAAAAAATGGCCCAAATGGAAAAATGATA

AAAAAATTCTATTTAACAAATGGTCAACTAACCTTGTCTACAAATGGACACTGAAAA

AGCAGTGGAACGTTTGGATTAAGGAAGCAAATACTGCACCCCAAGTT
```

X5

(SEQ ID NO: 131)
```
AAGGGTGTCACCTTGAGTTGCGTTTTTTCCCATGCGAGTGAGGAACGTGAGG

GTGGCACAGGGACATTTGCTTTGAGCAATGAGCCGATTTATTACGCCCCTAGTGGGG

GGCTGGCGCCGTGCGCGCTCATCAGCAGAGGGTTAAGCGGGGATGAGGAGGGTAGC

GGCGAGGACGGCGGTGAAGATGGCGACGGAGATGGTGGTGAAGACAGCGCTGAGG

ACAACGCTGAGGATGGAGACGATGATGGTGGCGAAGATGGCGGCTTGCCCGGGGA

CGCTTCCCATACGAAGAAGGAAAAAAGAGTAGCCTTGTGAGCGACGCACCCAGCGA

CCTCCTGGATGGAGATGCGGATGAACATGCCGCCGAAGATGGGGGAGCGAAGCGAA

AGATGAGTAAGAAGGAGGAAGAGGCGGAGGATAACAAAATTGACAAGTTGGTAAA

TGCGGAAATGAAAAAGCTCGAGGCAGGGGAAGAGGCGAACAAGGATCCCGACGCA

GAACCAGAAAAAGAGGACCAGGGAAGTGGCCAAGGACAAAGGGCGAAGCTGAGGT

GCTCAAACAAGCTAAATTACATACAGGTGACGGCGAATGGCCAAAGGGAGGGCGAC

CTCTTTGGCGAGAACGACGGGGAGAGCGCCCCAGCTTTCGTGGAGATACCCCACGA

GGTTGAGGAGGAAAGCGGCGGTGTGCCCACAAAGCATGACGAAGCGGGGGAAGCA

GCTGCGGCGGAGGAACCACATAACCGCGTCGACCGAGCGGAAAAAGAAAACAACG

CGAAGGACTTAAAATTTGTGGAGGGGGAGCGAGAAAGACAAAGGAGCAGCCCCCC

CTCGAATGGATATTCCCAAAACAGCTTTGTCGAACTGAAAGGTGTGCCCGATAAATT

GCCCCCTAATTTTACCAACTCGCTTGGTAGCTCCCCAACGCACAGTAATTTGGAGAA

ACCAGTTTATAAGCACTTACCCTGGTCTATCCTGGCATCCGACTCTGGTTCGAACAC

CGGGTCCTGGGCAGACGTCAACAGTAGTACCTACAATGTGAGTCCATTCAGTTTCAC

CTCAATACGTAGTGGTAACTCTCTGCATCTACTGCCGATGAATTTCCAAATCCAAAA

CTCCATCGTGAAAGTAACTGATGAGGAGTATGACAAATTGAAGCTTAAAAACAGCG

TCAAAGTGTATGACAAAAATGCCCTGGTAGATTATAAGTATGAAATTTTTGAGGTGA

AGGAAGGGGAGGAATATAATGATGGGAATGACCCTTATGAGGAAAGGAATGGGGA

AGAAGGGGATGCAGGTGGAGAGGGGGGTTCCGATGGGGAGGGAGATGCAGATTCT

AAATCATATCAAAATAACAAATCGGATGGACGTGGGTTCTTCGATGGGACCTTAGTA

ACCTACACCATTATCATTTTAGCTGGTGTTATAATTCTGCTGCTAAGTTTTGTCATTT
```

-continued

ATTACTACGATATAATAAATAAGGTGAAGAGGCGAATGAGTGCCAAGCGGAAGAAC

AACAAATCTATGGCCATCGCGAATGATACATCCGCGGGGATGTACATGGGCGACAC

CTACATGGAGAATCCCCACGTT

X6

(SEQ ID NO: 132)
TCACAAGGATGTTCAGGATACCGTTTACCACCACCAAAAAGATGGTTTACCTT

CACTTCTCGACCATACTGTAAAACAGCTGCATATTATGAACTTAAACATATGCCATA

TTATGTAGATGCAGTTAGTGCATCAGAAAACGTAAAACATGAGAAATGGAATAACT

GGTTAAAAGAAATGAAAATATCATTAACTGAAAAATTAGAAAAAGAATCACAAGAA

TATATGGAAAAATTGGAACAGCAATGGGATGAATTTATGAAAAATTCAGAAGATAA

ATGGAGGCATTATAATCCCCAAATGGAAGAAGAATATCAATGTAGTGTTTATCCACT

TGGATTAAAATGGGATGATGAAAAGTGGACTGCATGGTTTTATGAAAAAGGATTAT

GGTGTTTGAAGAAAAGCTTTAAAACATGGCTCACTGATTCTAAAAAAGGTTACAAC

ACCTACATGAAAAATCTTTTACAGGAATTTGGTAAACAATTTTATGAAGATTGGTGT

CGTAGACCTGAAAAACGTCGTGAAGATAAAATTTGCAAGAGATGGGGACAAAAAG

GATTACGTAATGACAATTACTATTCGTTAAAGTGGATGCAGTGGAGAAATTGGAAA

AACAGAAACCACGATCAAAAACATGTGTGGGTAACTCTTATGAAGGATGCGCTAAA

GGAATATACGGGGCCCGAATTCAAATTATGGACTGAGTTTAGAAAAGAAAAGATAG

ACTTTTACAAGCAATGGATGCAAGCTTTCGCCGAACAGTGGACACAAGACAAACAA

TGGAATACGTGGACTGAAGAAAGAAATGAATATATGAAAAAGAAAAAAGAAGAAG

AAGCAAAAAAAAAGCAGCATCAAAAAAAAAAGCAGCATCAAAAAAAGGAGGAG

CAGCAAAAAAGGCACCAGCAAAAAAGGCACCAACAAAAAAAGCCGCACCAGGAAC

AAAGGCACCAGCAAAAAAAGCAGCACCTAAAAAAGTTGCAGCACCAAATGCAGCA

X7

(SEQ ID NO: 133)
AAGGAGGCAGTGAAGAAGGGGTCCAAGAAGGCAATGAAGCAGCCCATGCAC

AAGCCGAACCTTCTTGAAGAGGAAGACTTTGAGGAGAAAGAATCCTTTTCGGATGA

CGAGATGAATGGGTTCATGGAGGAGAGCATGGATGCTTCTAAGTTGGATGCGAAGA

AGGCCAAGACGACCCTCAGGAGCTCGGAGAAGAAGAAGACTCCAACGAGCGGAAT

GAGTGGAATGAGTGGAAGCGGCGCCACCAGCGCAGCCACCGAGGCAGCCACGAAC

ATGAACGCCACCGCCATGAACGCCGCTGCTAAGGGCAACAGCGAGGCGAGCAAAA

AGCAAACCGACTTGTCCAACGAAGACCTGTTCAACGACGAGCTCACAGAAGAGGTC

ATTGCAGATTCGTACGAAGAGGGAGGAAACGTGGGAAGCGAGGAAGCCGAAAGCC

TCACAAATGCATTTGACGACAAGCTACTAGACCAAGGAGTGAATGAAAATACTCTG

CTGAACGACAACATGATTTACAACGTCAATATGGTTCCACATAAGAAGCGAGAATT

ATACATCTCCCCACACAAGCATACCTCTGCAGCAAGCAGTAAAAATGGCAAACATC

ATGCGGCGGACGCGGACGCTTTGGACAAAAAACTGAGGGCTCACGAGCTGCTCGAG

CTGGAAAACGGAGAAGGCAGCAACTCAGTCATTGTCGAAACGGAAGAAGTGGATGT

TGACCTAAACGGAGGAAAGTCAAGCGGCTCCGTGTCCTTCCTCAGCTCCGTAGTCTT

CTTGCTCATCGGATTGTTATGTTTCACCAAT

X8

(SEQ ID NO: 134)

AACCTGAGCAACGATTGCAAAAAAGGAGCCAACAACAGCTTTAAGTTAATCG

TGCACACCAGCGATGATATTTTGACACTCAAGTGGAAGGTCACTGGGGAAGGGGCA

GCTCCAGGCAACAAAGCAGATGTAAAGAAGTACAAACTCCCTACCCTAGAGAGGCC

TTTCACTTCCGTGCAAGTGCATTCAGCCAACGCCAAGTCGAAGATAATCGAAAGCAA

ATTTTACGACATTGGCAGCGGCATGCCAGCCCAGTGCAGCGCGATCGCCACGAACT

GCTTCCTCAGCGGCAGCCTCGAAATCGAGCACTGCTACCACTGCACCCTGTTGGAGA

AGAAGCTGGCCCAAGACAGCGAGTGCTTCAAGTACGTCTCGAGTGAAGCGAAGGAG

TTGATCGAGAAAGACACGCCGATTAAAGCTCAAGAAGAAGACGCCAACTCTGCAGA

CCACAAACTGATCGAGTCCATAGACGTGATACTAAAGGCAGTGTACAAATCAGATA

AGATGAGGAAAGAAGGAGCTCATCACCCCGGAGGAAGTGGACGAAAATTTGAA

GAAAGAGCTAGCCAATTATTGTACCCTACTGAAGGAGGTAGACACAAGTGGCACTC

TTAACAACCACCAGATGGCAAACGAAGAGGAAACGTTCAGAAATTTGACTCGACTG

TTGCGAATGCATAGCGAAGAAAACGTGGTGACCCTTCAGGACAAACTGAGAAACGC

AGCCATATGCATCAAGCACATCGACAAGTGGATTCTTAACAAGAGGGGGTTGACCC

TACCGGAAGAAGGGTACCCATCGGAAGGGTACCCCCCAGAAGAGTACCCCCCGGAG

GAACTCCTCAAAGAAATCGAGAAGGAAAAAAGCGCTCTGAATGATGAAGCGTTCGC

TAAAGATACCAACGGAGTCATCCACCTGGATAAGCCTCCCAACGAAATGAAATTTA

AATCCCCCTATTTTAAAAAGAGCAAATACTGTAACAATGAGTACTGTGATAGGTGGA

AAGATAAAACGAGTTGCATGTCAAATATAGAAGTGGAAGAGCAAGGGGATTGCGG

GCTCTGTTGGATTTTCGCCTCTAAGTTACACTTAGAAACGATCAGGTGCATGAGAGG

GTATGGCCACTTCCGCAGCTCCGCTCTGTTTGTGGCCAACTGCTCGAAGAGGAAGCC

AGAAGATAGATGCAACGTGGGTTCTAACCCTACAGAGTTTCTTCAAATTGTTAAGGA

CACGGGATTTTTACCTCTAGAGTCCGATCTCCCCTACAGCTATAGCGACGCGGGGAA

CTCCTGCCCCAATAAAAGAAACAAGTGGACCAACCTGTGGGGGGATACCAAACTGC

TGTATCATAAGAGACCCAATCAGTTTGCACAAACACTCGGGTACGTTTCCTACGAAA

GCAGTCGCTTTGAGCACAGCATCGACCTCTTCATAGACATCCTCAAAAGGGAAATTC

AAAACAAAGGCTCCGTTATCATTTACATAAAAACCAACAATGTCATCGATTATGACT

TTAATGGAAGAGTCGTCCACAGCCTATGTGGCCATAAGGATGCAGATCATGCCGCTA

ACCTGATCGGTTATGGTAACTACATCAGTGCTGGTGGGGAGAAGAGGTCCTATTGGA

TTGTGCGAAACAGCTGGGGGTACTACTGGGGAGATGAAGGCAACTTTAAGGTTGAC

ATGTACGGCCCGGAGGGATGCAAACGGAACTTCATCCACACGGCTGTTGTGTTTAAG

ATAGACCTGGGCATCGTCGAAGTCCCGAAGAAGGACGAGGGGTCCATTTATAGCTA

CTTCGTTCAGTACGTCCCCAACTTTTTGCACAGCCTTTTCTACGTGAGTTACGGTAAG

GGTGCTGATAAGGGAGCGGCGGTGGTGACAGGGCAGGCGGGAGGAGCGGTAGTCA

CAGGACAGACTGAAACGCCCACTCCGGAGGCCGCTAAAAATGGGGATCAGCCAGG

AGCACAGGGTAGCGAGGCAGAAGTCGCGGAGGGTGGCCAGGCAGGAAATGAAGCC

CCGGGAGGGTTGCAAGAGAGTGCTGTTTCGTCGCAAACGAGTGAGGTTACGCCGCA

ATCTAGTATAACTGCTCCGCAAATCGGTGCAGTTGCCCCACAAATCGGTGCAGCTGC

CCCACAAATCGATGTAGCCGCCCCACAAATCGATGTAGTCGCCCCACAAACGAGGT

-continued

CCGTTGACGCCCCCCAAACGAGCTCGGTTGCCGCCCACCCCCCAAACGTGACGCCGC

AGAACGTGACGCTTGGGGAGGGCCAGCACGCGGGGGGTGTAGGCTCCCTCATCCCC

GCGGACAAC

X9

(SEQ ID NO: 135)
GAAACCCTGCTAGACAGCGAAACGTTAAAGAACTACGAAAAGGAAACGAAC

GAATACATTCGCAAAAAAAAGTGGAGAAACTGTTCGATGTTATTTTAAAAAATGTT

CTGGTAAACAAACCGGAAAATGTATACCTGTACATATACAAGAACATTTATTCCTTC

CTTTTGAACAAAATTTTTGTGATCGGCCCTCCTTTGCTGAAAATTACTCCCACCTTAT

GTTCTGCGATTGCCAGCTGCTTTAGCTACTACCACCTCAGCGCCTCGCACATGATCG

AGTCTTACACTACTGGTGAAGTAGATGACGCTGCAGAGAGTTCCACAAGCAAAAAG

TTAGTCAGTGACGACTTAATCTGCTCCATCGTTAAAAGCAACATAAACCAGCTGAAC

GCGAAGCAAAAGCGGGGGTATGTAGTCGAAGGGTTCCCCGGCACCAATCTTCAGGC

AGACAGTTGCCTACGGCATTTGCCATCTTACGTTTTTGTCCTGTACGCCGACGAAGA

GTACATTTATGACAAGTACGAACAAGAGAACAACGTAAAAATTCGTTCAGACATGA

ACAGCCAAACTTTTGATGAAAACACACAGTTGTTCGAAGTGGCCGAGTTCAACACG

AATCCGCTGAAGGATGAGGTAAAGGTCTACTTAAGGAAC

X10

(SEQ ID NO: 136)
TATCCAAAAAAGAACTTCGACAAACCCGACCCAACTTCCCCATACCAAGGAC

AATATGGAGAGTCTGAGGAACAAAGACAAGGTTATGGAATCCCCCCCAACCCAACC

ATGATTAACCTTACTGGTAACCAAGACCAACGACCAAATGTATTGCAACAATTTGGA

ATAAACAACAAAAATGTAATGCAGTTTTTAATAAACATGTTTGTGTACGTTGCTGCT

ATATTAGTTAGTTTAAAAATATGGGACTACATGTCTTACAGCAAATGTGATTATTAC

AAAGATTTATTATTAAGAATTGTAAGATACCAATCACACATGAATGATGGTAAGATG

GCC

X11

(SEQ ID NO: 137)
AGCCGCATCGACAAGCAGCCCATCCAGAGCAGCTACCTCTTCCAGGATAACG

CAGTCCCGCCTGTTCGATTCTCCGCAGTAGATGCAGACCTGTTTTCCATTGGAGTAGT

TCACACAGAGGAGCAAATATTTATGGACGACGCCAACTGGGTGATTAGCAGCGTGC

CCAGTAAGTACCTGAACTTGCATCTACTCAAAACGGGTTCTAGACCCCATTTTTCGC

ACTTCTCCGTATCTATGAACACGGGTTGCAACCTATTCATCGCTTCACCGGTGGGGG

AAACCTTCCCCTTGAGTCCCTCCAAAGATGGAGCGACGTGGAAAGCATTTGAAACG

GACGACAGTGTAGAGGTGATTCACAGAGAGACGAAGGAAAAGAGAATCTATAAGC

TCAAGTTCATTCCTCTGAAGAGTGGGGCTCTCCTAAAGGTTGACGTTTTGAAGGGAA

TTCCCTTTTGGGTTATCTCACAAGGGAGGAAAATCCTACCAACGATTTGTTCTGGAG

ATGAGGAGGTGCTATCAAACCCACAGAATGAGGTCTTCAAAGAGTGCACATCGTCG

AGTAGTCTCTCTCCCGAATTTGATTGTCTAGCCGGGCTGAGCACCTACCATAGGGAT

AAGAAGAACCACACGTGGAAAACGTCTAGCGGATCTATAGGTCAGTTTATAAAGAT

CTTCTTCAATAAGCCCGTACAAATTACCAAGTTTAGGTTTAAGCCCAGAGACGACCT

GCTGTCTTGGCCCTCCGAAGTAGCTCTCCAATTCGATACCGATGAGGAGGTGATCAT

ACCAATTCTGCATACGCACAATATGGGGCAGAACACGACTAGGCTAGAACACCCAA

TCATCACCACCTCTGTTAAGGTAGAAGTGAGAGACATGTACGAACGGGCAAGTGAA

```
AATACAGGAGGTTCTTTCGAGGTAATTGGAAGCACATGCCAGATGATGGAAGACGA

CTACATGACGCACCATGCTGTTATAGACATCACCGAGTGTGATCGTAGGTTGGAGTC

CCTCCCAGATGTTATGCCCTTAACGAAGGGGAGCAAATTTCTGGCCATTTGTCCCCG

CCCCTGCTTGAGCAGCTCCAATGGGGGAGTCATTTACGGGTCAGATGTTTATTCCAC

AGATTCTGCCGTATGTGGGGCGGCCGTACACGCGGGGGTGTGCAGCCGTGAGGGGG

AGGGCAGCTGCCACTTCCTCGTTGTGGTGCGCGGCGGGCGGGCCAACTTCGTGGGG

GCTCTCCAGAACAACGTCCTGTCTCTCAGTCGGGGTGGTGGCGGTAGCGGTAGCGGT

AGCTCCACCAGTAGCGATGGCGATGGCGATAGCGATAGCTCCACCAGTAGGGCCAA

CTTCTCATTTTCCCTCTCCAGTGCGTCAGGGTTCGGGGGGGGTCCGCGCGGGGCCCA

CGCAGAAGCCGCGCCAAGCAGCTACTCCATTGTGTTCAAGCCGAGGGACCATTTGG

CTCCAACGAACGGCTTTCTAGTAGACTCAGGGAGAGAGTTCACCAGCTACGGAAGC

GTTGCCTACGGATGGAAGAGGGAGGTTTCTCCTTCGTCCTCTTTTTCCTCTCCTTCTC

CTAGCTACACTTCCCCCCCGTTGGAAGAACCGACGCTGCTTAGGGGGACTCCTCCT

CATTCAATGGGATTTACTCCGGGGGGATAGAATTCCCCCCCGCCTCGGCTAGCCAAA

ATTGCATTTCCCAACTGGATTGCCAGACCAACTTCTGGAAGTTTCAGATGCAAGAAA

ATGGCACCTACTTTGTGCAGGTGCTAGTGGGGAATAAAACTTCCCCTGAGAAGCAG

AAGGCCTTCGTCGAGCTGAATGGCGTTCCCATCATAAAGGGGGTGGACCTTGGCCCA

GACGAGGTCTTCGTCGCCACTGACCGCGTGCAGGTGACGAACCGGGCCCTCGTCCTC

ACGTCCACTTGCCTGGGCGGCGAGAGTGCCTGCTCGCGGGCGCGCGTCAGCATCAT

GGCGGTCCAGATTGTGAAGACG

X12
                                                     (SEQ ID NO: 138)
AACGGTATGAATAAAGACAAAGACGCAGAGATTACTCCCCCTCCGTTCATCG

TCTTGCCGGGTGGAAAAAAAATCCACATGCTGCAAAGCGAATACGAGTATGACGTT

CTGCGGGATATGTACCGAACGGATGAGGCGAATGGGGGAAGTGGTGAGAAGGAGA

GTCACCCCTCTGGGGATGGTGCAATCAGAAGAAACGAATTTTTTAAACTTTTTCACC

ACAGGGAGGGTCATTATAAGTTTGTTATCAAAAATGTTCCCACCAAATTGAGCGACC

TTTTGCAGAAAGGTGGCAACGAACAGGAGACAGACCTATTTCCTCTTTTATACAGGA

GTCTGCAATTCGCATGCAGCGCAGACGGGACGTGGCCATATGCCAGAAGAGAGGTG

GCCTTTTTAAAAACGGGAGCGTCCACTGCGAAGCGGAATTTCAAAACGAGTTATCA

GTGAGGAGAACCCCCCGAAGTGGGAAGAAATCATTTGGACGTTTTCCAAGGGGGAC

ACTAATAAAAGTAGCGACCTGAGGAGCAAAATTGTGGAGGGGAATTCTTATGATA

AAAGGGCCGCACCCCTGAAGAGTGAAAAAAAAAGAAGGCTCTCTTTTTACACCCA

GAAAGTGTGCTATACAAAATGGAAGAAATATTTTTTTATGAAAATCCAAGTGTCAAA

AGTGAAATTGTCGGGTTTGTTCTTTTTCATGATGTGTGCACAGTAACGTCCTTAGGAC

ATGGAGCACATCCCGTTAACTCCCCCTTTTTGGGAAGCGACCTGCTGGAGATGATAT

TTGGCTACTGCATTTTACACGGGTTTAAAAAAATCAGAGTGAAAAGCGAATCCTTAA

ATTACGAAACTGGGATAAGGACCTCATTCATTGAGATTTTACTCAACGGAAAAACA

GCACTTGAACATTTAGGGTTAAGACTTACAAACGTAGCGAAGTTTTCTAAAGAACTG

TATTATGTAATCACTGGGTATACGTGGAAAAGTGATTTGGTGCTATCACCCATAGTA

AGGTTTGAACATGATTTATACGTGCATCACGACATAGAGGAGCGATTTTTCCTTTAC
```

-continued

```
GTGAATAAAATGTATAGGAATATGCTCCACGATTTGTCCTTCTCTTGTGATGAAAAT

TATTATCCTTATAAAAATTGTTATGACATCTACCCCTCCGTGAGAAGGAGTCAAAAT

AATCTTTGTCTCTTCGAACTGAATCCCATATATGAAGAATTGAAGGAGCTCTTTCCA

GACTCTTGTAATATTGGCCAACGCGTTAGAAAATGCTATGAGGAGATAAAAAAAAA

CGTTGTCTGCACACATAACGGTGAAGGAGGAGAAGACGGATGTAAGTACTACCAAT

TTATTGTAAATACATTCATAAAGCCGAGGAGGAAAACGTCCTTTTTTATTTATCACA

ATATGTATGTACAGGAATATCTTTCAAAGAAATCCTACCCCTATTACTTGCTACTCA

GTGAGGTTATAAAAAATGAAGAAAATAACTTTCTCGAAAAAGGCAACTACGACTTA

GTGGCCGATGCACAGACGCACCTCTTCTTAAATTACGTTTTGCAAAATTCTACCTTTT

TTATCTTTTGGAATTTCTCTACCGAATTTTGGAAAAGGTTTCGGTACATCCAGGCTGG

CCCAACCGGGGCCACTTCCACACCGCAGAAGGGGCAAGCTGTGTTTTGCCCCATGG

CCTATGCGTACGAATTTGTGGAGCACCTCGACACGTTTTATGTGAGGGGG
```

V6

(SEQ ID NO: 139)
```
TCCGTTGAAGAGGCTAAAAAAAATACTCAGGAAGTTGTGACAAATGTGGACA

ATGCTGCTAAATCTCAGGCCACCAATTCAAATCCGATAAGTCAGCCTGTAGATAGTA

GTAAAGCGGAGAAGGTTCCAGGAGATTCTACGCATGGAAATGTTAACAGTGGCCAA

GATAGTTCTACCACAGGTAAAGCTGTTACGGGGGATGGTCAAATGGAAATCAGAC

ACCTGCAGAAAGCGATGTACAGCGAAGTGATATTGCCGAAAGTGTAAGTGCTAAAA

ATGTTGATCCGCAGAAATCTGTAAGTAAAAGAAGTGACGACACTGCAAGCGTTACA

GGTATTGCCGAAGCTGGAAAGGAAAACTTAGGCGCATCAAATAGTCGACCTTCTGA

GTCCACCGTTGAAGCAAATAGCCCAGGTGATGATACTGTGAACAGTGCATCTATACC

TGTAGTGAGTGGTGAAAACCCATTGGTAACCCCCTATAATGGTTTGAGGCATTCGAA

AGACAATAGTGATAGCGATGGACCTGCGGAATCAATGGCGAATCCTGATTCAAATA

GTAAAGGTGAGACGGGAAAGGGGCAAGATAATGATATGGCGAAGGCTACTAAAGA

TAGTAGTAATAGTTCAGATGGTACCAGCTCTGCTACGGGTGATACTACTGATGCAGT

TGATAGGGAAATTAATAAAGGTGTTCCTGAGGATAGGGATAAAACTGTAGGAAGTA

AAGATGGAGGGGGGAAGATAACTCTGCAAATAAGGATGCAGCGACTGTAGTTGGT

GAGGATAGAATTCGTGAGAACAGCGCTGGTGGTAGCACTAATGATAGATCAAAAAA

TGACACGGAAAAGAACGGGGCCTCTACCCCTGACAGTAAACAAAGTGAGGATGCAA

CTGCGCTAAGTAAAACCGAAAGTTTAGAATCAACAGAAAGTGGAGATAGAACTACT

AATGATACAACTAACAGTTTAGAAAATAAAAATGGAGGAAAAGAAAAGGATTTACA

AAAGCATGATTTTAAAAGTAATGATACGCCGAATGAAGAACCAAATTCTGATCAAA

CTACAGATGCAGAAGGACATGACAGGGATAGCATCAAAAATGATAAAGCAGAAAG

GAGAAAGCATATGAATAAAGATACTTTTACGAAAAATACAAATAGTCACCATTTAA

AT
```

V7

(SEQ ID NO: 140)
```
ATACGGAATGGAAACAACCCGCAGGCATTAGTTCCTGAAAAGGGCGCTGACC

CGAGTGGGGGCCAGAACAACCGCTCCGGAGAAAACCAAGACACGTGCGAAATTCA

AAAGATGGCCGAAGAAATGATGGAAAAAATGATGAAGGAAAAAGACGTGTTTAGC

TCCATCATGGAACCTCTCCAGAGCAAATTAACTGACGATCATCTGTGTTCAAAAATG

AAATATACGAACATTTGTCTTCACGAAAAGGACAAAACTCCCTTGACCTTCCCCTGC
```

-continued

```
ACAAGTCCGCAGTACGAACAGCTAATTCATCGCTTCACTTATAAAAAGTTGTGCAAC

TCCAAGGTGGCCTTTAGCAACGTCTTGCTCAAATCCTTCATCGATAAAAAAAATGAA

GAAAACACATTTAACACGATCATACAGAATTACAAAGTTCTGTCCACTTGCATTGAC

GATGATTTGAAGGACATTTATAATGCATCCATAGAGTTATTCTCCGACATAAGAACC

TCCGTCACAGAAATTACCGAAAAGTTGTGGTCCAAAAATATGATCGAAGTTTTAAAG

ACAAGAGAGCAAACCATTGCAGGCATTTTATGTGAGTTAAGAAATGGAAATAATTC

TCCCCTAGTATCGAACAGTTTTTCCTATGAAAATTTTGGAATTCTCAAGGTTAATTAT

GAGGGATTACTAAACCAGGCGTATGCGGCCTTTTCAGACTACTATTCATACTTTCCC

GCTTTTGCCATTAGCATGTTAGAAAAGGGAGGGTTGGTCGACCGCTTGGTCGCCATC

CATGAGAGCTTGACCAACTACAGGACGAGAAATATTCTCAAGAAGATCAATGAGAA

GTCCAAAAATGAGGTCCTCAATAATGAAGAAATTATGCACAGCTTGAGCAGTTACA

AGCACCATGCCGGGGGCACGCGTGGCGCCTTCCTGCAGTCCAGAGATGTGCGCGAA

GTTACGCAAGGAGATGTGAGCGTTGATGAGAAGGGCGACCGGGCCACCACCGCGGG

GGGCAACCAAAGCGCAAGCGTGGCTGCGGCGGCCCCGAAGGATGCGGGCCCAACC

GTGGCTGCTCCTAACACTGCTGCTACGCTCAAAACGGCTGCTTCCCCCAACGCGGCT

GCTACTAACACTGCTGCTCCCCCCAACATGGGTGCCACCTCCCCGCTGAGCAACCCC

CTGTACGGCACCAGCTCCCTGCAGCCAAAGGACGTCGCGGTGCTGGTCAGAGATCT

GCTCAAGAACACGAACATCATCAAGTTCGAGAATAACGAACCGACTAGCCAAATGG

ACGATGAAGAAATTAAGAAGCTCATTGAGAGCTCCTTTTTCGACTTGAGCGACAACA

CCATGTTAATGCGGTTGCTCATAAAGCCGCAGGCGGCCATCTTACTAATCATTGAGT

CCTTCATTATGATGACGCCCTCCCCCACGAGGGACGCCAAGACCTATTGCAAGAAA

GCCCTAGTTAATGGCCAGCTAATCGAAACCTCAGATTTAAACGCGGCGACGGAGGA

AGACGACCTCATAAACGAGTTTTCCAGCAGGTACAATTTATTCTACGAGAGGCTCAA

GCTGGAGGAGTTG
```

V8

(SEQ ID NO: 141)
```
AAGGAGTACTGCGACCAGCTTAGCTTTTGCGATGTGGGATTGACACACCACT

TTGATACGTATTGTAAGAATGACCAGTACCTGTTCGTTCACTACACTTGTGAGGACC

TCTGCAAAACGTGTGGCCCTAATTCGTCCTGCTACGGAAACAAGTACAAACATAAGT

GCCTGTGCAATAGCCCCTTCGAGAGTAAAAAGAACCATTCCATTTGCGAAGCACGA

GGTAGCTGCGATGCACAGGTATGCGGCAAGAATCAAATTTGCAAAATGGTAGACGC

TAAAGCAACATGCACATGTGCAGATAAATACCAAAATGTGAATGGGTGTGTCTAC

CGGAAGATAAGTGCGACCTTCTGTGCCCCTCAAACAAATCGTGCCTGCTGGAAAATG

GGAAAAAAATATGCAAGTGCATTAATGGGTTGACTCTACAGAACGGCGAGTGCGTC

TGCTCGGATAGCAGCCAAATTGAAGAAGGACACCTCTGTGTGCCCAAGAATAAATG

TAAACGGAAGGAGTACCAACAGCTCTGCACCAATGAGAAGGAACACTGTGTGTATG

ATGAGCAGACGGACATTGTGCGGTGCGACTGCGTGGACCACTTCAAGCGGAACGAA

CGGGGAATTTGCATCCCAGTCGACTACTGCAAAAATGTCACCTGCAAGGAAAATGA

GATTTGCAAAGTTGTTAATAATACACCCACATGTGAGTGTAAAGAAAATTTAAAAA

GAAATAGTAACAATGAATGTGTATTCAATAACATGTGTCTTGTTAATAAAGGGAACT

GCCCCATTGATTCGGAGTGCATTTATCACGAGAAAAAAAGGCATCAGTGTTTGTGCC
```

-continued

```
ATAAGAAGGGCCTCGTCGCCATTAATGGCAAGTGCGTCATGCAGGACATGTGCAGG

AGCGATCAGAACAAATGCTCCGAAAATTCCATTTGTGTAAATCAAGTGAATAAAGA

ACCGCTGTGCATATGTTTGTTTAATTATGTGAAGAGTCGGTCGGGCGACTCGCCCGA

GGGTGGACAGACGTGCGTGGTGGACAATCCCTGCCTCGCGCACAACGGGGGCTGCT

CGCCAAACGAGGTTTGCACGTTCAAAAATGGAAAGGTAAGTTGCGCCTGCGGGGAG

AACTACCGCCCCAGGGGGAAGGACAGCCCAACGGGACAAGCGGTCAAACGGGGGG

AAGCGACCAAACGGGGTGACGCGGGTCAGCCCGGGCAGGCGCACTCAGCAAATGA

GAACGCGTGCCTGCCCAAGACGTCCGAGGCGGACCAAACCTTCACCTTCCAGTACA

ACGACGACGCGGCCATCATTCTCGGGTCCTGCGGAATTATACAGTTTGTGCAAAAGA

GCGATCAGGTCATTTGGAAAATTAACAGCAACAATCACTTTTACATTTTTAATTATG

ACTATCCATCTGAGGGTCAGCTGTCGGCACAAGTCGTGAACAAGCAGGAGAGCAGC

ATTTTGTACTTAAAGAAAACCCACGCGGGGAAAGTCTTTTACGCCGACTTTGAGTTG

GGTCATCAGGGATGCTCCTACGGAAACATGTTTCTCTACGCCCACCGGGAGGAGGCT
```

V9

(SEQ ID NO: 142)
```
AGCAAAAACATTATTATTCTGAACGATGAAATTACCACCATTAAAAGCCCGA

TTCATTGCATTACCGATATTTATTTTCTGTTTCGCAACGAACTGTATAAAACCTGCAT

TCAGCATGTGATTAAAGGCCGCACCGAAATTCATGTGCTGGTGCAGAAAAAAATTA

ACAGCGCGTGGGAAACCCAGACCACCCTGTTTAAAGATCATATGTGGTTTGAACTGC

CGAGCGTGTTTAACTTTATTCATAACGATGAAATTATTATTGTGATTTGCCGCTATAA

ACAGCGCAGCAAACGCGAAGGCACCATTTGCAAACGCTGGAACAGCGTGACCGGCA

CCATTTATCAGAAAGAAGATGTGCAGATTGATAAAGAAGCGTTTGCGAACAAAAAC

CTGGAAAGCTATCAGAGCGTGCCGCTGACCGTGAAAAACAAAAAATTTCTGCTGAT

TTGCGGCATTCTGAGCTATGAATATAAAACCGCGAACAAAGATAACTTTATTAGCTG

CGTGGCGAGCGAAGATAAAGGCCGCACCTGGGGCACCAAAATTCTGATTAACTATG

AAGAACTGCAGAAAGGCGTGCCGTATTTTTATCTGCGCCCGATTATTTTTGGCGATG

AATTTGGCTTTTATTTTTATAGCCGCATTAGCACCAACAACACCGCGCGCGGCGGCA

ACTATATGACCTGCACCCTGGATGTGACCAACGAAGGCAAAAAAGAATATAAATTT

AAATGCAAACATGTGAGCCTGATTAAACCGGATAAAAGCCTGCAGAACGTGGCGAA

ACTGAACGGCTATTATATTACCAGCTATGTGAAAAAAGATAACTTTAACGAATGCTA

TCTGTATTATACCGAACAGAACGCGATTGTGGTGAAACCGAAAGTGCAGAACGATG

ATCTGAACGGCTGCTATGGCGGCAGCTTTGTGAAACTGGATGAAAGCAAAGCGCTG

TTTATTTATAGCACCGGCTATGGCGTGCAGAACATTCATACCCTGTATTATACCCGCT

ATGAT
```

TABLE 6 references associated with proteins

| Protein Code | 5' position to 3' (bp) | amino acid position | reference |
|---|---|---|---|
| X1 | (4-1845) | | Lu J Proteomics 2014 |
| X2 | (67-1161) | | Lu J Proteomics 2014 |
| X3 | (70-555) | | Lu J Proteomics 2014 |
| X4 | (4-948) | | Lu J Proteomics 2014 |
| X5 | (73-1659) | | Lu J Proteomics 2014 |
| X6 | (73-1074) | | Lu J Proteomics 2014 |
| X7 | (1384-2190) | | Lu J Proteomics 2014 |
| X8 | (559-2871) | | Lu J Proteomics 2014 |
| X9 | (4-660) | | Lu J Proteomics 2014 |
| X10 | (4-342) | | Lu J Proteomics 2014 |
| X11 | (1264-3261) | | Lu J Proteomics 2014 |
| X12 | (1957-3702) | | Lu J Proteomics 2014 |

TABLE 6-continued

| references associated with proteins | | | |
|---|---|---|---|
| Protein Code | 5' position to 3' (bp) | amino acid position | reference |
| V1 |  | 140 to 1275 | Hietanen 2015 Infection and Immunity PMID: 26712206 |
| V2 |  | 160 to 1135 | Hietanen 2015 Infection and Immunity PMID: 26712206 |
| V3 |  | 161 to 1454 | Hietanen 2015 Infection and Immunity PMID: 26712206 |
| V4 |  | 501 to 1300 | Hietanen 2015 Infection and Immunity PMID: 26712206 |
| V12 |  | 160 to 1170 | Hietanen 2015 Infection and Immunity PMID: 26712206 |
| V5 |  | 161-641 | Franca 2017 Elife PMID: 28949293 |
| V11 |  | Region II | Franca 2017 Elife PMID: 28949293 |
| V10 |  | Region II |  |
| V13 |  | Region II |  |
| V6 | (1522-2697) |  |  |
| V7 | (29-551) |  |  |
| V8 | (552-1075) |  |  |
| V9 | (30-366) |  |  |

APPENDIX IIIA

| | Area Under Curve (1 antigen) | | | Top 1% of 2 antigen combis | | | Top 1% of 3 antigen combis | | | Top 1% of 4 antigen combis | | | (<9 m GMT)/(12 m GMT) | | | (<9 m GMT)/(-ve control GMT) | | |
|---|---|---|---|---|---|---|---|---|---|---|---|---|---|---|---|---|---|---|
| | Thailand | Brazil | Solomons | Thailand | Brazil | Solomons | Thailand | Brazil | Solomons | Thailand | Brazil | Solomons | Thailand | Brazil | Solomons | Thailand | Brazil | Solomons |
| RBP2a | 0.849 | 0.818 | 0.868 | 100 | 100 | 100 | 95.3 | 96.2 | 100 | 89.7 | 98.5 | 100 | 10.85 | 8.53 | 11.84 | 31.33 | 26.31 | 13.91 |
| L01 | 0.812 | 0.787 | 0.697 | 5.9 | 5.9 | 0 | 21.1 | 13.5 | 2.3 | 43.5 | 23.9 | 4.3 | 7.41 | 4.49 | 4.09 | 10.73 | 17.26 | 2.1 |
| L31 | 0.805 | 0.762 | 0.766 | 0 | 0 | 0 | 2.6 | 2.6 | 2.3 | 5 | 2.7 | 3.7 | 3.9 | 3.05 | 2.56 | 8.62 | 12.32 | 5.1 |
| X087885 | 0.807 | 0.748 | 0.697 | 5.9 | 0 | 0 | 16.7 | 4.7 | 7 | 20.3 | 9.2 | 14.6 | 4.28 | 1.79 | 1.2 | 9.82 | 34.44 | 15.93 |
| PvEBP | 0.747 | 0.739 | 0.707 | 0 | 5.9 | 0 | 1.8 | 1.8 | 1.8 | 5 | 2.4 | 3.1 | 6.53 | 5.18 | 2.01 | 21.12 | 8.91 | 2.61 |
| L55 | 0.79 | 0.781 | 0.643 | 5.9 | 0 | 0 | 14.6 | 12.3 | 1.5 | 17.2 | 20.9 | 2.6 | 4.94 | 4.42 | 1.95 | 7.9 | 7.91 | 1.19 |
| PvRipr | 0.754 | 0.772 | 0.646 | 0 | 5.9 | 5.9 | 1.8 | 5.6 | 2 | 3 | 9.1 | 3.1 | 5.01 | 4.32 | 2.57 | 7.02 | 7.89 | 1.07 |
| L54 | 0.79 | 0.727 | 0.654 | 5.9 | 0 | 0 | 3.5 | 2.6 | 1.8 | 5.6 | 4.4 | 2.6 | 4.4 | 2.98 | 1.88 | 5.39 | 3.82 | 1.3 |
| L07 | 0.747 | 0.765 | 0.599 | 0 | 0 | 0 | 2.3 | 4.7 | 2.9 | 3.1 | 5.3 | 2.5 | 2.56 | 3.11 | 1.45 | 4.3 | 6.29 | 1.35 |
| L30 | 0.732 | 0.61 | 0.609 | 0 | 0 | 5.9 | 1.2 | 2.3 | 3.2 | 2.3 | 3.8 | 5.4 | 4.14 | 1.53 | 1.55 | 13.36 | 2.24 | 1.79 |
| PVDBPII | 0.74 | 0.773 | 0.639 | 0 | 0 | 0 | 0.6 | 3.2 | 0.6 | 1.7 | 2.6 | 4 | 2.76 | 4.89 | 1.79 | 5.14 | 15.42 | 1.34 |
| L34 | 0.767 | 0.746 | 0.67 | 5.9 | 0 | 5.9 | 3.8 | 7.3 | 2 | 4.5 | 16.6 | 2.2 | 3.22 | 2.99 | 1.84 | 3.87 | 4.78 | 1.46 |
| X092995 | 0.792 | 0.703 | 0.642 | 5.9 | 0 | 0 | 13.7 | 1.5 | 1.8 | 11.5 | 1.9 | 5.6 | 2.88 | 1.41 | 1.03 | 4.64 | 8.55 | 4.19 |
| L12 | 0.755 | 0.731 | 0.637 | 5.9 | 0 | 0 | 3.2 | 3.8 | 1.2 | 3.5 | 6.1 | 2.9 | 3.19 | 2.73 | 1.46 | 3.81 | 3.47 | 1.8 |
| rBP1b | 0.533 | 0.578 | 0.525 | 0 | 0 | 0 | 17.5 | 4.1 | 1.2 | 24.1 | 4.7 | 2.5 | 1.23 | 1.44 | 1.11 | 0.67 | 0.79 | 0.84 |
| L23 | 0.759 | 0.753 | 0.658 | 0 | 5.9 | 0 | 1.5 | 7 | 1.2 | 4 | 14.8 | 2.9 | 2.95 | 2.67 | 1.86 | 4.3 | 5.09 | 1.59 |
| L02 | 0.746 | 0.724 | 0.677 | 0 | 0 | 0 | 1.5 | 2.3 | 2.3 | 2.7 | 3.7 | 3.9 | 3.7 | 3 | 1.76 | 3.89 | 4.07 | 1.82 |
| L32 | 0.705 | 0.651 | 0.493 | 0 | 0 | 5.9 | 1.8 | 1.2 | 17 | 3.7 | 1.9 | 30.2 | 2.79 | 3.17 | 1.61 | 2.24 | 0.81 | 0.31 |
| L28 | 0.759 | 0.755 | 0.667 | 5.9 | 0 | 0 | 2.6 | 1.2 | 1.2 | 3.8 | 2.5 | 2.6 | 2.92 | 2.44 | 1.43 | 5.74 | 5.24 | 2.14 |
| L19 | 0.758 | 0.67 | 0.654 | 0 | 0 | 5.9 | 1.5 | 0.9 | 3.2 | 2.6 | 2.3 | 6.5 | 3.66 | 2.18 | 1.09 | 6.58 | 3.11 | 4.89 |
| L36 | 0.727 | 0.698 | 0.682 | 0 | 0 | 0 | 1.5 | 0.9 | 2 | 3.2 | 1.8 | 2.8 | 2.95 | 2.44 | 1.99 | 3.28 | 3.2 | 1.8 |
| L41 | 0.702 | 0.66 | 0.686 | 0 | 0 | 0 | 1.5 | 0.6 | 2 | 2.3 | 1.7 | 3.8 | 2.12 | 1.91 | 1.72 | 4.99 | 3.03 | 1.9 |
| X088820 | 0.723 | 0.666 | 0.633 | 5.9 | 0 | 0 | 4.4 | 0.6 | 3.8 | 4 | 1.8 | 6.7 | 1.9 | 1.28 | 0.99 | 4.04 | 8.58 | 5.87 |
| PvDBP.Sa | 0.716 | 0.751 | 0.616 | 0 | 0 | 0 | 0.3 | 2.6 | 8.8 | 1.7 | 2.6 | 7.2 | 3.01 | 4.78 | 1.85 | 3.96 | 12.35 | 0.83 |
| RBP2a | 0.692 | 0.731 | 0.662 | 0 | 5.9 | 5.9 | 3.5 | 1.2 | 0.9 | 5.4 | 1.8 | 1.6 | 2.42 | 2.49 | 1.47 | 2.46 | 4.6 | 1.5 |
| L18 | 0.736 | 0.663 | 0.622 | 5.9 | 0 | 0 | 2.3 | 2 | 2.3 | 3.1 | 4.5 | 3.8 | 2.22 | 1.41 | 0.93 | 2.53 | 2.33 | 4.31 |
| RBP2cNB | 0.744 | 0.7 | 0.551 | 0 | 0 | 5.9 | 1.5 | 1.2 | 11.1 | 3.6 | 1.9 | 6.6 | 3.02 | 2.3 | 1.57 | 3.87 | 3.23 | 0.64 |
| L27 | 0.735 | 0.663 | 0.585 | 0 | 5.9 | 5.9 | 2.9 | 1.5 | 2 | 4.5 | 2.4 | 2.7 | 2.34 | 2.24 | 1.66 | 1.67 | 1.2 | 0.63 |
| L42 | 0.697 | 0.632 | 0.593 | 0 | 0 | 0 | 1.5 | 0.9 | 1.5 | 2.9 | 1.8 | 3 | 2.81 | 1.91 | 1.85 | 4.44 | 2.89 | 1.19 |
| L14 | 0.701 | 0.637 | 0.581 | 0 | 0 | 0 | 3.5 | 1.2 | 1.5 | 3 | 2 | 3.1 | 1.94 | 1.51 | 1.33 | 2.85 | 2.23 | 1.07 |
| X099930 | 0.71 | 0.63 | 0.573 | 5.9 | 0 | 5.9 | 3.8 | 0.9 | 2.6 | 4.1 | 1.7 | 2.5 | 1.75 | 1.27 | 0.94 | 2.85 | 3.15 | 2.07 |
| PvDBP.R3 | 0.685 | 0.67 | 0.554 | 0 | 5.9 | 0 | 2 | 4.1 | 1.5 | 4.1 | 3 | 2.7 | 2.51 | 2.19 | 1.73 | 2.57 | 3.11 | 0.51 |
| L22 | 0.725 | 0.622 | 0.562 | 0 | 0 | 0 | 2.3 | 1.5 | 0.9 | 3 | 5.6 | 2.4 | 1.98 | 1.25 | 0.99 | 2.28 | 2.13 | 1.3 |
| RBP1a | 0.668 | 0.669 | 0.565 | 5.9 | 0 | 5.9 | 0 | 0.9 | 14 | 1.2 | 2.7 | 1.9 | 2.4 | 2.32 | 2.49 | 1.45 | 2.06 | 2.59 |
| PvCYRPA | 0.779 | 0.563 | 0.532 | 0 | 5.9 | 0 | 0.6 | 0.9 | 1.2 | 2 | 1.9 | 10.3 | 2.37 | 1.25 | 0.31 | 4.55 | 1.59 | 0.31 |
| L10 | 0.719 | 0.588 | 0.553 | 0 | 0 | 5.9 | 1.2 | 6.1 | 1.2 | 2.4 | 9.3 | 2.3 | 2.14 | 1.31 | 1.46 | 3.61 | 1.39 | 1.43 |
| L24 | 0.656 | 0.595 | 0.605 | 0 | 5.9 | 0 | 5.3 | 2.9 | 1.2 | 5.5 | 5.6 | 2.8 | 2.01 | 1.33 | 1.04 | 1.75 | 1.71 | 5.03 |
| L21 | 0.653 | 0.597 | 0.602 | 0 | 5.9 | 5.9 | 3 | 1.8 | 1.8 | 3 | 2.6 | 4.1 | 2 | 1.55 | 0.88 | 1.47 | 1.35 | 3.08 |
| L51 | 0.679 | 0.625 | 0.547 | 0 | 0 | 0 | 4.1 | 1.8 | 3.5 | 6.2 | 3.7 | 5.4 | 1.85 | 1.48 | 0.93 | 4.44 | 1.74 | 0.89 |
| L25 | 0.67 | 0.593 | 0.58 | 5.9 | 0 | 5.9 | 0.9 | 2.5 | 0.9 | 2.1 | 6 | 2.8 | 1.61 | 1.14 | 1.31 | 2.04 | 1.76 | 2.05 |
| L33 | 0.65 | 0.608 | 0.584 | 0 | 0 | 0 | 1.8 | 1.2 | 0.9 | 3.7 | 3.1 | 1.6 | 1.83 | 1.43 | 0.96 | 1.63 | 1.82 | 1.05 |
| L20 | 0.674 | 0.619 | 0.544 | 0 | 5.9 | 0 | 2 | 1.2 | 1.5 | 2.7 | 2.1 | 2.9 | 1.71 | 1.31 | 1.37 | 2.2 | 2.08 | 0.82 |
| X114330 | 0.666 | 0.594 | 0.577 | 0 | 0 | 0 | 2.3 | 1.2 | 2.6 | 2.2 | 2.6 | 3 | 1.44 | 1.15 | 1.23 | 2.35 | 1.34 | 1.78 |
| L50 | 0.713 | 0.604 | 0.494 | 0 | 0 | 5.9 | 0 | 6.4 | 1.5 | 2.9 | 8.6 | 7.3 | 2.15 | 1.55 | 1.03 | 2.53 | 1.41 | 0.45 |
| L06 | 0.686 | 0.583 | 0.54 | 0 | 0 | 0 | 1.2 | 1.8 | 1.2 | 2.5 | 3.1 | 2.3 | 1.91 | 1.33 | 1.4 | 2.23 | 1.9 | 1.57 |
| L05 | 0.686 | 0.607 | 0.499 | 0 | 5.9 | 0 | 2 | 2.3 | 2 | 3.9 | 4.7 | 3.4 | 2.23 | 1.44 | 0.92 | 2.1 | 1.9 | 0.72 |
| X080665 | 0.678 | 0.595 | 0.522 | 0 | 0 | 0 | 1.5 | 3.8 | 1.2 | 2.1 | 6.2 | 3.6 | 1.8 | 1.25 | 0.9 | 2.64 | 1.8 | 1.21 |

APPENDIX IIIA-continued

| | Area Under Curve (1 antigen) | | | Top 1% of 2 antigen combis | | | Top 1% of 3 antigen combis | | | Top 1% of 4 antigen combis | | | (<9 m GMT)/(12 m GMT) | | | (<9 m GMT)/(-ve control GMT) | | |
|---|---|---|---|---|---|---|---|---|---|---|---|---|---|---|---|---|---|---|
| | Thailand | Brazil | Solomons | Thailand | Brazil | Solomons | Thailand | Brazil | Solomons | Thailand | Brazil | Solomons | Thailand | Brazil | Solomons | Thailand | Brazil | Solomons |
| L39 | 0.673 | 0.56 | 0.537 | 5.9 | 0 | 0 | 4.1 | 1.2 | 1.5 | 4 | 2.4 | 2.8 | 1.64 | 1.12 | 0.96 | 2.96 | 1.57 | 1.5 |
| X094350 | 0.641 | 0.602 | 0.516 | 0 | 0 | 0 | 1.5 | 2 | 1.8 | 2.7 | 3.2 | 4.2 | 1.47 | 1.3 | 0.96 | 1.79 | 1.7 | 1.15 |
| L11 | 0.652 | 0.594 | 0.49 | 0 | 5.9 | 5.9 | 3.8 | 4.4 | 5 | 5.3 | 7.7 | 10.7 | 1.58 | 1.29 | 0.96 | 1.67 | 1.29 | 0.92 |
| L38 | 0.64 | 0.543 | 0.552 | 0 | 5.9 | 0 | 1.2 | 5.3 | 1.5 | 3 | 6.3 | 2.6 | 1.59 | 1.2 | 1.19 | 1.18 | 1 | 0.89 |
| L37 | 0.628 | 0.608 | 0.487 | 0 | 5.9 | 5.9 | 2.6 | 2 | 3.2 | 5.1 | 3.7 | 4.9 | 1.54 | 1.6 | 1.15 | 1.17 | 0.92 | 0.73 |
| PvGAMA | 0.646 | 0.57 | 0.495 | 0 | 0 | 5.9 | 2.3 | 1.2 | 6.7 | 5.3 | 2.5 | 6.5 | 1.64 | 1.49 | 1.32 | 1.45 | 0.74 | 0.53 |
| L49 | 0.577 | 0.532 | 0.6 | 0 | 5.9 | 5.9 | 1.8 | 19.6 | 8.2 | 2.5 | 11.9 | 13.6 | 1.26 | 1.08 | 0.89 | 1.24 | 0.4 | 0.34 |
| L47 | 0.641 | 0.513 | 0.539 | 0 | 5.9 | 5.9 | 0.9 | 5.8 | 4.7 | 1.9 | 6.8 | 4.8 | 1.52 | 1.29 | 1.21 | 1.73 | 0.51 | 0.38 |
| L48 | 0.552 | 0.586 | 0.523 | 5.9 | 0 | 0 | 2.9 | 1.2 | 1.2 | 4.8 | 2.4 | 2.7 | 1.16 | 1.23 | 0.98 | 1.3 | 1.56 | 1.23 |
| RBP2.P2 | 0.596 | 0.544 | 0.515 | 5.9 | 5.9 | 5.9 | 5 | 14.6 | 17 | 6.5 | 8.9 | 24.9 | 1.48 | 1.34 | 1.16 | 0.94 | 0.66 | 0.46 |
| L03 | 0.579 | 0.503 | 0.566 | 5.9 | 5.9 | 0 | 2.6 | 2.3 | 2 | 3.8 | 4.1 | 4.4 | 1.59 | 1.14 | 0.93 | 0.82 | 0.8 | 0.51 |
| L52 | 0.526 | 0.562 | 0.524 | 5.9 | 5.9 | 5.9 | 4.4 | 4.7 | 4.1 | 4.9 | 4.8 | 6.3 | 1.29 | 1.4 | 1.07 | 0.56 | 0.6 | 0.58 |
| L40 | 0.564 | 0.55 | 0.495 | 0 | 0 | 0 | 1.8 | 1.5 | 1.2 | 3.3 | 2.7 | 3.2 | 1.23 | 1.01 | 0.91 | 1.08 | 1.79 | 1.09 |

APPENDIX IIIB

| | (<9 m) > (>12 m GMT + 2*ds(>12 m)) | | | (<9 m) > (-ve cont GMT + 2*sd(-ve cont)) | | | age trend | | | age trend (P value) | | |
|---|---|---|---|---|---|---|---|---|---|---|---|---|
| | Thailand | Brazil | Solomons | Thailand | Brazil | Solomons | Thailand | Brazil | Solomons | Thailand | Brazil | Solomons |
| RBP2a | 34.7 | 19 | 47 | 70.8 | 64.4 | 45.7 | 1.02 | 0.63 | 1.06 | 0 | 0 | 0 |
| L01 | 36.1 | 0 | 24.3 | 51.4 | 56.6 | 14.3 | 0.39 | 0.52 | 0.24 | 0 | 0 | 0.0043 |
| L31 | 22.2 | 0 | 7.8 | 25 | 38 | 7.4 | 0.41 | 0.34 | 0.23 | 0 | 0 | 3.00E-04 |
| X087885 | 15.3 | 7.8 | 5.7 | 41.7 | 81 | 50.9 | 0.53 | 0.13 | -0.1 | 0 | 2.00E-04 | 0.0466 |
| PvEBP | 26.4 | 22.9 | 20 | 55.3 | 41 | 7.8 | 1.08 | 0.59 | 0.21 | 0 | 0 | 0 |
| L55 | 27.8 | 17.1 | 13.9 | 38.9 | 29.8 | 3.5 | 0.48 | 0.46 | 0.44 | 0 | 0 | 0 |
| PvRipr | 25 | 15.1 | 23.5 | 31.9 | 29.3 | 4.8 | 0.55 | 0.42 | 0.2 | 0 | 0 | 0.0013 |
| L54 | 23.6 | 16.1 | 14.3 | 26.4 | 19 | 2.2 | 0.48 | 0.33 | 0.24 | 0 | 0 | 0 |
| L07 | 22.2 | 0 | 8.3 | 27.8 | 41.5 | 3.9 | 0.22 | 0.34 | 0.19 | 0 | 0 | 4.00E-04 |
| L30 | 23.6 | 9.8 | 10.9 | 47.2 | 11.7 | 9.6 | 0.85 | 0.16 | 0.05 | 0 | 2.00E-04 | 0.4217 |
| PVDBPII | 15.3 | 19 | 10.4 | 20.8 | 47.3 | 3.5 | 0.4 | 0.63 | 0.1 | 0 | 0 | 0.076 |
| L34 | 15.3 | 12.2 | 10.9 | 12.5 | 19 | 3.9 | 0.35 | 0.35 | 0.18 | 0 | 0 | 2.00E-04 |
| X092995 | 12.5 | 3.4 | 1.7 | 15.3 | 34.1 | 10 | 0.33 | 0.09 | -0.03 | 0 | 0.0034 | 0.4924 |
| L12 | 23.6 | 12.7 | 5.2 | 16.7 | 15.1 | 3 | 0.36 | 0.22 | -0.07 | 0 | 0 | 0.1928 |
| rBP1b | 2.8 | 4.4 | 4.3 | 0 | 0 | 0 | -0.12 | 0.12 | -0.06 | 0.001 | 1.00E-04 | 0.1077 |
| L23 | 9.7 | 13.7 | 11.7 | 12.5 | 19.5 | 5.7 | 0.29 | 0.22 | 0.1 | 0 | 0 | 0.0824 |
| L02 | 15.3 | 10.7 | 7.4 | 15.3 | 13.7 | 2.6 | 0.31 | 0.4 | 0.02 | 0 | 0 | 0.6554 |
| L32 | 13.9 | 20.5 | 10 | 4.2 | 3.9 | 0.4 | 0.15 | 0.31 | 0.25 | 0.0016 | 0 | 1.00E-04 |
| L28 | 18.1 | 12.7 | 8.3 | 45.8 | 33.2 | 9.1 | 0.46 | 0.32 | 0.26 | 0 | 0 | 0 |
| L19 | 20.8 | 9.8 | 3.9 | 33.3 | 19.5 | 10.9 | 0.62 | 0.31 | -0.14 | 0 | 0 | 0.0036 |
| L36 | 18.1 | 14.6 | 11.3 | 36.1 | 22 | 10.4 | 0.63 | 0.36 | 0.3 | 0 | 0 | 0 |
| L41 | 9.7 | 9.3 | 7.8 | 29.2 | 17.6 | 8.3 | 0.39 | 0.41 | 0.32 | 0 | 0 | 0 |
| X088820 | 12.5 | 0 | 0 | 15.3 | 35.6 | 14.8 | 0.17 | 0.07 | -0.02 | 0 | 0.0032 | 0.5905 |
| PvDBP.Sa | 18.1 | 16.6 | 11.3 | 16.7 | 36.6 | 1.3 | 0.39 | 0.61 | 0.18 | 0 | 0 | 0.0016 |
| RBP2a | 18.1 | 13.2 | 9.1 | 18.1 | 22.4 | 3.5 | 0.3 | 0.34 | 0.1 | 0 | 0 | 0.0144 |
| L18 | 15.3 | 3.4 | 4.3 | 11.1 | 6.3 | 10.4 | 0.11 | 0.08 | -0.17 | 0.0022 | 0.0106 | 1.00E-04 |
| RBP2cNB | 23.6 | 16.6 | 10 | 18.1 | 17.6 | 1.7 | 0.43 | 0.35 | 0.44 | 0 | 0 | 0 |
| L27 | 15.3 | 13.2 | 10 | 0 | 0 | 0 | 0.1 | 0.3 | 0.15 | 0.0021 | 0 | 3.00E-04 |
| L42 | 16.7 | 12.7 | 16.1 | 29.2 | 20 | 7 | 0.5 | 0.3 | 0.27 | 0 | 0 | 0 |
| L14 | 12.5 | 3.9 | 5.2 | 9.7 | 5.9 | 1.3 | 0.05 | 0.18 | 0.02 | 0.1401 | 0 | 0.6094 |
| X099930 | 5.6 | 6.8 | 1.7 | 8.3 | 17.6 | 6.1 | 0.06 | 0.02 | -0.06 | 0.0734 | 0.4923 | 0.1513 |
| PvDBP.R3 | 13.9 | 9.8 | 8.7 | 13.9 | 11.2 | 0.9 | 0.36 | 0.33 | 0.16 | 0 | 0 | 0.0047 |
| L22 | 9.7 | 3.4 | 3 | 4.2 | 5.9 | 2.6 | 0.11 | 0.16 | -0.08 | 0.0012 | 0 | 0.0611 |
| RBP1a | 18.1 | 16.1 | 10.4 | 8.3 | 18 | 1.3 | 0.36 | 0.44 | 0.12 | 0 | 0 | 0.0239 |
| PvCYRPA | 16.7 | 0 | 4.8 | 29.2 | 11.7 | 0 | 0.43 | -0.02 | 0.15 | 0 | 0.6208 | 0.0046 |
| L10 | 8.3 | 4.4 | 3 | 12.5 | 4.4 | 1.3 | 0.47 | 0.16 | -0.17 | 0 | 0 | 3.00E-04 |
| L24 | 9.7 | 6.8 | 3.9 | 4.2 | 7.3 | 7 | 0.12 | 0.14 | -0.21 | 0.0069 | 3.00E-04 | 0 |
| L21 | 8.3 | 6.3 | 3.5 | 2.8 | 6.3 | 6.1 | 0.04 | 0.13 | -0.19 | 0.3593 | 4.00E-04 | 0 |
| L51 | 4.2 | 3.9 | 4.8 | 2.8 | 3.9 | 2.6 | 0.25 | 0.22 | 0.31 | 0 | 0 | 0 |
| L25 | 11.1 | 2.4 | 0.9 | 6.9 | 4.9 | 3.9 | 0.04 | 0.04 | -0.15 | 0.3008 | 0.232 | 0.0025 |
| L33 | 11.1 | 4.9 | 5.2 | 6.9 | 5.9 | 0.9 | 0.21 | 0.22 | 0.24 | 0 | 0 | 0 |
| L20 | 9.7 | 0 | 4.3 | 0 | 0 | 0 | 0.01 | 0.11 | 0.02 | 0.7715 | 1.00E-04 | 0.7011 |
| X114330 | 5.6 | 5.9 | 3 | 8.3 | 10.7 | 4.3 | 0.11 | 0.05 | -0.09 | 4.00E-04 | 0.103 | 0.054 |
| L50 | 11.1 | 5.4 | 6.5 | 5.6 | 4.4 | 0.9 | 0.13 | 0.27 | 0.2 | 6.00E-04 | 0 | 0 |
| L06 | 6.9 | 4.4 | 1.7 | 2.8 | 3.4 | 0.4 | -0.03 | 0.01 | -0.35 | 0.4684 | 0.6901 | 0 |
| L05 | 12.5 | 8.8 | 3.5 | 5.6 | 9.8 | 0.4 | 0.13 | 0.15 | -0.11 | 0.0018 | 1.00E-04 | 0.0232 |
| X080665 | 4.2 | 4.4 | 1.3 | 2.8 | 4.4 | 0.4 | 0.14 | 0.08 | -0.09 | 7.00E-04 | 0.0263 | 0.0757 |
| L39 | 6.9 | 3.9 | 3.5 | 6.9 | 4.4 | 3.5 | 0.04 | 0.07 | -0.15 | 0.2562 | 0.053 | 0.0064 |
| X094350 | 2.8 | 0 | 1.3 | 0 | 0 | 0 | 0.01 | 0.12 | 0.11 | 0.7336 | 0 | 0.0116 |
| L11 | 6.9 | 3.4 | 2.6 | 1.4 | 2.4 | 0 | 0.16 | 0.1 | -0.1 | 0 | 0.0027 | 0.0126 |
| L38 | 6.9 | 3.4 | 3.9 | 0 | 0 | 0 | -0.03 | 0.1 | 0.06 | 0.465 | 0.0011 | 0.0898 |
| L37 | 2.8 | 4.9 | 3.9 | 0 | 2.4 | 1.3 | -0.03 | 0.16 | 0.05 | 0.3436 | 0 | 0.2103 |
| PvGAMA | 9.7 | 6.8 | 9.1 | 6.9 | 2.9 | 0.9 | 0.19 | 0.14 | 0.05 | 0 | 0 | 0.1987 |
| L49 | 9.7 | 3.9 | 3 | 0 | 0 | 0 | -0.09 | 0 | -0.21 | 0.0088 | 0.9079 | 2.00E-04 |
| L47 | 12.5 | 4.4 | 5.2 | 5.6 | 1 | 0 | 0.02 | 0.15 | -0.06 | 0.5816 | 0 | 0.3004 |
| L48 | 0 | 0 | 3.5 | 0 | 0 | 0 | -0.08 | 0 | -0.14 | 0.0173 | 0.9939 | 0.0011 |
| RBP2.P2 | 5.6 | 4.9 | 4.3 | 0 | 0 | 0 | -0.01 | 0.13 | -0.02 | 0.7196 | 0 | 0.5467 |
| L03 | 2.8 | 0 | 3 | 1.4 | 4.4 | 0.4 | -0.03 | 0.03 | -0.16 | 0.4053 | 0 | 2.00E-04 |
| L52 | 1.4 | 5.9 | 3 | 0 | 0.5 | 0 | -0.15 | 0.15 | 0.01 | 2.00E-04 | 0.3609 | 0.8287 |
| L40 | 9.7 | 0 | 0 | 0 | 0 | 0 | -0.09 | 0.04 | -0.15 | 0.0058 | 0.1846 | 0.0018 |

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses which may further include any and all elements from any other disclosed methods, systems, and apparatuses, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A diagnostic test for *Plasmodium vivax*, to determine a likelihood of a specific timing of infection by *P. vivax* in a subject by determining a level of antibodies to a plurality of antigens in a sample from the subject, wherein the level is measured of antibody to protein PVX_084720 (SEQ ID NO:35) and of at least one antibody to protein selected from at least one protein selected from the group consisting of PVX_099980 (L01) (SEQ ID NO:1), PVX_112670 (SEQ ID NO: 23), PVX_087885 (SEQ ID NO:45), PVX_082650 (SEQ ID NO:59), PVX_088860 (SEQ ID NO: 5), PVX_112680 SEQ ID NO:11), PVX_112675 SEQ ID NO:21), PVX_092990 (SEQ ID NO: 39), PVX_091710 (SEQ ID NO:43), PVX_117385 SEQ ID NO:49), PVX_098915 (SEQ ID NO: 77), PVX_088820 (SEQ ID NO:79), PVX_117880 (SEQ ID NO:7), PVX_121897 (SEQ ID NO: 95), PVX_125728 (SEQ ID NO:97), PVX_001000 (SEQ ID NO:65), PVX_084340 SEQ ID NO: 75), PVX_090330 (SEQ ID NO:99), PVX_125738 (SEQ ID NO:103), PVX_096995 (SEQ ID NO: 3), PVX_097715 (SEQ ID NO:13), PVX_094830 (SEQ ID NO:19), PVX_101530 (SEQ ID NO: 9), PVX_090970 (SEQ ID NO:27), PVX_003770 (SEQ ID NO:37), PVX_112690 (SEQ ID NO: 41), PVX_003555 (SEQ ID NO:47), PVX_090265 (SEQ ID NO:53), PVX_099930 (SEQ ID NO: 73), PVX_123685 (SEQ ID NO:101), PVX_002550 (SEQ ID NO:25), PVX_082700 (SEQ ID NO:55), PVX_097680 (SEQ ID NO:63), PVX_097625 (SEQ ID NO:67), PVX_082670 (SEQ ID NO:41), PVX_082735 (SEQ ID NO:81), PVX_082645 (SEQ ID NO:83), PVX_097720 (SEQ ID NO:107), PVX_000930 (SEO ID NO: 109), PVX_088820 (SEQ ID NO:79), PVX_087885 (SEQ ID NO:45), PVX_087110 (SEQ ID NO:69), and RBP2b (P25) (PVX_094255) (SEQ ID NO:61), wherein the level of antibodies is measured at a plurality of time points and wherein a model of the decay of antibody titers over time is used to determine the time since last infection, wherein the level of antibody is correlated with the time since infection.

2. The test of claim 1, wherein the level is measured of antibody to protein PVX_084720 (SEQ ID NO:35) and of antibody to at least two proteins selected from the group consisting of PVX_099980 (L01) (SEQ ID NO:1), PVX_112670 (SEQ ID NO:23), PVX_087885 (SEQ ID NO:45), PVX_082650 (SEQ ID NO:59), PVX_088860 (SEQ ID NO:5), PVX_112680 SEQ ID NO:11), PVX_112675 SEQ ID NO:21), PVX_092990 (SEQ ID NO:39), PVX_091710 (SEQ ID NO:43), PVX_117385 SEQ ID NO:49), PVX_098915 (SEQ ID NO:77), PVX_088820 (SEQ ID NO:79), PVX_117880 (SEQ ID NO:7), PVX_121897 (SEQ ID NO:95), PVX_125728 (SEQ ID NO:97), PVX_001000 (SEQ ID NO:65), PVX_084340 SEQ ID NO:75), PVX_090330 (SEQ ID NO:99), PVX_125738 (SEQ ID NO:103), PVX_096995 (SEQ ID NO:3), PVX_097715 (SEQ ID NO:13), PVX_094830 (SEQ ID NO:19), PVX_101530 (SEQ ID NO:9), PVX_090970 (SEQ ID NO:27), PVX_003770 (SEQ ID NO:37), PVX_112690 (SEQ ID NO:41), PVX_003555 (SEQ ID NO:47), PVX_090265 (SEQ ID NO:53), PVX_099930 (SEQ ID NO:73), PVX_123685 (SEQ ID NO:101), PVX_002550 (SEQ ID NO: 25), PVX_082700 (SEQ ID NO:55), PVX_097680 (SEQ ID NO:63), PVX_097625 (SEQ ID NO: 67), PVX_082670 (SEQ ID NO:41), PVX_082735 (SEQ ID NO:81), PVX_082645 (SEQ ID NO: 83), PVX_097720 (SEQ ID NO:107), PVX_000930 (SEQ ID NO:109), PVX_088820 (SEQ ID NO:79), PVX_087885 (SEQ ID NO: 45), PVX_087110 (SEQ ID NO:69), and RBP2b (P25) (PVX_094255) (SEQ ID NO:61).

3. The test of claim 1, comprising determining a level of 2 to 8 antibodies.

4. The test of claim 1, wherein antibody levels are measured in the subject and time since infection is estimated continuously, wherein antibody level is compared with a titration curve to provide an estimate of antibody.

5. The test of claim 4, wherein antibody levels are measured according to a method selected from the group consisting of bead-based assays, the enzyme linked immuosorbent assay (ELISA), protein microarrays and the luminescence immunoprecipitation system (LIPS).

6. A method for diagnosis of *P. vivax*, comprising performing the diagnostic test of claim 1, wherein the level of antibody and the timing of infection identifies individuals with a high probability of being infected with liver-stage hypnozoites.

7. The test of claim 1, wherein said specific timing identifies whether and when an infection occurred within an elapsed time period of 0 to 12 months.

8. The test of claim 7, wherein said time period is differentiated by month, by week, or by day.

9. The test of claim 7, wherein a particular time period is determined as a binary decision of a more recent or an older infection, with each time point as a cut-off.

10. The test of claim 9, wherein said cut off determines whether an infection in a subject was within the past 9 months or later than the past 9 months.

11. The test of claim 1, comprising further determining an estimate of the time since last *P. vivax* blood-stage infection according to the time since last PCR-detectable blood-stage parasitemia, or as the time since last infective mosquito bite.

12. The test of claim 11 comprising determining a frequency of infections during a particular time period and/or time since last infection.

13. The test of claim 1 for detecting an asymptomatic infection by *P. vivax*.

14. The test of claim 1 for detecting a dormant infection, wherein the level of antibody indicates *P. vivax* is present in the liver but is not present at significant levels in the blood.

15. The test of claim 1 for detecting antibodies to malarial proteins that are present in the blood wherein the level of antibody and the timing of infection indicate a high degree of probability of liver-stage infection.

16. The test of claim 1 wherein the level of antibody and the timing of infection provides for determining progression of infection by *P. vivax* in a population of a plurality of subjects.

17. The test of claim 1 wherein the level of antibody and the timing of infection provides for determining whether the infection is starting or whether the infection has reached a peak in terms of exposure of individuals who are naïve to the particular strain of *P. vivax* causing the infection.

18. The test of claim 1 for measuring antibodies in the blood of the subject at a plurality of time points to determine decay in the level of each antibody in the blood; and fitting such decay to a suitable model to determine at least one infection parameter selected from probability of liver-stage infection, determination of the progression of infection, and rate of propagation of the *Plasmodium* species in a population.

19. The test of claim 18, wherein decay in the level of a plurality of different antibodies is determined and the different antibodies are selected to have a range of different half-lives.

20. The test of claim 18, wherein from two up to twenty different antibodies are measured.

21. The test of claim 1, wherein a model for determining at least one parameter about the infection in the subject is selected from the group consisting of linear discriminant analysis (LDA), quadratic discriminant analysis (QDA), combined antibody dynamics (CAD), decision trees, random forests, boosted trees and modified decision trees.

* * * * *

```
                              SEQUENCE LISTING

Sequence total quantity: 142
SEQ ID NO: 1            moltype = AA  length = 115
FEATURE                 Location/Qualifiers
source                  1..115
                        mol_type = protein
                        organism = Plasmodium vivax
SEQUENCE: 1
MNESKEILSQ LLNVQTQLLT MSSEHTCIDT NVPDNAACYR YLDGTEEWRC LLTFKEEGGK  60
CVPASNVTCK DNNGGCAPEA ECKMTDSNKI VCKCTKEGSE PLFEGVFCSH HHHHH       115

SEQ ID NO: 2            moltype = DNA  length = 348
FEATURE                 Location/Qualifiers
source                  1..348
                        mol_type = genomic DNA
                        organism = Plasmodium vivax
SEQUENCE: 2
atgaacgagt ccaaggagat cctcagccaa ctcctgaacg tgcaaaccca gctcctgacc   60
atgtccagcg agcacacctg catcgacacc aacgtcccag acaacgccgc ctgctacagg  120
tacctggacg gcaccgagga gtggcgctgc ctcctgacct tcaaggaaga gggcggcaag  180
tgcgtgccaa cctccaacgt cacctgcaag gacaacaacg gcggctgcgc tccagaggct  240
gagtgcaaga tgaccgacag caacaagatc gtgtgcaagt gcaccaagga aggctccgag  300
ccactcttcg agggcgtctt ctgcagccac caccaccacc accactga               348

SEQ ID NO: 3            moltype = AA  length = 427
FEATURE                 Location/Qualifiers
source                  1..427
                        mol_type = protein
                        organism = Plasmodium vivax
SEQUENCE: 3
MKTETVTSRS NPHQAIEYAN QGPSRDKVEE WKRNAWTDWM VQLDDDWKDF NAQIEEEKKA   60
WIEEKEGDWV ILLKHLQNKW LHFNPNLDAE YQTDMLAKSE TWDERQWKMW ISTEGKQLLE  120
MDLKKWFTNN EMIYCKWTMD EWNEWKNEKI KEWVTSEWKE SEDQYWSKYD DATIQTLTVA  180
ERNQWFKWKE RIYREGIEWK NWIAIKESKF VNANWNSWSE WKNEKRLEFN DWIEAFVEKW  240
IRQKQWLIWT DERKNFANRQ KAAPGGVAAA PGVFAPRPAF GAPSGFAPRP GFAAPSQPPR  300
YSFAAASGYV APSATSEAAP ATSEAPASAE ATTALSSETT TPVNPEETAA SPEAATPVNP  360
EETAASSETT TVNPEATPVN PEAPVAEPEK KEEEPAAEPL LAIEPAQTEP AALEAAPSTS  420
AHHHHHH                                                            427

SEQ ID NO: 4            moltype = DNA  length = 1284
FEATURE                 Location/Qualifiers
source                  1..1284
                        mol_type = genomic DNA
                        organism = Plasmodium vivax
SEQUENCE: 4
atgaagaccg agacggtgac ctccaggagc aacccacacc aagccatcga gtacgccaac   60
cagggcccat ccagggacaa ggtggaggag tggaagcgca acgcctggac cgactggatg  120
gtccaactcg acgacgactg gaaggacttc aacgcccaga tcgaggaaga gaagaaggcc  180
tggattgagg agaaggaagg cgactgggtc atcctcctga agcacctcca aaacaagtgg  240
ctgcacttca acccaaacct cgacgccgag taccagaccg acatgctggc caagtccgag  300
acgtgggacg agaggcagtg gaagatgtgg atcagcaccg agggcaagca gctcctggag  360
atggacctca agaagtggtt caccaacaac gagatgatct actgcaagtg gaccatggac  420
gagtggaacg agtggaagaa cgagaagatc aaggagtggg tgacctccga gtggaaggag  480
agcgaggacc aatactggtc caagtacgac gacgccacca tccaaaccct gaccgtcgcc  540
gagcgcaacc agtggttcaa gtggaaggag aggatctacc gcgagggcat cgagtggaag  600
aactggatcg ccatcaagga gagcaagttc gtgaacgcca actggaactc ctggtctgag  660
tggaagaacg agaaaaggct ggagttcaac gactggatcg aggccttcgt cgagaagtgg  720
atccgccaaa agcagtggct gatctggacc gacgagagga gaactttcgc caaccgccaa  780
aaggctgctc caggcggcgt ggctgccgcc ccaggcgtct cgccccacg  cccagccttc  840
ggcgccccat ccggcttcgc cccaaggcca ggcttcgctg ctccaagcca gccaccacgc  900
tactccttcg ctgccgccag cggctacgtg gctccatccg ctaccagcga ggctgctcca  960
gccacctccg aggcccagc cagcgccgag gctaccaccg ctctctccag cgagacgacc 1020
acccagtca acccagagga gacggctgct agccggagg ctgctacccc agtgaacccg 1080
gaggagacgg ctgcctccag cgagacgacg acggtcaacc cagaggccac cccggtgaac 1140
ccagaggctc cagtggctga gccagagaag aaggaagagg agccagctgc tgagccactg 1200
ctcgctatcg agccagctca aaccgagcca gctgctctgg aggctgctcc atccaccagc 1260
gcccaccacc accaccacca ctga                                        1284
```

```
SEQ ID NO: 5            moltype = AA  length = 387
FEATURE                 Location/Qualifiers
source                  1..387
                        mol_type = protein
                        organism = Plasmodium vivax
SEQUENCE: 5
MQLELEPAPD YESTSPTVPV RLLLHDDYAP NAEDMFGPEA SQVMTNLYET IDEDGTTTDG  60
YQNGSDDDQS NQSDSNDDAV MLNYLSNETD SFDELIDEID NHKKKKKIYS PLRKPVLKRS  120
DSSDSLSDYE LDEVLRQTEN EPEEDEDLDL SLEDSFEVIN YPWKDILESS PYSTDHTNEE  180
DFSSLEELEL EDPVQEMNFG KLKFFEIGDP DLLIRKTPIT PNTKTKSGLE KNGNNTEASN  240
INQHEKEKMD KRKRRTHKQF KNPIENFSVT TTYDDFLKQN GLRDHPSKHQ KDSSEPFVLD  300
QYNYRNAKFK NVRFYILRML YDNIKDIGLK EFQYLKSHKY EVEEFIKNIL RNNLICLTFS  360
QEDHLFNDAH LLIEKASIKS EHHHHHH                                     387

SEQ ID NO: 6            moltype = DNA  length = 1164
FEATURE                 Location/Qualifiers
source                  1..1164
                        mol_type = genomic DNA
                        organism = Plasmodium vivax
SEQUENCE: 6
atgcagctgg agctggagcc agccccagac tacgagtcca ccagcccaac cgtgccagtc  60
aggctcctgc tccacgacga ctacgcccca aacgccgagg acatgttcgg cccagaggcc  120
tcccaagtga tgaccaacct ctacgagacg atcgacgagg acggcaccac caccgacggc  180
taccaaaacg gctccgacga cgaccaaagc aaccagtccg acagcaacga cgacgccgtc  240
atgctcaact acctgtccaa cgagacggac agcttcgacg agctcatcga cgagatcgac  300
aaccacaaga agaagaagaa gatctactcc ccactcagga agccagtgct gaagcgcagc  360
gactccagcg actccctgag cgactacgag ctcgacgagg tcctgcgcca gaccgagaac  420
gagccagagg aagacgagga cctggacctc tccctggagg acagcttcga ggtcatcaac  480
tacccatgga aggacatcct ggagtccagc ccatacagca ccgaccacac caacgaggaa  540
gacttctcca gcctggagga gctggagctg gaggacccag tccaagagat gaacttcggc  600
aagctgaagt tcttcgagat cggcgaccca gacctgctca tcaggaagac cccaatcacc  660
ccaaacacca agaccaagtc cggcctggag aagaacggca acaacaccga ggccagcaac  720
atcaaccagc acgagaagga gaagatggac aagcgcaaga ggcgcaccca caagcaattc  780
aagaacccaa tcgagaactt ctccgtgacc accacctacg acgacttcct caagcaaaac  840
ggcctgaggg accacccaag caagcaccag aaggactcca gcgagccatt cgtgctcgac  900
caatacaact accgcaacgc caagttcaag aacgtcaggt tctacatcct ccgcatgctg  960
tacgacaaca tcaaggacat cggcctcaag gagttccagt acctgaagtc ccacaagtac  1020
gaggtcgagg agttcatcaa gaacatcctc aggaacaacc tcatctgcct gaccttcagc  1080
caagaggacc acctgttcaa cgacgcccac ctgctcatcg agaaggcctc catcaagagc  1140
gagcaccacc accaccacca ctga                                        1164

SEQ ID NO: 7            moltype = AA  length = 822
FEATURE                 Location/Qualifiers
source                  1..822
                        mol_type = protein
                        organism = Plasmodium vivax
SEQUENCE: 7
MNAGDGQGVY GGNGINNPLV YHVQHGVNIP NSNSDKKASD HTPDEDEDTY GRTRNKRYMH  60
RNPGEKYKGS NSPHDSNDDS GDTEYELNEG DVKRLTPKNK KGATTEEVDT YPYGKKTNGS  120
EFPRMNGSET GHYGYNNTGS GGHNDENGYT PIIVKYDNTH AKNRANEIEE NLNKGEYSRI  180
KMAKGKKGQK SGGYESDGED SDVDSSNVFY VDNGQDMLIK EKMSRSEGPD EMSEEGLNVK  240
YKAQRGPVNY HFSNYMNLDK RNTLSSNEIE LQKMIGPKFS EEVNKYCRLN EPSSKKGEFL  300
NVSFEYSRAL EELRSEMINE LQKRKAVGSN YYNNILNAIY TSMNRKNANF GRDAYEDKSF  360
ISEANSFRNE EMQPLSAKYN KILRQYLCHV FVGNPGVNQL ERLYFHNLAL GELIEPIRRK  420
YNKLASSSVG LNYEIYIASS SNIYLMGHLL MLSLAYLSYN SYFVQGLKPF YSLETMLMAN  480
SDYSFFMYNE VCNVYYHPKG TFNKDITFIP IESRPGRHST YVGERKVTCD LLELILNAYT  540
LINVHEIQKV FNTSEAYGYE NSISFGHNAV RIFSQVCPRD DAKNTFGCDF EKSTLYNSKV  600
LKMDEGDKEN QRSLKRAFDM LRTFAEIEST SHLGDPSPNY ISLIFEQNLY TDFYKYLFWY  660
DNRELINVQI RNAGRRKKGK KVKFVYDEFV KRGKQLKDKL IKIDAKYNAR SKALLVFYAL  720
VDKYANIFRK SENVRKFFLN DVSSIRHHLY LNSVLTKSPK SNLDSMKKTL EELQSLTNAP  780
LKFIVRGNNL KFLNNVAKFE NLFYVNLFIM SSLSRKHHHH HH                    822

SEQ ID NO: 8            moltype = DNA  length = 2469
FEATURE                 Location/Qualifiers
source                  1..2469
                        mol_type = genomic DNA
                        organism = Plasmodium vivax
SEQUENCE: 8
atgaacgctg gcgacggcca aggcgtgtac ggcggaaacg gcatcaacaa cccactcgtg  60
taccacgtcc agcacggcgt caacatccca aactccaaca gcgacaagaa ggccagcgac  120
cacaccccag acgaggacga ggacacctac ggcaggaccc gcaacaagag gtacatgcac  180
cgcaacccag gcgagaagta caagggctcc aacagcccac acgactccaa cgacgacagc  240
ggcgacaccg agtacgagct gaacgagggc gacgtgaaga ggctcacccc aaagaacaag  300
aagggcgcca ccaccgagga agtggacacc tacccatacg gcaagaagac caacggcagc  360
gagttcccac gcatgaacgg ctccgagacg ggccactacg gctacaacaa caccggcagc  420
ggcggccaca acgacgagaa cggctacacc ccaatcatcg tgaagtacga caacacccac  480
gccaagaaca gggccaacga gatcgaggag aacctcaaca agggcgagta ctcccgcatc  540
aagatggcca agggcaagaa gggccaaaag tccggcggct acgagagcga cggcgaggac  600
```

-continued

```
tccgacgtcg actccagcaa cgtgttctac gtcgacaacg gccaggacat gctgatcaag    660
gagaagatgt ccaggagcga gggcccagac gagatgagcg aggaaggcct caacgtgaag    720
tacaaggccc aaaggggccc agtcaactac cacttctcca actacatgaa cctggacaag    780
cgcaacaccc tctccagcaa cgagatcgag ctccagaaga tgatcggccc aaagttcagc    840
gaggaagtga acaagtactg caggctgaac gagccatcca gcaagaaggg cgagttcctc    900
aacgtctcct tcgagtacag cagggccctg gaggagctga ggtccgagat gatcaacgag    960
ctgcaaaagc gcaaggccgt gggcagcaac tactacaaca acatcctcaa cgccatctac   1020
acctccatga acaggaagaa cgccaacttc ggccgcgacg cctacgagga caagtccttc   1080
atcagcgagg ccaacagctt caggacgag gagatgcaac cactctccgc caagtacaac   1140
aagatcctgc gccagtacct ctgccacgtg ttcgtcggca acccaggcgt gaaccaactg   1200
gagcgcctgt acttccacaa cctgccctg ggcgagctga tcgagccaat caggcgcaag   1260
tacaacaagc tggcctccag ctccgtcggc ctcaactacg agatctacat cgccagctcc   1320
agcaacatct acctcatggg ccacctcctg atgctcagcc tggcctacct gtcctacaac   1380
agctacttcg tgcagggcct caagccattc tactccctga aaaccatgct catggccaac   1440
tccgactaca gcttcttcat gtacaacgag gtgtgcaacg tctactacca cccaaagggc   1500
accttcaaca aggacatcac cttcatccca atcgagagca ggccaggcag gcactccacc   1560
tacgtgggcg agaggaaggt cacctgcgac ctcctggagc tcatcctgaa cgcctacacc   1620
ctgatcaacg tgcacgagat ccaaaaggtc ttcaacacca gcgaggccta cggctacgag   1680
aactccatca gcttcggcca caacgccgtg aggatcttct cccaggtctg cccacgcgac   1740
gacgccaaga acaccttcgg ctgcgacttc gagaagagcc ccctgtacaa ctccaaggtg   1800
ctcaagatgg acgagggcga caaggagaac cagaggtccc tgaagcgcgc cttcgacatg   1860
ctccgcacct tcgccgagat cgagtccacc agccacctcg cgacccaagc cccaaactac   1920
atctccctga tcttcgagca aaacctctac accgacttct acaagtacct gttctgtgac   1980
gacaacaggg agctcatcaa cgtgcagatc cgcaacgccg gcaggcgcaa gaagggcaag   2040
aaggtgaagt tcgtctacga cgagttcgtc aagaggggca agcaactgaa ggacaagctc   2100
atcaagatca acgccaagta caacgcccgc agcaaggccc tcctggtgtt ctacgccctg   2160
gtcgacaagt acgccaacat cttcaggaag tccgagaacg tgcgcaagtt cttcctcaac   2220
gacgtctcca gcatcaggca ccacctctac ctgaacagcg tgctgaccaa gtccccaaag   2280
agcaacctcg acagcatgaa gaagaccctg gaggagctgc agtccctcac caacgcccca   2340
ctgaagttca tcgtcagggg caacaacctg aagttcctca caacgtggc caagttcgag   2400
aacctgttct acgtgaacct cttcatcatg tccgcctctc ccgcaagca ccaccaccac   2460
caccactga                                                            2469
```

SEQ ID NO: 9           moltype = AA   length = 337
FEATURE                Location/Qualifiers
source                 1..337
                       mol_type = protein
                       organism = Plasmodium vivax
SEQUENCE: 9
MNVNKKSSGE ENNTKQALGL RVSRTLAKDG ANENAEEGLS EEEEEAVEEG EEEAVEEGEE     60
EVVEEEGEEV VEGEEEEVVE GEEEVVEDEE VVEGEEYAEG EEPVEGEEYA EGEEPVEGEE    120
PVEVEEYAEG EEPVEGEEYA EGEEPVEGEE VVEGEEVVEG EEVAEGEEVA EGEEVAEGEE    180
AVEGEEVAEG EEVAEGEEVA EGEEAAEEGA AEEGATEEGA TEEGATKEEA TEKAAEGEET    240
AESEKPAEEQ PTTFVETVEK KVEPVSKPPF KPLFPVDEKY LETLEDIAQS FLKEFQEAEG    300
KRKQKKVKKR AKKITKKLAK EYAKKFKSKK KHHHHHH                             337

SEQ ID NO: 10          moltype = DNA   length = 1014
FEATURE                Location/Qualifiers
source                 1..1014
                       mol_type = genomic DNA
                       organism = Plasmodium vivax
SEQUENCE: 10
atgaacgtca acaagaagtc cagcggcgag gagaacaaca ccaagcaagc tctgggcctg     60
agggtgtccc gcacccctcgc taaggacgg gccaacgaga cgccgaggga ggcctcagcg    120
gaggagagg aagaggccgt cgaggaaggc gaggaaggga ccgtggagga aggcgaggaa    180
gaggtggtcg aggaagaggg cgaggaagtg gtcgagggcg aggaagagga agtggtggag    240
ggggaggaag aggtggtgga ggatgaggaa gtggtcgagg gcgaggagta cgctgagggc    300
gaggagccgc tggaggggga ggagtacgcc gagggggagg agccagtgga gggcgaggag    360
ccagtggagg tggaggagta cgcggagggg gaggagccgg tggaaggtga ggagtacgcc    420
gagggcgagg agcctgtcga gggggaggaa gtggtggaag gtggtgaaggt    480
gaggaagtgg ctgagggcga ggaagtggcc gagggggagg aagtggccga gggcgaggaa    540
gccgtggagg cgaggaagt ggcggagggg gaggaagtgg cggaaggcga ggaagtggcc    600
gaaggcgagg aagccgctga ggaaggcgct gccgaggaag gcgccacgga ggaaggcgct    660
accgaggaag gcgccaccaa ggaaggcgcc accgaaagcg ctgccgaggaa g acctgtgg    720
gctgagtccg agaagccagc tgaggagcaa ccaaccacct cgtggagac ggtcgagaag    780
aaggtggagc cagtcagcaa gccaccattc aagccactct cccagtcga cgagaagtac    840
ctcgaaaccc tggaggacat cgcccaatcc ttcctgaagg agttccaaga ggccgaggc    900
aagaggaagc agaagaaggt gaagaagcgc gccaagaaga tcaccaagaa gctcgccaag    960
gagtacgcca agaagttcaa gtccaagaag aagcaccacc accaccacca ctga          1014

SEQ ID NO: 11          moltype = AA   length = 288
FEATURE                Location/Qualifiers
source                 1..288
                       mol_type = protein
                       organism = Plasmodium vivax
SEQUENCE: 11
MPKPDQKNLK GGVKNAPLQQ RKGSVPINPP KPVNDKLKDG SNKTETKNAK NTLSKPPMQV     60
TDKSKDEAKK TPLQSTPKLT PKTKEVPKES NMEMWLKDTK DEYENLKCQY RTCLYDWFRK    120
INDEYNELLN KLEEKWAKFP NDPKNKDVFD NLKTSSLKND EKKAQWMRKN LKDLMREQVD    180

```
EWLEGKKKIY EGMSPTYWDA WEKKIAKGLM GAAWYKMNSS GRTKEWDKLR NELETRYNKK   240
IKSLWGGFHR DVYFRFKEWI EEVFNKWIEN KQIDTWMNSG KKHHHHHH               288

SEQ ID NO: 12           moltype = DNA   length = 867
FEATURE                 Location/Qualifiers
source                  1..867
                        mol_type = genomic DNA
                        organism = Plasmodium vivax
SEQUENCE: 12
atgccaaagc cagaccaaaa gaacctcaag ggcggcgtga agaacgcccc actgcaacag   60
aggaagggct ccgtgccaat caacccacca aagccagtca cgacaagct caaggacggc   120
agcaacaaga ccgagacgaa gaacgccaag aacaccctgt ccaagccacc aatgcaagtg   180
accgacaaga gcaaggacga ggccaagaag accccactcc agtccacccc aaagctgacc   240
ccaaagacca aggaagtgcc aaaggagagc aatatggaga tgtggctcaa ggacaccaag   300
gacgagtacg agaacctcaa gtgccagtac aggacctgcc tgtacgactg gttccgcaag   360
atcaacgacg agtacaacga gctcctgaac aagctggagg agaagtgggc caagttccca   420
aacgacccaa agaacaagga cgtgttcgac aacctcaaga cctccagcct gaagaacgac   480
gagaagaagg cccagtggat gaggaagaac ctcaaggacc tgatgaggga gcaggtggac   540
gagtggctgg agggcaagaa gaagatctac gagggcatgt ccccaaccta ctgggacgcc   600
tgggagaaga agatcgctaa gggcctgatg ggcgctgctt ggtacaagat gaactcctcc   660
ggcaggacca aggagtggga caagctcagg aacgagctcg aaaccgcta caacaagaag   720
atcaagtccc tctgggcgg cttccacagg gacgtgtact tccgcttcaa ggagtggatc   780
gaggaagtgt tcaacaagtg gatcgagaac aagcaaatcg acacctggat gaacagcggc   840
aagaagcacc accaccacca ccactga                                      867

SEQ ID NO: 13           moltype = AA   length = 438
FEATURE                 Location/Qualifiers
source                  1..438
                        mol_type = protein
                        organism = Plasmodium vivax
SEQUENCE: 13
MQYSIVKNEI TKRRKPKIRN ESPPDGNSPG GGKNNAAGNN GGGDNNAKNK AANKAANNAA   60
NKAANNAANN AANNAANNAA NNAANNAANN AANNAANNAA NNAANNANEQ NGNKKKKGKP   120
KKEEADLPVQ AQNENDRNKI EDIADEAELF AEEAKMLADL ASKRSKEVEQ ILSSIPENKF   180
GSEPKEDAIF AAKDAVRASE DAMKAAQKAR AAETVTQANE EKDKAKTAKE LAERSAQIVK   240
KNAVEALKEF GKIAEAAEME AIKIPIPENL KPKKKVKQPR AAAQKVEPTQ ATAHKVVPPP   300
AEPPRAPSPP PPPAKPEAAP PAKEVAPAVT TPEAPKEEAP KADAAPAAPQ PAAESKVAKE   360
PTDQSAENQS DSLYKETNIK EGTEEAGTGQ EQKQEPELQN LLEQQMNIFY ILVQFFKSKI   420
KALIKFLLIL VSHHHHHH                                                438

SEQ ID NO: 14           moltype = DNA   length = 1317
FEATURE                 Location/Qualifiers
source                  1..1317
                        mol_type = genomic DNA
                        organism = Plasmodium vivax
SEQUENCE: 14
atgcaatact ccatcgtgaa gaacgagatc accaagaggc gcaagccaaa gatcaggaac   60
gagtccccac cagacggcaa cagcccaggc ggcggcaaga acaacgctgc tggcaacaac   120
ggcggcggcg acaacaacgc caagaacaag gctgctaaca aggctgctaa caacgccgcc   180
aacaaggccg ccaacaacgc tgctaacaac gccgcgaaca acgccgccaa caacgccgcc   240
aacaacgcag ctaacaacgc cgctaacaac accgccgcca acaacgcggc caacaacgcc   300
aacaacgctg ccaacaacgc caacgagcaa aacggcaaca gaagaagaa gggcaagcca   360
aagaaggaag aggccgacct cccagtgcaa gcccagaacg agaacgacag gaacaagatc   420
gaggacatcg ctgacgaggc tgagctgttc gctgaggaag ccaagatgct cgccgacctg   480
gcctccaagc gcagcaagga agtggagcag atcctctcca gcatcccaga gaacaagttc   540
ggctccgagc caaaggaaga cgccatcttc gctgctaagg acgccgtgag ggctagcgag   600
gacgccatga aggctgctca aaaggccagg gccgctgaga cggtcaccca ggccaacgag   660
gagaaggaca aggctaagac cgctaaggag ctggctgaga ggtccgctca aatcgtgaag   720
aagaacgccg tcgaggccct gaaggagttc ggcaagatcg ccgaggccgc cgagatggag   780
gccatcaaga tcccaatccc agagaacctg aagccaaaga agaaggtgaa gcaaccaagg   840
gccgccgccc aaaaggtgga gccaacccaa gctaccgctc acaaggtggt gccaccacca   900
gctgagccac cacgcgcccc catccccacca ccaccaccag ctaagccaga ggctgcccca   960
ccagctaagg aagtggctcc agctgtcacc acccagagg ctccaaagga gaggcccca   1020
aagctgacg ctgctccagc tgccccacag ccagccgcg agtccaaggt gccaaggag   1080
ccaaccgacc agagcgccga gaaccaatcc gacagcctct acaaggagac gaacatcaag   1140
gaaggcaccg aggaagccgg caccggccaa gagcagaagc aagagccaga gctccaaaac   1200
ctcctggagc aacagatgaa catcttctac atcctggtgc agttcttcaa gtccaagatc   1260
aaggccctca tcaagttcct cctgatcctg gtcagccatc accaccacca ccactga      1317

SEQ ID NO: 15           moltype = AA   length = 355
FEATURE                 Location/Qualifiers
source                  1..355
                        mol_type = protein
                        organism = Plasmodium vivax
SEQUENCE: 15
MDENTGWPID YEFNSKTLPS IEVKLSPPEN PLPQVAAEIK LLESARLKLE EGMMQKLEDE   60
YNKSLSSAKI KIQDTVEKSL SIFNDPNMLG SVISNSVKML RSENVKKRTE NVQAKHNLKK   120
MQTVNQAKSG PLPPPELRKH TSFLEQNYVN RVLPSVKISL SELTEPSVEI KEKIEEMEQY   180
RTDEEVAMFE MAISEFSILT DITILELEKQ IQLQLNPPFLV DKKVVHRALT KELKELEQRE   240
```

```
EKQKIKENFQ RQSSFIEAGE DEDTGNILNV KISQTDYGYP TVDELVMQMQ KRRDISEKLE  300
RQKILDLQMK LLKAQSEMIK DALHFALSKV IAQYSPLVET MKLESMRMLH HHHHH       355

SEQ ID NO: 16          moltype = DNA  length = 1068
FEATURE                Location/Qualifiers
source                 1..1068
                       mol_type = genomic DNA
                       organism = Plasmodium vivax
SEQUENCE: 16
atggacgaga acaccggctg gccaatcgac tacgagttca actccaagac cctgccaagc  60
atcgaggtga agctctcccc accagagaac ccactgccac aagtcgccgc cgagatcaag  120
ctcctggaga gcgcccgcct caagctcgaa gagggcatga tgcagaagct ggaggacgag  180
tacaacaagt ccctgtccag cgccaagatc aagatccaag acaccgtgga gaagtccctc  240
agcatcttca acgacccaaa catgctgggc tccgtgatct ccaacagcgt caagatgctc  300
aggagcgaga acgtgaagaa gcgcaccgag aacgtccagg ccaagcacaa cctcaagaag  360
atgcagaccg tcaaccaagc caagagcggc ccactcccac caccagagct gcgcaagcac  420
acctccttcc tggagcaaaa ctacgtgaac agggtcctgc catccgtgaa gatctccctc  480
agcgagctga ccgagccaag cgtcgagatc aaggagaaga tcgaggagat ggagcagtac  540
aggaccgacg aggaagtggc catgttcgag atggccatct ccgagttcag catcctcacc  600
gacatcacca tcctggagct ggagaagcaa atccagctcc aactgaaccc attcctcgtc  660
gacaagaagg tggtccacag ggccctgacc aaggagctca aggagctgga gcagcgcgag  720
gagaagcaaa agatcaagga gaacttccag aggcaatcca gcttcatcga ggctggcgag  780
gacgaggaca ccggcaacat cctcaacgtg aagatctccc agaccgacta cggctaccca  840
accgtggacg agctcgtcat gcagatgcaa aagaggcgcg acatctccga gaagctggag  900
cgccagaaga tcctcgacct gcagatgaag ctcctgaagg cccagagcga gatgatcaag  960
gacgccctcc acttcgccct gtccaaggtc atcgcccaat acagcccact cgtcgagacg  1020
atgaagctgg agagcatgag gatgctccac caccaccacc accactga              1068

SEQ ID NO: 17          moltype = AA  length = 624
FEATURE                Location/Qualifiers
source                 1..624
                       mol_type = protein
                       organism = Plasmodium vivax
SEQUENCE: 17
MSSDGKSSAS AKSGSKSGSK YGGSSYSDYS AYDSGSASSV GSREFENEMY EFALQHPMEK  60
LTKEMDILKN DYTKVKEEEG KILDEEHKEI EEKRKEERLK MLAEGDVEKN KGDEEINFIK  120
HDYTDTRIRG GFTEFLSNLN PFKKEIKPMK KEISLITYIP DKIVNKEKIM RDLGISHKYE  180
PYQQSILYTC PNSVFFFDSM ENLRKELDKN HEKEAITNKI LDHNKECLKN FGLFDFELPD  240
NKTKLGNVIG SIGEYHVRLY EIENDLLKYQ PSLDYMTLAD DYKLVKNDVN TLENVNFCLL  300
NPKTLEDFLK KKEIMELMGE DPIAYEEKFT KYMEESINCH LESLIYEDLD SSQDTKIVLK  360
NVKSKLYLLQ NGLTYKSKKL INKLFNEIQK NPEPIFEKLT WIYENMYHLK RDYTFLAFKT  420
VCDKYVSHNS IYTSLQGMTS YIIEYTRLYG ACFKNITIYN AVISGIHEQM KNLMKLMPRS  480
GLLSDVHFEA LLHKENKKIT RTDYVLNDYD PSVKAYALTQ VERLPMVSVI NSFFEAKKKA  540
LSKMLAQMKL DLFTLTNEDL KIPNDKGANS KLTAKLISIY KAEIKKYFKE MRDDYVFLIK  600
ARYKGHYKKN YLLYKRLEHH HHHH                                         624

SEQ ID NO: 18          moltype = DNA  length = 1875
FEATURE                Location/Qualifiers
source                 1..1875
                       mol_type = genomic DNA
                       organism = Plasmodium vivax
SEQUENCE: 18
atgagcagcg acggcaagtc cagcgcttcc gctaagtccg gcagcaagtc cggcagcaag  60
tacggcggct ccagctactc cgactacagc gcctacgact ccggcagcgc ctccagcgtg  120
ggcagccgcg agttcgagaa cgagatgtac gagttcgccc tgcaacaccc gatggagaag  180
ctcaccaagg agatggacat cctgaagaac gactacacca aggtgaagga agaggaaggc  240
aagatcctcg acgaggagca caaggagatc gaggagaaga ggaaggaaga gcgcctcaag  300
atgctggccg agggcgacgt ggagaagaac aagggcgacg aggagatcaa cttcatcaag  360
cacgactaca ccgacaccag gatccgcggc ggcttcaccg agttcctctc caacctgaac  420
ccattcaaga aggagatcaa gccgatgaag aaggagatct ccctcatcac ctacatccca  480
gacaagatcg tcaacaagga gaagatcatg cgcgacctgg gcatctccca caagtacgag  540
ccataccaac agagcatcct ctacacctgc ccaaactccg tgttcttctt cgacagcatg  600
gagaacctca ggaaggagct ggacaagaac cacgagaagg aagccatcac caacaagatc  660
ctcgaccaca acaaggagtg cctcaagaac ttcggcctgt tcgacttcga gctcccagac  720
aacaagacca agctgggcaa cgtcatcggc tccatcggcg agtaccacgt gaggctctac  780
gagatcgaga acgacctcct gaagtaccaa ccaagcctgg actacatgac cctcgccgac  840
gactacaagc tggtgaagaa cgacgtcaac accctggaga acgtgaactt ctgcctcctg  900
aacccaaaga ccctggagga cttcctcaag aagaaggaga tcatggagct gatgggcgag  960
gacccaatcg cctacgagga gaagttcacc aagtacatgg aggagtccat caactgccac  1020
ctggagagcc tgatctacga ggacctcgac tccagccaag acaccaagat cgtgctcaag  1080
aacgtcaagt ccaagctgta cctcctgcag aacggcctca cctacaagag caagaagctc  1140
atcaacaagc tgttcaacga gatccagaag aacccagagc caatcttcga gaagctcacc  1200
tggatctacg agaacatgta ccacctgaag cgcgactaca ccttcctcgc cttcaagacc  1260
gtgtgcgaca agtatgtgtc ccacaacagc atctacacct ccctgcaagg catgaccagc  1320
tacatcatcg agtacaccag gctctacggc gcctgcttca agaacatcac catctacaac  1380
gccgtcatct ccggcatcca cgagcagatg aagaacctca tgaagctgat gccaaggtcc  1440
ggcctcctga gcgacgtgca cttcgaggcc ctcctgcaca aggagaacaa gaagatcacc  1500
cgcaccgact acgtgctcaa cgactacgac ccatccgtca aggcctacgc cctgacccaa  1560
gtggagaggc tcccaatggt gtccgtcatc aacagcttct tcgaggccaa gaagaaggcc  1620
```

```
ctcagcaaga tgctggccca gatgaagctc gacctgttca ccctgaccaa cgaggacctc    1680
aagatcccaa acgacaaggg cgccaactcc aagctcaccg ccaagctgat cagcatctac    1740
aaggccgaga tcaagaagta cttcaaggag atgagggacg actacgtctt cctgatcaag    1800
gcccgctaca aggggcacta caagaagaac tacctcctgt acaagcgcct ggagcaccac    1860
caccaccacc actga                                                     1875

SEQ ID NO: 19           moltype = AA   length = 239
FEATURE                 Location/Qualifiers
source                  1..239
                        mol_type = protein
                        organism = Plasmodium vivax
SEQUENCE: 19
MNTRASKFAN SKRKRNGNAM RENKLNNDDV DHYSFLSLRT ANEEKAATEN DSNNAKKEGE     60
ENTNGNEKKN EENGSGNEKR NEENNANEKK NEQTNDQSNG QSNSQTNIPK KNEAVPPEKK    120
INKENLLEYG THDKDGHFIP SYKTLTDEIL STNNSLERAS SFLKIACSHI MKIVEFIPES    180
KLSSQYIKVE SKNVYIKDIT SECQNIFFSL EKLTMTMIVL NSKMNKLVYV QDKHHHHHH    239

SEQ ID NO: 20           moltype = DNA   length = 720
FEATURE                 Location/Qualifiers
source                  1..720
                        mol_type = genomic DNA
                        organism = Plasmodium vivax
SEQUENCE: 20
atgaacacca gggcctccaa gttcgccaac agcaagagga gcgcaacgg caacgccatg      60
cgcgagaaca agctcaacaa cgacgacgtg gaccactact ccttcctcag cctgaggacc    120
gctaacgagg agaaggctgc taccgacaac gactccaaca acgccaagga ggaaggcgag    180
gagaacacca acggcaacga agaagaagaac gaggagaacg gcagcggcaa cgagaagcgc    240
aacgaggaga acaacgctaa cgagaagaag aacgagcaaa ccaacgacca gtccaacggc    300
caatccaaca gccagaccaa catcccaaag aagaacgagg ccgtcccacc agagaagaag    360
atcaacaagg agaacctcct ggagtacggc acccacgaca aggacggcca cttcatccca    420
agctacaaga ccctcaccga cgagatcctg tccaccaaca acagcctgga gagggcctcc    480
agcttcctga gatcgcctg ctcccacatc atgaagatcg tggagttcat cccagagtcc    540
aagctgtcca gccaatacat caaggtggag agcaagaacg tctacatcaa ggacatcacc    600
tccgagtgcc agaacatctt cttcagcctg gagaagctga ccatgaccat gatcgtcctc    660
aacagcaaga tgaacaagct ggtctacgtg caagacaagc accaccacca ccactga       720

SEQ ID NO: 21           moltype = AA   length = 287
FEATURE                 Location/Qualifiers
source                  1..287
                        mol_type = protein
                        organism = Plasmodium vivax
SEQUENCE: 21
MPKPAQNLKG GVKKPSLQQT KSPLPSKPPK PVNDKLKDDS NKTETKDAKN GLNKPPKNIN     60
DKVKDGENKT PSQDLNEPSF KLPMRQKASS WDAWLKGTKK DYENLKCFAK GNLYDWLCSV    120
RDSFELYLQS LESKWTSCSD NTTTVFLCEC LAESSGWGDP QWESWVKKEL KEQLKTEAQA    180
WISTKKKDFD GLTSKYFSLW KDHRRKELEE EAWKTKASSG GLSEWEELTD KMNTRYTNNL    240
DNMWSNYSGD LLFRFDEWSP EVLEKWIESK QWNQWVKKVR KHHHHHH                  287

SEQ ID NO: 22           moltype = DNA   length = 864
FEATURE                 Location/Qualifiers
source                  1..864
                        mol_type = genomic DNA
                        organism = Plasmodium vivax
SEQUENCE: 22
atgccaaagc cagcccaaaa cctcaagggc ggcgtgaaga agccatccct ccaacagacc     60
aagtccccac tgccaagcaa gccaccaaag ccagtcaacg acaagctcaa ggacgacagc    120
aacaagaccg agacgaagga cgccaagaac ggcctgaaca gccaccaaa gaacatcaac    180
gacaaggtga aggacggcga gaacaagacc ccatcccaag acctcaacga gccaagcttc    240
aagctgccaa tgaggcaaaa ggcctccagc tgggacgctt ggctcaaggg caccaagaag    300
gactacgaga acctgaagtg cttcgccaag ggcaacctct acgactggct gtgctccgtc    360
cgcgacagct tcgagctcta cctgcaatcc ctggagagca agtggacctc ctgcagcgac    420
aacaccacca ccgtgttcct ctgcgagtgc ctcgctgagt ccagcggctg ggcgaccca    480
cagtgggagt cctgggtcaa gaaggagctc aaggagcaac tgaagaccga ggcccaggcc    540
tggatcagca ccaagaagaa ggacttcgac ggcctcacct ccaagtactt cagcctgtgg    600
aaggaccaca gccgcaagga gctggaggaa gaggcctgga gaccaaggc ctccagcggc    660
ggcctctccg agtgggagga gctgaccgac aagatgaaca ccaggtacac caacaacctc    720
gacaacatgt ggtccaacta cagcggcgac ctcctgttcc gcttcgacga gtggtcccca    780
gaggtgctgg agaagtggat cgagagcaag cagtggaacc agtgggtgaa gaaggtcagg    840
aagcaccacc accaccacca ctga                                           864

SEQ ID NO: 23           moltype = AA   length = 309
FEATURE                 Location/Qualifiers
source                  1..309
                        mol_type = protein
                        organism = Plasmodium vivax
SEQUENCE: 23
MVTEGGDNLD DDLGGDLEGL LGDDAEGGAA GGEGAAAAS AEGLSGEVEN ELLYVKEDDD       60
DAPAATPDEK PSTSGEETPA AFVDLVNETV PPPAKAPLPL QTKAPQGPKI KDWNQWMKQA    120
KKDFSGYKGT MHTQRHEWTK EKEDELQKFC KYLEKRWMNY TGNIDRECRS DFLKSTQNWN    180
```

```
ESQWNKWVKS EGKHHMNKQF QKWLDYNKYK LQDWTNTEWN KWKTTVKEQL DDEEWKKKEA  240
AGKTKEWIKC TDKMEKKCLK KTKKHCKNWE KKANSSFKKW EGDFTKKWTS NKQWNSWCKE  300
LEKHHHHHH                                                         309

SEQ ID NO: 24              moltype = DNA  length = 930
FEATURE                    Location/Qualifiers
source                     1..930
                           mol_type = genomic DNA
                           organism = Plasmodium vivax
SEQUENCE: 24
atggtgaccg agggcggcga caacctcgac gacgacctcg gcggcgacct ggagggcctc   60
ctgggcgacg acgctgaggg cggcgccgcc ggcggcgagg gcgctgccgc cgccgcctcc  120
gccgagggc tgagcggcga ggtggagaac gagctcctct acgtgaagga agacgacgct  180
gacgctccag ctgctacccc agacgagaag ccatccacca gcggcgagga gacgccagct  240
gctttcgtgg acctcgtcaa cgagacggtg ccaccaccag ctaaggcccc actcccactg  300
caaaccaagg ccccacaggg cccaaagatc aaggactgga accagtggat gaagcaggcc  360
aagaaggact tctccggcta caagggcacc atgcacaccc aaaggcacga gtggaccaag  420
gagaaggaag acgagctgca gaagttctgc aagtacctgg agaacgctg gatgaactac  480
accggcaaca tcgacaggga gtgccgctcc gacttcctga gagcaccca aaactggaac  540
gagtcccagt ggaacaagtg ggtgaagagc gagggcaagc accacatgaa caagcaattc  600
cagaagtggc tggactacaa caagtacaag ctccaagact ggaccaacac cgagtggaac  660
aagtgaaga ccaccgtcaa ggagcagctg gacgagaagg agtggaagaa gaaggaagcc  720
gccggcaaga ccaaggagtg gatcaagtgc accgacaaga tggagaagaa gtgcctcaag  780
aagaccaaga agcactgcaa gaactgggag aagaaggcca ctccagcttt caagaagtgg  840
gagggcgact tcaccaagaa gtggacctcc aacaagcagt ggaacagctg gtgcaaggag  900
ctggagaagc accaccacca ccaccactga                                   930

SEQ ID NO: 25              moltype = AA  length = 933
FEATURE                    Location/Qualifiers
source                     1..933
                           mol_type = protein
                           organism = Plasmodium vivax
SEQUENCE: 25
MAVEVVQEAA DEVLEEEKIE EPLEIVEEEP VQVAAEEPVE EVLEEVVQEA ADEVMEEEKI   60
EEPLEIVAEE PLEIVAEEPV QVAAEEVLVE KEEVNENILN IVEEIKESIV DKLEANEEAS  120
EEGNEDLLES AEEEAAEEVAE EAVDTTTEAD VVETVEEEAA NATTEVSAEE SLEVSTEAPE  180
ETTESESHET FEEDILKNLE ENKEANENAL EDIKEMKEEF LDYVEQRVED NENVLVDLLQ  240
HLERNAHVNE SVLEDLEEIK EDLLANIQMA EETRKEVTDA SAESAEEVEE PVEVSAEVAA  300
EEPVEVAAEE PVEVTAEEPV EVTAEEPVEI PTEENIFDVI EEIKEKVLEN LEETTAESVA  360
ESVGEGADEN ALDVLKEMQE SLLENFGQKI EANENILASV LENIQEKVEL NKSVLVDVLA  420
ELKEEAVSQR ETAQEVAAEL VEEAAEVPAV EPVEEEVVEP AVEVVEEPVE EVVEPVVDV   480
IEEPAVEVVE VPVEETVEEP VEVTAEEPVE VTAEEPVEET VEEPVVEVVE EPVEEPVEA  540
IEEPVVEPVV EPAVEVIEDA TEEPVEEAAE EPDVEVAEGS AIESVEEAFE QIIEDAAQVI  600
AEESVEETAE QILEQATQAV TEEAADAADV ADAEEAVGTA QVVTEESVAE AIEDTVEEIS  660
AEPIQATIEG IVGEVVESVE ENIEAVEEAI KDIVEGAVEG APELSLEEMI EDVMVGTVAE  720
EDSAKEAAEE TVEEVVQEDA AEEEAAKEAA EETVEEAERE ATQEAVEETV EDVVEEVSAE  780
AVEEIVLETP EGTSDESVET VVEHAVEDSL GETIATIVDD VAEETTEKSE ESVVLDNLGV K  840
VEEVLDVDVE EVAQEAADDV IMRVSENESE GESGAESGEE VEELESALFE VEKDIKKKVL  900
DMFSGNVEFD EKESEKLALD LQKNLLSHHH HHH                               933

SEQ ID NO: 26              moltype = DNA  length = 2802
FEATURE                    Location/Qualifiers
source                     1..2802
                           mol_type = genomic DNA
                           organism = Plasmodium vivax
SEQUENCE: 26
atggctgtgg aggtggtcca agaggccgct gacgaggtgc tcgaagagga gaagatcgag   60
gagccactgg agatcgtgga ggaagagcca gtgcaagtcg ccgccgagga gccagtcgag  120
gaagtgctcg aagaggtggt gcaagaggcc gccgacgagg tcatgGagga gagaagatc   180
gaggagcctc tggagatcgt cgctgaagaa cctctgagta tcgtggctga ggagcctgtg  240
caggtggctg ccgaggaagt gctggtcgag aaggaagagg tgaacgagaa catcctcaac  300
atcgtggagg agatcaagga gagcatcgtc gacaagctgg aggccaacga ggaagccagc  360
gaggaaggca acgaggacct cctggagtcc gctgaggaag ccgctgagga agtggctgag  420
gaagccgtgg acaccaccac cgaggctgac gtggtggaga cggtggagga agaggccgct  480
aacgctacca ccgaggtgtc cgctgaggag agcctggagg tgtccaccga ggctccagag  540
gagacgaccg agtccgagag ccacgagacg ttcgaggaag acatcctgaa gaacctggag  600
gagaacaagg aagccaacga gaacgccctg aggacatca ggagatgaa ggaagagttc  660
ctcgactacg tggagcaaag ggtcgaggac aacgagaacg tgctggtcga cctcctgcag  720
cacctggagc gcaacgccca cgtgaacgag agcgtcctgg aggactgga gagagccagc  780
gaagacctcc tggccaacat ccaaatggcc gaggagacga ggaaggaagt gaccgacgct  840
tccgctgaga gcgctgagga agtggaggag ccgtcgagg tgtccgctga ggtggctgct  900
gaggagcctg tcgaggtggc cgccgaggag ccagtgagg tcaccgctga ggagcctgtt  960
gaggtgacgg ctgaggagcc agtggagatc ccaaccgagg agaacatctt cgacgtgatc 1020
gaggagatca aggagaaggt cctggagaa ctggaagaga gagccgctt cagcggtgtg 1080
gagtccgtgg gcgagggcgc tgacgagaac gccctggacg tgctcaagga gatgcaagag 1140
agcctcctgg agaacttcgg ccagaagatc gaggccaacg agaacatcct ggccagcgtg 1200
ctggagaaca tccaggagaa ggtcgagctg aacaagtccg tgctcgtcga cgtgctggcc 1260
gagctcaagg aagaggccgt gtcccaaagg gagacggctc aagaggtggc tgctgagctg 1320
gtggaggaag ccgctgaggt cccagctgtg agccagtcag gaagagagt ggtggagcca 1380
```

```
gctgtggagg tggtggagga gcctgtggag gaagaggtgg tcgagccagt ggtcgacgtg   1440
atcgaggagc ctgccgtgga ggtcgtggag gtcccagtgg aggagacggt cgaggagcct   1500
gtggaggtta ccgcggagga gcctgtggag gtcacggccg aggagcctgt cgaggagacg   1560
gtggaggagc cagtggtcga ggtggtcgag agccagttg aggagcctgt ggtcgaggcc    1620
atcgaggagc ccgtcgtcga gccagtggtc gagccagccg tcgaggtcat cgaggacgat   1680
acggaggagc ccgtcgtcga agccgccgag gagccggacg tggaggtggc tgagggcagc   1740
gctatcgagt ccgtggagga agccttcgag caaatcatcg aggacgccgc ccaagtgatc   1800
gctgaggaga gcgtggagga gacggctgag caaatcctgg agcaagccac ccaggccgtg   1860
accgaggaag ccgctgacgc tgctgacgtg gctgacgctg aggaagccgc gggcaccgct   1920
caagtcgtca ccgaggagag cgtggctgag gctatcgagg acaccgtcga ggagatctcc   1980
gccgagccaa tccaggccac catcgaggc atcgtgggcg aggtcgtcga gtccgtcgag   2040
gagaacatcg aggccgtgga ggaagccatc aaggacatcg tggagggcgc tgtggagggc   2100
gctccagagc tcagcctgga ggagatgatc gaggacgtca tggtgggcac cgtggctgag   2160
gaagactccg ctaaggaagc cgctgaggag acggtggagg aagtggtgca agaggacgct   2220
gctgaggaag aggccgccaa ggaagccgcc gaagagacgt ggaggaagc cgagagggag    2280
gctacccaag aggccgtcga ggagacggtt gaggacgtgg tcgaggaagt gtccgctgag   2340
gctgtggagg agatcgtcct cgaaacccgg agggcacct ccgacgagag cgtggagacg    2400
gtggtggagc acgctgtgga ggactcctg ggcgagacga tcgccaccat cgtgacgac    2460
gtcgccgagc agacgaccga gaagtccgag gagagcgtgg tcgacaacct gggcgtcaag   2520
gtggaggaag tgctcgacgt cgacgtggag gaagtggccc aagaggccgc cgacgacgtg   2580
atcatgcgcg tcagcgagaa cgagtccgag gcgagagcg cgctgagtc cggcgaggaa    2640
gtggaggagc tggagagcgc cctcttcgag gtggagaaga acatcaagaa gaaggtcctc   2700
gacatgttca gcggcaacgt ggagttcgac gagaaggagt ccgagaagct cgccctggac   2760
ctccagaaga acctcctgtc ccaccaccac caccaccact ga                      2802

SEQ ID NO: 27         moltype = AA   length = 242
FEATURE               Location/Qualifiers
source                1..242
                      mol_type = protein
                      organism = Plasmodium vivax
SEQUENCE: 27
MTYMLMKDDD SHDDKDDENE EKKKKEGKTN KDTNKIIKGE SMTREDLLQL LNEMLKLQTD    60
MKNIVKDLIV VAKKNSYDFM SVYNVAKTYN TVDPLGKYQI EMPEFDKVVE NYHFDPEVKE   120
TVSKLMSSQE NYYANMSETA TLNVDKIIEI HHFMLNELYK IDPEFKKIPN KHELDPKLIA   180
LVIQSIVSAK VEEEFNLTSE DVEASIANQQ YALTSNMEFA RVNIQMQTIM NKFMGDHHHH   240
HH                                                                  242

SEQ ID NO: 28         moltype = DNA   length = 729
FEATURE               Location/Qualifiers
source                1..729
                      mol_type = genomic DNA
                      organism = Plasmodium vivax
SEQUENCE: 28
atgacctaca tgctcatgaa ggacgacgac tcccacgacg acaaggacga cgagaacgag    60
gagaagaaga agaaggaagg caagaccaac aaggacacca acaagatcat caagggcgag   120
agcatgacca gggaggacct cctgcaactc ctgaacgaga tgctcaagct gcagaccgac   180
atgaagaaca tcgtcaagga cctcatcgtg gtcgccaaga agaactccta cgacttcatg   240
agcgtgtaca acgtcgccaa gacctacaac accgtggacc cactgggcaa gtaccaaatc   300
gagatgccag agttcgacaa ggtggtcgag aactaccact tcgacccaga ggtgaaggag   360
acggtgtcca agctcatgtc cagccaggag aactactacg ccaacatgag cgagacggcc   420
accctgaacg tcgacaagat catcgagatc caccacttca tgctcaacga gctgtacaag   480
atcgacccag agttcaagaa gatcccaaac aagcacgagc tggacccaaa gctcatcgcc   540
ctcgtgatcc aatccatcgt gagcgccaag gtcgaggaag agttcaacct cacctccgag   600
gacgtcgagg ccagcatcgc caaccaacag tacgccctga cctccaacat ggagttcgcc   660
cgcgtgaaca tccaaatgca gaccatcatg aacaagttca tgggcgacca ccaccaccac   720
caccactga                                                           729

SEQ ID NO: 29         moltype = AA   length = 245
FEATURE               Location/Qualifiers
source                1..245
                      mol_type = protein
                      organism = Plasmodium vivax
SEQUENCE: 29
MAGGVSEEAI KKLKEIKKLE LDILKDFMKQ DAGHADLYKK YHCIASDYIS GNPKGSSAEG    60
PNLAKKGEKS KKGEKHQNGE KPQNGEKPKK SFIEKIASFV SIFSYNNVSK IYSEHVQRIF   120
PKARDHAGDG SAGDAIYPDD KIETGKKQNQ SSYVQLSALN LMKRNMFLGG KDKSSEHFEV   180
GNLGSFYMIF GARNTDYPWA CSCDPLQLID YKEKKRNYVL CSNQVDMSIQ NADLFCNPKH   240
HHHHH                                                               245

SEQ ID NO: 30         moltype = DNA   length = 738
FEATURE               Location/Qualifiers
source                1..738
                      mol_type = genomic DNA
                      organism = Plasmodium vivax
SEQUENCE: 30
atggccggcg gcgtcagcga ggaagccatc aagaagctca aggagatcaa gaagctggag    60
ctggacatcc tgaaggactt catgaagcaa gacgccggcc acgccgacct ctacaagaag   120
taccactgca tcgccagcga ctacatctcc ggcaacccaa agggctccag cgctgagggc   180
ccaaacctgg ccaagaaggg cgagaagagc aagaaggcg agaagcacca aaacggcgag    240
```

-continued

```
aagccacaga acggcgagaa gccaaagaag tccttcatcg agaagatcgc ctccttcgtg  300
agcatcttct cctacaacaa cgtcagcaag atctactccg agcacgtgca aggatcttc   360
ccaaaggccc gcgaccacgc tggcgacggc agcgccggcg acgccatcta cccagacgac  420
aagatcgaga cgggcaagaa gcaaaaccag tccagctacg tccagctctc cgccctcaac  480
ctgatgaagc gcaacatgtt cctgggcggc aaggacaagt ccagcgagca cttcgaagtg  540
ggcaacctcg gcagcttcta catgatcttc ggcgccagga acaccgacta cccatgggcc  600
tgctcctgcg acccactcca gctgatcgac tacaaggaga agaagcgcaa ctacgtgctc  660
tgcagcaacc aagtcgacat gtccatccag aacgccgacc tgttctgcaa cccaaagcac  720
caccaccacc accactga                                                738

SEQ ID NO: 31          moltype = AA  length = 363
FEATURE                Location/Qualifiers
source                 1..363
                       mol_type = protein
                       organism = Plasmodium vivax
SEQUENCE: 31
MVSCTSLCLY IIYSLFLLNN VSLSIQVKTN EIKNGQNGSV QLKEKGGGVN LAPKVGTNIT   60
QKRDTKMAKK TVTKVAKKKV TKVAEKTGTK VADKTGTKVA DKTGTKVADK TGTKVAEKTG  120
TKVADKTGTK VAEKTGTNIS QKEDEKGPPK EDTQGTQKAD AKAIQQADAQ VSEKWKKKEW  180
KEWIKKAESD LDIFNALMDN EKEKKWYSEK EKEWNKWIKG VEKKWMHYNK NIYVEYRSLV  240
FWVGLKWVES QWEKWILSDG LEFLVMDWKK WIKENKSNFD EWLKSEWDTW TNSQMEEWKS  300
SNWKLNEDKR WEMWENDKKW IKWLYLKDWI NCSKWKKRIQ KESKEWLRWT KLKEEMYHHH  360
HHH                                                                363

SEQ ID NO: 32          moltype = DNA  length = 1092
FEATURE                Location/Qualifiers
source                 1..1092
                       mol_type = genomic DNA
                       organism = Plasmodium vivax
SEQUENCE: 32
atggtgtcct gcaccagcct ctgcctgtac atcatctaca gcctcttcct cctgaacaac   60
gtgtccctga gcatccaagt caagaccaac gagatcaaga acggcaaaaa cggctccgtc  120
cagctcaagg agaagggcgg cggcgtgaac ctggctccaa aggtcggcac caacatcacc  180
cagaagaggg acaccaagat ggccaagaag accgtgacca aggtcgccaa gaagaaggtc  240
acgaaggtcg ccgagaagac cggcaccaag gtggccgaca agaccggcac caaggtcgct  300
gataagacgg gcacgaaggt cgctgataag accgggacga aggtggctga aagacggggc  360
acgaaggttg ctgataagac ggggaccaag gtggctgaga gaccggcac caacatcagc   420
caaaaggaag acgagaaggg cccaccaaag gaagacaccc aaggcaccca agggccgac   480
gccaaggcca tccaacaggc cgacgcccag gtgagcgaga gtggaagaa gaaggagtgg   540
aaggagtgga tcaagaaggc cgagtccgac ctcgacatct tcaacgccct gatggacaac  600
gagaaggaga agaagtggta cagcgagaag gagaaggagt ggaacaagtg gatcaagggc  660
gtggagaaga agtggatgca ctacaacaag aacatctacg tcgagtacag gtccctcgtg  720
ttctgggtcg gcctgaagtg ggtggagtcc caatggagaa agtggatcct cagcgacggc  780
ctggagttcc tggtcatgga ctggaagaag tggatcaagg agaacaagtc caacttcgac  840
gagtggctca gagcgagtg ggacacctgg accaactccc agatggagga gtggaagtcc   900
agcaactgga agctgaacga ggacaagcgc tgggagatgt gggagaacga caagaagtgg  960
atcaagtggc tctacctgaa ggactggatc aactgcagca gtggaagaa gaggatccaa  1020
aaggagtcca aggagtggct ccgctggacc aagctgaagg aagagatgta ccaccaccac  1080
caccaccact ga                                                     1092

SEQ ID NO: 33          moltype = AA  length = 415
FEATURE                Location/Qualifiers
source                 1..415
                       mol_type = protein
                       organism = Plasmodium vivax
SEQUENCE: 33
MGEDAEVENA KYRIPAGRCP VFGKGIVIEN SDVSFLRPVA TGDQKLKDGG FAFPNANDHI   60
SPMTLANLKE RYKDNVEMMK LNDIALCRTH AASFVMAGDQ NSSYRHPAVY DEKEKTCHML  120
YLSAQENMGP RYCSPDAQNR DAVFCFKPDK NESFENLVYL SKNVRNDWDK KCPRKNLGNA  180
KFGLWVDGNC EEIPYVKEVE AEDLRECNRI VFGASASDQP TQYEEEMTDY QKIQQGFRQN  240
NREMIKSAFL PVGAFNSDNF KSKGRGFNWA NFDSVKKKCY IFNTKPTCLI NDKNFIATTA  300
LSHPQEVDLE FPCSIYKDEI EREIKKQSRN MNLYSVDGER IVLPRIFISN DKESIKCPCE  360
PERISNSTCN FYVCNCVEKR AEIKENNQVV IKEEFRDYYE NGEEKSNKQH HHHHH       415

SEQ ID NO: 34          moltype = DNA  length = 1248
FEATURE                Location/Qualifiers
source                 1..1248
                       mol_type = genomic DNA
                       organism = Plasmodium vivax
SEQUENCE: 34
atgggcgagg acgccgaggt ggagaacgcc aagtacagga tcccagctgg caggtgccca   60
gtgttcggca aggcatcgt catcgagaac tccgacgtga gcttcctccg cccagtggct  120
accggcgacc aaaagctgaa ggacggcgga ttcgccttcc caaacgccaa cgaccacatc  180
tccccaatga ccctcgccaa cctgaaggag aggtacaagg acaacgtgga gatgatgaag  240
ctcaacgaca tcgctctgtg caggacccac gctgctagct tcgtgatggc tggcgaccag  300
aactccagct acaggcaccc agccgtctac gacgagaagg agaagacctg ccacatgctc  360
tacctgtccg cccaagagaa catgggccca ggtactgct ccccagacgc tcagaacagg   420
gacgctgtct tctgcttcaa gccagacaag aacgagtcct tcgagaacct cgtgtacctg  480
agcaagaacg tcaggaacga ctgggacaag aagtgcccac gcaagaacct cggcaacgcc  540
```

```
aagttcggcc tgtgggtgga cggcaactgc gaggagatcc catacgtgaa ggaagtggag    600
gccgaggacc tcagggagtg caacaggatc gtcttcggcg cttccgctag cgaccaacca    660
acccagtacg aggaagagat gaccgactac caaaagatcc aacagggctt caggcagaac    720
aaccgcgaga tgatcaagtc cgccttcctc ccagtgggcg ccttcaactc cgacaacttc    780
aagagcaagg gccgcggctt caactgggcc aacttcgaca gcgtgaagaa gaagtgctac    840
atcttcaaca ccaagccaac ctgcctgatc aacgacaaga acttcatcgc caccaccgcc    900
ctctcccacc cacaagaggt cgacctggag ttcccatgca gcatctacaa ggacgagatc    960
gagagggaga tcaagaagca gtcccgcaac atgaacctct acagcgtgga cggcgagagg   1020
atcgtcctgc cacgcatctt catctccaac gacaaggaga gcatcaagtg cccatgcgag   1080
ccagagagga tctccaacag cacctgcaac ttctacgtgt gcaactgcgt cgagaagagg   1140
gccgagatca aggagaacaa ccaagtggtc atcaaggaag agttcaggga ctactacgag   1200
aacggcgagg agaagtccaa caagcagcac caccaccacc accactga                 1248

SEQ ID NO: 35           moltype = AA  length = 892
FEATURE                 Location/Qualifiers
source                  1..892
                        mol_type = protein
                        organism = Plasmodium vivax
SEQUENCE: 35
MNGNRNLNIK PTCHKSGKND KANGSDNIAN KGGAQHAANG ATGTPSGSSN GKKGATTTSA     60
SAGQAGASGG MAAPGMNPNF EQMMKPLNDM FKGNGEGLNI ENIMNSDMFQ NFFNSLMGGN    120
PHDGAGGGQE ILFKDMLNAM NAQGGGAPGA AATSGGANKD PNISVSPEQL NKINQLKDKL    180
ENVLKNVGVD VEQLKENMQN ENIMQNKDAL RDLLANLPMN PGMMQNMMAG KDGNMFNMDP    240
NQMMNMFNQL SQGKMNMKDF GMGDFMPPPV HANDQDAEDD SRGKAFVTNS SNNDINFAHK    300
LNAFEYSNGP SEGMFQLYGM NNDDGVIDDG MSDSVGKNSA LDVSGGSINR NLSDGDSAKE    360
DSDESNANAT SNSNATVPNK GGHEGGSANE VYSNEEELIT SSGSKGDANK LAGTGGYKNN    420
NAFLDLNNLK KDASAAKYGK DNSGDKSNGG NSNGGNNKVM NKRIGGKKKK TFKKKKNPGQ    480
IPFKMETLQK LVKEYTNTSN QKIMEKIIKK YVSMSNQSAR GNSEEEDDEE EAEDEKSAKD    540
KNSEKEAELN MNEFSVKDIK KLISEGILTY EDLTEEELKK LAKPDDMFYE LSPYANEEKD    600
LSLNETSGVS NEQLNAFLRK NGSYHMSYDS KAIDYLKQKK AEKKEEEQED DNFYDAYKQI    660
KNSYEGIPSN YYHDAPQLIG ENYVFTSVYD KKKELIDFLK RSNGATDSSN SSAGKDKGNS    720
AESGTYKSKY YDKYMKKLSE YRRREAFKIL KKRRAQEKKM QKKQEMQNNS SNEVDYSEYF    780
KKNGFINSSN GTVKTFSKDQ LDNMVKQFNS DGDDIPSSSG AGADLGDNYS GVSGGGQFSP    840
SGGSGNNPSG YVTFDGQNIV GPNENEEEEP TEDVLNEDDD NADDDDHHHH HH            892

SEQ ID NO: 36           moltype = DNA  length = 2679
FEATURE                 Location/Qualifiers
source                  1..2679
                        mol_type = genomic DNA
                        organism = Plasmodium vivax
SEQUENCE: 36
atgaacggca acaggaacct gaacatcaag ccaacctgcc acaagagcgg caagaacgac     60
aaggccaacg gctccgacaa catcgctaac aagggcgggc ccaacacgtg tgctaacggc    120
gccaccggca ccccaagcgg ctccagcaac ggcaagaagg gcgctacgac caccagcgct    180
tccgctggcc aagctggcgc ttccggcggc atggccgccc aggcatgaa cccaaacttc    240
gagcagatga tgaagccact gaacgacatg ttcaagggca acggcgaggg cctcaacatc    300
gagaacatca tgaacagcga catgttccag aacttcttca atccctgag ggcggcaac     360
ccacacgacg gcgctggcgg cggcaagag atcctgttca aggacatgct caacgccatg    420
aacgcccaag gcgcggcgc cccaggcgct gccgccacct ccggcggcgc caacaaggac    480
ccaaacatca gcgtctcccc agagcagctg aacaagatca ccaactcaa ggacaagctg    540
gagacgtgc tcaagaacgt gggcgtcgac gtggagcagc tcaaggagaa catgcaaaac    600
gagaacatca tgcagaacaa ggacgctctg agggacctcc tggctaacct cccgatgaac    660
ccaggcatga tgcaaaacat gatggccggc aaggacggca acatgttcaa catgacccca    720
aaccagatga tgaacatgtt caaccaactc agccagggca agatgaacat gaaggacttc    780
ggcatgggcg acttcatgcc accaccagtc cacgccaacg accaagacgc tgaggacgac    840
tcccgcggca aggcttttcgt gaccaactcc agcaacaacg acatcaactt cgcccacaag    900
ctgaacgcct tcgagtacag caacggccca tccgagggca tgttccagct ctacggcatg    960
aacaacgacg acggcgtcat cgacgacggc atgagcgact ccgtcggcaa gaacagcgct   1020
ctgacgtga gcgcggctc catcaacagg aacctcagcg acggcgactc cgccaaggaa   1080
gacgacgacg agtccaacgc caacgccacc agcaactcca acgccaccgt cccaaacaag   1140
ggcggccacg agggcggcag cgctaacgag gtgtactcca acgaggaaga gctgatcacc   1200
tccagcggct ccaagggcga cgctaacaag ctggctggca ccggcggcta caagaacaac   1260
aacgccttcc tcgacctgaa caacctgaag aaggacgcca gcgccgccaa gtacggcaag   1320
gacaacagcg gcgacaagtc caacggcggc aactccaacg gcggcaacaa caaggtcatg   1380
aacaagcgca tcggcggcaa gaagaagaag accttcaaga agaagaagaa cccaggccaa   1440
atcccattca agatggagac gctccagaag ctggtcaagg agtacaccaa caccagcaac   1500
caaaagatca tggagaagat catcaagaag tatgtgtcca tgtccaacca gagcgccagg   1560
ggcaactccg aggaagagga cgacgaggaa gaggccgagg acgaagagag cgccaaggac   1620
aagaactccg agaaggaagc cgagctgaac atgaacgagt tcagcgtcaa ggacatcaag   1680
aagctcatct ccgagggcat cctgacctac gaggacctca ccgaggaaga gctcaagaag   1740
ctggccaagc cagacgacat gttctacgag ctcagcccat acgccaacga ggagaaggac   1800
ctctcccctga acgagacgag cggcgtgtcc aacgagcaac tgaacgcctt cctccgcaag   1860
aacggctcct accacatgag ctacgactcc aaggccatcg actacctgaa gcaaaagaag   1920
gccgagaaga aggaaggaag gcaagaggac gacaatttcta caagcaaaatc            1980
aagaacagct acgagggcat cccatcaac tactaccacg acgccccaca gctcatcggc   2040
gagaactacg tcttcaccag cgtgtacgac aagaagaagg agctgatcga cttcctcaag   2100
aggtccaacg gcgctaccga ctccagcaac tccagcgctg gcaaggacaa gggcaacagc   2160
gctgagtccg gcacctacaa gagcaagtac tacgacaagt acatgaagaa gctgtccgag   2220
tacaggcgca gggaggcctt caagatcctc aagaagcgca gggcccagga gaagaagatg   2280
```

```
caaaagaagc aggagatgca aaacaactcc agcaacgagg tggactactc cgagtacttc   2340
aagaagaacg gcttcatcaa ctccagcaac ggcaccgtca agaccttcag caaggaccaa   2400
ctggacaaca tggtgaagca gttcaactcc gacggcgacg acatcccatc cagctccggc   2460
gctggcgctg acctcggcga caactacagc ggcgtgtccg gcggcggcca attcagccca   2520
tccggcggca gcggcaacaa cccatccggc tacgtcacct tcgacggcca gaacatcgtg   2580
ggcccaaacg agaacggaga agaggagcca accgaggacg tgctcaacga ggacgacgac   2640
aacgccgacg acgacgacca ccaccaccac caccactga                          2679

SEQ ID NO: 37              moltype = AA  length = 350
FEATURE                    Location/Qualifiers
source                     1..350
                           mol_type = protein
                           organism = Plasmodium vivax
SEQUENCE: 37
MPLEVSLWGQ GNAHLGTQTS RLLRESGRNG QANRVNQADQ ADQVASPPIS GKERRRGIGM    60
TSNLQLLSGE DEKDSTSEEA PNLEGKDNAD AGKDGEKEPS EKQSGDVDPT VTDAERAKDE   120
NASVSEEEQM KTLDSGEDHT DDGNADGGQG GGDGNDENQK GDGKEKEGGE EKKEDGKDDH   180
EKGEKGSEGE SGEKDEAAPK GDAAEKDKKL ESKTADAKVS EHKADDANPG GNKDSPEGES   240
PKEGNPDDPS QKNPEAAGDD DSRLHLDNLD DKVPHYSALR NNRVEKGVTD TMVLNDIIGE   300
NAKSCSVDNG GCADDQICIR IDNIGIKCIC KEGHLFGDKC ILTKHHHHHH               350

SEQ ID NO: 38              moltype = DNA  length = 1053
FEATURE                    Location/Qualifiers
source                     1..1053
                           mol_type = genomic DNA
                           organism = Plasmodium vivax
SEQUENCE: 38
atgccgctgg aggtgtccct gtggggccag ggcaacgctc acctcggcac ccaaacctcc    60
cgcctgctca gggagtccgg caggaacggc caggccaaca gggtgaacca ggctgaccag   120
gctgaccaag tggcttcccc accaatctcc ggcaaggaga ggcgcagggg catcggcatg   180
acctccaacc tccaactcct gagcggcgag gacgagaagg actccaccag cgaggaagcc   240
ccaaacctgg agggcaagga caacgctgac gctggcaagg atggcgagaa ggagccatcc   300
gagaagcaga gcggcgacgt ggacccaacc gtcaccgacg ctgagagggc taaggacgag   360
aacgcttccg tcagcgagga agagcagatg aagaccctgg acagcggcga ggaccacacc   420
gacgacggca acgctgacgg cggacaaggc ggcggcgacg gcaacgacga ggaaccaaaag   480
ggcgacggca aggagaagga aggcggcgag gagaagaagg aagacggcaa ggacgaccac   540
gagaagggcg agaagggctc cgagggcgag agcggcgaga aggacgaggc tgctccaaag   600
ggcgacgctg ccgagaagga caagaagctg agtccaaga ccgccgacgc caaggtgagc   660
gagcacaagg ctgacgacgc taaccaggc ggcaacaagg actcccccga gggcgagagc   720
ccaaaggaag gcaacccaga cgacccatcc cagaagaacc cggaggctgc tggcgacgac   780
gacagccgcc tccacctgga caacctcgac gacaaggtcc cacactactc cgccctgcgc   840
aacaacaggg tggagaaggg cgtcaccgac accatggtgc tgaacgacat catcggcgag   900
aacgccaagt cctgcagcgt ggacaacggc ggctgcgctg acgaccaaat ctgcatcagg   960
atcgacaaca tcggcatcaa gtgcatctgc aaggaaggcc acctcttcgg cgacaagtgc  1020
atcctgacca gcaccacca ccaccaccac tga                                 1053

SEQ ID NO: 39              moltype = AA  length = 296
FEATURE                    Location/Qualifiers
source                     1..296
                           mol_type = protein
                           organism = Plasmodium vivax
SEQUENCE: 39
MDVLQLVIPS EEDIQLDKPK KDELGSGILS ILDVHYQDVP KEFMEEEEET AVYPLKPEDF    60
AKEDSQSTEW LTFIQGLEGD WERLEVSLNK ARERWMEQRN KEWAGWLRLI ENKWSEYSQI   120
STKGKDPAGL RKREWSDEKW KKWFKAEVKS QIDSHLKKWM NDTHSNLFKI LVKDMSQFEN   180
KKTKEWLMNH WKKNERGYGS ESFEVMTTSK LLNVAKSREW YRANPNINRE RRELMKWFLL   240
KENEYLGQEW KKWTHWKKVK FFVFNSMCTT FSGKRLTKEE WNQFVNEIKV HHHHHH       296

SEQ ID NO: 40              moltype = DNA  length = 891
FEATURE                    Location/Qualifiers
source                     1..891
                           mol_type = genomic DNA
                           organism = Plasmodium vivax
SEQUENCE: 40
atggacgtgc tccaactggt catcccaagc gaggaagaca tccagctcga caagccaaag    60
aaggacgagc tgggcagcgg catcctctcc atcctggacg tgcactacca agacgtccca   120
aaggagttca tggaggaaga ggaagagacg gccgtgtacc cactcaagcc agaggacttc   180
gccaaggaag actcccaaag caccgagtgg ctcaccttca tccaaggcct ggagggcgac   240
tgggaggagc tggaggtgtc cctgaacaag gccagggaga gctggatgga gcaaaggaac   300
aaggagtggg ctggctggct caggctgatc gagaacaagt ggtccgagta cagccagatc   360
tccaccaagg gcaaggaccc ggctggcctc aggaagcgcg agtggtccga cgaaaagtgg   420
aagaagtggt tcaaggccga ggtgaagagc caaatcgact cccacctgaa gaagtggatg   480
aacgacaccc acagcaacct cttcaagatc ctggtcaagg acatgtccca gttcgagaac   540
aagaagacca aggagtggct catgaaccac tggaagaaga acgagaggg ctacggctcc   600
gagagcttcg aggtcatgac caccagcaag ctcctgaacg tcgccaagtc cagggagtgg   660
taccgcgcca acccaaacat caaccgcgag aggcgcgagc tcatgaagtg gttcctcctg   720
aaggagaacg agtacctggg ccaagagtgg aagaagtgga cccactggaa gaaggtgaag   780
ttcttcgtct tcaacagcat gtgcaccacc ttctccggca gcgcctgac caggaagag   840
tggaaccagt tcgtgaacga gatcaaggtc caccaccacc accaccactg a            891
```

```
SEQ ID NO: 41            moltype = AA   length = 291
FEATURE                  Location/Qualifiers
source                   1..291
                         mol_type = protein
                         organism = Plasmodium vivax
SEQUENCE: 41
MEAMPKFPQN NLKGGLKDSP LKQPKSPLIN GPPKPVNDKL KDDSNKTETK DAKNGLNKPP    60
KNINDKVKDG ENKTPSQDLN EPSFKLPMRQ KESSWYTWLK GTKKDYETLK CFAKGNLYDW   120
LCNVRESFDL YLQSLEKKWT TCSDSATTLF LCECFAESSG WNDSQWGNWM NNQLKEQLKT   180
EAEAWISTKK KDFDGLTSKY FSLWKDHRRK ELDADEWKNK VSSGGLSEWE ELTNKMNTRY   240
RNNLDNMWSH FSRDLFFNFD EWAPQVLEKW IENKQWNRWV KKVRKHHHHH H            291

SEQ ID NO: 42            moltype = DNA   length = 876
FEATURE                  Location/Qualifiers
source                   1..876
                         mol_type = genomic DNA
                         organism = Plasmodium vivax
SEQUENCE: 42
atggaggcca tgccaaagtt cccacaaaac aacctcaagg gcggcctgaa ggactcccca    60
ctcaagcagc caaagagccc actgatcaac ggcccaccaa agccagtgaa cgacaagctc   120
aaggacgact ccaacaagac cgagacgaag gacgccaaga acggcctgaa caagccacca   180
aagaacatca cgacaaggt caaggacggc gagaacaaga ccccatccca agacctcaac   240
gagccaagct tcaagctgcc aatgaggcag aaggagtcca gctggtacac ctggctcaag   300
ggcaccaaga aggactacga gacgctgaag tgcttcgcca agggcaacct ctacgactgg   360
ctgtgcaacg tgcgcgaagt cttcgacctc tacctgcaaa gcctggagaa gaagtggacc   420
acctgctccg acagcgctac caccctcttc ctgtgcgagt gcttcgccga gtccagcggc   480
tggaacgact cccagtgggg caactggatg aacaaccaac tcaaggagca gctgaagacc   540
gaggccgagg cctggatcag caccaagaag aaggacttcg acggcctcac ctccaagtac   600
ttcagcctgt ggaaggacca caggcgcaag gagctcgacg ccgacgagtg gaagaacaag   660
gtgtccagcg gcggcctcag cgagtgggag gagctgacca acaagatgaa caccaggtac   720
cgcaacaacc tcgacaacat gtggtcccac ttcagcaggg acctgttctt caacttcgac   780
gagtgggccc cacaagtcct ggagaagtgg atcgagaaca gcagtggaa ccgctgggtg    840
aagaaggtcc gcaagcacca ccaccaccac cactga                             876

SEQ ID NO: 43            moltype = AA   length = 866
FEATURE                  Location/Qualifiers
source                   1..866
                         mol_type = protein
                         organism = Plasmodium vivax
SEQUENCE: 43
MQKAPNNGKN NYGLNDDELG AILFGLNYDS IAKNKDNLEK RKNVENESIF LRNFANEDTS    60
KNTQSEKAQK EIKIETETES VNSNEKEVAT SQKSDTSNKN SSVENEKIEL KNDELLGKNF   120
EKDKVNKKGD NTNTTNNHDL TNSSEKQGVD IRGSKNMNNY LQKTGDTNIE KSESLQKDVN   180
IKNHNEEAND AKRLDSAQTN NEKSKISKDT IDKDVQSNEL TNLASNRSNK KSQGLAKKEN   240
ELKSANLEEN HNAKKDLLKK DQKREDGKKI THPENSNSDQ YGVQVSLNDE EKNTNTKSVS   300
HSEDHSASYS GEKFGTHVSN SQKDMLKNIR PVQFDESAYG KLNGGSPEND ENEILNKINK   360
NNENNFSEKV ALRKGTKDRN EYEYFKLKSN DFKVLGIINK YSSRGGFSIS VDCGGYDDFD   420
EVPGVSNLLQ HAIFYKSEKR NTTLLSELGK YSSEYNSCTS ESSTSYYATA HSEDIYHLLN   480
LFAENLFYPV FSEEHIQNEV KEINNKYISI ENNLESCLKI ASQYITNFKY SKFFVNGNYT   540
TLCENVLKNR LSIKNILTEF HKKCYQPRNM SLTILLGNKV NTADHYNMKD VENMVVHIFG   600
KIKNESYPID GDVIGKRINR MESERVNLYG KKDSYNDANF IHIEGRNEKE AAFLQSMNEL   660
HYALDLNQKS RYVEIIKKEE WGDQLYLYWS SKTNAELCKK IEEFGSMTFL REIFSDFRRN   720
GLYYKISVEN KYVYDLEVTS ICNKYYLNFG ILVKLTQRGR TNLAHLIHIC NVFVNEIGKL   780
FDRDSLDKGI SKYILDYYRE KALVTDLKFN SDNVNVSLDD LVIYSKRLLV HADDPSSLLT   840
IHSLIEDKHK NDFRNHIKIT HHHHHH                                        866

SEQ ID NO: 44            moltype = DNA   length = 2601
FEATURE                  Location/Qualifiers
source                   1..2601
                         mol_type = genomic DNA
                         organism = Plasmodium vivax
SEQUENCE: 44
atgcaaaagg ccccaaacaa cggcaagaac aactacggcc tcaacgacga cgagctgggc    60
gccatcctct tcggcctgaa ctacgacagc atcgccaaga caaggacaa cctggagaag   120
aggaagaacg tcgagaacga gtccatcttc ctgcgcaact tcgccaacga ggacaccagc   180
aagaacaccc aatccgagaa ggcccagaag gagatcaaga tcgagacgga gacggagtcc   240
gtcaacagca acgagaagga agtggccacc tcccagaaga gcgacaccag caacaagaac   300
tccagcgtcg agaacgagaa gatcgagctg aagaacgacg agctcctggg caagaacttc   360
gagaaggaca aggtgaacaa gaagggcgac aacaccaaca ccaccaacaa ccacgacctc   420
accaactcca gcgagaagca aggcgtcgac atcaggggca agaacat gaacaactac      480
ctccaaaaga ccggcgacac caacatcgag aagtccgaga gcctgcagaa ggacgtgaac   540
atcaagaacc acaacgagga agccaacgac gccaagaggc tggacagcgc ccagaccaac   600
aacgagaaga gcaagatctc caaggacacc atcgacaagg acgtgcaatc caacgagctc   660
accaacctgg ccagcaaccg ctccaacaag aagagccagg gcctcgccaa gaaggagaac   720
gagctcaagt ccgccaacct ggaggagaac cacaacgcca agaaggacct cctgaagaag   780
gaccaaaaga gggaggacgg caagaagatc acccaccag agaactccaa cagcgaccaa   840
tacggcgtgc aagtgtccct gaacgacgag gagaagaaca ccaacaccaa gtccgtcagc   900
cactccgagg accacagcgc ttcctacagc ggcgagaagt tcggcaccca cgtctccaac   960
```

-continued

```
agccaaaagg acatgctcaa gaacatccgc ccagtgcagt tcgacgagag cgcttacggc   1020
aagctcaacg gcggctcccc agagaacgac gagaacgaga tcctgaacaa gatcaacaag   1080
aacaacgaga acaacttcag cgagaaggtg gccctcagga agggcaccaa ggaccgcaac   1140
gagtacgagt acttcaagct caagtccaac gacttcaagg tcctgggcat catcaacaag   1200
tactccagca ggggcggctt ctccatcagc gtggactgcg cggatacga cgacttcgac   1260
gaggtgccag gcgtctccaa cctcctgcaa cacgccatct tctacaagag cgagaagcgc   1320
aacaccaccc tcctgtccga gctcggcaag tactccagcg agtacaacag ctgcacctcc   1380
gagtccagca ccagctacta cgccaccgcc cactccgagg acatctacca cctcctgaac   1440
ctcttcgccg agaacctgtt ctacccagtc ttcagcgagg agcacatcca aaacgaggtg   1500
aaggagatca acaacaagta catctccatc gagaacaacc tggagagctg cctgaagatc   1560
gcctcccagt acatcaccaa cttcaagtac agcaagttct tcgtcaacgg caactacacc   1620
accctctgcg agaacgtgct caagaacagg ctgagcatca gaacatcct gaccgagttc   1680
cacaagaagt gctaccagcc acgcaacatg tccctcacca tcctcctggg caacaaggtc   1740
aacaccgccg accactacaa catgaaggac gtggagaacg tggtggtcca catcttcggc   1800
aagatcaaga acgagtccta cccaatcgac ggcgacgtca tcggcaagag gatcaaccgc   1860
atggagagcg agagggtcaa cctctacggc aagaaggact cctacaacga cgccaacttc   1920
atccacatcg agggccgcaa cgagaaggaa gccgccttcc tccaaagcat gaacgagctg   1980
cactacgccc tcgacctgaa ccagaagtcc cgctacgtgg agatcatcaa gaaggaagag   2040
tggggcgacc aactctacct gtactggtcc agcaagacca cgccgagct ctgcaagaag   2100
atcgaggagt tcggcagcat gaccttcctc cgcgagatct tctccgactt caggcgcaac   2160
ggcctgtact acaagatcag cgtggagaac aagtatgtgt acgacctgga ggtgacctcc   2220
atctgcaaca agtactacct gaacttcggc atcctcgacc agctgaccca aaggggccgc   2280
accaacctcg ctcacctgat ccacatctgc aacgtgttcg tcaacgagat cggcaagctc   2340
ttcgacaggg acagcctgga caagggcatc tccaagtaca tcctcgacta ctaccgcgag   2400
aaggccctcg tgaccgacct gaagttcaac agcgacaacg tgaacgtctc cctcgatgac   2460
ctggtcatct acagcaagag gctcctggtg cacgccgacg acccatccag cctcctgacc   2520
atccactccc tcatcgagga caagcataag aacgacttcc gcaaccacat caagatcacc   2580
caccaccacc accaccactg a                                             2601

SEQ ID NO: 45            moltype = AA   length = 276
FEATURE                  Location/Qualifiers
source                   1..276
                         mol_type = protein
                         organism = Plasmodium vivax
SEQUENCE: 45
MKEAVKKGSK KAMKQPMHKP NLLEEEDFEE KESFSDDEMN GFMEESMDAS KLDAKKAKTT    60
LRSSEKKKTP TSGMSGMSGS GATSAATEAA TNMNATAMNA AAKGNSEASK KQTDLSNEDL   120
FNDELTEEVI ADSYEEGGNV GSEEAESLTN AFDDKLLDQG VNENTLLNDN MIYNVNMVPH   180
KKRELYISPH KHTSAASSKN GKHHAADADA LDKKLRAHEL LELENGEGSN SVIVETEEVD   240
VDLNGGKSSG SVSFLSSVVF LLIGLLCFTN HHHHHH                             276

SEQ ID NO: 46            moltype = DNA   length = 831
FEATURE                  Location/Qualifiers
source                   1..831
                         mol_type = genomic DNA
                         organism = Plasmodium vivax
SEQUENCE: 46
atgaaggaag ccgtgaagaa gggctccaag aaggccatga agcaaccaat gcacaagcca    60
aacctcctgg aggaagagga cttcgaggag aaggagtcct tcagcgacga cgagatgaac   120
ggcttcatgg aggagtccat ggacgccagc aagctggacg ccaagaaggc caagaccacc   180
ctcaggtcca gcgagaagaa gaagacccca acctccgtca tgagcggcat gtccggcagc   240
ggcgctacca cgctgctac cgaggccgcc accaacatga acgctaccgc catgaacgct   300
gccgccaagg gcaactccga ggctagcaag aagcaaaccg acctctccaa cgaggacctg   360
ttcaacgacg agctcaccga ggaagtgatc gccgacagct acgaggaagg cggcaacgtg   420
ggctccgagg aagccgagag cctgaccaac gccttcgacg acaagctcct ggaccagggc   480
gtgaacgaga acacactcct gaacgacaac atgatctaca cgtgaacat ggtcccacac   540
aagaagagg agctctacat ctccccacac aagcacacca cgccgcctc cagcaagaac   600
ggcaagcacc acgctgctga cgctgacgct ctggacaaga agctcagggc tcacgagctc   660
ctggagctgg agaacggcga gggctccaac agcgtgatcg tcgagacgga ggaagtggac   720
gtggacctga acggcggcaa gtcctccggc tccgtcagct tcctctccag cgtggtcttc   780
ctcctgatcg gcctcctgtg cttcaccaac caccaccacc accaccactg a            831

SEQ ID NO: 47            moltype = AA   length = 649
FEATURE                  Location/Qualifiers
source                   1..649
                         mol_type = protein
                         organism = Plasmodium vivax
SEQUENCE: 47
MDDNGRRLPR KAAPPVDKAK QDVMKDIVNY LSKNMLAFVR QKRNVSGKEG EAPTGPSGAQ    60
GGDSSQYASK FTFTDHSVDF SKYNKLDKEK FAAKDDLKSR LKNEVVASML DTEGDILTEE   120
FGYLLRNYFD KVKLEEKKSQ EAESAKPAEQ EEEAEEAPEQ KEEATAEKAT EETTEAATEE   180
TTEAATEETT EAATEETTEA ATEETTEAAT EETTEAATEE TTEAATEETT EAATEEATEG   240
ATEEGAEETT EEATEEGAEE ATEEGAEEAT EEGAEEETT EEGAEETT EETTEEGAEE   300
EATEEGAEET TEEGAEEEAE EGAEEGAEAA TEEATEEATE EATEEATEEA TEEATEEATA   360
EVAEAATPEK VTEEATEEAT EEGDNEPAEQ AAEKEEDVKG GLMDNETYYN TLQELYEEIE   420
NDDKKEKEKI QKAKEQEELE KKLFKESKKG KKKEKKRRKK LCKMAKIVEK YAEEIPKDSE   480
RSLRYDKEEH IDDPDEMDDL LFGEFKTLEK YGTHKTSTFY YEMTCFDERL RDFEINTKLK   540
EMEEVPEKWE LLSLYWQSYR NERHKYLAVK KYLLEKFLEL KTNQSTEALP KYNKKWKQCE   600
EIVDNNFTKQ HEHVNDVFYT FVAKENLSRD EFKEILNDVR ASWHHHHHH               649
```

```
SEQ ID NO: 48          moltype = DNA  length = 1950
FEATURE                Location/Qualifiers
source                 1..1950
                       mol_type = genomic DNA
                       organism = Plasmodium vivax
SEQUENCE: 48
atggacgaca acggcaggcg cctcccaagg aaggctgccc caccagtgga caaggccaag  60
caggacgtga tgaaggacat cgtcaactac ctctccaaga acatgctggc cttcgtgagg  120
caaaagcgca acgtctccgg caaggaaggc gaggctccaa ccggcccaag cggcgctcaa  180
ggcggcgact ccagccagta cgccagcaag ttcaccttca ccgaccactc cgtggacttc  240
agcaagtaca acaagctcga caaggagaag ttcgccgcca aggacgacct caagtccagg  300
ctgaagaacg aggtggtcgc cagcatgctc gacaccgagg gcgacatcct gaccgaggag  360
ttcggctacc tcctgcgcaa ctacttcgac aaggtcaagc tggaggagaa gaagtcccaa  420
gaggccgaga gcgctaagcc agctgagcaa gaggaagagg ccgaggaagc cccagagcaa  480
aaggaagagg ccaccgctga gaaggctacc gaggagacga ccgaggctgc cacggaggag  540
acgacggagg ccgccacgga ggagacgacc gaggccgcca ccgaggagac gacggaggct  600
gccactgaag agacgaccga ggctgcgacg gaagagacga ccgaggccgc gacggaagag  660
acgactgagg ctgccactga ggagacgacg gaagctgcta ccgaggaagc caccgagggc  720
gctaccgagg aaggcgctga ggagacgacg gaggaagcca cggaggaagg cgctgaggaa  780
gccaccgagg aaggcgccga ggaagccacg gaggaaggcg cagaggagac gacagaggaa  840
gccacggagg aaggcgccga agagacgacc gaagagacga ccgaggaagg cgcggaggaa  900
gaggccactg aggaaggcgc cgaggagacg actgaggaag gcgcagagga agccgctgag  960
gaaggcgctg aggaaggcgc tgaggccgcc acggaggaag ccaccgagga agccacggag  1020
gaagccacgg aggaagccac agaggaagcc actgaggaag ccacagagga agccacagct  1080
gaggtggctg aggctgctac cccagagaag gtcacagagg aagccacaga ggaagccacc  1140
gaggaaggcg acaacgagcc agctgagcag gctgctgaga aggaagagga cgtgaagggc  1200
ggcctcatgg acaacgagac gtactacaac accctccaag agctgtacga ggagatcgag  1260
aacgacgaca agaaggagaa ggagaagatc caaaaggcca aggagcaaga ggagctggag  1320
aagaagctgt tcaaggagtc caagaagggc aagaagaagg agaagaagag gcgcaagaag  1380
ctctgcaaga tggccaagat cgtcgagaag tacgccgagg agatcccaaa ggactccgag  1440
aggagcctgc gctacgacaa ggaagagcac atcgacgacc cagacgagat ggacgacctc  1500
ctgttcggcg agttcaagac cctggagaag tacggcaccc acaagacctc caccttctac  1560
tacgagatga cctgcttcga cgagaggctc cgcgacttcg agatcaacac caagctgaag  1620
gagatggagg aagtgccaga gaagtgggag ctcctgtccc tctactggca gagctacagg  1680
aacgagcgcc acaagtacct ggccgtcaag aagtacctcc tggagaagtt cctggagctg  1740
aagaccaacc aaagcaccga ggccctgcca aagtacaaca agaagtggaa gcagtgcgag  1800
gagatcgtcg acaacaactt caccaagcaa cacgagcacg tgaacgacgt cttctacacc  1860
ttcgtggcca aggagaacct ctccagggac gagttcaagg agatcctgaa cgacgtccgc  1920
gccagctggc accaccacca ccaccactga                                   1950

SEQ ID NO: 49          moltype = AA  length = 332
FEATURE                Location/Qualifiers
source                 1..332
                       mol_type = protein
                       organism = Plasmodium vivax
SEQUENCE: 49
MRCCTKDAVN VESPKKVVVG ETEEDTREEE NPYEDLPTVT VTLSDGSVYT GTTKDNRVHG  60
RGVLKYVNGD QYEGEFVDGK KEGKGKWTDK ENNTYEGDWV KDKRHGHGVY KTAEGFIFEG  120
EFANNKREGK GTIITPEKTK YVCSFQDDEE VGEVEFFFAN GDHALGYIKD GYLCQNGRYE  180
FKNGDIYVGN FEKGLFHGEG YYKWNNDANY TIYEGNYSEG KKHGKGQLIN KDGRILCGMF  240
RDNNMDGEFL EISPQGNQTK VLYDKGFFVK VLDKIEENLD VQEFLKDSII HTTIFSDPTT  300
YKKLYEITEK KKPQFRLNLK RTQPTSHHHH HH                                332

SEQ ID NO: 50          moltype = DNA  length = 999
FEATURE                Location/Qualifiers
source                 1..999
                       mol_type = genomic DNA
                       organism = Plasmodium vivax
SEQUENCE: 50
atgaggtgct gcaccaagga cgccgtcaac gtggagtccc caaagaaggt ggtcgtgggc  60
gagacggagg aagacaccag ggaggaagag aacccatacg aggacctccc aaccgtcacc  120
gtgaccctgt ccgacggcag cgtctacacc ggcaccacca aggacaacag ggtgcacggc  180
cgcggcgtcc tcaagtatgt gaacggcgac caatacgagg gcgagttcgt cgacggcaag  240
aaggaaggca agggcaagtg gaccgacaag gagaacaaca cctacgaggg cgactgggtc  300
aaggacaaga ggcacggcca cggcgtgtac aagaccgctg agggcttcat cttcgagggc  360
gagttcgcca acaacaagcg cgagggcaag ggcaccatca tcaccccaga gaagaccaag  420
tatgtgtgca gcttccaaga cgacgaggaa gtgggcgagg tggagttctt cttcgccaac  480
ggcgaccacg ccctcggcta catcaaggac ggctacctgt gccagaacgg ccgctacgag  540
ttcaagaacg gcgacatcta cgtgggcaac ttcgagaagg gcctgttcca cggcgagggc  600
tactacaagt ggaacaacga cgccaactac accatctacg agggcaacta ctccgagggc  660
aagaagcacg gcaagggcca actcatcaac aaggacggca ggatcctgtg cggcatgttc  720
cgcgacaaca acatggacgg cgagttcctg gagatcagcc cacaaggcaa ccagaccaag  780
gtcctctacg acaagggctt cttcgtcaag gtgctggaca agatcgagga gaacctcgac  840
gtgcaggagt tcctgaagga ctccatcatc cacaccacca tcttcagcga cccaaccacc  900
tacaagaagc tgtacgagat caccgagaag aagaagccac aattcaggct caacctgaag  960
cgcacccagc caacctccca ccaccaccac caccactga                        999

SEQ ID NO: 51          moltype = AA  length = 309

-continued

```
FEATURE                 Location/Qualifiers
source                  1..309
                        mol_type = protein
                        organism = Plasmodium vivax
SEQUENCE: 51
MNKLGTSLVE DATANGEFGL RVQRLLGGSR SSRDSIFADS FYDDDDDDDD NNDKLFDYDS  60
DHKSRREVKD RHHRHRHSHS HRHKRRHSHK HRTSSRSRRE KEESSTTNDD DDEVLSLSRF  120
DVDDDKDDRS HSRYSVDYDD ENDDEPSSSR PASTDYDDII DLTNARRSGS KYRISSMDIE  180
LYPEHEDEYL FEGKRRSGGV LKKADNYCEN KIFDALSALD KYKEYYGEER RVMKQAAYRK  240
ATKVFAIPGA AALSPLIITL FLTTSNVVAL PLAASAVILG GILYKKSKDK SDYGRPHLKS  300
ITYHHHHHH                                                         309

SEQ ID NO: 52           moltype = DNA  length = 930
FEATURE                 Location/Qualifiers
source                  1..930
                        mol_type = genomic DNA
                        organism = Plasmodium vivax
SEQUENCE: 52
atgaacaagc tgggcaccag cctcgtggag gacgctaccg ctaacggcga gttcggcctc  60
cgcgtccaaa ggctgctggg cggctccagg tccagccgcg acagcatctt cgccgactcc  120
ttctacgatg atgacgacga cgacgacgac aacaacgaca agctgttcga ctacgacagc  180
gaccacaagt ccaggcgcga ggtgaaggac aggcaccaca ggcacaggca cagccactcc  240
caccgccaca agaggcgcca cagccacaag cacaggacct ccagccgctc caggcgcgag  300
aaggaagagt ccagcaccac caacgacgac gacgacgagg tgctcagcct gtccaggttc  360
gacgtcgacg acgacaagga cgacaggagc cactcccgct acagcgtgga ctacgacgac  420
gagaacgacg acgagccatc cagctccagg ccagcctcca ccgactacga cgacatcatc  480
gacctcacca acgctaggcg cagcggctcc aagtaccgca tcagctccat ggacatcgag  540
ctctacccag agcacgagga cgagtacctg ttcgagggca agaggcgcag cggcggcgtc  600
ctgaagaagg ctgacaacta ctgcgagaac aagatcttcg acgccctctc cgccctggac  660
aagtacaagg agtactacgg cgaggagagg cgcgtgatga agcaggccgc ctacaggaag  720
gccaccaagg tcttcgctat cccaggcgct gccgccctca gcccactgat catcaccctc  780
ttcctgacca ccagcaacgt ggtggctctc ccactggctg cttccgccgt catcctcggc  840
ggcatcctgt acaagaagag caaggacaag tccgactacg gccgcccaca cctcaagtcc  900
atcacctacc accaccacca ccaccactga                                  930

SEQ ID NO: 53           moltype = AA  length = 332
FEATURE                 Location/Qualifiers
source                  1..332
                        mol_type = protein
                        organism = Plasmodium vivax
SEQUENCE: 53
MEAARGVSGL VPSSNSLQEI TLRYKDKLLN MDKEQMILTL GVTMIAITSA VAFGVLATHG  60
DINDFLGVES DEESEKKKEI VEKSEEWKRK EWSNWLKKLE QDWKVFNEKL QNEKKTFLEE  120
KEEDWNTWIK SVEKKWTHFN PNMDKEFHTN MMRRSINWTE SQWREWIQTE GRLYLDIEWK  180
KWFFENQSRL DELIVKKWIQ WKKDKIINWL MSDWKRAEQE HWEEFEEKSW SSKFFQIFEK  240
RNYEDFKDRV SDEWEDWFEW VKRKDNIFIT NVLDQWIKWK EEKNLLYNNW ADAFVTNWIN  300
KKQWVVWVNE RRNLAAKAKA ALNKKKHHHH HH                               332

SEQ ID NO: 54           moltype = DNA  length = 999
FEATURE                 Location/Qualifiers
source                  1..999
                        mol_type = genomic DNA
                        organism = Plasmodium vivax
SEQUENCE: 54
atggaggctg ccaggggcgt gtccggcctc gtcccatcca gcaacagcct ccaagagatc  60
accctgcgct acaaggacaa gctcctgaac atggacaagg agcagatgat cctcaccctg  120
ggcgtcacca tgatcgctat cacctccgct gtggctttcg gcgtcctggc tacccacggc  180
gacatcaacg acttcctggg cgtcgagtcc gacgaggaga gcgagaagaa gaaggagatc  240
gtggagaagt ccgaggagtg gaagaggaag gagtggagca actggctcaa gaagctggag  300
caagactgga aggtcttcaa cgagaagctc cagaacgaga agaagacctt cctggaggag  360
aaggaagagg actggaacac ctggatcaag tccgtggaga agaagtggac ccacttcaac  420
ccaaacatgg acaaggagtt ccacaccaac atgatgaggc gctccatcaa ctggaccgag  480
agccaatggc gcgagtggat ccagaccgag ggcaggctct acctggacat cgagtggaag  540
aagtggttct tcgagaacca aagcaggctc gacgagctga tcgtgaagaa gtggatccag  600
tggaagaagg acaagatcat caactggctc atgtccgact ggaagcgcgc cgagcaagag  660
cactgggagg agttcgagga gaagagctgg tccagcaagt tcttccagat cttcgagaag  720
cgcaactacg aggacttcaa ggaccgcgtg agcgacgagt gggaggactg gttcgagtgg  780
gtcaagcgca aggacaacat cttcatcacc aacgtgctgg accagtggat caagtggaag  840
gaagagaaga acctcctgta caacaactgg gccgacgcct tcgtcaccaa ctggatcaac  900
aagaagcagt gggtggtctg ggtgaacgag aggcgcaacc tcgctgctaa ggctaaggct  960
gccctgaaca agaagaagca ccaccaccac caccactga                        999

SEQ ID NO: 55           moltype = AA  length = 405
FEATURE                 Location/Qualifiers
source                  1..405
                        mol_type = protein
                        organism = Plasmodium vivax
SEQUENCE: 55
MTKGPSGPPP NKKLNANALH FLRGKLELLN KISEEQVVSP DFKKNVELLK KKIEELQGKA  60
```

```
EKDKSKTDGE DTTPKEQQED QNVSQNGLEE QAPSDSNEGE AQEENTQVKN VIFTEKEEAV    120
DEEAEKEDTA VISEKANFPN EESQGNDETQ TQESIEGEAS PGVVVDETDD SPEGEPLSGL    180
ETEGNSSAES APNEPDVNTT HTAVDTHMPA DANIGVDTNM PFDTPPHPSG ENPGAPQETH    240
LPSIDENANR RASRMKHMSS FLNGLLTNQS NNKKEIFFHP YYGPYFNHGG YYNYDPYYNY    300
APAYNPFVSQ ARDYEVIKKL LDACFNKGEG ADPNVPCIID IFKKVLDDER FRNELKTFMY    360
DLYEFLKKND VLSDDEKKNE LMRFFFDNAF QLVNPMFYYH HHHHH                    405

SEQ ID NO: 56           moltype = DNA   length = 1218
FEATURE                 Location/Qualifiers
source                  1..1218
                        mol_type = genomic DNA
                        organism = Plasmodium vivax
SEQUENCE: 56
atgaccaagg gcccatccgg cccaccacca aacaagaagc tcaacgccaa cgccctccac     60
ttcctgaggg gcaagctgga gctcctgaac aagatctccg aggagcaagt ggtcagccca    120
gacttcaaga gaacgtcga gctcctcaag aagaagatcg aggagctcca gggcaaggcc    180
gagaaggaca agtccaagac cgacggcgag gacaccaccc caaaggagca acaagaggac    240
caaaacgtga gccagaacgg cctggaggag caagctccgt ccgacagcaa cgagggcgag    300
gctcaagagg agaacaccca ggtcaagaac gtgatcttca ccgagaagga agaggccgtc    360
gacgaggaag ccgagaagga agacaccgcc gtgatcctcg agaaggccaa cttcccaaac    420
gaggagagcc agggcaacga cgagacgcaa acccaagagt ccatcgaggg cgaggctagc    480
ccgggcgtgg tggtggacga gacggacgac tccccggagg gcgagccact cagcggcctc    540
gaaaccgagg gcaactccag cgctgagtcc gctccaaacg agccagacgt caacaccacc    600
cacaccgctg tggacaccca catgccagct gacgccaaca tcggcgtcga caccaacatg    660
ccattcgaca ccccaccaca cccaagcggc gagaacccgg gcgccccaca agagacgcac    720
ctcccatcca tcgacgagaa cgccaacagg cgcgccaacg ggatgaagca catgtccagc    780
ttcctgaacg gcctcctgac caaccagtcc aacaacaaga aggagatctt cttcccccca    840
tactacggcc catacttcaa ccacggcgga tactacaact acgacccata ctacaactac    900
gccccagcct acaacccatt cgtcagccaa gcccgcgact acgaggtcat caagaagctc    960
ctggacgcct gcttcaacaa gggcgagggc gctgacccaa acgtcccatg catcatcgac   1020
atcttcaaga aggtgctcga cgacgagagg ttccgcaacg agctgaagac cttcatgtac   1080
gacctctacg agttcctgaa gaagaacgac gtcctcagcg acgacgagaa gaagaacgag   1140
ctgatgaggt tcttcttcga caacgccttc agctcgtga acccaatgtt ctactaccac   1200
caccaccacc accactga                                                1218

SEQ ID NO: 57           moltype = AA   length = 875
FEATURE                 Location/Qualifiers
source                  1..875
                        mol_type = protein
                        organism = Plasmodium vivax
SEQUENCE: 57
MFSGGVGDDE EEEEEEEGEE GESERDDSER DYAGRDDAGR DDAERNDAER DDAERNDAER     60
DDAERDHAER DHADKAESDR ESSLEANENR LVKLSEGGES EPALLEVEED IKQTVLGMFS    120
LKGEFDEAES EKLALDLQKN LLSMLSGNME DNDDEYEDID EEYEEVEEDY EEEKLGKPVE    180
VVVEDATEEA VDEVVGVVQE PEEEGAEESD KDTGEVSEEE VAKEAADEVM EEEKKEEAGE    240
PSVVVEEPSV VVKEPSVVVK EPSVVVEEPS VVVEEPSVVV EEPSVVVEEP AFTVEEPAFT    300
VEEPAITVEE PAITVEEPVF TVEEPVFTVE EPAFTVEEPA FTVEEPATTV EEPATTVEEL    360
VEEVLKVAEE EVATEAVEKD GEEAEEQVTE ESVEEDEEES GEEEGEESEE EETEESAEEE    420
VAKESVEEEV AKEAEESEES GEESAEEEKE KAEEPVAPVD EVLKEGMQKI EESVKEALGV    480
VQEAVDKVAE EEQTEQAQGP AEAGPVGVVK EPEEEEESEE EGEEGEEGEE GEEEEEESE    540
EEESEEGEES AGESEAGKSD AAESEVAESE AGEPAEDQEG MDAKMKDELL GMLSEKMKAE    600
GKDLDKLPPE VKKNLLDMLA GNMEMDDEEE EGEEEGEDLG NEELDLQKNL LEMLSGKGGF    660
NPNMLGNLKE LEALQKSVPG LMGKAQGISP AEIESLKSMF SGAFDSRGFK GMPQMKLPAE    720
LQSIMMPKKE EKGKPQGAQA KAKVPAKAGQ VQKPKAQDIM PSRRIRDLFV LPKEIFGSLK    780
NFKESALKFA NHIGLNLETI KKHLTTVKNF LLRVDAVVDK EIGNIIEAGK SPQNVVQANE    840
GFLDKMKRLV NKYKIFSIPF FAGMGSFGFH HHHHH                              875

SEQ ID NO: 58           moltype = DNA   length = 2628
FEATURE                 Location/Qualifiers
source                  1..2628
                        mol_type = genomic DNA
                        organism = Plasmodium vivax
SEQUENCE: 58
atgttcagcg gcggcgtggg cgacgacgag gaagaggaag aggaagagga aggcgaggaa     60
ggcgagagcg agagggacga ctccgagagg gactacgctg gcagggacga tgccggcagg    120
gacgacgccg agaggaacga cgccgagcgc gatgatgctg agcgcaacga cgccgagcgc    180
gacgacgccg agagggacca cgccgagcgc gaccacgccg acaaggccga gtccgacagg    240
gagtccagcc tggaggccaa cgagaacagg ctggtgaagc tcagcgaggg cggcgagtcc    300
gagccagctc tcctggaggt ggaggaagac atcaagcaaa ccgtcctggg catgttcagc    360
ctcaagggcg agttcgacga ggccgagtcc gagaagctcg ccctggacct ccagaagaac    420
ctcctgtcca tgctcagcgg caacatggag gacaacgacg acgagtacga ggacatcgac    480
gaggagtacg aggaagtgga ggaagactac gaggaagaga gctcggcaa gccagtggag    540
gtggtcgtgg aggacgccac cgaggaagcc gtggacgagg tggtgggcgt cgtgcaagag    600
ccagagaagg agggcgctga ggaagacag aaggacaccg gcgaggtgtc cgaggaagag    660
gtggccaaga agccgccga cgaggtcatg aggaagaga agaaggaaga ggccggcgag    720
ccatccgtgg tggtggagga gccaagcgtg gtcgtgaagg agccatccgt cgtggtcaag    780
gagccttccg tggtcgtgga ggagcctagc gtcgtcgtcg aggagccttc cgtcgtggtg    840
gaggagccca gcgtggtcgt cgaggagcca gccttcaccg tggaggagcc tgccttcacc    900
gtcgaggagc cagccatcac cgtggaggag cccgctatca cggtggagga gccagtgttc    960
```

```
accgtggaag aacccgtgtt caccgtggaa gagcccgcct tcaccgttga ggagcccgcc   1020
ttcaccgtag aagagcctgc cttcaccgtt gaagaaccag ctaccaccgt ggaggagctg   1080
gtggaggaag tgctcaaggt ggctgaggaa gaggtggcta ccgaggctgt ggagaaggac   1140
ggcgaggaag ccgaggagca agtcaccgag gagagcgtcg aggaagacga ggaagagtcc   1200
ggcgaggaag agggcgagga gagcgaggaa gaggagaccg aggagtccgc tgaggaagag   1260
gtggcgaagg agagcgtgga ggaagaggtg gctaaggaag ccgaggagtc cgaggagagc   1320
ggggaggaga gcgctgagga agagaaggag aaggccgagg agccagtggc tccagtggac   1380
gaggtcctga aggaaggcat gcagaagatc gaggagagcg tgaaggaagc cctgggcgtg   1440
gtccaagagg ccgtggacaa ggtcgccgag gaagagcaga ccgagcaggc tcagggccca   1500
gctgaggctg gcccagtcgg cgtggtcaag gagcctgagg aagaggaaga gtctgaggaa   1560
gagggcgagg aaggcgagga aggcgaggaa ggcgaggaag aggaagagga agagagtgag   1620
gaagaggagt ctgaggaagg cgagtccgag gctgggagaa gcgaggctgg caagagcgac   1680
gccgccgagt ccgaggtggc cgagagcgag gccggcgagc cggctgagga ccaagctggc   1740
atggacgcca agatgaagga cgagctcctg ggcatgctga gaggaagat gaaggccgag   1800
```
*(Note: some line values may be imperfectly OCRed)*

```
accgtggaag aacccgtgtt caccgtggaa gagcccgcct tcaccgttga ggagcccgcc   1020
ttcaccgtag aagagcctgc cttcaccgtt gaagaaccag ctaccaccgt ggaggagctg   1080
gtggaggaag tgctcaaggt ggctgaggaa gaggtggcta ccgaggctgt ggagaaggac   1140
ggcgaggaag ccgaggagca agtcaccgag gagagcgtcg aggaagacga ggaagagtcc   1200
ggcgaggaag agggcgagga gagcgaggaa gaggagaccg aggagtccgc tgaggaagag   1260
gtggcgaagg agagcgtgga ggaagaggtg gctaaggaag ccgaggagtc cgaggagagc   1320
ggggaggaga gcgctgagga agagaaggag aaggccgagg agccagtggc tccagtggac   1380
gaggtcctga aggaaggcat gcagaagatc gaggagagcg tgaaggaagc cctgggcgtg   1440
gtccaagagg ccgtggacaa ggtcgccgag gaagagcaga ccgagcaggc tcagggccca   1500
gctgaggctg gcccagtcgg cgtggtcaag gagcctgagg aagaggaaga gtctgaggaa   1560
gagggcgagg aaggcgagga aggcgaggaa ggcgaggaag aggaagagga agagagtgag   1620
gaagaggagt ctgaggaagg cgagtccgag gctgggagaa gcgaggctgg caagagcgac   1680
gccgccgagt ccgaggtggc cgagagcgag gccggcgagc cggctgagga ccaagctggc   1740
atggacgcca agatgaagga cgagctcctg ggcatgctga gaggaagat gaaggccgag   1800
ggcaaggacc tggacaagct cccaccagag gtcaagaaga acctcctgga catgctcgcc   1860
ggcaacatgg agatggacga tgaggaagag gaaggcgagg aagagggcga agacctgggc   1920
aacgaggagc tcgacctcca gaagaacctc ctggagatgc tctccggcaa gggcggcttc   1980
aacccaaaca tgctgggcaa cctcaaggag ctggagccc tccaaaagag cgtgccaggc   2040
ctgatgggca aggctcaggg catctcccca gctgagatcg agtccctcaa gagcatgttc   2100
tccggcgcct tcgacagcag gggcttcaag ggcatgccac agatgaagct gccagccgag   2160
ctccagtcca tcatgatgcc aaagaaggaa gagaagggca agcacaaggc cgctcaagct   2220
aaggctaagg tgccagctaa ggctggccaa gtccagaagc caagtcccga ggacatcatg   2280
ccaagcaggc gcatccgcga cctgttcgtg ctcccaaagg agatcttcgg cagcctgaag   2340
aacttcaagg agtccgccct caagttcgcc aaccacatcg gcctgaacct ggagaccatc   2400
aagaagcacc tcaccaccgt gaagaacttc ctcctgaggg tcgacgccgt ggtcgacaag   2460
gagatcgaca acatcatcga ggccggcaag tccccacaaa cgtggtcca ggccaacgag   2520
ggcttcctgg acaagatgaa gcgcctcgtg aacaagtaca gatcttcag catcccattc   2580
ttcgccggca tgggctcctt cggcttccac catcaccacc atcactga             2628

SEQ ID NO: 59         moltype = AA  length = 437
FEATURE               Location/Qualifiers
source                1..437
                      mol_type = protein
                      organism = Plasmodium vivax
SEQUENCE: 59
MQLGIQKKKK NLEQDAMHAL MKKLESLYKL SATDNGEIFN KEIDALKKQI DQLHQHGGGN    60
EGESLGHLLE SEAADDSGKK TIFGVDEDDL DNYDADFIGQ SKGKIKGQAD TTAVAKPPTG   120
SGAGAHGSHS PPKPSVLVVP GKSGKEDSVA TLENGYESIH GEDEPREDST SHDSPPALPV   180
GRSEGDSSAS GGGTEGQQPD PASARGSQAS GGRGGGDQTN TTQPAGGQQS SSAARSLQAP   240
HAGDSQLPNA GGDPQSPAAA GHQQPPTSPP ANNEGTTVTQ ESALAATPPK GTADSNDAKI   300
KYLDKLYDEV LTTSDNTSGI HVPDYHSKYN TIRQKYEYSM NPVEYEIVKN LFNVGFKNDG   360
AASSDATPLV DVFKKALADE KFQAEFDNFV HGLYGFAKRH SYLSEARMKD NKLYSDLLKN   420
AISLMSTLQV SHHHHHH                                                  437

SEQ ID NO: 60         moltype = DNA  length = 1314
FEATURE               Location/Qualifiers
source                1..1314
                      mol_type = genomic DNA
                      organism = Plasmodium vivax
SEQUENCE: 60
atgcagctcg gcatccaaaa gaagaagaag aacctggagc aggacgccat gcacgccctc    60
atgaagaagc tggagagcct gtacaagctc tccgccaccg acaacggcga gatcttcaac   120
aaggagatcg acgccctgaa gaagcaaatc gaccagctcc accaacacgg cggcggaaac   180
gagggcgaga gcctgggcca cctcctggag agcgaggctg ctgacgactc cggcaagaag   240
accatcttcg gcgtggacga ggacgacctg gacaactacg acgccgactt catcggccag   300
tccaagggca agatcaaggg ccaggctgac accaccgctg tggctaagcc accaaccggc   360
agcggcgctg cgctcacgg cagccactcc ccaccaaagc catccgtgct cgtggtccca   420
ggcaagagcg gcaaggaaga ctccgtcgcc accctggaga acggctacga gagcatccac   480
ggcgaggacg agcccaaggga ggacagcacc tcccacgact ccccaccagc tctcccagtg   540
ggccgcagcg agggcgactc cagcgcttcc ggcggcggca ccgagggcca acagccagac   600
ccagctagcg ccaggggcag ccaggcttcc ggcggcaggg gcggcggcga ccaaaccaac   660
accacccaac cagctggcgg ccaacagtcc agctccgctg ctaggagcct gcaggcccca   720
cacgctggcg acagccagct cccaaacgcc ggcggcgacc cacaatcccc agctgccgcc   780
ggccaccaac agctccccca gccaacaacg gccaacagcc cgtgaccaca   840
gagtccgctc tggctgctac cccaccaaag ggcaccgccg actccaacga cgccaagatc   900
aagtacctgg acaagctcta cgacgaggtg ctgaccacca gcgacaacac ctccggcatc   960
cacgtcccag actaccacag caagtacaac accatccgcc aaaagtacga gtactccatg  1020
aacccagtgg agtacgagat cgtcaagaac ctcttcaacg tgggcttcaa gaacgacggc  1080
gctgccagct ccgacgctac cccactggtg gacgtcttca agaaggccct cgccgacgag  1140
aagttccagg ccgagttcga caacttcgtc cacggcctgt acggcttcgc caagaggcac  1200
agctacctct ccgaggcccg catgaaggac aacaagctgt acagcgacct cctgaagaac  1260
gccatcagcc tgatgtccac cctccaagtg tcccaccacc accaccacca ctga         1314

SEQ ID NO: 61         moltype = AA  length = 675
FEATURE               Location/Qualifiers
source                1..675
                      mol_type = protein
                      organism = Plasmodium vivax
SEQUENCE: 61
```

```
MAAYNTVLQI YKYSDDIVRK QEKCEQLVKD GKDICLKFKS INEIKVMIQN SKGKESTLSA    60
KVSHSFNKLS ELNKIKCNDE SYDAILETPS REELNKLRST FKQEKDTIAN QAKLSGYKTD   120
FETHIGKLND LAKIVDNLKA SETLPKNIEE KKTSINLIST KLETIEKEIE SINSSFDQLL   180
EKGKKCEMTK YKLVRDSLST KINDHSAIIK DNQKKATEYL TYIQNNHISI FKDIDMLNEN   240
LGEKSVSRYA IAKIEEANDL SAQLTAAVSE YEAIANSIRK EFTNISDHTE MDTLENEAKM   300
LKEHYDNLIN KKNIITELHN KINLIKLLEI RATSDKYVDI AELLGEVVKD QKKKLQEAKN   360
KLDTLKDHIA VKEKELINHD SSFTLVSIKA FDEIYDDIKY NVGQLHTLEV TNFDELKKGK   420
TYEENVTHLL NRRETLQNDL HNYEEKDKLK NTNIEMSNEE NNQIRQTSEV IKKLESEFQN   480
LLKIIQQSNT LCSNDNIKQF ISDILKKVET IRERFVKNFP EREKYHQIEI NYNEIKGVIE   540
EVDTNPEISI FTEKINTYIR QKIRSAHHLE DAQKIKDIIE DVTSNYRKIK SKLSQVNNAL   600
DRIKIKKSEM DTLFESLSKE NANNYNSAKY FLVDSDKIIK HLEDQVSKMS SLISYAEREI   660
KELEEKVYSH HHHHH                                                   675

SEQ ID NO: 62           moltype = DNA   length = 2028
FEATURE                 Location/Qualifiers
source                  1..2028
                        mol_type = genomic DNA
                        organism = Plasmodium vivax
SEQUENCE: 62
atggccgcct acaacaccgt gctccaaatc tacaagtact ccgacgacat cgtgaggaag    60
caagagaagt gcgagcagct ggtcaaggac ggcaaggaca tctgcctcaa gttcaagtcc   120
atcaacgaga tcaaggtcat gatccagaac agcaaggcga aggagtccac cctcagcgcc   180
aaggtgtccc acagcttcaa caagctcagc gagctgaaca agatcaagtg caacgacgag   240
agctacgacg ccatcctcga acccccatcc agggaggagc tcaacaagct gcgcagcacc   300
ttcaagcaag agaaggacac catcgccaac caggccaagc tctccggcta caagaccgac   360
ttcgagcacg acatcggcaa gctcaacgac ctggccaaga tcgtggacaa cctcaaggcc   420
agcgagacgc tgccaaagaa catcgaggag aagaagacct ccatcaacct catcagcacc   480
aagctcgaaa ccatcgagaa ggagatcgag tccatcaact ccagcttcga ccaactcctg   540
gagaagggca agaagtgcga gatgaccaag tacaagctcg tcagggactc cctgagcacc   600
aagatcaacg accactccgc catcatcaag gacaaccaaa agaaggccac cgagtacctc   660
acctacatcc agaacaacca catcagcatc ttcaaggaca tcgacatgct caacgagaac   720
ctgggcgaga gtccgtgag caggtacgcc atcgccaaga tcgaggaagc caacgacctc   780
tccgctcaac tcaccgctgc cgtcagcgag tacgaggcta tcgccaactc catccgcaag   840
gagttcacca acatctccga ccacaccgag atggacaccc tggagaacga ggccaagatg   900
ctgaaggagc actacgacaa cctcatcaac aagaagaaca tcatcaccga gctccacaac   960
aagatcaacc tgatcaagct cctggagatc cgcgccacca gcgacaagta tgtggacatc  1020
gccgagctcc tgggcgaggt ggtcaaggac caaagaagaa gctgcaaga ggccaagaac  1080
aagctcgaca ccctgaagga ccacatcgcc gtgaaggaga aggagctgat caaccacgac  1140
tccagcttca ccctcgtcag catcaaggcc ttcgacgaga tctacgacga catcaagtac  1200
aacgtgggcc aactccacac cctggaggtc accaacttcg acgagctcaa gaagggcaag  1260
acctacgagg agaacgtgac ccaccctcctg aacaggcgcg agacgctcca gaacgacctg  1320
cacaactacg aggagaagga caagctcaag aacaccaaca tcgagatgtc caacgaggag  1380
aacaaccaaa tcaggcagc cagcgaggtc atcaagagc tggactccga gttccaaaac  1440
ctcctgaaga tcatccaaca gtccaacacc ctctgcagca acgataacat caagcagttc  1500
atcagcgaca tcctgaagaa ggtggagacg atcagggagc gcttcgtcaa gaacttccca  1560
gagcgcgaga gtaccacca atcgagatc aactacaacg agatcaaggg catcgtgaag  1620
gaagtggaca cacccccaga gatctccatc ttcaccgaga agatcaacac ctacatcagg  1680
caaaagatca ggagcgctca ccacctggag gacgctcaga agatcaagga catcatcgag  1740
gacgtgacct ccaactacag gaagatcaag tccaagctga gccaagtcaa caacgccctc  1800
gaccgcatca agatcaagaa gagcgagatg gacaccctct cgagtccct gagcaaggag  1860
aacgccaaca actacaacag cgccaagtac ttcctggtgg actccgacaa gatcatcaag  1920
cacctggagg accaagtgtc caagatgtcc agcctgatca gctacgccga gcgcgagatc  1980
aaggagctgg aggagaaggt ctactcccac caccaccacc accactga               2028

SEQ ID NO: 63           moltype = AA   length = 1003
FEATURE                 Location/Qualifiers
source                  1..1003
                        mol_type = protein
                        organism = Plasmodium vivax
SEQUENCE: 63
MNVATRGEIV NLKNPNLRNG WSMKNLSAQN EENIVHSDGS DDVTDKEEDG EVLEGQKGSP    60
KKSAEQKVHA QEEVNKESLK SKAQNAKAEA EKAAKAAESA KENTLDALEK VNVPTELNNE   120
KNFAESAATE AKKQEKISTE AAEEVKEIEV DGQLEKLKNE EKTAKKARK QEIKTEIAEQ   180
AAKAQAAKTE AETAQKDATT AKDEAIKETG KPKSQNTTKA VTMATEEEKK TKDEAQTASE   240
KAGKTAEEAQ KEVGKETADD DKEVSQLEEE IKELERILKI VKDLASEEASS ASDNAKKAKL   300
KTQIAAEVVK AEKARIEAEE AEKEAGEAKT KTEATEKEVL KISDESKAAK VKKAVEKAKE   360
AEKQAKSEAE KAKGMADDAG GKGTTNLEDV LTKLSEVLTS VKSLASNAEV ASKNAKKEMT   420
KAQIAAEVAK AEKAKIEAEN AKLLADTASK AAENIAKSSK AAKIANNVST IAAEKSKVAT   480
EAADEAAKAL DETENPESKI AEVTEKATKA VNAAEEAKKE KAKAEVAVEV AHAEVAKEKA   540
QEAKEAAKQV ADKSKLEKAI QAADKASEKA NEASKLAEEA LSNLESLEKE TGEIVEKVNA   600
IEQKVQTAKN AAIEAHKEKT KAEIAVEVAK AEEAKKEADN AKVAAEKAKE TAEKIAKTSK   660
STEKITEEVR KATEFAKTAG DETTLAATKA ESEIPSEEKN QKELLDSIKQ KAESAFQASQ   720
EAIKAKTEAE NFLEIAKEVP KAEAAKEEAQ KAATAAEEAK TEVLKIAEEV NKSDASESEK   780
KKIETAANET AGEAEKAATF AKEAADAAKD TNKAVTLAVA KEKVEKALKA AKEAKKANEK   840
ASYALIRTKK QYALEPLEIT SEAGYNITEK EEQVKEEIEE QDDKASEEEE EDTQQIDQTQ   900
IDEVDISVDN EEEEGAAEE QIEGEKDTPT KEAKEEQTSG EKILDDKEAH KTLAEKFKDS   960
NTAKTGGVEF LETLISDVGE DTLKNLQQDL HQYFKGKHHH HHH                    1003

SEQ ID NO: 64           moltype = DNA   length = 3012
```

```
FEATURE                 Location/Qualifiers
source                  1..3012
                        mol_type = genomic DNA
                        organism = Plasmodium vivax
SEQUENCE: 64
atgaacgtcg ccaccagggg cgagatcgtg aacctgaaga acccaaacct ccgcaacggc    60
tggagcatga agaacctgtc cgcccaaaac gaggagaaca tcgtccactc cgacggcagc   120
gacgacgtga ccgacaagga agaggacggc gaggtgctgg agggcagaa gggcagccca    180
aagaagtccg ccgagcaaaa ggtccacgcc caagaggaag tgaacaagga gtccctcaag   240
agcaaggccc aaaacgccaa ggctgaggct gagaaggctg ctaaggctgc cgagtccgcc   300
aaggagaaca ccctcgacgc cctggagaag gtgaacgtcc aaccgagct caacaacgag    360
aagaacttcg ctgagagcgc tgctaccgag gccaagaagc aggagaagat ctccaccgag   420
gccgccgagg aagtgaagga gatcgaggtg acggcgaac tggagaagct gaagaacgag    480
gaagagaaga ccgccaagaa ggccaaggaa caggagatca agaccgagat cgctgagcaa   540
gctgctaagg ctcaggctgc taagaccgag gccgagacgg cccaaaagga cgccaccacc   600
gccaaggacg aggccatcaa ggagacgggc aagccaaaga ccagaacac caccaaggcc    660
gtcaccatgg ccaccgagga agagaagaag accaaggacg aggctcaaac cgcttccgag   720
aaggctggca agaccgctga ggaagcccag aaggaagtgg gcaaggagac ggccgacgag   780
gacaaggaag tgtcccaact cgaagaggag atcaaggagc tggagaggat cctcaagatc   840
gtgaaggacc tggctagcga ggcctccagc gcttccgaca cgccaagaa ggccaagctc    900
aagacccaaa tcgctgctga ggtggtcaag gctgagaagg ctaggatcga ggctgaggaa   960
gccgaagg aagccggcga ggctaagacc aagaccgaga ctaccgagaa ggaagtgctg     1020
aagatctccg acgagagcaa ggccgccaag gtcaagaagg ccgtggagaa ggccaaggaa   1080
gccgagaagc aagccaagtc cgaggctgag aaggctaagg gcatggctga cgacgccggc   1140
ggcaagggca ccaccaacct ggaggacgtg ctcaccaagc tgagcgaggt cctgacctcc   1200
gtgaagtccc tggcttccaa cgctgaggtg gcttccaaga acgccaagaa ggagatgacc   1260
aaggctcaga tcgctgctga ggtgctaag gctgaagag ccaagatcga ggccgagaac     1320
gccaagctgc tggctgacac cgctagcaag gctgccgaga acatcgccaa gtccagcaag   1380
gccgccaaga tcgccaacaa cgtcagcacc atcgccgccg agagtccaa ggtggctacc    1440
gaggctgctg acgaggctgc caaggccctc gacgagacgg agaacccaga gtccaagatc   1500
gccgaggtga ccgagaaggc taccaaggct gtgaacgctg ctgaggaagc caagaaggag   1560
aaggccaagg ctgaggtggc tgtggaggtg gctcacgctg aggtggctaa ggagaaggcc   1620
caagaggcca aggaagccgc caagcaggtg gccgacaaga gcaagctgga aggccatc     1680
caagccgccg acaaggccag cgaaagggcc aacgaggcct ccaagctcgc cgaggaagcc   1740
ctcagcaacc tggagtccct ggagaaggag acgggcgaga tcgtcgagga ggtgaacgcc   1800
atcgagcaaa aggtgcagac cgccaagaac gccgccatcg aggcccacaa ggagaagacc   1860
aaggctgaga tcgctgtgga ggtcgccaag gccgaggaag ccaagaagga agccgacaac   1920
gccaaggtgg ctgctgagaa ggctaaggag acggccgaga gatcgccaa gacctccaag    1980
agcaccggac agatcaccga ggaagtgagg aaggctaccg agttcgctaa gaccgctggc   2040
gacgagcga ccctggctgc taccaaggct gagagcgaga tcccatccga ggagaagaac    2100
caaaaggagc tcctggacag catcaagcag aaggccgaga gcgccttcca gcctcccaa    2160
gaggccatca aggccaagac cgaggccgag aacttcctgg agatcgccaa ggaagtgcca   2220
aaggccgagg ccgccaagga agagccaa aagctgcta ccgccgctga ggaagccaag      2280
accgaggtcc tcaagatcgc cgaggaagtg aacaagtccg acgcctccga gagcgagaag   2340
aagaagatcg agacggctgc taacgagacg gctggcgagg ccgagaaggc cgctaccttc   2400
gctaaggaag ccgctgacgc tgctaaggac caacaagg ccgtcaccct ggccgtggcc     2460
aaggagaagg tcgagaaggc cctcaaggcc gccaagaaga ccaaggagca acgagag      2520
gccagctacg ccctgatccg caccaagaag cagtacgccc tggagccact ggagatcacc   2580
tccgaggccg gctacaacat caccgagaag gaagagcaag tgaaggaaga gatcgaggag   2640
caggacgaca aggccagcga ggaagaggaa gaggacaccc aacagatcga ccaaacccag   2700
atcgaggagg tcgacatctc cgtggacaac gaggaagagg aagagggcc tgctgaggga   2760
caaatcgagg gcgagaagga caccccaacc aaggaagcca aggaagagca gacctccgga   2820
gagaagatcc tggacgacaa ggaagcccac aagaccctcg ccgagaagtt caaggacagc   2880
aacaccgcta gaccggcgg cgtcgagttc ctcgaaaccc tcatctccga cgtgggcgag    2940
gacaccctga gaacctcca acaggacctc accagtact tcaagggcaa gcaccaccac    3000
caccaccact ga                                                       3012

SEQ ID NO: 65          moltype = AA length = 656
FEATURE                Location/Qualifiers
source                 1..656
                       mol_type = protein
                       organism = Plasmodium vivax
SEQUENCE: 65
MNNYGKLKHG KWDDGSYSER TRWRMLSGDD HDDLLPSCDS PGGRNDEHQV NKEVSRTAPS    60
EKVKVVDKET GESMLVDVGE SGGKSSPGVA EESGPSLRGR DVRDVRVDQE TRETLQGGAT   120
NRRDLTQHGE EETGDDSKRA KQDDEAGVRS MLNDTVTAIK DNGSNLLRSV IGQINFVQGS   180
AELLKVANEE ERQPSGGSVL SKEGEEATPG DFLGGNNPNG GEKGELPNGT KNDVMIKGYA   240
NVLLNEGKHV LVGNVRNFLS RVFNLIVREK IMTRMCHRGG EASIERSGEP VGERSGEPTG   300
ERSGDPTGER SGDPTGERSG EPTGERSGEP TGERSGEPTA ERSGEPTAER SDEPTAERSD   360
EPTADPKGDP TNCRLPKRSA TKFYQSEDLY NYYSSLEEML KGRGIRWKTD RVSRYFTFSP   420
SKKIKDNFEE VMNNKVFIES VRSILFDSHK KNKKAVFSSF AVVVETLFSL IKEEKVIADM   480
YSYVKLFFQD LDILNLKVLH FLSSSSTENT QFVGPPDLSL TNFEYILAKI YSRSVLANIL   540
SPKMNHSDSK KLSKLLTRRE NNLKFSFLEG VKMVHSAIPS EGVSAVVLGN AGGQVNVPIP   600
GADDTLCKFI PIRKKLLYER LSVTRKVAEE VILDYLFRLL LRKVHEYVLE HHHHHH       656

SEQ ID NO: 66          moltype = DNA length = 1971
FEATURE                Location/Qualifiers
source                 1..1971
                       mol_type = genomic DNA
```

```
                          organism = Plasmodium vivax
SEQUENCE: 66
atgaacaact acggcaagct caagcacggc aagtgggacg acggctccta cagcgagagg    60
accaggtgga ggatgctgtc cggcgacgac cacgacgacc tcctcccatc ctgcgacagc   120
ccaggcggca ggaacgacga gcaccaagtc aacaaggaag tgtccaggac cgccccaagc   180
gagaaggtga aggtggtcga caaggagacc ggcgagtcca tgctggtgga cgtgggcgaa   240
agcggcggca agtcctcccc aggcgtggct gaggagtccg gcccaagcct gcgcggcagg   300
gacgtgcgcg acgtcagggt ggaccaagag acccgcgaga ccctgcaggg cggcgccacc   360
aacaggcgcg acctcaccca cacgcggag gaagagaccg gcgacgacag caagcgcgct   420
aagcaggacg acgaggctgg cgtcaggtcc atgctcaacg acaccgtgac cgccatcaag   480
gacaacggct ccaacctcct cgcgcagcgtc atcggccaaa tcaacttcgt gcaaggcagc   540
gctgagctcc tgaaggtcgc caacgaggaa gagcgccagc catccggcgg cagcgtgctg   600
tccaaggaag gcgaggaagc caccccaggc gacttcctcg gcggcaacaa cccgaacggc   660
ggcgagaagg gcgagctgcc aaacggcacc aagaacgacg tcatgatcaa gggctacgcc   720
aacgtgctcc tgaacgaggg caagcacgtc ctcgtgggca acgtccgcaa cttcctgtcc   780
agggtgttca acctcatcgt cagggagaag atcatgacca ggatgtgcca caggggcggc   840
gaggctagca tcgagaggtc cggcgagcca gtggggagc gctccggcga gccaaccggc   900
gagaggaccg agacccaac cggcgaggag tctggcgacc ctacggggga gaggagcggg   960
gagcctaccg gcgagcgcag cggggagcct acgggcgaga ggtccgggga gcctaccgct  1020
gagagaagcg gcgagccaac cgctgagagg agcgatgagc ctaccgctga gaggtccgac  1080
gagccaaccg ctgacccaaa gggcgaccca accaactgcc gcctcccaaa gaggtccgcc  1140
accaagttct accaaagcga ggacctgtac aactactacc ccagcctgga ggagatgctc  1200
aagggcaggg gcatcaggtg gaagaccgac cgcgtcagca ggtacttcac cttctcccca  1260
agcaagaaga tcaaggacaa cttcgaggaa gtgatgaaca caaggtcttc atcgagagc   1320
gtgcgctcca tcctcttcga ctcccacaag aagaacaaga aggccgtgtt ctccagcttc  1380
gccgtggtcg tggagaccct gttcagcctc atcaaggaag agaaggtcat cgccgacatg  1440
tactcctacg tgaagctgtt cttccaagac ctcgacatcc tgaacctcaa ggtcctgcac  1500
ttcctctcca gctccagcac cgagaacacc cagttcgtgg gcccaccaga cctgagcctc  1560
accaacttcg agtacatcct cgccaagatc tactcccgca gcgtcctggc caacatcctc  1620
agcccaaaga tgaaccactc cgacaccaag aagctgtcca agtcctgac caggcgcgag  1680
aacaacctga agttctcctt cctggagggc gtcaagatgg tgcacagcgc tatcccatcc  1740
gagggcgtga cgcgctgtgg gctgggcaac gctggcggcc aggtcaacgt gccaatccca  1800
ggcgccgacg acaccctctg caagttcatc ccaatcagga gaagctcct gtacgagcgc  1860
ctgtccgtca ccaggaaggt ggccgaggaa gtgatcctgg actacctctt ccgcctcctg  1920
ctcaggaagg tgcacgagta tgtgctggag caccatcacc accatcactg a            1971

SEQ ID NO: 67           moltype = AA  length = 447
FEATURE                 Location/Qualifiers
source                  1..447
                        mol_type = protein
                        organism = Plasmodium vivax
SEQUENCE: 67
MGNVSPPNFN DNRVNGNNGN KGNGNDNDVP SFIGGNNNNV NGNNDDNIFN KNGKDVTRND    60
GDAKDGENRN NKKNENGSGS NENNSIANAD NGSGKSDANA NQIDEDGNKM DEASLKKILK   120
IVDEMENIQG LLDGDYSILD KYSVKLVDED DGETNKRKII GEYDLKMLKN ILLFREKISR   180
VCENKYNKNL PVLLKKCSNV DDPKLSKSRE KIKKGLAKNN MSIEDFVVGL LEDLFEKINE   240
HPIKDDSFDL SDYLADFELI NYIIMHETSE LIDELLNIIE SMNFRLESGS LEKMVKSAES   300
GMNLNCKMKE DIIHLLKKSS AKFFKIEIDR KTKMIYPVQA THKGANMKQL ALSFLQKNNV   360
CEHKKCPLNS NCYVINGEEV CRCLPGFSDV KIDNVMNCVR DDTLDCSNNN GGCDVNATCT   420
LIDKKIVCEC KDNFEGDGIY CHHHHHH                                      447

SEQ ID NO: 68           moltype = DNA  length = 1344
FEATURE                 Location/Qualifiers
source                  1..1344
                        mol_type = genomic DNA
                        organism = Plasmodium vivax
SEQUENCE: 68
atgggcaacg tgtccccacc aaacttcaac gacaacaggg tcaacggcaa caacggcaac    60
aagggcaacg gcaacgacaa cgacgtgcca agcttcatcg gcggcaacaa caacaacgtc   120
aacggcaaca acgacgacaa catcttcaac aagaacggca aggacgtgac ccgcaacgac   180
ggcgacgcta aggacggcga gaaccgcaac aacaagaaga acgagaacgg ctccggcagc   240
aacgagaaca actccatcgc caacgctgac aacggctccg gcaagagcga cgccaacgcc   300
aaccaaatcg acgaggacgg caacaagatg gacgaggcca gcctcaagaa gatcctgaag   360
atcgtggacg agatggagaa catccagggc ctcctggacg gcgactactc catcctcgac   420
aagtacagcg tgaagctggt cgacgaggac gacggcgaga cgaacaagcg gaagatcatc   480
ggcgagtacg acctcaagat gctgaagaac atcctcctgt tcagggagaa gatctcccgc   540
gtctgcgaga acaagtacaa caagaacctc ccagtgctcc tgaagaagtg cagcaacgtc   600
gacgacccaa agctctccaa gagccgcgag aagatcaaga agggcctggc taagaacaac   660
atgtccatcg aggacttcgt ggtcggcctc ctggaggacc tgttcgagaa gatcaacgag   720
cacttcatca aggacgactc cttcgacctc agcgactacc tggccgactt cgagctcatc   780
aactacatca tcatgcacga gacgtccgag ctgatcgacg agctcctgaa catcatcgag   840
agcatgaact tcaggctgga gtccggcagc ctggagaaga tggtgaagtc cgccgagagc   900
ggcatgaacc tcaactgcaa gatgaaggaa gacatcatcc acctcctgaa gaagtccagc   960
gccaagttct tcaagatcga gatcgaccgc aagaccaaga tgatctaccc agtgcaagcc  1020
acccacaagg gcgccaacat gaagcaactc gccctgtcct tcctccagaa gaacaacgtc  1080
tgcgagcaca agaagtgccc actgaacagc aactgctacg tgatcaacgg cgaggaagtg  1140
tgcaggtgcc tcccaggctt ctccgacgtc aagatcgaca acgtgatgaa ctgcgtccgc  1200
gacgacaccc tcgactgcag caacaacaac ggcggctgcg acgtgaacgc tacctgcacc  1260
ctgatcgaca agaagatcgt ctgcgagtgc aaggacaact tcgagggcga cggcatctac  1320
```

```
tgccaccacc accaccacca ctga                                              1344

SEQ ID NO: 69           moltype = AA  length = 226
FEATURE                 Location/Qualifiers
source                  1..226
                        mol_type = protein
                        organism = Plasmodium vivax
SEQUENCE: 69
METLLDSETL KNYEKETNEY IRKKKVEKLF DVILKNVLVN KPENVYLYIY KNIYSFLLNK         60
IFVIGPPLLK ITPTLCSAIA SCFSYYHLSA SHMIESYTTG EVDDAAESST SKKLVSDDLI        120
CSIVKSNINQ LNAKQKRGYV VEGFPGTNLQ ADSCLRHLPS YVFVLYADEE YIYDKYEQEN        180
NVKIRSDMNS QTFDENTQLF EVAEFNTNPL KDEVKVYLRN HHHHHH                      226

SEQ ID NO: 70           moltype = DNA  length = 681
FEATURE                 Location/Qualifiers
source                  1..681
                        mol_type = genomic DNA
                        organism = Plasmodium vivax
SEQUENCE: 70
atggagacgc tcctggactc cgagacgctc aagaactacg agaaggagac gaacgagtac         60
atcaggaaga gaaggtgga gaagctcttc gacgtcatcc tcaagaacgt gctggtcaac        120
aagccagaga acgtgtacct gtacatctac aagaacatct acagcttcct cctgaacaag        180
atcttcgtca tcggcccacc actcctgaag atcaccccaa ccctctgctc cgccatcgcc        240
tcctgcttca gctactacca cctgtccgcc agccacatga tcgagagcta caccaccggc        300
gaggtggacg acgctgctga gtccagcacc tccaagaagc tcgtgagcga cgacctgatc        360
tgctccatcg tcaagagcaa catcaaccaa ctcaacgcca agcagaagag gggctacgtg        420
gtcgagggct tcccaggcac caacctccag gctgactcct gcctcaggca cctgccaagc        480
tacgtgttcg tcctgtacgc cgacgaggag tacatctacg acaagtacga gcaggagaac        540
aacgtgaaga tcaggtccga catgaacagc caaaccttcg acgagaacac ccagctgttc        600
gaggtcgccg agttcaacac caacccactc aaggacgagg tgaaggtcta cctgcgcaac        660
caccaccacc accaccactg a                                                  681

SEQ ID NO: 71           moltype = AA  length = 395
FEATURE                 Location/Qualifiers
source                  1..395
                        mol_type = protein
                        organism = Plasmodium vivax
SEQUENCE: 71
MKPGVEKKKK LEEDVIGILR RKLESLQKRS LTNSDGKLKK EIELVKKQIQ ELQKYEKGEA         60
GKKVDATLGE EPGVESAEEQ PLSVEEAGDT QDEDRLDELE GVEDFEEENL EQSEQVEEAE        120
VVEEAEEEAG DAEEEQPAEA EEDGSLLEEA PNSVERKAEG AIAEFEEADV EEGAEAEDEGV       180
ETDEGADADE ASLGSFDLEG ELIEEDLQES FDLEGEQEEE DLQEGFKSEE EANQGGQLPR        240
EIPPHGEEAV EPPLRGSNQP MEYVGNLHSD VGPTEGSANQ ISPPSVDEKG KEDGDKYKSA        300
SQDGGNSVGI NNFGGCFQGG NSNGICPLDI FKKVLEDENF LQEFDSFIHN LYGSSKNNTP        360
WGGDKMGNEN LYMDLFTNAL SFLNTIEVIH HHHHH                                  395

SEQ ID NO: 72           moltype = DNA  length = 1188
FEATURE                 Location/Qualifiers
source                  1..1188
                        mol_type = genomic DNA
                        organism = Plasmodium vivax
SEQUENCE: 72
atgaagccag gcgtggagaa gaagaagaag ctcgaagagg acgtcatcgg catcctgcgc         60
aggaagctga gtccctgca aaagaggtcc ctcaccaaca gcgacggcaa gctcaagaag        120
gagatcgagc tggtcaagaa gcaaatccag gagctgcaga agtacgagaa gggcgaggct        180
ggcaagaagg tggacgctac cctgggcgag gagccgggcg tggagtccgc tgaggagcaa        240
ccactgagcg tggaggaagc cggcgacacc caggacgagg acaggctcga cgagctggag        300
ggcgtcgagg acttcgagga agagaacctg agcaaagcg agcaggtgga ggaagccgag        360
gtggtggagg aagccgagga agaggccggc gacgctgagg aagagcaacc ggctgaggct        420
gaggaagacg gctccctcct cgaagaggcc ccaaacagc tggagggaa cgagaactc        480
gctatcgctg agttcgagga agccgacgtc gaggaaggcg ccgaggccga cgagggcgtg        540
gagacggacg agggcgctga cgctgacgag gcttccctgg gcagcttcga cctggagggc        600
gagctgatcg aggaagacct ccaggagtct ttcgacctgg aggggagca agaggaagag        660
gacctccaag agggcttcaa gagcgaggaa gaggccaacc aagggggcca gctgccaagg        720
gagatcccac cacacggcga ggaagccgtg gagccaccac tccgcggcaa caagccatcc        780
atggagtatg tgggcaacct gcacagcgac gtgggcccaa ccgagggcag cgccaaccaa        840
atctccccac caagcgtcga cgagaagggc aaggaagacg gcgacaagta caagtccgcc        900
agccaagacg gcggaaactc cgtgggcatc aacaacttcg gcggatgctt ccagggcggc        960
aacagcaacg gcatctgccc actcgacatc ttcaagaagg tcctggagga cgagaacttc       1020
ctgcaggagt tcgactcctt catccacaac ctgtacggct ccagcaagaa caacaccca       1080
tggggcggcg acaagatggg caacgagaac ctctacatgg acctgttcac caacgccctc       1140
agcttcctga acaccatcga ggtcatccac caccaccacc accactga                   1188

SEQ ID NO: 73           moltype = AA  length = 372
FEATURE                 Location/Qualifiers
source                  1..372
                        mol_type = protein
                        organism = Plasmodium vivax
SEQUENCE: 73
```

-continued

```
MELSHSLSVK NAPDASALNI EVEKDKKKIC KNAFQYINVA ELLSPREEET YVQKCEEVLD  60
TIKNDSPDES AEAEINEFIL SLLHARSKYT IINDSDEEVL SKLLRSINGS ISEEAALKRA  120
KQLITFNRFI KDKAKVKNVQ EMLVISSKAD DFMNEPKQKM LQKIIDSFEL YNDYLVILGS  180
NINIAKRYSS ETFLSIKNEK FCSDHIHLCQ KFYEQSIIYY RLKVIFDNLV TYVDQNSKHF  240
KKEKLLELLN MDYRVNRESK VHENYVLEDE TVIPTMRITD IYDQDRLIVE VVQDGNSKLM  300
HGRDIEKREI SERYIVTVKN LRKDLNDEGL YADLMKTVKN YVLSITQIDN DISNLVRELD  360
HEDVEKHHHH HH                                                     372

SEQ ID NO: 74           moltype = DNA  length = 1119
FEATURE                 Location/Qualifiers
source                  1..1119
                        mol_type = genomic DNA
                        organism = Plasmodium vivax
SEQUENCE: 74
atggagctct cccacagcct gtccgtgaag aacgctccag acgctagcgc tctcaacatc  60
gaggtcgaga aggacaagaa gaagatctgc aagaacgcct tccaatacat caacgtcgcc  120
gagctcctgt ccccaaggga ggaagagact tacgtgcaga agtgcgagga agtgctggac  180
accatcaaga acgacagccc agacgagtcc gctgaggctg agatcaacga gttcatcctc  240
agcctcctgc acgcccgctc caagtacacc atcatcaacg acagcgacga ggaagtgctg  300
agcaagctcc tgaggtccat caacggcagc atctccgagg aagccgctct caagagggct  360
aagcaactga tcaccttcaa caggttcatc aaggacaagg ccaaggtgaa gaacgtccag  420
gagatgctcg tcatctccag caaggccgac gacttcatga acgagccaaa gcaaaagatg  480
ctccagaaga tcatcgacag cttcgagctg tacaacgact acctcgtgat cctgggctcc  540
aacatcaaca tcgccaagcg ctactccagc gagacgttcc tcagcatcaa gaacgagaag  600
ttctgctccg accacatcca cctgtgccaa aagttctacg agcagagcat catctactac  660
aggctcaagg tcatcttcga caacctggtg acctacgtcg accaaaactc caagcacttc  720
aagaaggaga agctcctgga gctcctgaac atggactaca gggtgaaccg cgagtccaag  780
gtgcacgaga actacgtcct ggaggacgag actgtgatcc caaccatgcg catcaccgac  840
atctacgacc aagacaggct catcgtggag gtggtccagg acggcaacag caagctgatg  900
cacggcaggg acatcgagaa gcgcgagatc tccgagaggt acatcgtgac cgtcaagaac  960
ctccgcaagg acctgaacga cgagggcctc tacgccgacc tgatgaagac cgtgaagaac  1020
tacgtcctca gcatcaccca gatcgacaac gacatctcca acctcgtgag ggagctggac  1080
cacgaggacg tcgagaagca ccaccaccac caccactga                         1119

SEQ ID NO: 75           moltype = AA  length = 450
FEATURE                 Location/Qualifiers
source                  1..450
                        mol_type = protein
                        organism = Plasmodium vivax
SEQUENCE: 75
MEKLDIPPHE MYEDMQQAFR EQDKYDFLAI SDGSVINSYM KKNVVDWNNR YSYNQLKNKD  60
SLIMFLVDIF RSLFLSNCID KNIDNVLSSI EEMFTDHYYN PMHSRLKYLI DDVGIFFTKL  120
PITKAFHTYN KKYRITKRLY APPTFNEVRH ILNLAQILSL EDGLDLLTFD ADETLYPDGY  180
DFHDEVLASY ISSLLKKMNI AIVTAASYSN DAEKYQKRLE NLLRYFSKHN IEDGSYENFY  240
VMGGESNYLF KCNEDANLYS VPEEEWYHYK KYVNKETVEQ ILDISQKCLQ QVITDFKLCA  300
QIQRKEKSIG LVPNKIPSAN NQKEQKNYMI KYEVLEEAVI RVKKEIVKNK ITAPYCAFNG  360
GQDLWVDIGN KAEGLIILQK LLKIEKKKCC HIGDQFLHSG NDFPTRFCSL TLWISNPQET  420
KACLKSIMNL NMKSFIPEVL YENEHHHHHH                                  450

SEQ ID NO: 76           moltype = DNA  length = 1353
FEATURE                 Location/Qualifiers
source                  1..1353
                        mol_type = genomic DNA
                        organism = Plasmodium vivax
SEQUENCE: 76
atggagaagc tcgacatccc accacacgag atgtacgagg acatgcaaca ggccttcagg  60
gagcaagaca agtacgactt cctggccatc tccgacggca gcgtgatcaa ctcctacatg  120
aagaagaacg tggtcgactg gaacaacagg tactcctaca accagctcaa gaacaaggac  180
agcctcatca tgttcctggt ggacatcttc cgctccctct tcctgagcaa ctgcatcgac  240
aagaacatcg acaacgtcct gtccagcatc gaggagatgt tcaccgacca ctactacaac  300
ccaatgcaca gcaggctcaa gtacctgatc gacgacgtgg gcatcttctt caccaagctc  360
ccaatcacca aggccttcca cacctacaac aagaagtaca ggatcaccaa gcgcctgtac  420
gccccaccaa ccttcaacga ggtccgccac atcctcaacc tggcccaaat cctctccctg  480
gaggacggcc tcgacctcct gaccttcgac gccgacgaga cgctgtaccc agacggctac  540
gacttccacg acgaggtgct cgccagctac atctccagcc tcctgaagaa gatgaacatc  600
gccatcgtca ccgccgcctc ctacagcaac gacgccgaga agtaccagaa gaggctggag  660
aacctcctgc gctacttctc caagcacaac atcgaggacg gcagctacga gaacttctac  720
gtgatgggcg gcgagtccaa ctacctcttc aagtgcaacg aggacgccaa cctgtacagc  780
gtcccagagg aagagtggta ccactacaag aagtatgtga acaaggagac ggtcgagcaa  840
atcctcgaca tctcccagaa gtgcctgcaa caagtgatca ccgacttcaa gctctgcgcc  900
caaatccaga ggaaggagaa gtccatcggc ctggtcccaa acaagatccc aagcgccaac  960
aaccaaaagg agcagaagaa ctacatgatc aagtacgagg tgctcgaaga ggccgtgatc  1020
cgcgtcaaga aggagatcgt caagaacaag atcaccgctc catactgcgc cttcaacggc  1080
ggccaagacc tgtgggtgga catcggcaac aaggccgagg gcctcatcat cctgcaaaag  1140
ctcctgaaga tcgagaagaa gaagtgctgc cacatcggcg accagttcct ccacagcggc  1200
aacgacttcc caacccgctt ctgctccctc accctgtgga tcagcaaccc acaggagacg  1260
aaggcctgcc tcaagtccat catgaacctg aacatgaaga gcttcatccc agaggtcctc  1320
tacgagaacg agcaccacca ccaccaccac tga                              1353
```

-continued

```
SEQ ID NO: 77           moltype = AA  length = 527
FEATURE                 Location/Qualifiers
source                  1..527
                        mol_type = protein
                        organism = Plasmodium vivax
SEQUENCE: 77
MEIIAEKPKV KFNFASEEYK NCDSSDYSEC AEDYGRPNGK DYFYANRILS LDRNSEQRRK  60
ESPSKRPGLC VDEICTCGFH RCPKIVKSLP FDGESNYRSE FGPKPLPELP PRQEAKLTRS  120
LPFEGESNYR SEFGPKPLPE LPPRVEQKPP KSLPFDGESN YRSEFGPKPL PELPPRVEQK  180
PPKSLPFDGE SNYRSEFGPK PLPELPPRVE QKPPKSLPFE GESNYRSEFG PKPLPELPPR  240
VEQKPPKSLP FEGESNYRSE FGPKALPELP PRVEQKPPKS LPFEGESNYR SEFGPKPLPA  300
LPPRVETKLV KSLPFEGESN YRSEFGPKPL PELPPRVEQK PPKSLPFEGE SNYRSEFGPK  360
PLPALPPRVV TKLVKSLPFE GESNYRSEFG PKPLPEIPPR VEQKPPKSLP FEGESNYRSE  420
FGPKPLPELP PRVEQKPPKS LPFEGESNYR SEFGPKQLPE LPPRQEAKLT RSLPFEGESS  480
YRSEYVRKAI PICPVNLLPK YPAPTYPSEH VFWDSACKRW YHHHHHH                527

SEQ ID NO: 78           moltype = DNA  length = 1584
FEATURE                 Location/Qualifiers
source                  1..1584
                        mol_type = genomic DNA
                        organism = Plasmodium vivax
SEQUENCE: 78
atggagatca tcgccgagaa gccaaaggtc aagttcaact tcgcctccga ggagtacaag  60
aactgcgact ccagcgacta ctccgagtgc gctgaggact acggcaggcc aaacggcaag  120
gactacttct acgccaacag gatcctctcc ctggaccgca acagcgagca gaggcgcaag  180
gagtccccaa gcaagaggcc aggcctctgc gtggacgaga tctgcacctg cggcttccac  240
cgctgcccaa agatcgtcaa gtccctgcca ttcgacggcg agtccaacta ccgcagcgag  300
ttcggcccaa agccactccc agagctgcca ccaaggcaag aggccaagct cacccgcagc  360
ctgccattcg agggcgagtc caactacagg tccgagttcg ggcctaagcc tctgcctgag  420
ctgccaccac gcgtggagca aaagccacca aagtccctcc ctttcgatgg ggagagcaac  480
tacaggagtg aattcgggcc taagccgctg cccgagctgc caccacgcgt cgagcagaag  540
ccaccaaaga gcctcccttt cgatggcgag agcaactaca ggagcgaatt tgggcctaag  600
ccgctgccgg aactgccacc acgcgtggaa caaaagccac caaagagcct gcctttcgag  660
ggggagtcca actacaggag tgagtttggg cctaagccgt tgcctgaact gccaccacgc  720
gtcgaacaga aaccaccaaa aagcctccct ttcgagggcg agagcaacta ccgctccgag  780
ttcggcccaa aggctctgcc ggagctgcca ccacgcgtgg aacagaaacc accaaagagc  840
ctccccttcg agggggagag caattatcgc tctgagttcg ggccaaagcc gctgccggct  900
ctgccaccac gcgtggagac gaagctcgtc aagagcctcc cgttcgaggg ggagagcaac  960
tatcgctccg aatttgggcc taaaccactg cctgaactgc caccacgcgt ggaacagaag  1020
ccaccaaaaa gcctcccctt tgaaggggag agcaattacc gctccgagtt cgggcccaag  1080
ccgctgccgg ccctgccacc acgcgtggtc accaagctcg tgaagtccct cccctttgaa  1140
ggcgagagca actacagatc tgagttcggg cctaagccac tcccagagat cccaccacgc  1200
gtcgagcaaa aaccaccaaa atctctcccc tttgagggtg agagcaatta tcgctcagag  1260
ttcgggccca agcctctgcc ggagctgcca ccacgcgtcg aacagaagcc accaaagagc  1320
ttaccttttg aaggggagag caactaccgc agtgaattcg gcccaaagca gctgccagaa  1380
ctgccaccaa ggcaagaggc caaactcacc cgctccctgc ctttcgaggg cgagtccagc  1440
tacaggagcg agtatgtgag gaaggccatc ccaatctgcc cagtcaacct cctgccaaag  1500
tacccagccc caacctaccc atccgagcac gtgttctggg acagcgcctg caagcgctgg  1560
taccaccacc accaccacca ctga                                         1584

SEQ ID NO: 79           moltype = AA  length = 266
FEATURE                 Location/Qualifiers
source                  1..266
                        mol_type = protein
                        organism = Plasmodium vivax
SEQUENCE: 79
MAAANRPNAN GFVSPTLIGF GELSIQESEE FKRMAWNNWM LRLESDWKHF NDSVEEAKTK  60
WLHERDSAWS DWLRSLQSKW SHYSEKMLKE HKSNVMEKSA NWNDTQWGNW IKTEGRKILE  120
AQWEKWIKKG DDQLQKLILD KWVQWKNDKI RSWLSSEWKT EEDYYWANVE RATTAKWLQE  180
AEKMHWLKWK ERINRESEQW VNWVQMKESV YINVEWKKWP KWKNDKKILF NKWSTNLVYK  240
WTLKKQWNVW IKEANTAPQV HHHHHH                                       266

SEQ ID NO: 80           moltype = DNA  length = 801
FEATURE                 Location/Qualifiers
source                  1..801
                        mol_type = genomic DNA
                        organism = Plasmodium vivax
SEQUENCE: 80
atggctgccg ccaacaggcc aaacgccaac ggcttcgtct ccccaaccct catcggcttc  60
ggcgagctgt ccatccaaga gagcgaggag ttcaagagga tggcctggaa caactggatg  120
ctccgcctgg agtccgactg gaagcacttc aacgacagcg tggaggaagc caagaccaag  180
tggctgcacg agagggactc cgcttggagc gactggctcc gctccctgca gagcaagtgg  240
tcccactaca gcgagaagat gctgaaggag cacaagtcca acgtcatgga gaagagcgcc  300
aactggaacg acacccaatg gggcaactgg atcaagaccg agggccgcaa gatcctggag  360
gcccagtggg agaagtggat caagaagggc gacgaccaac tgcagaagct catcctggac  420
aagtgggtcc agtggaagaa cgacaagatc aggtcctggc tctccagcga gtggaagacc  480
gaggaagact actactgggc taacgtggag agggctacca ccgctaagtg gctccaagag  540
gccgagaaga tgcactggct gaagtggaag gagaggatca accgcgagtc cgagcaatgg  600
gtgaactggg tccagatgaa ggagagcgtg tacatcaacg tcgagtggaa gaagtggcca  660
```

```
aagtggaaga acgataagaa gatcctgttc aacaagtgga gcaccaacct cgtgtacaag   720
tggaccctga agaagcagtg gaacgtctgg atcaaggaag ccaacaccgc cccacaggtg   780
caccaccacc accaccactg a                                             801

SEQ ID NO: 81           moltype = AA   length = 475
FEATURE                 Location/Qualifiers
source                  1..475
                        mol_type = protein
                        organism = Plasmodium vivax
SEQUENCE: 81
MEKVVDEVKY SEEVCNESVD LYLLVDGSGS IGYPNWITKV IPMLNGLINS LSLSRDTINL    60
YMNLFGNYTT ELIRLGSGQS IDKRQALSKV TELRKTYTPY GTTNMTAALD EVQKHLNDRV   120
NREKAIQLVI LMTDGVPNSK YRALEVANKL KQRNVSLAVI GVGQGINHQF NRLIAGCRPR   180
EPNCKFYSYA DWNEAVALIK PFIAKVCTEV ERVANCGPWD PWTACSVTCG RGTHSRSRPS   240
LHEKCTTHMV SECEEGECPV EPEPLPVPAP LPTVPEDVNP RDTDDENENP NFNKGLDVPD   300
EDDDEVPPAN EGADGNPVEE NVFPPADDSV PDESNVLPLP PAVPGGSSEE FPADVQNNPD   360
SPEELPMEQE VPQDNNVNEP ERSDSNGYGV NEKVIPNPLD NERDMANKNK TVHPGRKDSA   420
RDRYARPHGS THVNNNRANE NSDIPNNPVP SDYEQPEDKA KKSSNNGYKH HHHHH        475

SEQ ID NO: 82           moltype = DNA   length = 1428
FEATURE                 Location/Qualifiers
source                  1..1428
                        mol_type = genomic DNA
                        organism = Plasmodium vivax
SEQUENCE: 82
atggagaagg tggtcgacga ggtgaagtac agcgaggaag tgtgcaacga gtccgtcgac    60
ctctacctcc tggtggacgg ctccggcagc atcggctacc caaactggat caccaaggtc   120
atcccaatgc tcaacggcct gatcaactcc ctcagcctgt cccgcgacac catcaacctc   180
tacatgaacc tgttcggcaa ctacaccacc gagctcatca ggctgggcag cggccaatcc   240
atcgacaagc gccaggccct cagcaaggtg accgagctga ggaagaccta cacccctac    300
ggcaccacca acatgaccgc cgccctcgac gaggtgcaaa agcacctgaa cgacagggtc   360
aaccgcgaga aggccatcca gctcgtgatc ctgatgaccg acggcgtccc aaacagcaag   420
taccgcgccc tggaggtggc caacaagctg aagcaaagga acgtctccct ggccgtgatc   480
ggcgtggggc aaggcatcaa ccaccagttc aacaggctga tcgctggctg caggccacgc   540
gagccaaact gcaagttcta cagctacgct gactgaacg aggctgtgc tctcatcaag    600
ccattcatcg ccaaggtctg caccgaggtg gagagggtgg ctaactcggg cccatgggac   660
ccgtggaccg cttgctccgt gacctgcggc aggggcaccc acagcaggtc ccgcccaagc   720
ctgcacgaga agtgcaccac ccacatggtg tccgagtgcg aggaaggcga gtgcccagtg   780
gagccagcc cactgccggt cccagccca ctgccaacca tgccagagga cgtcaaccca    840
agggacaccg acgacgagaa cgagaaccca aacttcaaca agggcctcga cgtgccagac   900
gaggacgacg acgaggtccc accagctaac gagggcgctg acggcaaccc agtggaggag   960
aacgtcttcc caccagccga cgacagcgtg ccagacgagt ccaacgtgct gccactgcca  1020
ccagctgtgc caggcgggtc cagcgaggag ttcccagctg acgtccaaaa caacccagac  1080
tcccagagg agctcccgat ggagcaagag gtgccacagg acaacaacgt caacgagcca   1140
gagcgcagcg actccaacgg ctacggcgtg aacgagaagg tcatcccaaa cccactggac  1200
aacgagaggg acatggccaa caagaacaag accgtgcacc cgggcaggaa ggacagcgcc  1260
agggaccgct acgccaggcc acacggctcc acccacgtga acaacaacgg ggccaacgag  1320
aacagcgaca tcccaaacaa cccagtccca tccgactacg agcagccaga ggacaaggcc  1380
aagaagtcca gcaacaacgg ctacaagcac caccaccacc accactga             1428

SEQ ID NO: 83           moltype = AA   length = 362
FEATURE                 Location/Qualifiers
source                  1..362
                        mol_type = protein
                        organism = Plasmodium vivax
SEQUENCE: 83
MDDKKDKENE HKEDADKKNN DELKT

```
ggcccatcca agccagcttc cggcgcttcc ggcagccagg gcgcttccga ctccagcaac  600
gactccgccg agccaaccag cgctgccgcc gccgccgccc cagctggccc aaccgctgcc  660
gccgccagcc cacaggtgaa gcacgtggac accctctgcg acgagctcct ggctggcgag  720
aacaagaaga acgtgctgga cgagggcgag gaccactccc aatacaacat cttcaggaag  780
cagtacgaca agatggtcct caacaagacc gagtacaaca tcagcctcaa gctcctggac  840
accatgctga ccaacggcca agtggagcgc gagaagaaga acaccctcat caagaccttc  900
aagaaggccc tgtacgacaa gcagtactcc gagaagctca ggaacctgat cagcggcgtg  960
tacgccttcg ccaagcgcaa caacttcatc gacggcgaca aggtgaagga aggcgactac 1020
agcaagctct tcgagtacat cggctgcatg atgaacaccc tggagctgca ccaccaccac 1080
caccactga                                                         1089

SEQ ID NO: 85            moltype = AA  length = 723
FEATURE                  Location/Qualifiers
source                   1..723
                         mol_type = protein
                         organism = Plasmodium vivax
SEQUENCE: 85
MKRHATRGAL HSLKSIEHEV QRKKNKKKKI ILYSIGSILA LAAVIATGVG IGMYIKKKKK  60
NSLEKLQQIE PQKLESKTDE SDPLLGKSEA AKVEVKGDSE EVPQEVSSPS EALDVEPPVS 120
EALNMEPAVG ESANFEDSAK GEVDIEPVSE VESIEPVSEV ESIEPVSEVE SIEPSVDEVM 180
DAAEPISTEP VNVEPAGNET ENIVPTSFEQ VNIEPAVSEA FSQERSGEET ADFEDSVKED 240
VIPESPPVES VTIEAENIQP MNVEQMNVDP TVSDAESIEP TPVEAVDIEP VNVEPVNVEP 300
AVSETMSQEP SLDEVENVES AVNEMMSQEP SAEETANFAH SIKEDVSPES TSVESLDVES 360
SVSEPMSTDP SPVESVSMES VDSETVNVES IDSETVNVEP SDETSKVEAD VQQFTDEELS 420
TIGNVADKAS DGPAPEASDF PDSIFEENLD NANPPLKLED ALVDPPASDE AQPEPSHPNE 480
AVGAAKSAES AEADQISHSG SGDASPSAPS SSDDTSGSKN SGTSGKDRLF KTYDSDVEPP 540
IVPEKYPTVG VKEAPKMGFA EMAFKNIFDT FSKVADASKV LTPEKQSAPE KQSAPEKQSA 600
PEKQSAPEKH STPPKQSTSP KESTSPKQPA PPKPSTSPKQ SAPAKQSAPP KQSAPAKQSA 660
PAKNAAPPQS ASSSRFFSSS SNGNKGFGLR LFSDASSSNN KKGRAGNPII RFKRRANHHH 720
HHH                                                               723

SEQ ID NO: 86            moltype = DNA  length = 2172
FEATURE                  Location/Qualifiers
source                   1..2172
                         mol_type = genomic DNA
                         organism = Plasmodium vivax
SEQUENCE: 86
atgaagaggc acgctacccg cggcgccctc cactccctga agagcatcga gcacgaggtg   60
caaaggaaga agaacaagaa gaagaagatc atcctctact ccatcggcag catcctggct  120
ctggctgccg tgatcgctac cggcgtcggc atcggcatgt acatcaagaa gaagaagaag  180
aacagcctgg agaagctgca acagatcgag ccacaaaagc tggagtccaa gaccgacgag  240
agcgacccac tcctgggcaa gagcgaggct gctaaggtgg aggtcaaggg cgactccgag  300
gaagtgccac aagaggtgtc ctccccgagc gaggctctgg acgtggagcc accagtctcc  360
gaggccctga acatggagcc agccgtgggc gagtccgcca acttcgagga cagcgccaag  420
ggcgaggtcg acatcgagcc agtgtccgag gtcgagtcta ttgaaccagt gtccgaggtg  480
gagtctattg agccagtgtc cgaagtcgag agcatcgagc catccgtgga cgaggtcatg  540
gacgctgctg agccaatcag caccgagcca gtgaacgtcg agccagccgg caacgagacg  600
gagaacatcg tgccaacctc cttcgagcaa gtgaacatcg agccagccgt cagcgaggcc  660
ttctcccaag agaggagcgg cgaggagacg gctgacttcg aggactccgt gaaggaagac  720
gtcatcccag agtccccacc agtggagagc gtcaccatcg aggccgagaa catccaaccg  780
atgaacgtgg agcagatgaa cgtggaccca accgtctccg acgccgagag catcgagcca  840
accccagtgg aggccgtgga tatcgagcct gtcaacgtgg agcctgtcaa cgttgagcca  900
gccgtgtccg agacgatgag ccaagagcca tccctgacgt aggtggagaa cgtcgagagc  960
gccgtcaacg agatgatgtc ccaggagcca tccgctgagg agacgccaa cttcgcccac 1020
tccatcaagg aagacgtgag cccagagagc acctccgtcg agtccctgga cgtggagtcc 1080
agcgtcagcg agccaatgtc caccgaccca agcccagtgg agagcgtctc catggagtcc 1140
gtggacagcg agacggtgaa cgtcgagtcc atcgattccg agacggtcaa cgtggagcca 1200
tccgacgaga cgagcaaggt ggaggccgac gtccaacagt tcaccgacga ggagctcagc 1260
accatcggca acgtggctga caaggcttcc gacggcccag ctccagaggc ctccgacttc 1320
ccagacagca tcttcgagga gaacctcgac aacgccaacc caccactcaa gctcgaggac 1380
gctctggtgg acccaccagc tagcgacgag gctcaaccag agccatccca cccaaacgag 1440
gctgtggggc ctgctaagtc cgctgagagc gctgaggctg accaaatcag ccactccggc 1500
agcggcgacg cttccccaag cgctccatcc agctccgacg acacctccgg cagcaagaac 1560
tccggcacca gcggcaagga caggctcttc aagacctacg actccgacgt ggagccacca 1620
atcgtcccag agaagtaccc aaccgtgggc gtgaaggaag ccccaaagat gggcttcgcc 1680
gagatggcct tcaagaacat cttcgacacc ttctccaagg tggctgacgc tagcaaggtc 1740
ctgaccccag agaagcaatc cgccccagag aagcagagcg ctcctgagaa gcagagcgct 1800
cccgagaagc agagcgcccc agagaagcac tccacccgac caaagcaatc caccagccca 1860
aaggagtcca ccagcccaaa gcagcagccc accaaagcag catccaccag cctaagcag 1920
tccgctccag ctaagcagtc cgccccacca aagcagagcg ctccagctaa gcaatccgct 1980
ccagctaaga cgctgcccc accacagagc gccagctcca gcaggttctt ctccagctcc 2040
agcaacggca caagggctt cggctcagg ctgttctccg acgcctccag ctccaacaac 2100
aagaagggca gggccggcaa cccaatcatc cgcttcaaga ggcgcgccaa ccaccaccac 2160
caccaccact ga                                                     2172

SEQ ID NO: 87            moltype = AA  length = 373
FEATURE                  Location/Qualifiers
source                   1..373
                         mol_type = protein
```

-continued

```
                         organism = Plasmodium vivax
SEQUENCE: 87
MNNPAEVVAA HLRRTGNSNE IRQASHVESV GGSANSSLDD DDGGGYDSAA PPGELHTTGD  60
APPGEFRTTG VVPPGRQKGG KKRMFKIKKK KSLTPLHIDD GGFTQGGEAK GPDVALESFA  120
ITRKRRRPPL LGRGVVESSN IELTSKLGGK LGSKLGGKLN PTLSLVASRA VDGLLGGVHK  180
HMQGPFSLDL DGTNNSPLAT PIVTPNLYSN ISTPFNMHNG IPPSAPAPMA LPPQGVQVPL  240
PNAQPQPPPS VATTATAAPA ATSPMASPTT PTPAASTGVP PPPGIQLATN AMTYPQMNMQ  300
NVMTANQMAQ NPAFNIHPTA TNLRDDPGNV NYNEVVTITI GIVICLFLFC FVFGCIVKMC  360
KPAKRRRHHH HHH                                                     373

SEQ ID NO: 88            moltype = DNA  length = 1122
FEATURE                  Location/Qualifiers
source                   1..1122
                         mol_type = genomic DNA
                         organism = Plasmodium vivax
SEQUENCE: 88
atgaacaacc cagctgaggt ggtggctgct cacctgaggc gcaccggcaa ctccaacgag  60
atcaggcagg ctagccacgt ggagagcgtc ggcggctccg ctaactccag cctcgacgac  120
gacgacggcg gcggatacga cagcgctgcc ccaccaggcg agctccacac caccggcgac  180
gccccaccag gcgagttccg caccaccggc gtggtcccac caggcaggca aaagggcggc  240
aagaagcgca tgttcaagat caagaagaag aagtccctca ccccactgca catcgacgac  300
ggcggcttca cccagggcgg cgaggctaag ggcccagacg tggctctgga gtccttcgcc  360
atcaccagga agaggcgcag gccaccactc ctgggccgcg gcgtggtcga gtccagcaac  420
atcgagctca ccagcaagct gggcggcaag ctcggctcca agctgggcgg caagctcaac  480
ccgaccctca gcctggtggc ctccagggcc gtggacggcc tcctgggcgg cgtgcacaag  540
cacatgcaag gcccattcag cctcgacctg gacggcacca acaactcccc actggccacc  600
ccaatcgtca ccccaaacct ctactccaac atcagcaccc cattcaacat gcacaacggc  660
atcccaccaa gcgctccagc tccaatggct ctgccaccac aaggcgtgca ggtcccactc  720
ccaaacgccc aaccacaacc accaccatcc gtggctacca ccgctaccgc tgctccagct  780
gctaccagcc caatggcttc cccaaccacc ccaaccccag ctgctagcac cggcgtgcca  840
ccaccaccag gcatccagct ggccaccaac gccatgacct acccacagat gaacatgcag  900
aacgtcatga ccgccaacca aatggcccag aacccagcct tcaacatcca cccgaccgct  960
accaacctca gggacgaccc aggcaacgtg aactacaacg aggtggtcac catcaccatc  1020
ggcatcgtca tctgcctctt cctgttctgc ttcgtgttcg gctgcatcgt caagatgtgc  1080
aagccggcta agcgcaggcg ccatcaccac caccaccact ga                     1122

SEQ ID NO: 89            moltype = AA  length = 361
FEATURE                  Location/Qualifiers
source                   1..361
                         mol_type = protein
                         organism = Plasmodium vivax
SEQUENCE: 89
MSKTGNNNRN AKNAKGGGGG GKRGNNEANK NDGMSGKGSQ KGKKKDPGGG GTPKGQGKGP  60
EQGKQKNKKG EDSHFDEYIK DMKNSQDEDN FMDELNRFEK NFHDEDFESD ENLFNYGKGG  120
THSGEFNKIG ELNSGNYNEM KPDANDYQYF DNEDILEGDE DLTNIWNKNM QNFEPSTLLT  180
FEIQGNSEEY LFEEVTSLNT YFRGVFYSNN ESDDNKILFF ITDPDGEVIY KKEASEGIFY  240
FYTQKIGVYT ITLKNSKWMG KKLTTVALGL GESPSLKSEH IKDFTNYIDK IVAETKRLKN  300
ELKYLSSKHM THIEKMKKIT NKAFLYCFIK LFVLVFLSLF TIYYIKNLVS NKRVLHHHHH  360
H                                                                  361

SEQ ID NO: 90            moltype = DNA  length = 1086
FEATURE                  Location/Qualifiers
source                   1..1086
                         mol_type = genomic DNA
                         organism = Plasmodium vivax
SEQUENCE: 90
atgtccaaga ccggcaacaa caacaggaac gccaagaacg ctaagggcgg cggcggcggc  60
ggcaagaggg gcaacaacga ggccaacaag aacgacggca tgtccggcaa gggcagccaa  120
aagggcaaga agaaggaccc aggcggcggc ggcaccccga agggccaggg caagggccca  180
gagcaaggca agcagaagaa caagaagggc gaggactccc acttcgacga gtacatcaag  240
gacatgaaga acagccaaga cgaggacaac ttcatggacg agctcaacag gttcgagaag  300
aacttccacg acgaggactt cgagtccgac gagaacctgt tcaactacgg caagggcggc  360
acccactccg gcgagttcaa caagatcggc gagctcaaca gcggcaacta caacgagatg  420
aagccagacg ccaacgacta ccagtacttc gacaacgagg acatcctgga gggcgacgag  480
gacctgacca acatctggaa caagaacatg caaaacttcg agccaagcac cctcctgacc  540
ttcgagatcc agggcaactc cgaggagtac ctcttcgagg aagtgaccag cctgaacacc  600
tacttccgcg gcgtcttcta ctccaacaac gagagcgacg acaacaagat cctgttcttc  660
atcaccgacc cagacggcga ggtcatctac aagaaggaag cctccgaggg catcttctac  720
ttctacaccc aaaagatcgg cgtgtacacc atcaccctca agaacagcaa gtggatgggc  780
aagaagctga ccaccgtggc tctgggcctg ggcgagtccc caagcctcaa gagcgagcac  840
atcaaggact tcaccaacta catcgacaag atcgtcgccg agacgaagag gctgaagaac  900
gagctcaagt acctgtccag caagcacatg acccacatcg agaagatgaa gaagatcacc  960
aacaaggcct tcctctactg cttcatcaag ctcttcgtgc tggtcttcct ctccctgttc  1020
accatctact acatcaagaa cctcgtgagc aacaagcgcg tcctgcacca ccaccaccac  1080
cactga                                                             1086

SEQ ID NO: 91            moltype = AA  length = 501
FEATURE                  Location/Qualifiers
source                   1..501
```

```
                        mol_type = protein
                        organism = Plasmodium vivax
SEQUENCE: 91
MNNHQAVKQQ MNPKGSKEQN RMVAPNSNMP GGMRDLAYHR NNGNNEMGKM NMNANGQQHN    60
AGSSNTYNSN SINNNNYSLG LYIDNPQNAF VFDENDLKTL FSHYKGAKNI RILNDKAAAQ   120
ITFNDKNMIQ QVRKDINGLT ITDIGTIRCI ILNEGKIVEQ FLPFSANDPA SAQQKGGSNQ   180
SGDSTVDMLK KLANLLQPER AMDSSMAPKM GDNGGLSATG SVNMGASIAT NVGMGGNMPT   240
NANMGGVITT NANVSANVSA NVSANPMPGK NQVKNKMGNH AIYNNGGSHF NQAHMNKGEP   300
GENNPYATKR LSRIELIDIF GFPVEFDVMK KILGKNNSNI SYIKEQTNNS VSIEIKGKPF   360
NEAPIVERMH VSVSSDDLIG YKKATELIVK LLNSIFEEFY DFCYEKNYPV PENLSFKRHE   420
YMYNPDGSTK YVGFKDKWHV MKDSYRTDYS FRKNKGLQKN DKDKRMHGGA FGGHPNLSIG   480
YANQNAPQGD FKEMNHHHHH H                                             501

SEQ ID NO: 92           moltype = DNA  length = 1506
FEATURE                 Location/Qualifiers
source                  1..1506
                        mol_type = genomic DNA
                        organism = Plasmodium vivax
SEQUENCE: 92
atgaacaacc accaagccgt caagcaacag atgaacccaa agggctccaa ggagcagaac    60
aggatggtgg ccccaaacag caacatgcca ggcggcatga gggacctcgc ttaccacagg   120
aacaacggca caacgagat gggcaagatg aacatgaacg ccaacggcca acagcacaac   180
gccggctcca gcaacaccta caactccaac tccatcaaca caacaactac tctccctcgg   240
ctgtacatcg acaacccaca aaacgccttc gtcttgacg agaacgacct caagaccctg   300
ttcagccact acaagggcgc caagaacatc aggatcctca cgacaaggc tgccgcccag   360
atcaccttca acgacaagaa catgatccaa caggtacgga aggacatcaa cggcctgacc   420
atcaccgaca tcggcaccat ccgctgcatc atcctcaacg agggcaagat cgtggagcaa   480
ttcctgccat tctccgccaa cgacccggct agcgctcaac agaagggcgg ctccaaccaa   540
agcggcgact ccaccgtgga catgctcaag aagctcgcta acctcctgca gccagagagg   600
gccatggact ccagcatggc cccaaagatg ggcgacaacg gcggcctctc cgctaccggc   660
tccgtcaaca tgggcgcctc catcgccacc aacgtgggca tgggcggcaa catgccaacc   720
aacgccaaca tgggcggcgt catcaccacc aacgccaacg tgagcgccaa cgtctccgct   780
aacgtgagcg ctaacccaat gccaggcaag aaccaagtga agaacaagat gggcaaccac   840
gccatctaca caacggcgg ctcccacttc aaccaggcca acatgaacaa gggcgagcca   900
ggcgagaaca acccatacg caccaagagg ctcagccgca tcgagctgat cgacatcttc   960
ggcttcccag tcgagttcga cgtgatgaag aagatcctcg gcaagaacaa cagcaacatc  1020
tcctacatca aggagcaaac caacaactcc gtcagcatcg agatcaaggg caagccattc  1080
aacgaggccc aatcgtggaa gcgcatgcac gtgtccgtct ccagcgacga cctcatcggc  1140
tacaagaagg ccaccgagct gatcgtcaag ctcctgaaca gcatcttcga ggagttctac  1200
gacttctgct acgagaagaa ctacccagtg ccagagaacc tgtccttcaa gaggcacgag  1260
tacatgtaca cccagacgg cagcaccaag tatgtgggct tcaaggacaa gtggcacgtg  1320
atgaaggact cctacaggac cgactacagc ttccgcaaga caagggcct ccagaagaac  1380
gacaaggcaa agaggatgca cggcggcgct ttcggcggac acccaaacct gagcatcggc  1440
tacgccaacc aaaacgcccc acagggcgac ttcaaggaga tgaaccacca ccaccaccac  1500
cactga                                                              1506

SEQ ID NO: 93           moltype = AA  length = 185
FEATURE                 Location/Qualifiers
source                  1..185
                        mol_type = protein
                        organism = Plasmodium vivax
SEQUENCE: 93
MREAKGSVRD GKQYVKTKSP TYTPQKKTKV IFYMPGQEQE EEEDDNDPNG SKKNGKSDTG    60
ANKGTHMGSK TDAGNSPSGL NKGSGVGSGS RPASNNYKGN AGGGINIDMS PHGDNSNKGQ   120
QGNAGLNKNQ EDTLRDEYEK IRKQEEEEEE RINNQRRADM KRAQRGKNKF GDDKGVQDSH   180
HHHHH                                                               185

SEQ ID NO: 94           moltype = DNA  length = 558
FEATURE                 Location/Qualifiers
source                  1..558
                        mol_type = genomic DNA
                        organism = Plasmodium vivax
SEQUENCE: 94
atgcgcgagg ctaagggctc cgtgcgcgac ggcaagcaat acgtcaagac caagagccca    60
acctacaccc cacagaagaa gaccaaggtc atcttctaca tgccaggcca agagcaagag   120
gaagaggaag acgacaacga cccaaacggc tccaagaaga acggcaagag cgacaccggc   180
gccaacaagg gcacccacat gggctccaag accgacgctg gcaactcccc gagcggcctc   240
aacaagggct ccggcgtggg ctccggcagc aggccagcga gcaacaacta caagggcaac   300
gccggcggcg gcatcaacat cgacatgtcc ccacacggcg acaacagcaa caagggcaac   360
cagggcaacg ccggcctcaa caagaaccaa gaggacaccc tgagggacga gtacgagaag   420
atccgcaaac aagaggaaga ggaagaggag cgcatcaaca accaaaggcg cgctgacatg   480
aagagggctc agaggggcaa gaacaagttc ggcgacgaca agggcgtgca agacagccac   540
caccaccacc accactga                                                 558

SEQ ID NO: 95           moltype = AA  length = 259
FEATURE                 Location/Qualifiers
source                  1..259
                        mol_type = protein
                        organism = Plasmodium vivax
```

```
SEQUENCE: 95
MSSQSAVDYI  EQEPLDILNL  EEGDLEVTEQ  WKDNEWHNWK  LKLEEDWDSF  STSLIRDKKD   60
FMKIKTDELN  GWLNLEENKW  NNFSGYLSDG  YKNYLLKKSE  KWNDADWENW  ANTEMVAHLD  120
KDYHLWSLNT  ERSVNALVRG  EWNQWQHDKM  SSWLSSDWKK  VGAMYWDLQE  SRNWASYSHT  180
DDMKEHWIKW  NDRNARENIE  WSKWVQNKEY  FIMYARHSDI  EQWKYDNYAL  YSTWRNDFIN  240
RWVSEKKWNS  ILNHHHHHH                                                   259

SEQ ID NO: 96           moltype = DNA   length = 780
FEATURE                 Location/Qualifiers
source                  1..780
                        mol_type = genomic DNA
                        organism = Plasmodium vivax
SEQUENCE: 96
atgtccagcc aaagcgccgt ggactacatc gagcaggagc cactcgacat cctcaacctc    60
gaagagggcg acctggaggt caccgagcag tggaaggaca cgagtggca caactggaag   120
ctcaagctcg aagaggactg ggactccttc agcacctccc tcatcaggga caagaaggac   180
ttcatgaaga tcaagaccga cgagctgaac ggctggctca acctggagga aacaagtgg    240
aacaacttca gcggctacct ctccgacggc tacaagaact acctcctgaa gaagtccgag   300
aagtggaacg acgccgactg ggagaactgg gccaacaccg agatggtggc ccacctcgac   360
aaggactacc acctctggag cctgaacacc gagaggtccg tgaacgctct ggtccgcggc   420
gagtggaacc aatggcagca cgacaagatg tccagctggc tctccagcga ctggaagaag   480
gtcggcgcca tgtactggga cctgcaggag agcaggaact gggcgagcta ctcccacacc   540
gacgacatga aggagcactg gatcaagtgg aacgacagga cgccgcga   aacatcgag   600
tggtccaagt gggtgcaaaa caaggagtac ttcatcatgt acgcccgcca cagcgacatc   660
gagcagtgga agtacgacaa ctacgccctc tactccaccct ggaggaacga cttcatcaac   720
cgctgggtca gcgagaagaa gtggaactcc atcctgaacc accaccacca ccaccactga   780

SEQ ID NO: 97           moltype = AA   length = 257
FEATURE                 Location/Qualifiers
source                  1..257
                        mol_type = protein
                        organism = Plasmodium vivax
SEQUENCE: 97
MKSSNEIERL  THVKLKDTSE  WTENVEEWVK  DEWHEWMDEV  QMDWKEFNSS  LESEKNKWFG   60
KKEKEMMELI  KSIEDKWLDF  NENMHEVLNY  AILKISLMWS  FSEWQKWINK  DGKRIIENQW  120
ERWTISNKNL  YYKIIMKEWF  KWKNKKIKQW  LKRNWLHHEG  RILENWERLP  YTKILAMSEK  180
KPWFNSNAQV  INERDYFLIW  IKKKEDFLVN  EERDKWENWE  YYKNDFFQTW  MDSFLSHWLN  240
IKKRDILHSQ  SHHHHHH                                                    257

SEQ ID NO: 98           moltype = DNA   length = 774
FEATURE                 Location/Qualifiers
source                  1..774
                        mol_type = genomic DNA
                        organism = Plasmodium vivax
SEQUENCE: 98
atgaagtcca gcaacgagat cgagaggctc acccacgtga agctgaagga cacctccgag    60
tggaccgaga acgtggagga gtgggtcaag gacgagtgga tggacgaggtc             120
cagatggact ggaaggagtt caactccagc ctggagtccg agaagaacaa gtggttcggc   180
aagaaggaga aggagatgat ggagctgatc aagagcatcg aggacaagtg gctcgacttc   240
aacgagaaca tgcacgaggt gctcaactac gccatcctca gatctccct gatgtggtcc    300
ttcagcgagt ggcaaaagtg gatcaacaag gacggcaaga ggatcatcga aaccagtgga   360
gagcgctgga ccatcagcaa caagaacctg tactacaaga tcatcatgaa ggagtggttc   420
aagtggaaga acaagaagat caagcaatgg ctcaagagga ctggctgca  ccacgagggc   480
aggatcctgg agaactggga gcgcctgcca tacaccaaga tcctcgccat gtccgagaag   540
aagccatggt tcaacagcaa cgcccaagtg atcaacgagg gggactactt cctgatctgg   600
atcaagaaga aggaagactt cctcgtgaac gaggagcgcg acaagtggga gaactgggag   660
tactacaaga acgacttctt ccaaacctgg atggactcct tcctcagcca ctggctgaac   720
atcaagaagc gcgacatcct ccactcccag agccaccacc accaccacca ctga         774

SEQ ID NO: 99           moltype = AA   length = 118
FEATURE                 Location/Qualifiers
source                  1..118
                        mol_type = protein
                        organism = Plasmodium vivax
SEQUENCE: 99
MRLKHDHNLL  PNYANLMRDD  QNGQNSENRG  DNINNHNKNH  NDQNNHNGNN  DNSINSEYLK   60
TSHLQNSSAM  VHLNDHKITT  KPARYSYIQR  SKIYAFNPNN  KKIENINNEL  HSHHHHHH   118

SEQ ID NO: 100          moltype = DNA   length = 357
FEATURE                 Location/Qualifiers
source                  1..357
                        mol_type = genomic DNA
                        organism = Plasmodium vivax
SEQUENCE: 100
atgaggctca agcacgacca caacctcctg ccaaactacg ccaacctgat gagggacgac    60
caaaacggcc agaactccga gaaccgcggc gacaacatca caaccacaa caagaaccac   120
aacgaccaaa acaaccacaa cggcaacaac gacaactcca tcaacagcga gtacctcaag   180
accagccacc tgcagaactc cagcgccatg gtgcacctca cgaccacaa gatcaccacc   240
aagccagcca ggtactccta catccaacgc agcaagatct acgccttcaa cccaaacaac   300
```

```
aagaagatcg agaacatcaa caacgagctg cactcccacc accaccacca ccactga      357

SEQ ID NO: 101              moltype = AA   length = 651
FEATURE                     Location/Qualifiers
source                      1..651
                            mol_type = protein
                            organism = Plasmodium vivax
SEQUENCE: 101
MSMEQGTPIV FPHKEGTILT KGTNNLAVAH KEEVHRSEEE TTLKGLKEEL PHEHTLAIQK     60
YDPSFGRGGS PGSGSTEHTN GSFSNSYETI LYNKSNDVVK NLKEIKKGAP FGGVISDAVS    120
CPASSSSNTG GNKNLCFSNM MKLSKKILGF PLLTDFERGM STNQPCLPLS DHLKRLSVCT    180
VCYSKHNDLA KAIICRVTKM HFEANYNDGL GDEDMFKTSS ECIQSVIREL ANTIKEYRKR    240
ELSGAYVQEL ARSGSSSYRS CSSSSYSSRG GSCAGSRGDG LAGSHGEIHA VIAGPPLTDD    300
HNDIGAEAHS PSSSLKLPPQ KPFYGMMSDP PCSDRRPGDT NNPFENNTPP LLWDNKVNYT    360
DDYTCKRGEV NSTLGKRPHE EDNKGSSQKK SKLRTKPSND TIGGENGDSL KGGTDEGKTH    420
EGGGNVGSCT AQGGADQLPR SDLCRDPRGD PCVDPLPEQH AHRSKDENQK GDKNDIHFAG    480
EKLDEIEAPG DQKGNYVTLE NISKASNFIP LLGVELGSTK IQREFTNGTY VGTVTEQIKD    540
EHGNPFFVVT YEDGDAEWMT PCFLFQELLK QSTNSVDYPL ATTFKEVFNP EFKKDLKLSN    600
CSLELKIERR KRKSNCESAS NNNSVSKRQK HAQEENSSRK KKQRFHHHHH H             651

SEQ ID NO: 102              moltype = DNA   length = 1956
FEATURE                     Location/Qualifiers
source                      1..1956
                            mol_type = genomic DNA
                            organism = Plasmodium vivax
SEQUENCE: 102
atgtccatgg agcaaggcac cccaatcgtg ttcccacaca aggaaggcac catcctcacc     60
aagggcacca caaacctggc cgtggcccac aaggaagagg tgcacaggag cgaggaagag    120
acgaccctca agggcctgaa ggaagagctc ccacacgagc acaccctggc catccagaag    180
tacgacccaa gcttcggccg cggcggctcc ccaggcagca gcaccgagca cacgaacaac    240
ggctccttca gcaactccta cgagacgatc ctctacaaca agtccaacga cgtggtcaag    300
aacctgaagg agatcaagaa gggcgctcca ttcggcggcg tgatctccga cgccgtctcc    360
tgcccggcct ccagctccag caacaccggc ggcaacaaga acctctgctt cagcaacatg    420
atgaagctct ccaagaagat cctgggcttc ccactcctga ccgacttcga gagggcatg    480
agcaccaacc aaccatgcct cccactgagc gacctcctca agcgcctgtc cgtgtgcacc    540
gtctgctaca gcaagcacaa cgacctggcc aaggccatca tctgcagggt gaccaagatg    600
cacttcgagg ccaactacaa cgacggcctc ggcgacgagg acatgttcaa gacctccagc    660
gagtgcatcc aatccgtgat ccgcgagctg gccaacacca tcaaggagta caggaagcgc    720
gagctgtccg gcgcctacgt ccaagagctc gctaggtccg gctccagctc ctacaggagc    780
tgcagctcca gctcctacag ctccaggggc ggcagctgcg ctggctcccg cggcgacggc    840
ctcgccggct cccacggcga gatccacgcc gtcatcgctg gcccaccact gaccgacgac    900
cacaacgaca tcggcgctga ggctcacagc ccaagctcca gcctcaagct gccaccacaa    960
aagccattct acggcatgat gtccgaccca ccatgctcca acaggcgccc aggcgacacc   1020
aacaacccat tcgagaacaa caccccacca ctcctgtggg acaacaaggt gaactacacc   1080
gacgactaca cctgcaagag gggcgaggtc aactccaccc tcggcaagcg cccacacgag   1140
gaagacaaca agggctccag ccagaagaag tccaagctca ggaccaagcc aagcaacgac   1200
accatcggcg gcgagaacgg cgacagcctc aagggcggca ccgacgaggg caagacccac   1260
gagggcggcg gcaacgtggg ctcctgcacc gccaaggcgg cgccgaccag ctcccaagg    1320
tccgacctgt gcagggaccc acgcggcgac ccatgcgtcg acccactccc agagcaacac   1380
gcccaccgct ccaaggacga gaaccagaag ggcgacaaga acgacatcca cttcgccggc   1440
gagaagctcg acgagatcga ggcccaggc gaccaaaagg gcaactacgt gaccctggag   1500
aacatcagca aggcctccaa cttcatcccg ctcctgggcg tggagctggg cagcaccaag   1560
atccaacgcg agttcaccaa cggcacctac gtgggcaccg tcaccgagca gatcaaggac   1620
gagcacggca cccattcttc cgtggtcacc tacgaggacg gcgacgctga gtggatgacc   1680
ccatgcttcc tcttccagga gctcctgaag cagagcacca actccgtcga ctacccactg   1740
gccaccacct tcaaggaagt gttcaaccca gagttcaaga aggacctcaa gctgagcaac   1800
tgctccctgg agctgaagat cgagaggcgc aagaggaagt ccaactgcga gagcgcctcc   1860
aacaacaaca gcgtgtccaa gcgccaaaag cacgcccaag aggagaactc ctccaggaag   1920
aagaagcagc gcttccacca ccaccaccac cactga                             1956

SEQ ID NO: 103              moltype = AA   length = 793
FEATURE                     Location/Qualifiers
source                      1..793
                            mol_type = protein
                            organism = Plasmodium vivax
SEQUENCE: 103
MTFNDGSDEI STAQKYKTDV EGIIDKLNVI DETINGINST LDELLELGNN CQLHRTFLIS     60
SSLNNKIAKF LVEIREQKEN TKKCFQYVKR NHQHLANFVS ELHKTQGGIF ENVNLVDNTP    120
DADKYYHEFM EIEQEATKIV KDIKKEIYHL NDDVDEPVLE KRIKDVINTY NKLKTKKVQM    180
DQSYKNMYIT KLREVEGSHD LFNQVAQLIR GETDKKGKAL SERENNLHSI YNFVKLHETE    240
LHNLYAKYTP EYMEKINKIF DDINARMIAV DLNDDHSSEY SDVKRHEHEA MLLMDATNNL    300
SKEVEMMQNE SGGKNDGING GKSQLVEDYT NTMSEFTEQA KTVAKKIHDS KGDYANMFDH    360
IRENEAMLER IDLKKKDIKE ILAHLNRMKE YLLKKLSEEE KLHHMREKLE EVNTSTDEIV    420
KKFRTYDQMV DISQNIDIKN VQSKRYDSVD EIDKEMSYIK THNKDLIDSK FIVERALEND    480
KRKKSEMAQI FSTISRDNSS MYEYAKSFFD SVLKEIEKLT QMIRNMDKLI NENEAVMEKL    540
KDQRRELQNV ENASTDLGKL EEVDKMAQTK SETELSERND SRNAKDGATY STLMDDKETD    600
SVNGEETKQE NVVVKKGLPP QTDIYTSVVL KNDRNDQKSE KIGEKKSNKP VGTEENIQHS    660
SYLNNDNSNN DIDVGTLYTL GGYNAPNDNY NTNESGDDIN EEAKKKRNAV LFVYVGGLFS    720
ALFICIGAVF YLLHRKIGIE GVGKSDHEKK PTIEDTKIEV FEETNGSKRN VKDEVIDVPF    780
```

VDMEDNLHHH HHH                                                                          793

SEQ ID NO: 104          moltype = DNA   length = 2382
FEATURE                 Location/Qualifiers
source                  1..2382
                        mol_type = genomic DNA
                        organism = Plasmodium vivax
SEQUENCE: 104
atgaccttca acgacggcag cgacgagatc tccaccgccc aaaagtacaa gaccgacgtg    60
gagggcatca tcgacaagct gaacgtcatc gacgagacga tcaacggcat caacagcacc   120
ctggacgagc tcctggagct cggcaacaac tgccaactcc acaggacctt cctgatctcc   180
agctccctca caacaagat cgccaagttc tcgtggaga tcaggagca gaaggagaac      240
accaagaagt gcttccaata cgtgaagcgc aaccaccagc acctggccaa cttcgtctcc   300
gagctccaca agacccaagg cggcatcttc gagaacgtca acctggtgga caacacccca   360
gacgccgaca agtactacca cgagttcatg gagatcgagc aagaggccac caagatcgtc   420
aaggacatca gaaggagat ctaccacctg aacgacgacg tggacgagcc agtcctggag    480
aagaggatca aggacgtgat caacacctac aacaagctga gaccaagaa ggtccagatg    540
gaccagtcct acaagaacat gtacatcacc aagctgaggg aggtggaggg cagccacgac   600
ctgttcaacc aagtcgccca gctcatcagg ggcgagacgg acaagaaggg caaggccctg   660
tccgagcgcg agaacaacct ccacagcatc tacaacttcg tgaagctgca cgagacggag   720
ctccacaacc tgtacgccaa gtacaccca gagtacatgg agaagatcaa caagatcttc   780
gacgacatca acgccaggat gatcgccgtg gacctcaacg acgaccacag ctccgagtac   840
agcgacgtca agcgccacga gcacgaggcc atgctcctga tggacgccac caacaacctg   900
tccaaggaag tggagatgat gcagaacgag agcggcggca agaacgacgg catcaacggc   960
ggcaagtccc aactcgtgga ggactacacc aacaccatga gcgagttcac cgagcaggcc  1020
aagaccgtcc caagaagat ccacgactcc aagggcgact acgccaaact gttcgaccac   1080
atcagggaga acgaggccat gctggagcgc atcgacctca gaagaagga catcaaggag   1140
atcctcgccc acctgaacag gatgaaggag tacctcctga agaagctgtc gaggaagag   1200
aagctccacc acatgcgcga gaagctcgaa gaggtgaaca cgagcaccga cgagatcgtc   1260
aagaagttcc gcacctacga ccaaatggtg gacatctccc agaacatcga catcaagaac   1320
gtgcaaagca agcgctacga ctccgtcgac gagatcgaca aggagatgtc ctacatcaag   1380
acccacaaca aggacctgat cgacagcaag ttcatcgtcg agagggccct ggagaacgac   1440
aagcgcaaga gagcgagat ggcccaaatc ttcagcacca tctccaggga caacagctcc    1500
atgtacgagt acgccaagag cttcttcgac tccgtgctga aggagatcga gaagctcacc   1560
cagatgatcc gcaacatgga caagctcatc aacgagaacg aggccgtcat ggagaagctg   1620
aaggaccaaa ggcgcgagct ccagaacgtg gagaacgcct ccaccgacct cggcaagctc   1680
gaagaggtgg acaagatggc ccagaccaag agcgagacgg agctgtccga gaggaacgac   1740
agccgcaacg ctaaggacgg cgctacctac tccaccctca tggacgacaa ggagacggac   1800
agcgtgaacg gcgaggagac gaagcaagag aacgtggtcg tgaagaaggg cctgccacca   1860
cagaccgaca tctacaccag cgtcgtgctc aagaacgaca ggaacgacca aaagtccgga   1920
aagatcggcg agaagaagag caacaagcca gtgggcaccg aggagaacat ccagcacagc   1980
tcctacctca caacgacaa ctccaacaac gacatcgacg tgggcaccct ctacccctg    2040
ggcggctaca acgccccaaa cgacaactac aacaccaacg agagcggcga cgacatcaac   2100
gaggaagcca agaagaagag gaacgccgtg ctcttcgtct acgtgggcgg cctcttctcc   2160
gccctgttca tctgcatcgg cgccgtgttc tacctcctgc accgcaagat cggcatcgag   2220
ggcgtcggca agagcgacca cgagaagaag ccaaccatcg aggacaccaa gatcgaggtg   2280
ttcgaggaga cgaacggctc caagcgcaac gtcaaggacg aggtcatcga cgtgccattc   2340
gtcgacatgg aggacaacct ccaccaccac caccaccact ga                     2382

SEQ ID NO: 105          moltype = AA   length = 396
FEATURE                 Location/Qualifiers
source                  1..396
                        mol_type = protein
                        organism = Plasmodium vivax
SEQUENCE: 105
MGEHKTDSKT DNGKGANNLV MLDYETSSNG QPAGTLDNVL EFVTGHEGNS RKNSSNGGNP    60
YDIDHKKTIS SAIINHAFLQ NTVMKNCNYK RKRRERDWDC NTKKDVCIPD RRYQLCMKEL   120
TNLVNNTDTN FHRDITFRKL YLKRKLIYDA AVEGDLLLKL NNYRYNKDFC KDIRWSLGDF   180
GDIIMGTDME GIGYSKVVEN NLRSIFGTDE KAQQRRKQWW NESKAQIWTA MMYSVKKRLK   240
GNFIWICKLN VAVNIEPQIY RWIREWGRDY VSELPTEVQK LKEKCDGKIN YTDKKVCKVP   300
PCQNACKSYD QWITRKKNQW DVLSNKFISV KNAEKVQTAG IVTPYDILKQ ELDEFNEVAF   360
ENEINKRDGA YIELCVCSVE EAKKNTQEVV HHHHHH                             396

SEQ ID NO: 106          moltype = DNA   length = 1191
FEATURE                 Location/Qualifiers
source                  1..1191
                        mol_type = genomic DNA
                        organism = Plasmodium vivax
SEQUENCE: 106
atgggcgagc acaagaccga ctccaagacc gacaacggca agggcgccaa caacctggtc    60
atgctcgact acgagacgtc ctccaacggc cagccagctg gcaccctgga caacgtgctg   120
gagttcgtca ccggccacga gggcaacagc aggaagaact ccagcaacgg cggcaaccca   180
tacgacatcg accacaagaa gaccatctcc agcgccatca tcaaccacgc cttcctgcag   240
aacaccgtga tgaagaactg caactacaag aggaagagc gcgagcgcga ctgggactgc   300
aacaccaaga aggacgtctg catcccagac aggcgctacc aactctgcat gaaggagctg   360
accaacctcg tgaacaacac cgacaccaac ttccacaggg acatcacctt ccgcaagctg   420
tacctcaaga ggaagctgat ctacgacgct gctgtggagg gcgacctcct gctcaagctc   480
aacaactaca ggtacaacaa ggacttctgc aaggacatcc gctggtccct gggcgacttc   540
ggcgacatca tcatgggcac cgacatggag ggcatcggct actccaaggt ggtcgagaac   600

-continued

```
aacctccgca gcatcttcgg caccgacgag aaggcccaac agaggcgcaa gcaatggtgg    660
aacgagtcca aggcccagat ctggaccgcc atgatgtaca gcgtgaagaa gaggctgaag    720
ggcaacttca tctggatctg caagctcaac gtggccgtca acatcgagcc acagatctac    780
aggtggatca gggagtgggg cagggactac gtctccgagc tgccaaccga ggtgcaaaag    840
ctcaaggaga agtgcgacgg caagatcaac tacaccgaca agaaggtgtg caaggtccca    900
ccatgccaaa acgcctgcaa gagctacgac cagtggatca ccaggaagaa gaaccaatgg    960
gacgtcctgt ccaacaagtt catcagcgtg aagaacgccg agaaggtcca gaccgccggc    1020
atcgtgaccc catacgacat cctgaagcaa gagctcgacg agttcaacga ggtggccttc    1080
gagaacgaga tcaacaagcg cgacggcgcc tacatcgagc tgcgcgtgtg cagcgtcgag    1140
gaagccaaga gaacacccca gaggtggtc caccaccacc accaccactg a             1191

SEQ ID NO: 107           moltype = AA   length = 835
FEATURE                  Location/Qualifiers
source                   1..835
                         mol_type = protein
                         organism = Plasmodium vivax
SEQUENCE: 107
MVIGGSPNNE APNSSRHHLR NGFPGKNDSL PHEEPNNLEG KNESSDQCDT INLGQVTEKE     60
KKTIEQASVQ AQDATKPEAN NAEQIQAELQ KVKTAKDESA TAAKDAETAK KNAVDAGKGL   120
DAAKGAIKKA EEAAAEAKKQ AGIAEKAEKD AEAAGKKDKL EDVNSQVQIA VEASTKAKDK   180
KTEAEIAVEI VKAVVAKEEA QKASDEAQKA CEKAQKAHAK AQKASDTTKT VETFKTNAEA   240
AAKNAKEKAG NANKAATEAE SANELSVAKQ KAKDAEEAAK EAKKEQVKAE IAAEVAKAKV   300
AKEEADAAQK KAEAAKKIVD KIAQDTKVPE AQREAKLATQ TASKATEAAT EAGKKAQEAE   360
ESSKEAEEKA ETSDAVKGKA DAAEKAAGEA KKASIETEIA IEVAKAEVLN AEVKKTAQEA   420
EKDATEAKEQ AEKAKAAAEE AKTHGEKAEK VGESTKAHSD EAQQENKNAK DASEEAENRA   480
VDALEEAYAV EAHLARTKNA AESAKSATDM SELEKAKEEA IDAANIAHQK WLKATQAATI   540
AKEKKEAAKV AAEKAQTAAN VVKDKAAKAE AKKAETEAVK AAVEARAAAE EAKQEAAKVG   600
ASKEPQETKN KANVEAEATG NEAKKAEDAA EEAKEAAKKA NEATDANVAR SEADKAIAAA   660
KKAKKAREKA AYGLLKTKNQ YVLEPLDISP ESADNITSKE EQVKEEMEDQ GDEDSNEAEV   720
EEALPNGSGA QEEDVNLEMD DEEEVEEVEE NVATNQQTGG KREKRNTNDT VDDTNADKQF   780
GDEFDTYNDI KKVTEALVKS MTSLVSDDPS VGDTINEFLS DMNHLFLSWH HHHHH        835

SEQ ID NO: 108           moltype = DNA   length = 2508
FEATURE                  Location/Qualifiers
source                   1..2508
                         mol_type = genomic DNA
                         organism = Plasmodium vivax
SEQUENCE: 108
atggtcatcg gcggctcccc aaacaacgag gccccaaact ccagcaggca ccacctccgc     60
aacggcttcc caggcaagaa cgactccctc ccacacgagg agccaaacaa cctggagggc    120
aagaacgagt ccagcgacca atgcgacacc atcaacctgg gccaggtgac cgagaaggag    180
aagaagacca tcgagcaagc tagcgtccaa gctcaggacg ctaccaagcc agaggccaac    240
aacgccgaca aaatccaggc cgagctccaa aaggtgaaga ccgctaagga cgagtccgca    300
accgctgcta aggacgctga cgcgccaag aagaacgctg tggacgctgg caagggcctg    360
gacgccgcca agggcgccat caagaaggct gaggaagccg ccgccgaggc caaggaagcag   420
gctggcatcg ccgagaaggc tgagaaggac gctgaggctg ctggcaagaa ggacaagctg   480
gaggacgtga acagccaagt ccagatcgcc gtggagtcc aagaagacaag             540
aagaccgagg ccgagatcgc cgtggagatc gtcaaggccg tggtcgccaa ggaagaggcc    600
caaaaggcta gcgacgaggc tcagaaggct tgcgagaagg cccaaaaggc tcacgctaag    660
gctcagaagg cttccgacac caccaagacc gtggagacgt tcaagaccaa cgccgaggct    720
gccgccaaga acgccaagga aaaggctggc aacgctaaca aggctgctac aggctgct     780
agcgctaacg agctctccgt ggccaagcag aaggccaagg acgccgagga agccgccaag    840
gaagccaaga aggagcaagt caaggctgag atcgctgctg aggtggctaa ggctaaggtg    900
gctaaggaag aggccgacgc tgctcagaag aaggctgagg ccgccaagaa gatcgtggac    960
aagatcgccc aagacaccaa ggtgccggag gctcagaagg aggctaccag gctacccag   1020
accgctagca aggctaccga ggccgccacc gaggctggca agaaggtcca gagggccgag    1080
gagtccagca aggaagccga ggagaaggct gagacgagcg acgctgtgaa gggcaaggct    1140
gacgctgctg agaaggctgc tggcgaggcc aagaaggctt ccatcgagac ggagatcgcc    1200
atcgaggtcg ccaaggccga ggtgctcaac gccgagtca agaagaccgc tcaagaggcc    1260
gagaaggacg ctaccgaggc caaggacgaa gccaaggctgc cgccgaggaa              1320
gccaagaccc acggcgagaa ggctgagaag gtgggcgaga gcaccaaggc ccactccgac    1380
gaggcccaac aggagaacaa gaacgccaag gacgccagcg aggaagccga gaacagggct    1440
gtggacgctc tcgaagaggc ctacgctgtg gaggctcacc tggctaggac caagaacgct    1500
gctgagtccg ctaagagcgc taccgacatg tccgagctgg agaaggccaa ggaagaggcc    1560
atcgacgccc caacatcgc ccaccaaaag tggctcaagg ctaccaggc tgctaccatc    1620
gctaaggaga agaggaagc cgccaaggtg gctgctgaga aggctcagac cgctgccaac    1680
gtggtcaagg acaaggctgc taaggctgag gccaagaagg ctgagacgga ggccgtcaag    1740
gctgctgtgg aggccagggc cgccgccgag aagccaaac aaggccgc taaggtcggc      1800
gctagcaagg agccacaaga gacgaagaac aaggctaacg tggagctga ggctaccggc    1860
aacgaggcca agaaggccga ggacgctgct gaggaagcca aggaagccgc caagaaggct    1920
aacgaggcta ccgacgctaa cgtggctagg tccgaggctg acaaggctat cgccgccgcc    1980
aagaaggcca agaaggcccg cgagaaggct gcttacggcc tcctgaagac caagaaccaa    2040
tacgtgctgg agccactgga catctcccca gagcgccg acaacatcac ctccaaggaa    2100
gagcaggtga aggaagat ggaggaccaa ggcgacgag agcaatgaag                2160
gaggaagccc tgccaaacgg ctccggcgct caagaggaag acgtcaacct ggagatggac    2220
gacgaggaag aggtgaagga agtggaggag aacgtggcca ccaaccaaca gaccggcgc    2280
aagagggaga agcgcaacac caacgacacc gtcgacgaca ccaacgccga caagcaattc    2340
ggcgacgagt tcgacaccta caacgacatc aagaaggtga ccgaggccct cgtcaagtcc    2400
atgaccagcc tggtgtccga cgacccatcc gtgggcgaca ccatcaacga gttcctcagc    2460
```

```
gacatgaacc acctcttcct gtcctggcac caccaccacc accactga        2508

SEQ ID NO: 109          moltype = AA  length = 117
FEATURE                 Location/Qualifiers
source                  1..117
                        mol_type = protein
                        organism = Plasmodium vivax
SEQUENCE: 109
MENNKIKGGK VPPPSVPTGN NSDNNVPKKD GGENNPPPDA ENALQELKNF TKNLEKKTTT   60
NRNIIISTTV INMVLLVLLS GLIGYNTKKG FKKGQMGSVK EVTPEAQKGK LHHHHHH     117

SEQ ID NO: 110          moltype = DNA  length = 354
FEATURE                 Location/Qualifiers
source                  1..354
                        mol_type = genomic DNA
                        organism = Plasmodium vivax
SEQUENCE: 110
atggagaaca acaagatcaa gggcggcaag gtgccaccac catccgtccc aaccggcaac   60
aactccgaca acaacgtgcc aaagaaggac ggcggcgaga acaacccacc accagacgcc  120
gagaacgccc tccaagagct gaagaacttc accaagaacc tggagaagaa gaccaccacc  180
aacaggaaca tcatcatctc caccaccgtc atcaacatgg tgctcctggt cctcctgagc  240
ggcctgatcg gctacaacac caagaagggc ttcaagaagg gccaaatggg ctccgtgaag  300
gaagtgaccc cagaggccca aaagggcaag ctccaccacc accaccacca ctga        354

SEQ ID NO: 111          moltype = AA  length = 614
FEATURE                 Location/Qualifiers
source                  1..614
                        mol_type = protein
                        organism = Plasmodium vivax
SEQUENCE: 111
ENPVRHSVDI KSEDFVVLIS LQNLQTFIMI GYTAVNKDHL NFDFSYLWAL CIGTGLFIYS   60
LISFVLIRSL ALSKIDIGKY VLELLFSLSI IATCSLSIII DSPKIANMQL LPFFSFALTGY 120
AYYNLMSLFF FCTLVGMTIQ YNLSFTGFRA HSTSFFFLDM LSYLVQMIGG NILYFRMYEL  180
CTLIVISKRN PCKYVVASKE VKQVEKQIFS SLFNSYMCIK SKTYSDLTCT NDLLNKDSQS  240
VVGRDTNPKW NSPIGTSYQD KVNHTKKLLL RRGKRDKRYP KGGGGARLTC AKHSAYHNSR  300
SLANCASKNT PICTTNFRIS NTLSLKNHFN PNLTLEASPP VCKKCVSEKN SHKDNEYKNG  360
EERRKAKRGI KSGTANKSNQ LGNHGGDATQ VANPTYRTTS HGGDATQVAY PTYRTTSHGG  420
DATQVDSPTH PTTSHGGNNS SSGHPQDDEV LIPIRGTNAT NDAAATYNSN ASWIKTAAVI  480
DVSVEGKQKK GGHQTFAGNP VNSSANFPSD KKPSYNSHRN GGTPPPNEQL RYYACPCYQT  540
HSSGSSLSEV PSGQTTKRKN SAHNSVEGGN PKMDNQQSRR VSNKRVDGAT GEEHDHPSDP  600
PADNPNGNSN TYHC                                                    614

SEQ ID NO: 112          moltype = AA  length = 365
FEATURE                 Location/Qualifiers
source                  1..365
                        mol_type = protein
                        organism = Plasmodium vivax
SEQUENCE: 112
ELSHSLSVKN APDASALNIE VEKDKKKICK NAFQYINVAE LLSPREEETY VQKCEEVLDT   60
IKNDSPDESA EAEINEFILS LLHARSKYTI INDSDEEVLS KLLRSINGSI SEEAALKRAK  120
QLITFNRFIK DKAKVKNVQE MLVISSKADD FMNEPKQKML QKIIDSFELY NDYLVILGSN  180
INIAKRYSSE TFLSIKNEKF CSDHIHLCQK FYEQSIIYYR LKVIFDNLVT YVDQNSKHFK  240
KEKLLELLNM DYRVNRESKV HENYVLEDET VIPTMRITDI YDQDRLIEVV VQDGNSKLMH  300
GRDIEKREIS ERYIVTVKNL RKDLNDEGLY ADLMKTVKNY VLSITQIDND ISNLVRELDH  360
EDVEK                                                              365

SEQ ID NO: 113          moltype = AA  length = 162
FEATURE                 Location/Qualifiers
source                  1..162
                        mol_type = protein
                        organism = Plasmodium vivax
SEQUENCE: 113
LPWTKKRKAV NQMGIIKDMS QELRTKAEQL PTPEDISAKI HRVDKEVIDK LNKDIIEEEN   60
LDKHKPHVCQ EPAYERDYSY LCPEDWVKNS NDQCWGIDYD GHCEALKYFQ DYSVEEKKEF  120
EMNCCVLWPK LKNEGMKGAH KKDLLRGSIS SNNGLIIKPK YL                     162

SEQ ID NO: 114          moltype = AA  length = 315
FEATURE                 Location/Qualifiers
source                  1..315
                        mol_type = protein
                        organism = Plasmodium vivax
SEQUENCE: 114
ELKKNNAALT SQRSSSRTTS TRSYKNAPKN STSFLSRLSI LIFALSCAIF VNTASGAAAN   60
RPNANGFVSP TLIGFGELSI QESEEFKRMA WNNWMLRLES DWKHFNDSVE EAKTKWLHER  120
DSAWSDWLRS LQSKWSHYSE KMLKEHKSNV MEKSANWNDT QWGNWIKTEG RKILEAQWEK  180
WIKKGDDQLQ KLILDKVQQW KNDKIRSWLS SEWKTEEDYY WANVERATTA KWLQEAEKMH  240
WLKWKERINR ESEQWVNWVQ MKESVYINVE WKKWPKWKND KKILFNKWST NLVYKWTLKK  300
QWNVWIKEAN TAPQV                                                   315
```

```
SEQ ID NO: 115              moltype = AA  length = 529
FEATURE                     Location/Qualifiers
source                      1..529
                            mol_type = protein
                            organism = Plasmodium vivax
SEQUENCE: 115
KGVTLSCVFS HASEEREGGT GTFALSNEPI YYAPSGGLAP CALISRGLSG DEEGSGEDGG    60
EDGDGDGGED SAEDNAEGDG DDGGEDGGLP GGRFPYEEGK KSSLVSDAPS DLLDGDADEH   120
AAEDGGAKRK MSKKEEEAED NKIDKLVNAE MKKLEAGEEA NKDPDAEPEK EDQGSGQGQR   180
AKLRCSNKLN YIQVTANGQR EGDLFGENDG ESAPAFVEIP HEVEEESGGV PTKHDEAGEA   240
AAAEEPHNRV DRAEKENNAK DLKFVEGERE RQRSSPPSNG YSQNSFVELK GVPDKLPPNF   300
TNSLGSSPTH SNLEKPVYKH LPWSILASDS GSNTGSWADV NSSTYNVSPF SFTSIRSGNS   360
LHLLPMNFQI QNSIVKVTDE EYDKLKLKNS VKVYDKNALV DYKYEIFEVK EGEEYNDGND   420
PYEERNGEEG DAGGEGGSDG EGDADSKSYQ NNKSDGRGFF DGTLVTYTII ILAGVIILLL   480
SFVIYYYDII NKVKRRMSAK RKNNKSMAIA NDTSAGMYMG DTYMENPHV              529

SEQ ID NO: 116              moltype = AA  length = 334
FEATURE                     Location/Qualifiers
source                      1..334
                            mol_type = protein
                            organism = Plasmodium vivax
SEQUENCE: 116
SQGCSGYRLP PPKRWFTFTS RPYCKTAAYY ELKHMPYYVD AVSASENVKH EKWNNWLKEM    60
KISLTEKLEK ESQEYMEKLE QQWDEFMKNS EDKWRHYNPQ MEEEYQCSVY PLGLKWDDEK   120
WTAWFYEKGL WCLKKSFKTW LTDSKKGYNT YMKNLLQEFG KQFYEDWCRR PEKRREDKIC   180
KRWGQKGLRN DNYYSLKWMQ WRNWKNRNHD QKHVWVTLMK DALKEYTGPE FKLWTEFRKE   240
KIDFYKQWMQ AFAEQWTQDK QWNTWTEERN EYMKKKKEEE AKKKAASKKK AASKKGGAAK   300
KAPAKKAPTK KAAPGTKAPA KKAAPKKVAA PNAA                              334

SEQ ID NO: 117              moltype = AA  length = 269
FEATURE                     Location/Qualifiers
source                      1..269
                            mol_type = protein
                            organism = Plasmodium vivax
SEQUENCE: 117
KEAVKKGSKK AMKQPMHKPN LLEEEDFEEK ESFSDDEMNG FMEESMDASK LDAKKAKTTL    60
RSSEKKKTPT SGMSGMSGSG ATSAATEAAT NMNATAMNAA AKGNSEASKK QTDLSNEDLF   120
NDELTEEVIA DSYEEGGNVG SEEAESLTNA FDDKLLDQGV NENTLLNDNM IYNVNMVPHK   180
KRELYISPHK HTSAASSKNG KHHAADADAL DKKLRAHELL ELENGEGSNS VIVETEEVDV   240
DLNGGKSSGS VSFLSSVVFL LIGLLCFTN                                    269

SEQ ID NO: 118              moltype = AA  length = 771
FEATURE                     Location/Qualifiers
source                      1..771
                            mol_type = protein
                            organism = Plasmodium vivax
SEQUENCE: 118
NLSNDCKKGA NNSFKLIVHT SDDILTLKWK VTGEGAAPGN KADVKKYKLP TLERPFTSVQ    60
VHSANAKSKI IESKFYDIGS GMPAQCSAIA TNCFLSGSLE IEHCYHCTLL EKKLAQDSEC   120
FKYVSSEAKE LIEKDTPIKA QEEDANSADH KLIESIDVIL KAVYKSDKDE EKKELITPEE   180
VDENLKKELA NYCTLLKEVD TSGTLNNHQM ANEEETFRNL TRLLRMHSEE NVVTLQDKLR   240
NAAICIKHID KWILNKRGLT LPEEGYPSEG YPPEEYPPEE LLKEIEKEKS ALNDEAFAKD   300
TNGVIHLDKP PNEMKFKSPY FKKSKYCNNE YCDRWKDKTS CMSNIEVEEQ GDCGLCWIFA   360
SKLHLETIRC MRGYGHFRSS ALFVANCSKR KPEDRCNVGS NPTEFLQIVK DTGFLPLESD   420
LPYSYSDAGN SCPNKRNKWT NLWGDTKLLY HKRPNQFAQT LGYVSYESSR FEHSIDLFID   480
ILKREIQNKG SVIIYIKTNN VIDYDFNGRV VHSLCGHKDA DHAANLIGYG NYISAGGEKR   540
SYWIVRNSWG YYWGDEGNFK VDMYGPEGCK RNFIHTAVVF KIDLGIVEVP KKDEGSIYSY   600
FVQYVPNFLH SLFYVSYGKG ADKGAAVVTG QAGGAVVTGQ TETPTPEAAK NGDQPGAQGS   660
EAEVAEGGQA GNEAPGGLQE SAVSSQTSEV TPQSSITAPQ IGAVAPQIGA AAPQIDVAAP   720
QIDVVAPQTR SVDAPQTSSV AAHPPNVTPQ NVTLGEGQHA GGVGSLIPAD N           771

SEQ ID NO: 119              moltype = AA  length = 219
FEATURE                     Location/Qualifiers
source                      1..219
                            mol_type = protein
                            organism = Plasmodium vivax
SEQUENCE: 119
ETLLDSETLK NYEKETNEYI RKKKVEKLFD VILKNVLVNK PENVYLYIYK NIYSFLLNKI    60
FVIGPPLLKI TPTLCSAIAS CFSYYHLSAS HMIESYTTGE VDDAAESSTS KKLVSDDLIC   120
SIVKSNINQL NAKQKRGYVV EGFPGTNLQA DSCLRHLPSY VFVLYADEEY IYDKYEQENN   180
VKIRSDMNSQ TFDENTQLFE VAEFNTNPLK DEVKVYLRN                         219

SEQ ID NO: 120              moltype = AA  length = 113
FEATURE                     Location/Qualifiers
source                      1..113
                            mol_type = protein
                            organism = Plasmodium vivax
SEQUENCE: 120
YPKKNFDKPD PTSPYQGQYG ESEEQRQGYG IPPNPTMINL TGNQDQRPNV LQQFGINNKN    60
```

```
VMQFLINMFV YVAAILVSLK IWDYMSYSKC DYYKDLLLRI VRYQSHMNDG KMA         113

SEQ ID NO: 121              moltype = AA  length = 666
FEATURE                     Location/Qualifiers
source                      1..666
                            mol_type = protein
                            organism = Plasmodium vivax
SEQUENCE: 121
SRIDKQPIQS SYLFQDNAVP PVRFSAVDAD LFSIGVVHTE EQIFMDDANW VISSVPSKYL   60
NLHLLKTGSR PHFSHFSVSM NTGCNLFIAS PVGETFPLSP SKDGATWKAF ETDDSVEVIH  120
RETKEKRIYK LKFIPLKSGA LLKVDVLKGI PFWVISQGRK ILPTICSGDE EVLSNPQNEV  180
FKECTSSSSL SPEFDCLAGL STYHRDKKNH TWKTSSGSIG QFIKIFFNKP VQITKFRFKP  240
RDDLLSWPSE VALQFDTDEE VIIPILHTHN MGQNTTRLEH PIITTSVKVE VRDMYERASE  300
NTGGSFEVIG STCQMMEDDY MTHHAVIDIT ECDRRLESLP DVMPLTKGSK FLAICPRPCL  360
SSSNGGVIYG SDVYSTDSAV CGAAVHAGVC SREGEGSCHF LVVVRGGRAN FVGALQNNVL  420
SLSRGGGGSG SGSSTSSDGD GDSDSSTSRA NFSFSLSSAS GFGGGPRGAH AEAAPSSYSI  480
VFKPRDHLAP TNGFLVDSGR EFTSYGSVAY GWKREVSPSS SFSSPSPSYT SPPLEEPTLL  540
RGDSSSFNGI YSGGIEFPPA SASQNCISQL DCQTNFWKFQ MQENGTYFVQ VLVGNKTSPE  600
KQKAFVELNG VPIIKGVDLG PDEVFVATDR VQVTNRALVL TSTCLGGESA CSRARVSIMA  660
VQIVKT                                                             666

SEQ ID NO: 122              moltype = AA  length = 582
FEATURE                     Location/Qualifiers
source                      1..582
                            mol_type = protein
                            organism = Plasmodium vivax
SEQUENCE: 122
NGMNKDKDAE ITPPPFIVLP GGKKIHMLQS EYEYDVLRDM YRTDEANGGS GEKESHPSGD   60
GAIRRNEFFK LFHHREGHYK FVIKNVPTKL SDLLQKGGNE QETDLFPLLY RSLQFACSAD  120
GTWPYARREV AFFKNGSVHC EAEFQNELSV RRTPRSGKKS RGRFPRGTLI KSSDLRSKIV  180
EGNSYDKRAA PLKSEKKKKA LFLHPESVLY KMEEIFFYEN PSVKSEIVGF VLFHDVCTVT  240
SLGHGAHPVN SPFLGSDLLE MIFGYCILHG FKKIRVKSES LNYETGIRTS FIEILLNGKT  300
ALEHLGLRLT NVAKFSKELY YVITGYTWKS DLVLSPIVRF EHDLYVHHDI EERFFLYVNK  360
MYRNMLHDLS FSCDENYYPY KNCYDIYPSV RRSQNNLCLF ELNPIYEELK ELFPDSCNIG  420
QRVRKCYEEI KKNVVCTHNG EGGEDGCKYY QFIVNTFIKP RRKTSFFIYH NMYVQEYLSK  480
KSYPYYLLLS EVIKNEENNF LEKGNYDLVA DAQTHLFLNY VLQNSTFFIF WNFSTEFWKR  540
FRYIQAGPTG ATSTPQKGQA VFCPMAYAYE FVEHLDTFYV RG                     582

SEQ ID NO: 123              moltype = AA  length = 392
FEATURE                     Location/Qualifiers
source                      1..392
                            mol_type = protein
                            organism = Plasmodium vivax
SEQUENCE: 123
SVEEAKKNTQ EVVTNVDNAA KSQATNSNPI SQPVDSSKAE KVPGDSTHGN VNSGQDSSTT   60
GKAVTGDGQN GNQTPAESDV QRSDIAESVS AKNVDPQKSV SKRSDDTASV TGIAEAGKEN  120
LGASNSRPSE STVEANSPGD DTVNSASIPV VSGENPLVTP YNGLRHSKDN SDSDGPAESM  180
ANPDSNSKGE TGKGQNDMA KATKDSSNSS DGTSSATGDT TDAVDREINK GVPEDRDKTV  240
GSKDGGGEDN SANKDAATVV GEDRIRENSA GGSTNDRSKN DTEKNGASTP DSKQSEDATA  300
LSKTESLEST ESGDRTTNDT TNSLENKNGG KEKDLQKHDF KSNDTPNEEP NSDQTTDAEG  360
HDRDSIKNDK AERRKHMNKD TFTKNTNSHH LN                                392

SEQ ID NO: 124              moltype = AA  length = 530
FEATURE                     Location/Qualifiers
source                      1..530
                            mol_type = protein
                            organism = Plasmodium vivax
SEQUENCE: 124
IRNGNNPQAL VPEKGADPSG GQNNRSGENQ DTCEIQKMAE EMMEKMMKEK DVFSSIMEPL   60
QSKLTDDHLC SKMKYTNICL HEKDKTPLTF PCTSPQYEQL IHRFTYKKLC NSKVAFSNVL  120
LKSFIDKKNE ENTFNTIIQN YKVLSTCIDD DLKDIYNASI ELFSDIRTSV TEITEKLWSK  180
NMIEVLKTRE QTIAGILCEL RNGNNSPLVS NSFSYENFGI LKVNYEGLLN QAYAAFSDYY  240
SYFPAFAISM LEKGGLVDRL VAIHESLTNY RTRNILKKIN EKSKNEVLNN EEIMHSLSSY  300
KHHAGGTRGA FLQSRDVREV TQGDVSVDEK GDRATTAGGN QSASVAAAAP KDAGPTVAAP  360
NTAATLKTAA SPNAAATNTA APPNMGATSP LSNPLYGTSS LQPKDVAVLV RDLLKNTNII  420
KPENNEPTSQ MDDEEIKKLI ESSFFDLSDN TMLMRLLIKP QAAILLIIES FIMMTPSPTR  480
DAKTYCKKAL VNGQLIETSD LNAATEEDDL INEFSSRYNL FYERLKLEEL             530

SEQ ID NO: 125              moltype = AA  length = 524
FEATURE                     Location/Qualifiers
source                      1..524
                            mol_type = protein
                            organism = Plasmodium vivax
SEQUENCE: 125
KEYCDQLSFC DVGLTHHFDT YCKNDQYLFV HYTCEDLCKT CGPNSSCYGN KYKHKCLCNS   60
PPFESKKNHSI CEARGSCDAQ VCGKNQICKM VDAKATCTCA DKYQNVNGVC LPEDKCDLLC  120
PSNKSCLLEN GKKICKCING LTLQNGECVC SDSSQIEEGH LCVPKNKCKR KEYQQLCTNE  180
KEHCVYDEQT DIVRCDCVDH FKRNERGICI PVDYCKNVTC KENEICKVVN NTPTCECEKN  240
LKRNSNNECV FNNMCLVNKG NCPIDSECIY HEKKRHQCLC HKKGLVAING KCVMQDMCRS  300
```

```
DQNKCSENSI CVNQVNKEPL CICLFNYVKS RSGDSPEGGQ TCVVDNPCLA HNGGCSPNEV    360
CTFKNGKVSC ACGENYRPRG KDSPTGQAVK RGEATKRGDA GQPGQAHSAN ENACLPKTSE    420
ADQTFTFQYN DDAAIILGSC GIIQFVQKSD QVIWKINSNN HFYIFNYDYP SEGQLSAQVV    480
NKQESSILYL KKTHAGKVFY ADFELGHQGC SYGNMFLYAH REEA                     524

SEQ ID NO: 126          moltype = AA  length = 340
FEATURE                 Location/Qualifiers
source                  1..340
                        mol_type = protein
                        organism = Plasmodium vivax
SEQUENCE: 126
SKNIIILNDE ITTIKSPIHC ITDIYFLFRN ELYKTCIQHV IKGRTEIHVL VQKKINSAWE     60
TQTTLFKDHM WFELPSVFNF IHNDEIIIVI CRYKQRSKRE GTICKRWNSV TGTIYQKEDV    120
QIDKEAFANK NLESYQSVPL TVKNKKFLLI CGILSYEYKT ANKDNFISCV ASEDKGRTWG    180
TKILINYEEL QKGVPYFYLR PIIFGDEFGF YFYSRISTNN TARGGNYMTC TLDVTNEGKK    240
EYKFKCKHVS LIKPDKSLQN VAKLNGYYIT SYVKKDNFNE CYLYYTEQNA IVVKPKVQND    300
DLNGCYGGSF VKLDESKALF IYSTGYGVQN IHTLYYTRYD                          340

SEQ ID NO: 127          moltype = DNA  length = 1842
FEATURE                 Location/Qualifiers
source                  1..1842
                        mol_type = genomic DNA
                        organism = Plasmodium vivax
SEQUENCE: 127
gagaaccccg tgaggcactc ggtggacata aagtcggaag acttcgtcgt cctgatttcg     60
ctccaaaacc tgcagacctt catcatgata gggtacacag ccgtgaacaa agaccacctg    120
aatttcgact tctcctactt atgggccctc tgcatcggga cgggcctctt catatactcc    180
ctcatcagct ttgtactcat aagatcccta gcactgtcaa aaatagacat aggcaaatac    240
gtcctggagc tgctattcag tttgagtata atcgccacat gttcactctc cataataatt    300
gactctttca aaatagccaa catgcagttg ctttttttttt cgttcgcttt aacgggctat    360
gcctactaca atttgatgag cctcttcttt ttctgcacac tggtaggaat gaccattcag    420
tacaatttaa gttcactggg gttcagagcg cattcgactt cttttcttctt tttagatatg    480
ctatcttacc tagtgcaaat gataggaggg aacatcctct actttcgcat gtacgagctg    540
tgtaccctaa tcgtcatttc gaagaggaac ccctgcaagt atgttgtcgc atcgaaggaa    600
gtgaaacaag tggagaagca aatttttctct tctttatttta attcttacat gtgcatcaag    660
tccaaaactt attcagattt aacctgcact aatgatctgt taaataaaga cagtcaatct    720
gttgtcggta gggatacgaa ccctaagtgg aactccccca ttggtacttc ctaccaggat    780
aaggtcaatc atacgaagaa gttactcctt cggagggg aacgggacaa acgctacccc    840
aaaggggag gggagctcg actaacatgt gcaaaacata gtgcctacca taatagccga    900
agtcttgcca actgtgccag taagaatacc cccattgca caactaactt taggatatct    960
aacaccctt cacttaaaaa tcatttcaac cctaacctaa cctagaagc gtctcccccc   1020
gtttgtaaaa aatgcgttc ggaaaagaat agccataagg ataatgagta caaaaacggg   1080
gaagagagaa aaaagcaaa acgtggtatc aagtcgggca ctgcaaacaa gtctaaccag   1140
ttgggcaacc acgggggga cgctacgcag gtgctaatc ctacctacag aactacttcc   1200
cacggggggg acgcaaccca ggtggctat cctacctaca gaactacttc ccacggggg    1260
gacgcaacgc aggtggatag tcctacccac ccaactacct cccatggggg gaacaactcg   1320
tcgagcgggc accccaaga cgacgaagtg ctcatcccca ttagggggaac caacgccact   1380
aacgatgcag ccgccaccta caactcgaac gctagttgga tcaaaaccgc tgcggttatt   1440
gacgtgtctg tggaggggaa gcagaaaaag gggggacatc aaacgttcgc gggcaatccc   1500
gtaaattcat ccgctaattt cccatcggac aagaaaccat cctacaactc gcaccgcaac   1560
ggaggtactc ccccccaaa tgaacaactc aggtactacg cctgcccctg ctaccagaca   1620
cactccagcg gatcgtccct cagtgaggtg ccctcgggac aaacgacgaa gcggaaaaat   1680
agtgcgcaca actcggttga aggggaaac cccaaaatgg ataatcagca aagtcgccgc   1740
gtgagtaaca agcgggtaga tggcgcaacg ggtgaggaac atgaccaccc aagtgacccc   1800
cccgcagata acccaaatgg aaactccaac acctaccact gc                     1842

SEQ ID NO: 128          moltype = DNA  length = 1095
FEATURE                 Location/Qualifiers
source                  1..1095
                        mol_type = genomic DNA
                        organism = Plasmodium vivax
SEQUENCE: 128
gagctgagcc acagcttgtc cgtgaagaac gcgccggacg cgagcgcgct gaacatcgag     60
gtggagaagg acaaaaagaa gatctgcaaa aacgcattcc aatacataaa cgtagctgag    120
ctgttgtccc caaggaggga agaaacctac gtgcagaaat gtgaagaggt cctagacaca    180
ataaagaatg acagtccaga tgaatcggca gaagcagaga taaacgaatt tatactgagc    240
ttactgcacg ctcgttctaa gtataccata taaatgact cagatgagga ggtactgagc    300
aagctcctga ggagtatcaa cggatcgata agtgaagagg cagcgttgaa gagagccaaa    360
cagctaatca cattcaatcg gtttataaaa gacaaagcga aggtaaaaaa tgtgcaagag    420
atgctagtaa taagtagcaa agcagatgac ttcatgaatg agccgaagca aaaaatgctc    480
caaaaaatta tagattcgtt tgaactgtat aatgattacc tagtcatttt agggtcaaat    540
attaacatcg ccaagaggta ctcctcagaa acgtttcttt ctattaaaaa tgaaaagttc    600
tgctcagacc acatccactt atgccagaag ttctacgagc agtctatcat ttactacaga    660
ttgaaggtta ttttttgataa cctggtgact tatgtagatc aaaattccaa gcattttaaa    720
aaggaaaagt tgctggagct tctaaatatg gattataggg tcaatcgaga gtcgaaggtg    780
catgaaaatt acgtgctgga ggatgagacg gtcatcccca cgatgcgcat tacagacatt    840
tacgatcaag ataggctaat tgttgaggtc gttcaggatg aaatagcaa gctgatgcac    900
ggcagggata ttgagaagag ggaaatcagc gagaggtaca tcgtcaccgt gaagaacctg    960
cgcaaggacc tcaacgacga ggggctctac gccgacttga tgaagaccgt caagaactac   1020
```

```
gtgctctcca tcacgcagat cgacaacgac atttccaacc tcgtgcgcga gctcgaccac  1080
gaggatgtgg agaag                                                   1095

SEQ ID NO: 129          moltype = DNA  length = 486
FEATURE                 Location/Qualifiers
source                  1..486
                        mol_type = genomic DNA
                        organism = Plasmodium vivax
SEQUENCE: 129
ctaccatgga cgaagaaaag aaaggcggtg aaccaaatgg gcatcataaa agatatgtcg  60
caggagctta ggactaaggc cgaacagctt ccaacccccg aggatatatc agccaaaatt  120
cacagagtag ataaagaggt catcgataag ttaaacaaag acatcataga ggaagaaaat  180
ttagacaagc acaaaccgca cgtctgccag gagccagcat acgagaggga ctattcgtac  240
ctatgtcccg aagactgggt gaagaactcc aacgatcagt gctggggcat agactacgat  300
ggtcactgtg aagcgctaaa atatttccaa gattattctg tagaggagaa aaaagaattt  360
gaaatgaact gctgcgtctt gtggcctaag ctaaaaaatg aaggcatgaa aggagcgcac  420
aagaaggacc tcctaagggg atcgataagt tcaaacaatg ggttaataat aaagccgaaa  480
tatttg                                                             486

SEQ ID NO: 130          moltype = DNA  length = 945
FEATURE                 Location/Qualifiers
source                  1..945
                        mol_type = genomic DNA
                        organism = Plasmodium vivax
SEQUENCE: 130
gaattgaaga agaacaatgc cgcgttgacc tcacaaaggt catcttctag aaccacatcc  60
acaaggagct acaaaaatgc cccaaaaaat tccacttcat tcctttctcg tttatctatt  120
ctgatatttg ccttatcatg tgctattttt gtaaatactg catcaggggc ggcagctaat  180
agaccaaacg cgaatggctt tgtgtcacct actttaatag gatttggcga attaagcatc  240
caagaatcag aagaattcaa aagaatggct tggaataatt ggatgttgcg attggagtcc  300
gactggaaac attttaacga ttctgttgaa gaagccaaaa ccaaatggct tcatgaaaga  360
gactcagctt ggtctgattg gcttcgttcc ttgcaaagta aatggtctca ctatagtgaa  420
aaaatgctta aagaacacaa aagtaatgtt atggaaaaat cagccaactg gaatgacacg  480
caatggggaa attggataaa aactgaagga agaaaaattc tagaagcgca atgggaaaaa  540
tggattaaaa aaggtgatga ccaattacaa aagttaattt tagataaatg ggttcaatgg  600
aaaaatgata agatccgatc ctggttatcc agtgaatgga aaaccgaaga agattactac  660
tgggcaaatg tagagcgcgc tacaacagca aaatggttgc aagaagcaga gaaaatgcat  720
tggcttaaat ggaaagaaag aattaacaga gagtctgaac aatgggtgaa ctgggtccaa  780
atgaaagaaa gcgtttacat caatgtagaa tggaaaaaat ggcccaaatg gaaaaatgat  840
aaaaaaattc tatttaacaa atggtcaact aaccttgtct acaaatggac actgaaaaag  900
cagtggaacg tttggattaa ggaagcaaat actgcacccc aagtt                   945

SEQ ID NO: 131          moltype = DNA  length = 1587
FEATURE                 Location/Qualifiers
source                  1..1587
                        mol_type = genomic DNA
                        organism = Plasmodium vivax
SEQUENCE: 131
aagggtgtca ccttgagttg cgttttttcc catgcgagtg aggaacgtga gggtggcaca  60
gggacatttg ctttgagcaa tgagccgatt tattacgccc ctagtggggg gctggcgccg  120
tgcgcgctca tcagcagagg gttaagcggg gatgaggagg gtagcggcga ggacggcggt  180
gaagatggcg acggagatgg tggtgaagac agcgctgagg acaacgctga ggatggagac  240
gatgatggtg gcgaagatgg cggcttgccc gggggacgct tcccatacga agaaggaaaa  300
aagagtagcc ttgtgagcga cgcacccagc gacctcctgg atggagatgc ggatgaacat  360
gccgccgaag atgggggagc gaagcgaaag atgagtaaga aggaggaaga ggcggaggat  420
aacaaaattg acaagttggt aaatgcggaa atgaaaaagc tcgaggcagg ggaagaggcg  480
aacaaggatc ccgacgcaga accagaaaaa gaggaccagg gaagtggcca aggacaaagg  540
gcgaagctga ggtgctcaaa caagctaaat tacatacagg tgacggcgaa tggccaaagg  600
gagggcgacc tctttggcga gaacgacggg gagagcgccc cagctttcgt ggagataccc  660
cacgaggttg aggaggaaag cggcggtgtg cccacaaagc atgacgaagc gggggaagca  720
gctgcggcgg aggaaccaca taaccgcgtc gaccgagcgg aaaaagaaaa caacgcgaag  780
gacttaaaat ttgtggaggg ggagcgagaa agacaaagga gcagcccccc ctcgaatgga  840
tattcccaaa acagctttgt cgaactgaaa ggtgtgcccg ataaattgcc ccctaatttt  900
accaactcgc ttggtagctc cccaacgcac agtaatttgg agaaaccagt ttataagcac  960
ttaccctggt ctatcctggc atccgactct ggttcgaaca ccgggtcctg ggcagacgtc  1020
aacagtagta cctacaatgt gagtccattc agtttcacct caatacgtag tggtaactct  1080
ctgcatctac tgccgatgaa tttccaaatc caaaactcca tcgtgaaagt aactgatgag  1140
gagtatgaca aattgaagct taaaaacagc gtcaaagtgt atgacaaaaa tgccctggta  1200
gattataagt atgaaatttt tgaggtgaag gaaggggagg aatataatga tgggaatgac  1260
ccttatgagg aaaggaatgg ggaagaaggg gatgcaggtg gagagggggg ttccgatggg  1320
gagggagatg cagattctaa atcatatcaa aataacaaat cggatggacg tgggttcttc  1380
gatgggacct tagtaaccta caccattatc attttagctg gtgttataat tctgctgcta  1440
agttttgtca tttattacta cgatataata aataaggtga agaggcgaat gagtgccaag  1500
cggaagaaca acaaatctat ggccatcgcg aatgatacat ccgcggggat gtacatgggc  1560
gacacctaca tggagaatcc ccacgtt                                      1587

SEQ ID NO: 132          moltype = DNA  length = 1002
FEATURE                 Location/Qualifiers
source                  1..1002
```

```
                        mol_type = genomic DNA
                        organism = Plasmodium vivax
SEQUENCE: 132
tcacaaggat gttcaggata ccgtttacca ccaccaaaaa gatggtttac cttcacttct    60
cgaccatact gtaaaacagc tgcatatttat gaacttaaac atatgccata ttatgtagat   120
gcagttagtg catcagaaaa cgtaaaacat gagaaatgga ataactggtt aaaagaaatg    180
aaatatcat taactgaaaa attagaaaaa gaatcacaag aatatatgga aaaattggaa     240
cagcaatggg atgaatttat gaaaaattca gaagataaat ggaggcatta taatccccaa    300
atggaagaag aatatcaatg tagtgtttat ccacttggat taaaatggga tgatgaaaag    360
tggactgcat ggttttatga aaaaggatta tggtgtttga agaaaagctt taaacatgg    420
ctcactgatt ctaaaaaagg ttacaacacc tacatgaaaa atcttttaca ggaatttggt    480
aaacaatttt atgaagattg gtgtcgtaga cctgaaaaac gtcgtgaaga taaaatttgc    540
aagagatggg gacaaaaagg attacgtaat gacaattact attcgttaaa gtggatgcag    600
tggagaaatt ggaaaaacag aaaccacgat caaaaacatg tgtgggtaac tcttatgaag    660
gatgcgctaa aggaatatac ggggcccgaa ttcaaattat ggactgagtt tagaaaagaa    720
aagatagact tttacaagca atggatgcaa gctttcgccg aacagtggac acaagacaaa    780
caatggaata cgtggactga agaaagaaat gaatatatga aaaagaaaaa agaagaagaa    840
gcaaaaaaaa aagcagcatc aaaaaaaaaa gcagcatcaa aaaaaggagg agcagcagca    900
aaggcaccag caaaaaaggc accaacaaaa aaagccgcac caggaacgaa ggcaccagca    960
aaaaaagcag cacctaaaaa agttgcagca ccaaatgcag ca                     1002

SEQ ID NO: 133       moltype = DNA  length = 807
FEATURE              Location/Qualifiers
source               1..807
                     mol_type = genomic DNA
                     organism = Plasmodium vivax
SEQUENCE: 133
aaggaggcag tgaagaaggg gtccaagaag gcaatgaagc agcccatgca caagccgaac    60
cttcttgaag aggaagactt tgaggagaaa gaatccttttt cggatgacga gatgaatggg   120
ttcatggagg agagcatgga tgcttctaag ttggatgcga agaaggccaa gacgaccctc    180
aggagctcgg agaagaagaa gactccaacg agcggaatga gtggaatgag tggaagcggc    240
gccaccagcg cagccaccga ggcagccacg aacatgaacg ccaccgccat gaacgccgct    300
gctaagggca cagcgaggc gagcaaaaag caaaccgact tgtccaacga agacctgttc    360
aacgacgagc tcacagaaga ggtcattgca gattcgtacg aagagggagg aaacgtggga    420
agcgaggaag ccgaaaagcct cacaaatgca tttgacgaca agctactaga ccaaggagtg    480
aatgaaaata ctctgctgaa cgacaacatg atttacaacg tcaatatggt tccacataag    540
aagcgagaat tatacatctc cccacacaag catacctctg cagcaagcag taaaaatggc    600
aaacatcatg cggcggacgc ggacgctttg gacaaaaaac tgagggctca cgagctgctc    660
gagctggaaa acggagaagg cagcaactca gtcattgtcg aaacggaaga agtggatgtt    720
gacctaaacg gaggaaagtc aagcggctcc gtgtcccttcc tcagctccgt agtcttcttg    780
ctcatcggat tgttatgttt caccaat                                       807

SEQ ID NO: 134       moltype = DNA  length = 2313
FEATURE              Location/Qualifiers
source               1..2313
                     mol_type = genomic DNA
                     organism = Plasmodium vivax
SEQUENCE: 134
aacctgagca acgattgcaa aaaaggagcc aacaacagct ttaagttaat cgtgcacacc    60
agcgatgata ttttgacact caagtggaag gtcactgggg aaggggcagc tccaggcaac   120
aaagcagatg taaagaagta caaactccct accctagaga ggcctttcac ttccgtcgaa    180
gtgcattcag ccaacgccaa gtcgaagata atcgaaagca aattttacga cattggcagc    240
ggcatgccag cccagtgcag cgcgatcgcc acgaactgct tcctcagcgg cagcctcgaa    300
atcgagcact gctaccactg caccctgttg gagaagaagc tggcccaaga cagcgagtgc    360
ttcaagtacg tctcgagtga agcgaaggag ttgatcgaga aagacacgcc gattaaagct    420
caagaagaag acgccaactc tgcagaccac aaactgatcg agtccataga cgtgatacta    480
aaggcagtgt acaatcagat aaagatgag gaaagaagg agctcatcac cccggaggaa     540
gtggacgaaa atttgaagaa agagctagcc aattattgta ccctactgaa ggaggtagac    600
acaagtggca ctcttaacaa ccaccagatg gcaaacgaag aggaaacgtt cagaaatttg    660
actcgactgt tgcgaatgca tagcgaagaa aacgtggtga cccttcagga caaactgaga    720
aacgcagcca tatgcatcaa gcacatcgac aagtggattc ttaacaagag ggggttgacc    780
ctaccggaag aagggtaccc atcggaaggg taccccccag aagagtaccc ccggaggaa    840
ctcctcaaag aaatcgagaa ggaaaaaagc gctctgaatg atgaagcgtt cgctaaagat    900
accaacggag tcatccaccct ggataagcct cccaacgaaa tgaaatttaa atcccccat    960
tttaaaaaga gcaaatactg taacaatgag tactgtgata ggtggaaaga taaaacgagt   1020
tgcatgtcaa atatagaagt ggaagagcaa ggggattgcg ggctctgttg gattttcgcc   1080
tctaagttac acttagaaac gatcaggtgc atgagagggt atggccactt ccgcagctcc   1140
gctctgtttg tggccaactg ctcgaagagg aagcaagag atagatgcaa cgtgggtct    1200
aaccctacag agttttcttca aattgttaag gacacgggat tttttacctct agagtccgat   1260
ctccctaca gctatagcga cgcggggaac tcctgcccca ataaaagaaa caagtcgacc    1320
aacctgtggg gggataccaa actgctgtat cataagagac ccaatcagtt tgcacaaaca    1380
ctcgggtacg tttcctacga aagcagtcgc tttgagcaca gcatcgacct cttcatagac    1440
atcctcaaaa gggaaattca aaacaaaggc tccgttatca tttacataaa aaccaacaat    1500
gtcatcgatt gtgactttaa tggaagagtc gtccacagcc tatggtggcca taagatgca    1560
gatcatgccg ctaacctgat cggttatggt aactacatca gtgctggtgg ggagaagagg    1620
tcctattgga ttgtgcgaaa cagctggggg tactactggg gagatgaagg caactttaag    1680
gttgacatgt acgccccgga gggatgcaaa cggaacttca tccacacggc tgttgtgttt    1740
aagatagacc tgggcatcgt cgaagtcccg aagaaggacg aggggtccat ttatagctac    1800
ttcgttcagt acgtccccaa cttttttgcac agcctttctc acgtgagtta cggtaagggt    1860
```

```
gctgataagg gagcggcggt ggtgacaggg caggcgggag gagcggtagt cacaggacag  1920
actgaaacgc ccactccgga ggccgctaaa aatggggatc agccaggagc acagggtagc  1980
gaggcagaag tcgcggaggg tggccaggca ggaaatgaag cccgggaggg gttgcaagag  2040
agtgctgttt cgtcgcaaac gagtgaggtt acgccgcaat ctagtataac tgctccgcaa  2100
atcggtgcag ttgccccaca aatcggtgca gctgccccac aaatcgatgt agccgcccca  2160
caaatcgatg tagtcgcccc acaaacgagg tccgttgacg ccccccaaac gagctcggtt  2220
gccgcccacc ccccaaacgt gacgccgcag aacgtgacgc ttggggaggg ccagcacgcg  2280
gggggtgtag gctccctcat ccccgcggac aac                               2313

SEQ ID NO: 135          moltype = DNA  length = 657
FEATURE                 Location/Qualifiers
source                  1..657
                        mol_type = genomic DNA
                        organism = Plasmodium vivax
SEQUENCE: 135
gaaaccctgc tagacagcga aacgttaaag aactacgaaa aggaaacgaa cgaatacatt  60
cgcaaaaaaa aagtggagaa actgttcgat gttattttaa aaaatgttct ggtaaacaaa  120
ccggaaaatg tatacctgta catatacaag aacatttatt ccttcctttt gaacaaaatt  180
tttgtgatcg gccctccttt gctgaaaatt actcccacct tatgttctgc gattgccagc  240
tgctttagct actaccacct cagcgcctcg cacatgatcg agtcttacac tactggtgaa  300
gtagatgacg ctgcagagag ttccacaagc aaaaagttag tcagtgacga cttaatctgc  360
tccatcgtta aaagcaacat aaaccagctg aacgcgaaag aaaagcgggg gtatgtagtc  420
gaagggttcc ccggcaccaa tcttcaggca gacagttgcc tacggcattt gccatccttac  480
gtttttgtcc tgtacgccga cgaagagtac atttatgaca agtacgaaca agagaacaac  540
gtaaaaattc gttcagacat aacagccaa acttttgatg aaaacacaca gttgttcgaa  600
gtggccgagt caacacgaa tccgctgaag gatgaggtaa aggtctactt aaggaac     657

SEQ ID NO: 136          moltype = DNA  length = 339
FEATURE                 Location/Qualifiers
source                  1..339
                        mol_type = genomic DNA
                        organism = Plasmodium vivax
SEQUENCE: 136
tatccaaaaa agaacttcga caaacccgac ccaacttccc cataccaagg acaatatgga  60
gagtctgagg aacaaagaca aggttatgga atccccccca acccaaccat gattaacctt  120
actggtaacc aagaccaacg accaaatgta ttgcaacaat ttggaataaa caacaaaaat  180
gtaatgcagt ttttaataaa catgtttgtg tacgttgctg ctatattagt tagttttaaaa  240
atatgggact acatgtctta cagcaaatgt gattattaca aagatttatt attaagaatt  300
gtaagatacc aatcacacat gaatgatggt aagatggcc                         339

SEQ ID NO: 137          moltype = DNA  length = 1998
FEATURE                 Location/Qualifiers
source                  1..1998
                        mol_type = genomic DNA
                        organism = Plasmodium vivax
SEQUENCE: 137
agccgcatcg acaagcagcc catccagagc agctacctct tccaggataa cgcagtcccg  60
cctgttcgat tctccgcagt agatgcgac ctgttttcca ttggagtagt tcacacagag  120
gagcaaatat ttatgacga cgccaactgg tgattagca gcgtgcccag taagtacctg  180
aacttgcatc tactcaaaac gggttctaga ccccattttt cgcacttctc cgtatctatg  240
aacacgggtt gcaacctatt catcgcttca ccggtgggag aaaccttccc cttgagtcgc  300
tccaaagatg gagcgacgtg gaaagcattt gaaacggacg acagtgtaga ggtgattcac  360
agagagacga aggaaaagag aatctataag ctcaagttca ttcctctgaa gagtggggct  420
ctcctaaagg ttgacgtttt gaagggaatt cccttttggg ttatctcaca agggaggaaa  480
atcctaccaa cgatttgttc tggagatgag gaggtgctat caaacccaca gaatgaggtc  540
ttcaaagagt gcacatcgtc gagtagtctc tctcccgaat ttgattgtct agccgggctg  600
agcacctacc ataggggataa gagaaccac acgtggaaaa cgtctagcgg atctatagtg  660
cagtttataa agatcttctt caataagcc gtacaaatta ccaagtttag gtttaagccc  720
agagcgaaac tgctgtcttg gccctccgaa gtagctctcc aattcgatac cgatgaggag  780
gtgatcatac caattctgca tacgcacaat atgggggcaga acacgactag gctagaaacac  840
ccaatcatca ccacctctgt taaggtagaa gtgagagaca tgtacgaacg ggcaagtgaa  900
aatacaggag gttctttcga ggtaattgga agcacatgcc agatgatgga gacgactac  960
atgacgcacc atgctgttat agacatcacc gagtgtgatc gtaggttgga gtccctccca  1020
gatgttatgc ccttaacgaa gggagcaaa tttctggcca tttgtccccg cccctgcttg  1080
agcagctcca atggggggagt catttacggg tcagatgttt attccacaga ttctgccgta  1140
tgtggggcgg ccgtacacgc ggggggtgtgc agccgtgagg gggagggcag ctgccacttc  1200
ctcgttgtgt tgcgcggcgg gcgggccaac ttcgtggggg ctctccagaa caacgtcctg  1260
tctctcagtc ggggtggtgg cggtagcggt agcgtagct ccaccagtag cgatgcgat  1320
ggcgatagcg atagctccac cagtagggcc aacttctcat tttccctctc cagtcgctca  1380
gggtcggggg ggggtccgcg cggggccac gcagaagccg cgccaagcag ctactccatt  1440
gtgttcaagc cgagggacca tttggctcca acgaacggct ttctagtaga ctcagggaga  1500
gagttcacca gctacggaag cgttgcctac ggatggaaga gggaggtttc tcctccgtcc  1560
tcttttttcct ctccttctcc tagctacact tccccccgt tggaagaacc gacgctgctt  1620
agggggggact cctccctcatt caatgggatt tactccgtag ggatagaatt cccccccgtg  1680
tcggctagcc aaaattgcat ttcccaactg gattgccaga ccaacttctg gaagtttcag  1740
atgcaagaaa atgcaccta ctttgtgcag gtgctagtgg ggaataaaac ttcccctgag  1800
aagcagaagg ccttcgtcga gctgaatggc gttcccatca taaggggggt ggaccttggc  1860
ccagacgagg tcttcgtcgc cactgaccgc gtgcaggtga cgaaccgggc cctcgtcctc  1920
acgtccactt gcctgggcgg cgagagtgcc tgctcgcggg cgcgcgtcag catcatgcg  1980
```

```
gtccagattg tgaagacg                                                         1998

SEQ ID NO: 138           moltype = DNA   length = 1746
FEATURE                  Location/Qualifiers
source                   1..1746
                         mol_type = genomic DNA
                         organism = Plasmodium vivax
SEQUENCE: 138
aacggtatga ataaagacaa agacgcagag attactcccc ctccgttcat cgtcttgccg    60
ggtggaaaaa aaatccacat gctgcaaagc gaatacgagt atgacgttct gcgggatatg    120
taccgaacgg atgaggcgaa tgggggaagt ggtgagaagg agagtcaccc ctctggggat    180
ggtgcaatca gaagaaacga atttttaaa ctttttcacc acagggaggg tcattataag    240
tttgttatca aaaatgttcc caccaaattg agcgaccttt tgcagaaagg tggcaacgaa    300
caggagacag acctatttcc tcttttatac aggagtctgc aattcgcatg cagcgcagac    360
gggacgtggc catatgccag aagagaggtg gccttttta aaaacgggag cgtccactgc    420
gaagcggaat tcaaaacga gttatcagtg aggagaaccc cccgaagtgg aagaaatca    480
tttggacgtt ttcaaggggg gacactaata aaaagtagcg acctgaggag caaaattgtg    540
gaggggaatt cttatgataa aagggccgca ccctgaaga gtgaaaaaaa aagaaggct    600
ctcttttac acccagaaag tgtgctatac aaaatggaag aaatatttt ttatgaaaat    660
ccaagtgtca aaagtgaaat tgtcgggttt gttcttttc atgatgtgtg cacagtaacg    720
tccttaggac atggagcaca tcccgttaac tccccctttt tgggaagcga cctgctggag    780
atgatatttg gctactgcat tttacacggg tttaaaaaaa tcagagtgaa aagcgaatcc    840
ttaaattacg aaactgggat aaggacctca ttcattgaga ttttactcaa cggaaaaaca    900
gcacttgaac atttagggtt aagacttaca acgtagcga agttttctaa agaactgtat    960
tatgtaatca ctgggtatac gtggaaaagt gatttggtgc tatcacccat agtaaggttt    1020
gaacatgatt tatacgtgca tcacgacata gaggagcgat ttttccttta cgtgaataaa    1080
atgtatagga atatgctcca cgatttgtcc ttctcttgtg atgaaaatta ttatcctat    1140
aaaaattgtt atgacatcta cccctccgtg agaaggagtc aaaataatct ttgtctcttc    1200
gaactgaatc ccatatatga agaattgaag agctctttc cagactcttg taatattggc    1260
caacgcgtta gaaaatgcta tgaggagata aaaaaaaacg ttgtctgcac acataacggt    1320
gaaggaggag aagacggatg taagtactac caatttattg taaatacatt cataaagccg    1380
aggaggaaaa cgtcctttt tatttatcac aatatgtatg tacaggaata tcttcaaag    1440
aaatcctacc cctattactt gctactcagt gaggttataa aaatgaaga aaataactt    1500
ctcgaaaaag gcaactacga cttagtggcc gatgcacaga cgcaccctctt cttaaattac    1560
gttttgcaaa attctacctt ttttatcttt tggaatttct ctaccgaatt ttggaaaagg    1620
tttcggtaca tccaggctgg cccaaccggg gccacttcca caccgcagaa ggggcaagct    1680
gtgttttgcc ccatggccta tgcgtacgaa tttgtggagc acctcgacac gttttatgtg    1740
aggggg                                                              1746

SEQ ID NO: 139           moltype = DNA   length = 1176
FEATURE                  Location/Qualifiers
source                   1..1176
                         mol_type = genomic DNA
                         organism = Plasmodium vivax
SEQUENCE: 139
tccgttgaag aggctaaaaa aaatactcag gaagttgtga caaatgtgga caatgctgct    60
aaatctcagg ccaccaattc aaatccgata agtcagcctg tagatagtaa taaagcggag    120
aaggttccag gagattctac gcatggaaat gttaacagtg gccaagatag ttctaccaca    180
ggtaaagctg ttacgggga tggtcaaaat ggaaatcaga cacctgcaga aagcgatgta    240
cagcgaagtg atattgccga aagtgtaagt gctaaaaatg ttgatccgca gaaatctgta    300
agtaaaagaa gtgacgacac tgcaagcgtt acaggtattg ccgaagctgg aaaggaaaac    360
ttaggcgcat caaatagtcg accttctgag tccaccgttg aagcaaatag cccaggtgat    420
gatactgtga acagtgcatc tatacctgta gtgagtggtg aaaacccatt ggtaccccc    480
tataatggtt tgaggcattc gaaagacaat agtgatagcg atggacctgc ggaatcaatg    540
gcgaatcctg attcaaatag taaaggtgag acgggaaagg ggcaagataa tgatatgccg    600
aaggctacta agatagtag taatagttca gatggtacca gctctgctac gggtgatact    660
actgatgcag ttgatagggaa aattaataaa ggtgttcctg aggatagga taaaactgta    720
ggaagtaaag atggagggg ggaagataac tctgcaaata aggatgcagc gactgtagtt    780
ggtgaggata gaattcgtga gaacagcgct ggtggtagca ctaatgatag atcaaaaat    840
gacacggaaa gagagcgggc ctctaccct gacagtaaac aaagtgagga tgcaactgcg    900
ctaagtaaaa ccgaaagttt agaatcaaca gaaagtggag atagaactac taatgataca    960
actaacagtt tagaaaataa aaatggagga aaagaaaagg atttacaaaa gcatgatttt    1020
aaaagtaatg atacgccgaa tgaagaacca aattctgatc aaactacaga tgcagaagga    1080
catgacaggg atagcatcaa aaatgataaa gcagaaagga gaaagcatat gaataaagat    1140
actttacga aaatacaaa tagtcaccat ttaaat                                1176

SEQ ID NO: 140           moltype = DNA   length = 1590
FEATURE                  Location/Qualifiers
source                   1..1590
                         mol_type = genomic DNA
                         organism = Plasmodium vivax
SEQUENCE: 140
atacggaatg gaaacaaccc gcaggcatta gttcctgaaa agggcgctga cccgagtggg    60
ggccagaaca accgctccgg agaaaaccaa gacacgtgcg aaattcaaaa gatgccgaa    120
gaaatgatgg aaaaaatgat gaaggaaaaa gacgtgttta gctccatcat ggaacctctc    180
cagagcaaat taactgacga tcatctgtgt tcaaaaatga aatatacgaa catttgtctt    240
cacgaaaagg acaaaactcc cttgaccttc ccctgcacaa gtccgcagta cgaacagcta    300
attcatcgct tcacttataa aaagttgtgc aactccaagg tggcctttag caacgtcttg    360
ctcaaatcct tcatcgataa aaaaaatgaa gaaaacacat ttaacacgat catacagaat    420
```

-continued

```
tacaaagttc tgtccacttg cattgacgat gatttgaagg acatttataa tgcatccata  480
gagttattct ccgacataag aacctccgtc acagaaatta ccgaaaagtt gtggtccaaa  540
aatatgatcg aagttttaaa gacaagagag caaaccattg caggcatttt atgtgagtta  600
agaaatggaa ataattctcc cctagtatcg aacagttttt cctatgaaaa ttttggaatt  660
ctcaaggtta attatgaggg attactaaac caggcgtatg cggccttttc agactactat  720
tcatactttc ccgcttttgc cattagcatg ttagaaaagg gagggttggt cgaccgcttg  780
gtcgccatcc atgagagctt gaccaactac aggacgagaa atattctcaa gaagatcaat  840
gagaagtcca aaaatgaggt cctcaataat gaagaaatta tgcacagctt gagcagttac  900
aagcaccatg ccgggggcac gcgtggcgcc ttcctgcagt ccagagatgt gcgcgaagtt  960
acgcaaggag atgtgagcgt tgatgagaag ggcgaccggg ccaccaccgc ggggggcaac  1020
caaagcgcaa gcgtggctgc ggcggccccg aaggatgcgg gcccaaccgt ggctgctcct  1080
aacactgctg ctacgctcaa aacggctgct tcccccaacg cggctgctac taacactgct  1140
gctcccccca acatgggtgc cacctccccg ctgagcaacc ccctgtacgg caccagctcc  1200
ctgcagccaa aggacgtcgc ggtgctggtc agagatctgc tcaagaacac gaacatcatc  1260
aagttcgaga ataacgaacc gactagccaa atggacgatg aagaaattaa gaagctcatt  1320
gagagctcct tttcgacttt gagcgacaac accatgttaa tgcggttgct cataaagccg  1380
caggcggcca tcttactaat cattgagtcc ttcattatga tgacgccctc ccccacgagg  1440
gacgccaaga cctattgcaa gaaagcccta gttaatggcc agctaatcga aacctcagat  1500
ttaaacgcgg cgacggagga agacgacctc ataaacgagt tttccagcag gtacaattta  1560
ttctacgaga ggctcaagct ggaggagttg                                   1590
```

```
SEQ ID NO: 141         moltype = DNA  length = 1572
FEATURE                Location/Qualifiers
source                 1..1572
                       mol_type = genomic DNA
                       organism = Plasmodium vivax
SEQUENCE: 141
aaggagtact gcgaccagct tagcttttgc gatgtgggat tgacacacca ctttgatacg  60
tattgtaaga atgaccagta cctgttcgtt cactacactt gtgaggacct ctgcaaaacg  120
tgtggcccta attcgtcctg ctacggaaac aagtacaaac ataagtgcct gtgcaatagc  180
cccttcgaga gtaaaaagaa ccattccatt tgcgaagcac gaggtagctg cgatgcacag  240
gtatgcggca agaatcaaat ttgcaaaatg gtagacgcta aagcaacatg cacatgtgca  300
gataaatacc aaaatgtgaa tggggtgtgt ctaccggaag ataagtgcga ccttctgtgc  360
ccctcaaaca aatcgtgcct gctggaaaat gggaaaaaaa tatgcaagtg cattaatggg  420
ttgactctac agaacggcga gtgcgtctgc tcggatagca gccaaattga agaaggacac  480
ctctgtgtgc ccaagaataa atgtaaacgg aaggagtacc aacagctctg caccaatgag  540
aaggaacact gtgtgtatga tgagcagacg gacattgtgc ggtgcgactg cgtggaccac  600
ttcaagcgga acgaacgggg aatttgcatc ccagtcgact actgcaaaaa tgtcacctgc  660
aaggaaaatg agatttgcaa agttgttaat aatacaccca catgtgagtg taaagaaaat  720
ttaaaaagaa atagtaacaa tgaatgtgta ttcaataaca tgtgtcttgt taataaaggg  780
aactgcccca ttgattcgga gtgcatttat cacgagaaaa aaaggcatca gtgtttgtgc  840
cataagaagg gcctcgtcgc cattaatggc aagtgcgtca tgcaggacat gtgcaggagc  900
gatcagaaca aatgctccga aaattccatt tgtgtaaatc aagtgaataa agaaccgctg  960
tgcatatgtt tgtttaatta tgtgaagagt cggtcgggcg actcgcccga gggtggacag  1020
acgtgcgtgg tggacaatcc ctgcctcgcg cacaacgggg gctgctcgcc aaacgaggtt  1080
tgcacgttca aaaatggaaa ggtaagttgc gcctgcgggg agaactaccg ccccaggggg  1140
aaggacagcc caacgggaca agcggtcaaa cgggggggaag cgaccaaacg gggtgacgcg  1200
ggtcagcccg ggcaggcgca ctcagcaaat gagaacgcgt gcctgcccaa gacgtccgag  1260
gcggaccaaa ccttcacctt ccagtacaac gacgacgcgg ccatcattct cgggtcctgc  1320
ggaattatac agtttgtgca aaagagcgat caggtcattt ggaaaattaa cagcaacaat  1380
cacttttaca tttttaatta tgactatcca tctgagggtc agctgtcggc acaagtcgtg  1440
aacaagcagg agagcagcat tttgtactta aagaaaaccc acgcggggaa agtcttttac  1500
gccgactttg agttgggtca tcagggatgc tcctacggaa acatgtttct ctacgcccac  1560
cgggaggagg ct                                                      1572
```

```
SEQ ID NO: 142         moltype = DNA  length = 1020
FEATURE                Location/Qualifiers
source                 1..1020
                       mol_type = genomic DNA
                       organism = Plasmodium vivax
SEQUENCE: 142
agcaaaaaca ttattattct gaacgatgaa attaccacca ttaaaagccc gattcattgc  60
attaccgata tttattttct gtttcgcaac gaactgtata aaacctgcat tcagcatgtg  120
attaaaggcc gcaccgaaat tcatgtgctg gtgcagaaaa aaattaacag cgcgtgggaa  180
acccagacca ccctgtttaa agatcatatg tggtttgaac tgccgagcgt gtttaacttt  240
attcataacg atgaaattat tattgtgatt tgccgctata aacagcgcag caaacgcgaa  300
ggcaccattt gcaaacgctg gaacagcgtg accggcacca tttatcagaa agaagatgtg  360
cagattgata aagaagcgtt tgcgaacaaa aacctggaaa gctatcagag cgtgccgctg  420
accgtgaaaa acaaaaaatt tctgctgatt tgcggcattc tgagctatga atataaaacc  480
gcgaacaaag ataactttat tagctgcgtg gcgagcgaag ataaaggccg cacctggggc  540
accaaaattc tgattaacta tgaagaactg cagaaaggcg tgccgtattt ttatctgcgc  600
ccgattattt ttggcgatga atttggcttt tatttttata gccgcattag caccaacaac  660
accgcgcgcg gcggcaacta tatgacctgc accctggatg tgaccaacga aggcaaaaaa  720
gaatataaat ttaaatgcaa acatgtgagc ctgattaaac cggataaaag cctgcagaac  780
gtggcgaaac tgaacggcta ttatattacc agctatgtga aaaaagataa ctttaacgaa  840
tgctatctgt attataccga acagaacgcg attgtggtga aaccgaaagt gcagaacgat  900
gatctgaacg gctgctatgg cggcagcttt gtgaaactgg atgaaagcaa agcgctgttt  960
atttatagca ccggctatgg cgtgcagaac attcataccc tgtattatac ccgctatgat  1020
```